(12) United States Patent
Thurieau et al.

(10) Patent No.: US 7,566,734 B2
(45) Date of Patent: *Jul. 28, 2009

(54) IMIDAZOLYL DERIVATIVES

(75) Inventors: Christophe Alain Thurieau, Paris (FR); Lydie Francine Poitout, Le Kremlin-Bicetre (FR); Marie-Odile Galcera, Bondoufle (FR); Thomas D. Gordon, Medway, MA (US); Barry A. Morgan, Franklin, MA (US); Christophe Philippe Moinet, Montréal (CA); Dennis C. H. Bigg, Gif sur Yvette (FR)

(73) Assignee: Societe de Conseils de Recherches et d'Applications Scientifiques, S.A.S., Paris (FR)

( * ) Notice: Subject to any disclaimer, the term of this patent is extended or adjusted under 35 U.S.C. 154(b) by 968 days.

This patent is subject to a terminal disclaimer.

(21) Appl. No.: 10/333,556

(22) PCT Filed: Jul. 31, 2001

(86) PCT No.: PCT/US01/23959

§ 371 (c)(1),
(2), (4) Date: Oct. 20, 2003

(87) PCT Pub. No.: WO02/10140

PCT Pub. Date: Feb. 7, 2002

(65) Prior Publication Data

US 2007/0032653 A1     Feb. 8, 2007

Related U.S. Application Data

(60) Provisional application No. 60/222,584, filed on Aug. 1, 2000.

(51) Int. Cl.
*A61K 31/4164* (2006.01)
*A61K 31/417* (2006.01)
*C07D 233/02* (2006.01)
*C07D 233/61* (2006.01)

(52) U.S. Cl. .................. 514/399; 514/400; 548/311.1; 548/315.1; 548/335.5

(58) Field of Classification Search .............. 548/335.5, 548/338.1, 311.1, 315.1; 514/400, 399
See application file for complete search history.

(56) References Cited

U.S. PATENT DOCUMENTS

| 5,128,355 | A | 7/1992 | Carini et al. |
| 5,733,882 | A | 3/1998 | Carr et al. |
| 6,852,725 | B1 | 2/2005 | Thurieau et al. |

FOREIGN PATENT DOCUMENTS

| EP | 0 166 609 | 1/1986 |
| FR | 2 132 632 | 11/1972 |
| HU | 218 460 B | 9/1987 |
| JP | 61-024594 | 2/1986 |
| JP | 01-203383 | 8/1989 |
| JP | 10-502670 | 3/1998 |
| JP | 10-504808 | 5/1998 |
| WO | 94/04494 | 3/1994 |
| WO | 95/08550 | 3/1995 |
| WO | 96/00730 | 1/1996 |
| WO | WO 96/11927 | 4/1996 |
| WO | 96/16040 | 5/1996 |
| WO | 97/24119 | 7/1997 |
| WO | 97/30053 | 8/1997 |
| WO | 97/43278 | 11/1997 |
| WO | 97/45425 | 12/1997 |
| WO | 98/27108 | 6/1998 |
| WO | WO 99/64401 | 12/1999 |
| WO | WO 99/65942 | 12/1999 |
| WO | WO 00/00477 | 1/2000 |

OTHER PUBLICATIONS

Von Geldern et al., "Azole endothelin antagonists. 1. A receptor model explains an unusual structure-activity profile," J. Med. Chem., 1996, 394(4): 957-967.
Al-Dabbagh et al., "Species differences I noxidative drug metabolism: some basic considerations," Archives of Toxicology, 1984Supplement 7:219-231.
Bundgaard, Hans, Design of Prodrugs, 1985, p1, Elsevier Science Publishers.
Silverman, R., The Organic Chemistry of Drug Design and Drug Action, 1992, p. 352-400, Academic Press, Inc.
Emery, P.T.J. et al., "Anti-secretory properties of non-peptide somatostatin receptor agonists in isolated rat colon: luminal activity and possible interaction with p-glycoprotein," Br. J. Pharm., 135:1443-1448, 2002.
Albert, Rainer, et al.; "Direct Synthesis of [DOTA-Dphe$^1$] - Octreotide (SMT487) : . . . "; Bioorganic & Medicinal Chemistry Letters, 1998,vol. 8; pp. 1207-1210; XP002124712.
Bornowski, Heinz et al.; Chem. Abstract 1973, 78:13689.
Gordon, Thomas D. et al.; Chem. Abstract 1997, 127:248417.
Gramberg, Dieter et al; "Synthesis of a Type Vibeta-Turn Peptide . . . "; Helvetica Chimica Acta; 1995, vol. 78, pp. 1588-1606; XP000612160.
Hirschmann, Ralph et al.; "De Novo Design and Synthesis of Somatostatin . . . "; Journal of the American Chemical Society; 1996, vol. 115, No. 26; pp. 12550-12568; XP002124710.

(Continued)

*Primary Examiner*—Kamal A. Saeed
(74) *Attorney, Agent, or Firm*—Fish & Richardson; Alan F. Feeney; Tony K. Uhm

(57) ABSTRACT

The present invention is directed to imidazolyl derivatives of formula (I) where the substituents are defined in the specification, which are useful as agonists or antagonists of somatostatin receptors.

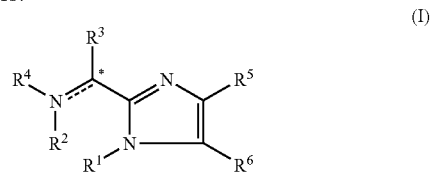

(I)

4 Claims, No Drawings

OTHER PUBLICATIONS

Hirschmann, Ralph et al.; "Nonpeptidal Peptidomimetics with a beta-D-glucose Scaffolding"; Journal of the American Chemical Society; 1992, vol. 114, No. 23; XP002124711.

Miller, William H. et al.; Chem. Abstract 1997, 127:161822.

Papageorgiou, Christos et al.; "A Non-peptide ligand for the Somatostatin Receptor having a Benzodiazepinone Structure"; Bioorganic & Medicinal Chemistry Letters; 1996, vol. 6, No. 3; pp. 267-272; XP004135075.

Stocker, Fred B. et al.; Chem. Abstract, 1970, 72:121434.

Towliati, Hossein; Chem. Abstract, 1971, 74:53642.

Von Geldern, Thomas W. et al.; Chem Abstract, 1996, 124:193276.

Von Geldern, Thomas W. et al.; Chem. Abstract, 1996, 124:127005.

Von Geldern, Thomas W. et al.; Chem. Abstract, 1996, 124:164291.

Ellinger and Goldberg; J. Chem. Soc.; 1949; 263, 266; Beilstein Registry No. 1965.

Ellinger and Goldberg; J. Chem. Soc.; 1949; 263, 266; Beilstein Registry No. 3689018.

Ellinger and Goldberg; J. Chem. Soc.; 1949; 263, 266; Beilstein Registry No. 3798855.

Gordon, T. D. et al., "Synthetic approaches to the "azole" peptide mimetics," Tet. Lett., 34:1901-1904, 1993.

English language abstract for JP 01-203383, published Aug. 16, 1989.

Avallone, L. et al., "Research on heterocyclic compounds, XXXV[1]. Synthesis of 2-phenylimidazo[1,2-a]-pyrazine-3-acetates", Monatshefte fur Chemie, 1996, 127:947-953.

Barraclough, P. et al., "Synthesis and pharmacological properties of BW315C and other inotropic 2-arylimidazo[1,2-a]pyrazines", Bioroganic & Med. Chem. Letters, 1993, 3:509-514.

Morgenstern, R. et al., "Zur antihistaminischen aktivitat einiger 4-phenylimidazole". Pharmazie, 1975, 30:103-105. (in German).

Morgenstern, R. et al., "Antihistamine activity of some 4-phenylimidazoles", Pharmazie, 1975, 30:103-105. (in English).

Spitzer, W. A. et al., "Imidazo[1,2-1]pyrimidines and imidazo[1,2-a]pyrazines: the role of nitrogen position in inotropic activity", J. Med. Chem., 1988, 31:1590-1595.

Towliati, H. "Notiz uber die synthese von imidazolderivaten", Chem. Ber., 1970, 103:3952-3953. (in German).

Towliati, H. "Report on the synthesis of imidazole derivatives", Chem. Reports., 1970, 103:3952-3953. (English translation).

Werbel, L. M. et al., "Synthesis of fused imidazo-heterocyclic systems", J. Heterocyclic Chem., 1965, 2:287-290.

IMIDAZOLYL DERIVATIVES

This application is a national phase application, under U.S.C. Section 371, of PCT/US01/23959 filed Jul. 31, 2001, which claims priority to U.S. Provisional Application No. 60/222,584 filed Aug. 1, 2000, the entire contents of which are incorporated herein by reference.

BACKGROUND OF THE INVENTION

The present invention is directed to compounds and compositions containing said compounds which bind selectively to somatostatin receptor subtypes and the use of said compounds for treating medical disorders which are mediated by somatostatin receptor subtypes. Somatostatin (somatotropin release inhibiting factor, SRIF), a tetradecapeptide hormone, originally isolated from bovine hypothalami (Brazesu, P. et al., Science 179, 77-79, 1973) has been shown to have a wide range of regulatory effects on the release of a variety of hormones such as growth hormone, prolactin, glucagon, insulin, gastrin (Bloom, S. R. and Poldack, J. M., Brit. Med. J. 295, 288-289, 1987). In addition, antiproliferative properties (Reichlin, S., N. Engl. J. Med. 309, 1495-1501, 1983) have been obtained with somatostatin analogs in metastatic prostatic cancer (Parmar, H. et al, Clin. Exp. Metastasis, 10, 3-11, 1992) and in several other neuroendocrine neoplasms in man (Anthony, L. et al. Acta Oncol., 32, 217-223, 1993). Metabolism of somatostatin by aminopeptidases and carboxypeptidases leads to a short duration of action.

The actions of somatostatin are mediated via membrane bound receptors. The heterogeneity of its biological functions has led to studies to identify structure-activity relationships of peptides analogs at the somatostatin receptors which resulted in the discovery of five receptor subtypes (Yamada, et al, Proc. Natl. Acad. Sci. U.S.A 89, 251-255, 1992; Raynor, K. et al. Mol. Pharmacol., 44, 385-392, 1993). The functional roles of these receptors are under extensive investigation. Binding to the different types of somatostatin subtypes have been associated with the treatment of the following conditions and/or diseases. Activation of types 2 and 5 have been associated with growth hormone suppression and more particularly GH secreting adenomas (Acromegaly) and TSH secreting adenomas. Activation of type 2 but not type 5 has been associated with treating prolactin secreting adenomas. Other indications associated with activation of the somatostatin subtypes are restenosis, inhibition of insulin and/or glucagon and more particularly diabetes mellitus, hyperlipidemia, insulin insensitivity. Syndrome X, angiopathy, proliferative retinopathy, dawn phenomenon and Nephropathy; inhibition of gastric acid secretion and more particularly peptic ulcers, entercutaneous and pancreaticocutaneous fistula, irritable bowel syndrome, Dumping syndrome, watery diarrhea syndrome, AIDS related diarrhea, chemotherapy-induced diarrhea, acute or chronic pancreatitis and gastrointestinal hormone secreting tumors; treatment of cancer such as hepatoma; inhibition of angiogenesis, treatment of inflammatory disorders such as arthritis; chronic allograft rejection; angioplasty; preventing graft vessel and gastrointestinal bleeding. Somatostatin agonists can also be used for decreasing body weight in a patent.

In drug research, it is a key issue to minimize side effects by developing highly potent and selective drug molecules. Recent work on the development of nonpeptide structures (Hirshmann, R. et al, J. Am. Chem. Soc. 115, 12550-12568, 1993; Papageorgiou, C. and Borer, X., Bioorg. Med. Chem. Lett. 6, 267-272, 1996) have described compounds with low somatostatin receptor affinity.

The present invention is directed to a family of nonpeptide compounds, which are selective and potent somatostatin receptor ligands.

SUMMARY OF THE INVENTION

In one aspect the present invention is directed to a compound of the formula (I),

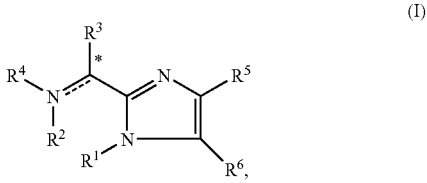

(I)

the racemic-diastereomeric mixtures and optical isomers of said compound of formula (I), the pharmaceutically-acceptable salts and prodrugs thereof or a pharmaceutically acceptable salt thereof, wherein ⎯⎯ represents an optional bond;

$R^1$ is H, $-(CH_2)_m-C(O)-(CH_2)_m-Z^1$, $-(CH_2)_m-Z^1$, $-(CH_2)_m-O-Z^1$ or $-(C_0-C_8)alkyl-C(O)-NH-(CH_2)_m-Z^3$;

$Z^1$ is an optionally substituted moiety selected from the group consisting of $(C_1-C_{12})alkyl$, benzo[b]thiophene, phenyl, naphthyl, benzo[b]furanyl, thiophene, isoxazolyl, indolyl,

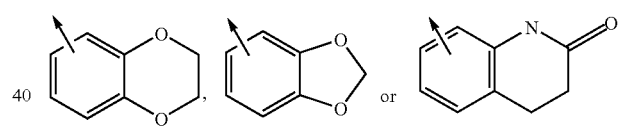

$R^2$ is H or $(C_1-C_8)alkyl$;

or $R^1$ and $R^2$ are taken together with the nitrogen atoms to which they are attached to form a compound of formula (Ia), (Ib) or (Ic),

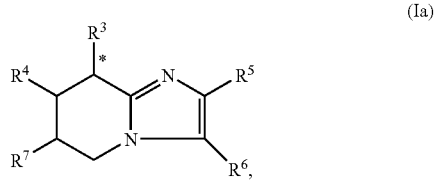

(Ia)

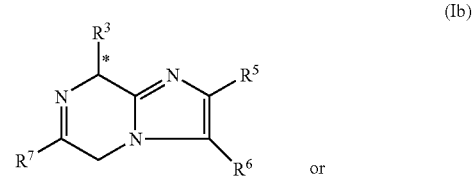

(Ib)

or

-continued

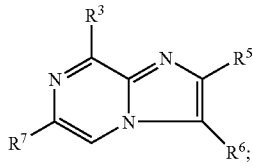
(Ic)

R³ is —(CH₂)ₘ-E-(CH₂)ₘ-Z²;
  E is O, S, —C(O)—, —C(O)—O—, —NH—C(O)—O— or a bond;
  Z² is H, (C₁-C₁₂)alkyl, amino, (C₁-C₁₂)alkylamino, N,N-di-(C₁-C₁₂)alkylamino, (C₁-C₁₂)alkylguanidino, or an optionally substituted moiety selected from the group consisting of phenyl, indolyl, imidazolyl, thiophene, benzothiophene, pyridinyl and naphthyl;
R⁴ is H or —(CH₂)ₘ-A¹;
  A¹ is —C(=Y)—N(X¹X²), —C(=Y)—X², —C(=NH)—X² or X²;
  Y is O or S;
  X¹ is H, (C₁-C₁₂)alkyl, —(CH₂)ₘ—NH—(C₁-C₈)alkyl, —(CH₂)ₘ—N-di-(C₁-C₈)alkyl or —(CH₂)ₘ-aryl;
  X² is —(CH₂)ₘ—Y¹—X³ or optionally substituted (C₁-C₁₂)alkyl;
    Y¹ is O, S, NH, C=O, (C₂-C₁₂)alkenyl having one or more double bonds, —NH—CO—, —CO—NH—, —NH—CO—O—(CH₂)ₘ—, —C≡C—, SO₂ or a bond;
    X³ is H, an optionally substituted moiety selected from the group consisting of (C₁-C₁₂)alkyl, (C₃-C₈)cycloalkyl, (C₁-C₁₂)alkoxy, aryloxy, (C₁-C₁₂)alkylamino, N,N-di-(C₁-C₁₂)alkylamino, —CH-di-(C₁-C₁₂)alkoxy, pyrrolidinyl, pyridinyl, thiophene, imidazolyl, piperidinyl, piperidinyl, benzothiazolyl, furanyl, indolyl, morpholino, benzo[b]furanyl, quinolinyl, isoquinolinyl, —(CH₂)ₘ-phenyl, naphthyl, fluorenyl, phthalamidyl, pyrimidinyl,

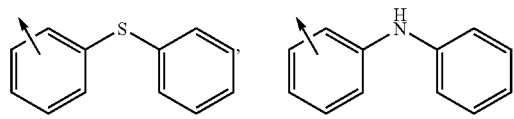

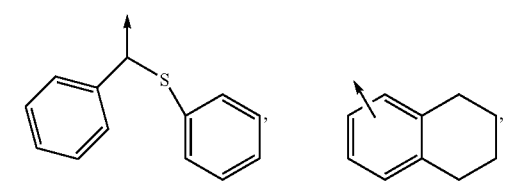

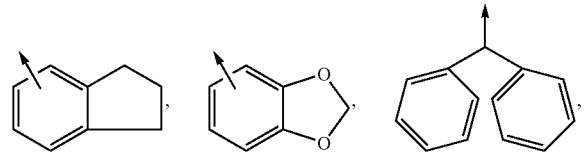

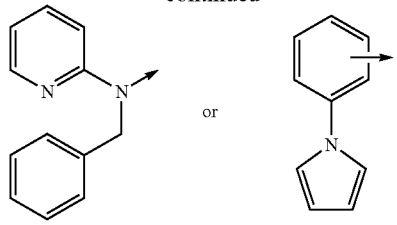

or X¹ and X² are taken together with the nitrogen to which they are attached to form an optionally substituted moiety selected from the group consisting of thiazolyl

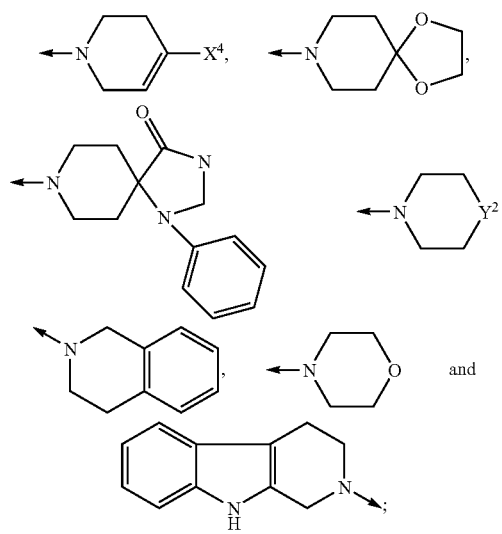

Y² is CH—X⁴, N—X⁴, —C(X⁴X⁴), O or S;
X⁴ for each occurrence is independently —(CH₂)ₘ—Y³—X⁵;
  Y³ is —C(O)—, —C(O)O— or a bond;
  X⁵ is hydroxy, (C₁-C₁₂)alkyl, amino, (C₁-C₁₂)alkylamino, N,N-di-(C₁-C₁₂)alkylamino, or an optionally substituted moiety selected from the group consisting of aryl, aryl(C₁-C₄)alkyl, furanyl, pyridinyl, indolyl, —CH(phenyl)₂,

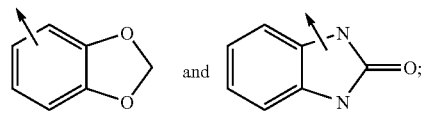

R⁵ is (C₁-C₁₂)alkyl, (C₀-C₆)alkyl-C(O)—O-Z⁵, (C₀-C₆)alkyl-C(O)—NH—(CH₂)ₘ-Z³ or optionally substituted aryl;
Z³ for each occurrence is independently amino, (C₁-C₁₂)alkylamino, N,N-di-(C₁-C₁₂)alkylamino, —NH—C(O)—O—(CH₂)ₘ-phenyl —NH—C(O)—O—(CH₂)ₘ—(C₁-C₆)alkyl or an optionally substituted moiety selected from the group consisting of imidazolyl, pyridinyl, morpholino, piperidinyl, piperazinyl, pyrazolidinyl, furanyl and thiophene;

$R^6$ is H or $(C_1-C_6)$alkyl;

$R^7$ is $(C_1-C_{12})$alkyl or $-(CH_2)_m-Z^4$;

$Z^4$ is an optionally substituted moiety selected from the group consisting of phenyl, naphthyl, indolyl, thiophene, benzo[b]furan, benzo[b]thiophene, isoxazolyl,

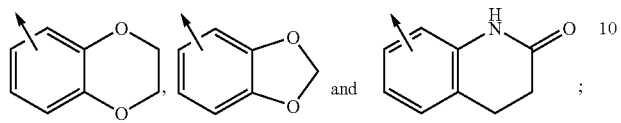

$Z^5$ is H, $(C_1-C_{12})$alkyl, $(CH_2)_m$-aryl;

wherein an optionally substituted moiety is optionally substituted by one or more substituents, each independently selected from the group consisting of Cl, F, Br, I, $CF_3$, CN, $N_3$, $NO_2$, OH, $SO_2NH_2$, $-OCF_3$, $(C_1-C_{12})$alkoxy, $-(CH_2)_m$-phenyl-$(X^4)_m$, $-S$-phenyl-$(X^4)_m$, $-S-(C_1-C_{12})$alkyl, $-O-(CH_2)_m$-phenyl-$(X^4)_m$, $-(CH_2)_m-C(O)-O-(C_1-C_8)$alkyl, $-(CH_2)_m-C(O)-(C_1-C_8)$alkyl, $-O-(CH_2)_m-NH_2$, $-O-(CH_2)_m-NH-(C_1-C_8)$alkyl, $-O-(CH_2)_m-N$-di-$((C_1-C_8)$alkyl) and $-(C_6-C_{12})$alkyl-$(X^4)_m$;

$X^4$ for each occurrence is independently selected from the group consisting of hydrogen, Cl, F, Br, I, $NO_2$, $N_3$, CN, OH, $-CF_3$, $-OCF_3$, $(C_1-C_{12})$alkyl, $(C_1-C_{12})$alkoxy, $-(CH_2)_m-NH_2$, $-(CH_2)_m-NH-(CH_2-C_8)$alkyl, $-(CH_2)_m-N$-di-$((C_1-C_8)$alkyl) and $-(CH_2)_m$-phenyl;

m for each occurrence is independently 0 or an integer from 1 to 6; and n for each occurrence is independently an integer from 1 to 5;

provided that:

(a) when $R^5$ is $(C_1-C_{12})$alkyl, or $-C(O)-O-Z^5$ and $Z^5$ is $(C_1-C_{12})$alkyl or optionally substituted aryl; $R^6$ is H or $(C_1-C_8)$alkyl; $R^7$ is $(C_1-C_{12})$alkyl or $Z^4$ and $Z^4$ is thiophene or optionally substituted phenyl, then $R^3$ is not $-C(O)-O-(CH_2)_m-Z$ where m is 0 and Z is H or $(C_1-C_{12})$alkyl or where m is 1 to 6 and Z is H;

(b) when $R^5$ is $(C_1-C_{12})$alkyl or optionally substituted phenyl; $R^1$ is H or $(C_1-C_6)$alkyl; $R^7$ is $(C_1-C_{12})$alkyl and $R^3$ is $-O-(CH_2)-Z^2$, then $Z^2$ is not an optionally substituted moiety selected from the group consisting of phenyl, indolyl, imidazolyl, thiophene, benzothiophene, pyridinyl, and naphthyl; and (c) when $R^5$ is H or $(C_1-C_{12})$alkyl; $R^1$ is $(C_1-C_8)$alkyl; $R^7$ is $(C_1-C_{12})$alkyl; and $R^3$ is $-O-Z^2$ or $-S-Z^2$, then $Z^2$ is not an optionally substituted moiety selected from the group consisting of phenyl, naphthyl, thiophene, benzothienyl and indolyl.

A preferred compound of formula I is where $R^1$ is H; $R^2$ is H; $R^3$ is $-CH_2$-phenyl; $R^4$ is $-(CH_2)_m-A^1$ where m in the definition of $R^4$ is 0; $R^5$ is phenyl; $R^6$ is H;

where $A^1$ is $-C(=Y)-N(X^1X^2)$;

Y is O; $X^1$ is H or methyl;

$X^2$ is $-(CH_2)_m-Y^1-X^3$;

m in the definition of $X^2$ is 0, 1, 2 or 3; $Y^1$ is a bond or O; and $X^3$ is N-methylpyrrolidin-2-yl, diethylamino, pyridinyl, thiophene, imidazolyl, diethoxymethyl, 1-benzyl-piperidin-4-yl, optionally substituted phenyl or

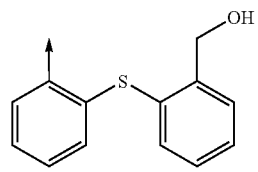

Another preferred compound of formula (I) is where $R^1$ is H; $R^2$ is H; $R^3$ is $-CH_2$-phenyl; $R^4$ is $-(CH_2)_m-A^1$ where m in the definition of $R^4$ is 0; $R^5$ is phenyl; $R^4$ is H;

where $A^1$ is $-C(=Y)-N(X^1X^2)$;

Y is O;

$X^1$ is benzyl and $X^2$ is 2-hydroxyethyl;

or $X^1$ and $X^2$ are taken together with the nitrogen atom to which they are attached to form

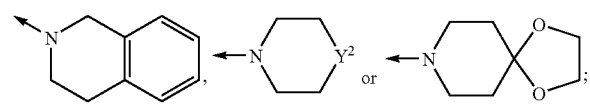

where $Y^2$ is $C-X^4$ or $N-X^4$;

$X^4$ is $-(CH_2)_m-Y^3-X^5$ where m in the definition of $X^4$ is 0 or 1; and $X^5$ is selected from the group consisting of furanyl, benzyl, phenyl, amino,

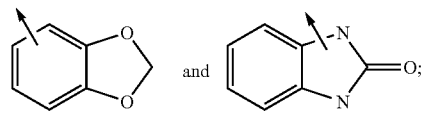

Another preferred compound of formula (I) is where $R^1$ is H; $R^2$ is H; $R^3$ is $-CH_2$-phenyl; $R^4$ is $-(CH_2)_m-A^1$ where m in the definition of $R^4$ is 0; $R^5$ is phenyl; $R^4$ is H;

where $A^1$ is $-C(=Y)-X^2$,

Y is O; $X^2$ is $-(CH_2)_m-Y^1-X^3$;

where m in the definition of $X^2$ is 0, 1 or 2;

$Y^1$ is O, $-NH-CO-$, $-CO-NH-$, $-NH-CO-O-CH_2$, $SO_2$ or a bond; and $X^3$ is methyl, furanyl, pentyl, phenyl, indolyl, p-$NO_2$-phenyl, naphthyl, fluorenyl, $-CH(phenyl)_2$, benzothiazolyl, phthalamidyl, N,N-dimethylamino,

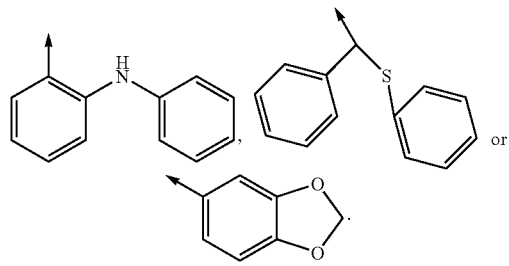

Another preferred compound of formula (I) is where $R^1$ is H; $R^2$ is H; $R^3$ is $-CH_2$-indol-3-yl; $R^4$ is $-(CH_2)_m-A^1$ where m in the definition of $R^4$ is 0; $R^5$ is phenyl or t-Bu; $R^6$ is H;

A¹ is —C(=Y)—N(X¹X²);
  Y is O or S; X¹ is H; X² is 0, 1 or 2;
    m in the definition of X² is 0, 1 or 2;
      Y¹ is a bond, and X³ is phenyl, o-Cl-phenyl, m-Cl-phenyl, p-phenyloxy-phenyl, 2,6-di-isopropylphenyl, m-CF₃-phenyl, p-ethoxycarbonyl-phenyl, 2,4-difluorophenyl, m-NO₂-phenyl, p-benzyloxyphenyl, o-isopropylphenyl, n-hexyl, 4-morpholino, naphthyl or

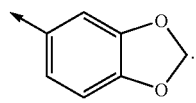

Another compound of formula (I) is where R¹ is H; R² is H; R³ is —CH₂-indol-3-yl; R⁴ is —(CH₂)ₘ-A¹ where m in the definition of R⁴ is 0; R⁵ is phenyl or t-Bu; R⁶ is H;
where A¹ is —C(=Y)—X²,
  Y is O; X² is —(CH₂)ₘ—Y¹—X³;
    where m in the definition of X² is 0, 1 or 2;
      Y¹ is O, —CO—NH—, —NH—CO—O—CH₂— or a bond; and X³ is methyl, 3-pentyl, phenyl, p-NO₂-phenyl, phthalamidyl, N,N-dimethylamino, p-aminophenyl, fluorenyl or

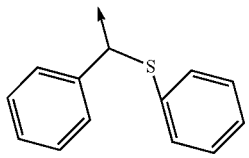

Another preferred compound of formula (I) is where R¹ is H; R² is H; R³ is —CH₂-indol-3-yl; R⁴ is —(CH₂)ₘ-A¹ where m in the definition of R⁴ is 0; R⁵ is phenyl or t-Bu; R⁶ is H;
where A¹ is —C(=Y)—N(X¹X²);
  Y is O; X¹ is hydrogen; X² is —(CH₂)ₘ—Y¹—X³;
    where m in the definition of X² is 0, 1, 2 or 3;
      Y¹ is O, or a bond; and X³ is cyclopentyl, 4-OH-butyl, N,N-diethylamino, N-methyl-pyrrolidin-3-yl, —CH(ethoxy)₂, phenyl, p-SO₂NH₂phenyl p-OH-phenyl, o-CF₃-phenyl, p-Cl-phenyl, —CH(phenyl)₂,

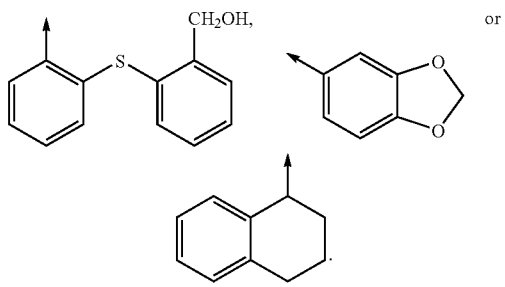

Another preferred compound of formula (I) is where R¹ is H; R² is H; R³ is —CH₂-indol-3-yl; R⁴ is —(CH₂)ₘ-A¹ where m in the definition of R⁴ is 0; R⁵ is phenyl or t-Bu; R⁶ is H;
where A¹ is —C(=Y)—X²;

Y is O; X² is —(CH₂)ₘ—Y¹—X²;
  where m in the definition of X² is 0, 1, 2 or 3;
    Y¹ is —NH—CO, —C=C—, —C≡C— or a bond; and X³ is t-butyl, 1-methylcarbonyl-piperidin-4-yl, phenyl, p-Cl-phenyl, m-CF₃-phenyl, 4-nitro-naphthyl, p-methoxy-phenyl, m-(phenylethyl)-phenyl, indol-3-yl or p-aminophenyl.

Another preferred compound of formula (I) is where R¹ is H; R² is H; R³ is —CH₂-indol-3-yl, —(CH₂)₄—NH—CO—O-t-Bu or —(CH₂)₄—NH₂; R⁴ is —(CH₂)ₘ-A¹ where m in the definition of R⁴ is 0; R⁵ is phenyl, o-methoxyphenyl, p-Br-phenyl, p-nitro-phenyl or p-N,N-diethylamino-phenyl; R⁴ is H;
where A¹ is —C(=Y)—N(X¹X²);
  Y is O; X¹ is H; X² is —(CH₂)ₘ—Y¹—X³;
    where m in the definition of X² is 0;
      Y¹ is a bond; and X³ is o-Br-phenyl, m-Br-phenyl, p-Br-phenyl, o-Cl-phenyl, m-Cl-phenyl, p-Cl-phenyl, o-nitro-phenyl, m-nitro-phenyl, p-nitro-phenyl, o-CF₃-phenyl, m-CF₃-phenyl, p-CF₃-phenyl, p-F-phenyl, 2,4-di-F-phenyl, 2,5-di-F-phenyl, 2,5-di-methoxy-phenyl, m-OMe-phenyl, p-OMe-phenyl, 2-CF₃-4-Cl-phenyl or 3-nitro-4-F-phenyl.

Of the immediately above compounds it is preferred that when R⁵ is phenyl and R³ is —(CH₂)-indol-3-yl that the stereochemistry at the carbon to which R³ is attached is in the R-configuration.

Another preferred compound of formula (I) is where R¹ is H; R² is H; R³ is —CH₂-indol-3-yl, —(CH₂)₄—NH—CO—O-t-Bu or —(CH₂)₄—NH₂; R⁴ is —(CH₂)ₘ-A¹ where m in the definition of R⁴ is 0; R⁵ is phenyl, o-methoxyphenyl, p-methoxyphenyl, p-Br-phenyl, p-nitro-phenyl or p-N,N-diethylamino-phenyl; R¹ is H;
where A¹ is —C(=Y)—X²;
  Y is O; X² is —(CH₂)ₘ—Y¹—X³;
    where m in the definition of X² is 1;
      Y¹ is a bond; and X³ is phenyl, o-Br-phenyl, m-Br-phenyl, p-Br-phenyl, o-Cl-phenyl, m-Cl-phenyl, p-Cl-phenyl, o-nitro-phenyl, m-nitro-phenyl, p-nitro-phenyl, o-CF₃-phenyl, m-CF₃-phenyl, p-CF₃-phenyl, o-F-phenyl, m-F-phenyl, p-F-phenyl, N,N-di-methylamino-phenyl, o-OMe-phenyl, m-OMe-phenyl, p-OMe-phenyl, 3,4-di-Cl-phenyl, 3,4,5-tri-OMe-phenyl, p-Me-phenyl, p-OH-phenyl or 2,4-di-F-phenyl.

Of the immediately foregoing compounds when R⁵ is phenyl or o-OMe-phenyl and R³ is —(CH₂)-indol-3-yl; it is preferred that the compounds are the separated enantiomers (R or S configuration) according to the carbon to which R³ is attached.

Another preferred compound of formula (I) is where R¹ is H; R³ is —(CH₂)₄—NH—CO—O-t-Bu or —(CH₂)₄—NH₂; R⁴ is —(CH₂)ₘ-A¹ where m in the definition of R⁴ is 0; R⁵ is phenyl; R⁶ is H;
where A¹ is —C(=Y)—X²;
  Y is O; X² is —(CH₂)ₘ—Y¹—X³;
    where m in the definition of X² is 0, 1 or 2;
      Y¹ is S, SO₂ or a bond; and X³ is phenyl, 3,4-di-Cl-phenyl, 3,4,5-tri-OMe-phenyl, p-Me-phenyl, p-OH-phenyl, 2,4-di-F-phenyl, 2-furanyl, 2-pyridinyl, 3-pyridinyl, naphthyl, 2-quinolinyl, 3-quinolinyl, 4-quinolinyl, 8-quinolinyl, 1-isoquinolinyl, 2-thiophene or 2-pyrimidinyl.

Another preferred compound of formula (I) is where R¹ is H; R² is H; R³ is —(CH₂)₄—NH—CO—O-t-Bu or —(CH₂)₄—NH₂; R⁴ is —(CH₂)ₘ-A¹ where m in the definition of R⁴ is 0; R⁵ is phenyl; R⁶ is H;

where $A^1$ is —C(=Y)—$X^2$;
Y is O; $X^2$ is —$(CH_2)_m$—$Y^1$—$X^3$;
where m in the definition of $X^2$ is 0, 1, 2 or 3;
$Y^1$ is a bond; and $X^3$ is 5-indolyl, 3-indolyl, 4-indolyl, 2-indolyl, 5-OMe-indol-3-yl, 5-OMe-indol-2-yl, 5-OH-indol-2-yl, 5-OH-indol-3-yl, 5-Br-indol-3-yl, 2-Me-indol-3-yl, 2-benzothiophene, 3-benzothiophene or 2-benzofuran.

Another preferred compound of formula (I) is where $R^1$ is H; $R^2$ is H; $R^3$ is —$(CH_2)_m$-indol-3-yl, —$(CH_2)_4$—NH—CO—O-t-Bu or —$(CH_2)_4$—$NH_2$; $R^4$ is —$(CH_2)_m$-$A^1$ where m in the definition of $R^4$ is 0; $R^5$ is phenyl, o-OMe-phenyl or p-OMe-phenyl; $R^4$ is H;
where $A^1$ is $X^2$;
$X^2$ is —$(CH_2)_m$—$Y^1$—$X^3$;
where m in the definition of $X^2$ is 1, 2, or 3;
$Y^1$ is S, O or a bond; and $X^3$ is phenyl, o-OH-phenyl, p-OH-phenyl, o-F-phenyl, m-F-phenyl, p-F-phenyl, o-$CF_3$-phenyl, o-OMe-phenyl, m-OMe-phenyl, o-nitro-phenyl, p-nitro-phenyl, 3,4-di-Cl-phenyl, 2-nitro-3-OMe-phenyl, o-Br-phenyl, m-Br-phenyl, p-Br-phenyl, 2-thiophene, 3,4,5-tri-OMe-phenyl, p-N,N-dimethylamino-phenyl, p-$OCF_3$-phenyl, p-(3-N,N-dimethylamino)propoxy)phenyl, 3-F-4-OMe-phenyl, 2-pyridinyl, 3-pyridinyl, 4-pyridinyl, 2-Cl-quinolin-3-yl, 2-quinolinly, methyl, n-butyl, n-pentyl, n-hexyl, 3,3-dimethyl-butyl, benzyl, cyclohexyl or p-t-Bu-phenyl.

Another preferred compound of formula (I) is where $R^1$ is H; $R^2$ is H; $R^3$ is —$(CH_2)_4$—NH—CO—O-t-Bu or —$(CH_2)_4$—$NH_2$; $R^4$ is —$(CH_2)_m$-$A^1$ where m in the definition of $R^4$ is 0; $R^5$ is phenyl; $R^6$ is H;
where $A^1$ is $X^2$;
$X^2$ is —$(CH_2)_m$—$Y^1$—$X^3$—;
where m in the definition of $X^2$ is 1, 2 or 3;
$Y^1$ is O or a bond; and $X^3$ is phenyl, o-OH-phenyl, p-OH-phenyl, o-F-phenyl, m-F-phenyl, p-F-phenyl, o-$CF_3$-phenyl, o-OMe-phenyl, m-OMe-phenyl, p-OMe-phenyl, o-nitro-phenyl, p-nitro-phenyl, 3,4-di-Cl-phenyl, 2-nitro-3-OMe-phenyl, o-Br-phenyl, m-Br-phenyl, p-Br-phenyl, p-phenyl-phenyl, 2-thiophene, 3,4,5-tri-OMe-phenyl, p-N,N-dimethylamino-phenyl, p-benzyloxy-phenyl, p-$OCF_3$-phenyl, p-(3-(N,N-dimethylamino)propoxy)phenyl, 3-F-4-OMe-phenyl, 2-pyridinyl, 3-pyridinyl, 4-pyridinyl, 2-Cl-quinolin-3-yl, 2-quinoliny, 3-indolyl, 6-methoxycarbonyl-indol-3-yl, 1-methyl-indol-3-yl, 2-methyl-indol-3-yl, methyl, n-butyl, n-pentyl, n-hexyl, 3,3-dimethyl-butyl, benzyl, cyclohexyl or p-t-Bu-phenyl.

Another preferred compound of formula (I) is where $R^1$ is —$(CH_2)$—CO-$Z^1$; $R^2$ is H; $R^3$ is —$(CH_2)_4$—NH—CO—O-t-Bu, —$(CH_2)_4$—NH—CO—O-benzyl, —$(CH_2)$-phenyl or —$(CH_2)$-indol-3-yl; $R^4$ is —$(CH_2)_m$-$A^1$ where m in the definition of $R^4$ is 0; $R^5$ is phenyl; $R^6$ is H;
where $Z^1$ is ethyl, phenyl, p-OMe-phenyl, p-phenyl-phenyl, p-Cl-phenyl, p-Br-phenyl, p-$N_3$-phenyl, p-F-phenyl, m-nitro-phenyl, p-nitro-phenyl, p-CN-phenyl, 2,5-di-OMe-phenyl, 3,4-di-Cl-phenyl, N,N-dimethylamino-phenyl, 3-methyl-4-Cl-phenyl or napththyl;
$A^1$ is —C(=Y)—$X^2$;
Y is O; $X^2$ is —$(CH_2)_m$—$Y^1$—$X^3$;
where m in the definition of $X^2$ is 0;
$Y^1$ is O; and $X^3$ is t-bu.

Another preferred compound of formula (I) is where $R^1$ is —$(CH_2)$—CO—$(CH_2)_m$-$Z^1$ where m in the definition of $R^1$ is 0, 1 or 2; $R^2$ is H; $R^3$ is —$(CH_2)$-indol-3-yl or —$(CH_2)_4$—NH—CO—O-t-Bu; $R^4$ is H or —$(CH_2)_m$-$A^1$ where m in the definition of $R^4$ is 0; $R^5$ is phenyl, o-OMe-phenyl, p-nitro-phenyl, p-Br-phenyl, t-Bu, —CH$(CH_3)_2$—CO—NH—$(CH_2)_2$—CO—O-t-Bu, —CH$(CH_3)_2$—CO—NH—$(CH_2)_3$-imidazol-1-yl, —CH$(CH_3)_2$—CO—NH—$(CH_2)_2$-pyridin-2-yl, —CH$(CH_3)_2$—CO—NH—$(CH_2)_3$-4-morpholino, —CH$(CH_3)_2$—CO—NH—$(CH_2)$-pyridin-4-yl or —CH$(CH_3)_2$—CO—NH—$(CH_2)_2$—N,N-diethylamino; $R^3$ is H;
where $Z^1$ is ethyl, propyl, phenyl, p-OMe-phenyl, p-Cl-phenyl, p-Br-phenyl, p-F-phenyl, p-nitro-phenyl, m-nitro-phenyl, p-CN-phenyl, p-$N_3$-phenyl, p-phenyl-phenyl, 3-Me-4-Cl-phenyl, p-N,N-diethylamino-phenyl, 2,5-di-OMe-phenyl, 3,4-di-Cl-phenyl, 3,4-di-F-phenyl, p-$OCF_3$-phenyl, p-benzyloxy-phenyl, p-pentyl-phenyl, 3,4,5-tri-OMe-phenyl, 3-nitro-4-Cl-phenyl, 3-Cl-4-nitro-phenyl, 3-methyl-5-chloro-benzothiophen-2-yl, 2-benzofuranyl, 3-benzothiophene, 3-phenyl-isoxazol-5-yl, 3-(2,4-di-Cl-phenyl)-isoxazol-5-yl, 3-indolyl, 5-Br-thiophen-2-yl, naphthyl,

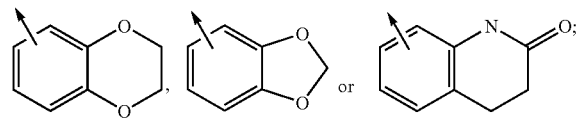

$A^1$ is —C(=Y)—$X^2$;
Y is O; $X^2$ is —$(CH_2)_m$—$Y^1$—$X^3$;
where m in the definition of $X^2$ is 0;
$Y^1$ is O; and $X^3$ is t-Bu.

Another preferred compound of formula (I) is where $R^1$ and $R^2$ are taken together to form a compound of formula (Ib) or (Ic);
$R^3$ is —$(CH_2)$-indol-3-yl, —$(CH_2)$-phenyl, —$(CH_2)_4$—NH—CO—O-benzyl or —$(CH_2)_4$—$NH_2$;
$R^5$ is phenyl, o-OMe-phenyl, p-OMe-phenyl, p-Br-phenyl, p-nitro-phenyl, t-Bu or —CH$(CH_3)_2$—CO—NH—$(CH_2)_2$—$NH_2$; $R^5$ is H;
$R^7$ is ethyl, propyl, phenyl, p-OMe-phenyl, p-Cl-phenyl, p-Br-phenyl, p-F-phenyl, p-nitro-phenyl, m-nitro-phenyl, p-CN-phenyl, p-$N_3$-phenyl, p-phenyl-phenyl, 3-Me-4-Cl-phenyl, p-N,N-diethylaminophenyl, 2,5-di-OMe-phenyl, 3,4-di-Cl-phenyl, 3,4-di-F-phenyl, p-$OCF_3$-phenyl, p-benzyloxy-phenyl, p-pentyl-phenyl, 3,4,5-tri-OMe-phenyl, 3-nitro-4-Cl-phenyl, 3-Cl-4-nitro-phenyl, 3-methyl-5-chloro-benzothiophen-2-yl, 2-bezofuranyl, 3-benzothiophene, 3-phenyl-isoxazol-5-yl, 3-(2,4-di-Cl-phenyl)-isoxazol-5-yl, 3-indolyl, 5-Br-thiophen-2-yl, naphthyl,

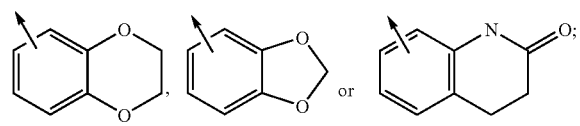

In another respect, the present invention is directed to a compound of the formula (II),

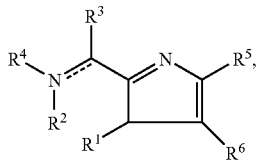

(II)

the racemic-diastereomeric mixtures and optical isomers of said compound of formula (II), the pharmaceutically-acceptable salts or prodrugs thereof or a pharmaceutically acceptable salt of said prodrug, wherein ——— represents an optional bond;

$R^1$ is H, —$(CH_2)_m$—C(O)—$(CH_2)_m$-$Z^1$, —$(CH_2)_m$-$Z^1$, —$(CH_2)_m$—O-$Z^1$ or —$(C_0$-$C_6)$alkyl-C(O)—NH—$(CH_2)_m$-$Z^3$;

$Z^1$ is an optionally substituted moiety selected from the group consisting of $(C_1$-$C_{12})$alkyl, benzo[b]thiophene, phenyl, naphthyl, benzo[b]furanyl, thiophene, isoxazolyl, indolyl,

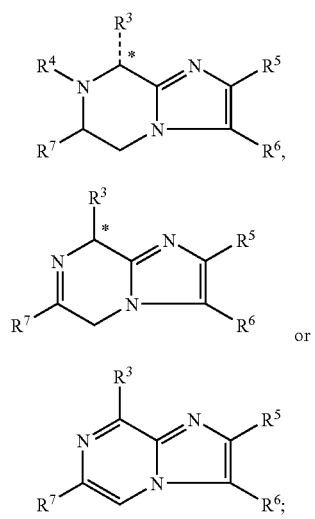

$R^2$ is H or $(C_1$-$C_8)$alkyl;

or $R^1$ and $R^2$ are taken together with the nitrogen atoms to which they are attached to form a compound of formula (IIa), (IIb) or (IIc),

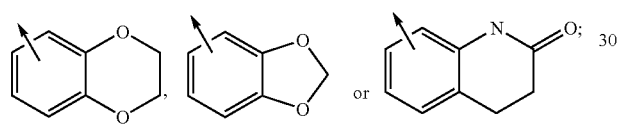

$R^3$ is —$(CH_2)_m$-E-$(CH_2)_m$-$Z^2$;

E is O, S, —C(O)—, —C(O)—O—, —NH—C(O)—O—, —N($C_1$-$C_8$)alkyl-C(O)—O— or a bond;

$Z^2$ is H, $(C_1$-$C_{12})$alkyl, amino, $(C_1$-$C_{12})$alkylamino, N,N-di-$(C_1$-$C_{12})$alkylamino, $(C_1$-$C_{12})$alkylguanidino, or an optionally substituted moiety selected from the group consisting of phenyl, indolyl, imidazolyl, thiophene, benzothiophene, pyridinyl and naphthyl;

$R^4$ is H or —$(CH_2)_m$-$A^1$;

$A^1$ is —C(=Y)—N($X^1X^2$), —C(=Y)—$X^2$, —C(=NH)—$X^2$ or $X^2$;

Y is O or S;

$X^1$ is H, $(C_1$-$C_{12})$alkyl, —$(CH_2)_m$—NH—$(C_1$-$C_8)$alkyl, —$(CH_2)_m$-N-di-$(C_1$-$C_8)$alkyl or —$(CH_2)_m$-aryl;

$X^2$ is —$(CH_2)_m$—$Y^1$—$X^3$ or optionally substituted $(C_1$-$C_{12})$alkyl;

$Y^1$ is O, S, NH, C=O, $(C_2$-$C_{12})$alkenyl having one or more double bonds, —NH—CO—, —CO—NH—, —NH—CO—O—$(CH_2)_m$—, —C≡C—, $SO_2$ or a bond;

$X^3$ is H, an optionally substituted moiety selected from the group consisting of $(C_1$-$C_{12})$alkyl, $(C_3$-$C_8)$cycloalkyl, $(C_1$-$C_{12})$alkoxy, aryloxy, $(C_1$-$C_{12})$alkylamino, N,N-di-$(C_1$-$C_{12})$alkylamino, —CH-di-$(C_1$-$C_{12})$alkoxy, pyrrolidinyl, pyridinyl, thiophene, imidazolyl, piperidinyl, piperazinyl, benzothiazolyl, furanyl, indolyl, morpholino, benzo[b]furanyl, quinolinyl, isoquinolinyl, —$(CH_2)_m$-phenyl, naphthyl, fluorenyl, phthalamidyl, pyrimidinyl.

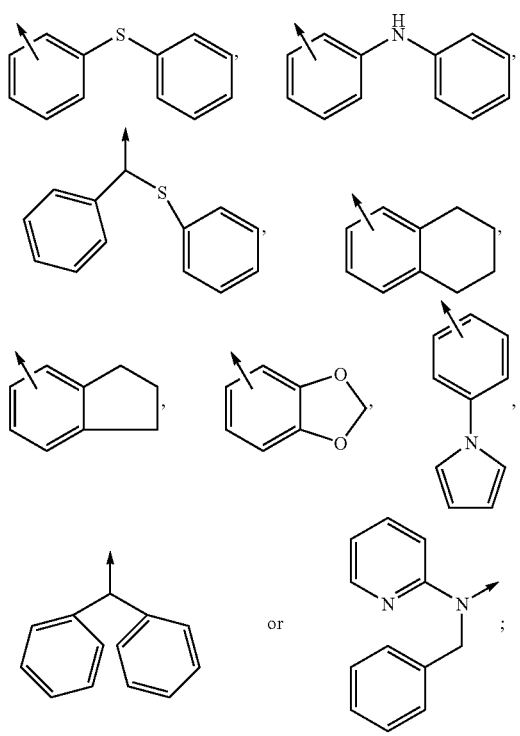

or $X^1$ and $X^2$ are taken together with the nitrogen to which they are attached to form an optionally substituted moiety selected from the group consisting of thiazolyl,

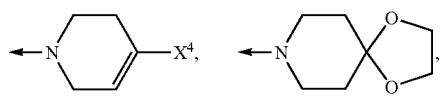

-continued

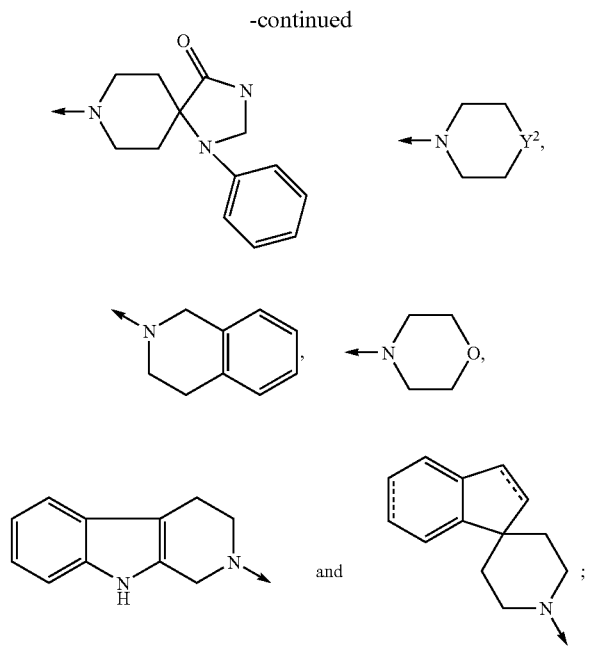

Y² is CH—X⁴, N—X⁴, —C(X⁴X⁴), O or S.

X⁴ for each occurrence is independently H or —(CH₂)$_m$—Y³—X⁵;

Y³ is —C(O)—, —C(O)O— or a bond;

X⁵ is hydroxy, (C₁-C₁₂)alkyl, amino, (C₁-C₁₂) alkylamino, N,N-di-(C₁-C₁₂)alkylamino, or an optionally substituted moiety selected from the group consisting of aryl, aryl(C₁-C₄)alkyl, furanyl, pyridinyl, indolyl, piperidinyl, —CH(phenyl)₂,

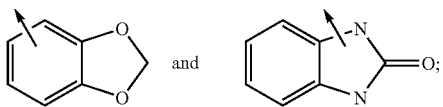

R⁵ is (C₁-C₁₂)alkyl, (C₀-C₆)alkyl-C(O)—O-Z⁵, (C₀-C₆)alkyl-C(O)—NH—(CH₂)$_m$-Z³ or optionally substituted aryl;

Z³ for each occurrence is independently amino, (C₁-C₁₂) alkylamino, amino(C₁-C₁₂)alkyl, (C₅-C₇)cycloalkylamino, amino(C₅-C₇)cycloalkyl, N—(C₁-C₁₂)alkylamino, N,N-di-(C₁-C₁₂)alkylamino, —NH—C(O)—O—(CH₂)$_m$-phenyl, —NH—C(O)—O—(CH₂)$_m$—(C₁-C₈)alkyl, or an optionally substituted moiety selected from the group consisting of imidazolyl, pyridinyl, morpholino, piperidinyl, piperazinyl, pyrazolidinyl, furanyl, phenyl, indolyl and thiophene, provided that when m is 0 in the formula for R⁶ then Z³ is not —NH—C(O)—O—(CH₂)$_m$- phenyl or —NH—C(O)—O—(CH₂)$_m$—(C₁-C₆)alkyl;

R⁶ is H or (C₁-C₆)alkyl;

R⁷ is (C₁-C₁₂)alkyl or —(CH₂)$_m$-Z⁴;

Z⁴ is an optionally substituted moiety selected from the group consisting of phenyl, naphthyl, indolyl, thiophene, benzo[b]furan, benzo[b]thiophene, isoxazolyl,

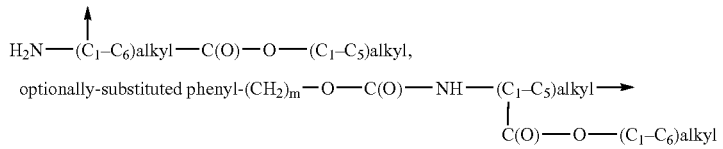

Z⁵ is H, (C₁-C₁₂)alkyl, or —(CH₂)$_m$-aryl;

wherein an optionally substituted moiety is optionally substituted by one or more substituents, each independently selected from the group consisting of Cl, F, Br, I, CF₃, CN, N₃, NO₂, OH, SO₂NH₂, —OCF₃, (C₁-C₁₂)alkoxy, —(CH₂)$_m$-phenyl-(X⁶)$_n$, —S-phenyl-(X⁶)$_n$, —S—(C₁-C₁₂)alkyl, —O—(CH₂)$_m$-phenyl-(X⁶)$_n$, —(CH₂)$_m$—C(O)—O—(C₁-C₈)alkyl, —(CH₂)$_m$—C(O)—(C₁-C₈) alkyl, —O—(CH₂)$_m$—NH₂, —O—(CH₂)$_m$—NH—(C₁-C₈)alkyl, —O—(CH₂)$_m$—N-di-((C₁-C₈)alkyl), —(C₀-C₁₂)alkyl-(X₆)$_n$ and —(CH₂)$_m$-phenyl-X⁷;

X⁴ for each occurrence is independently selected from the group consisting of hydrogen, Cl, F, Br, I, NO₂, N₃, CN, OH, —CF₃, —OCF₃, (C₁-C₁₂)alkyl, (C₁-C₁₂)alkoxy, —(CH₂)$_m$—NH₂, —(CH₂)$_m$—NH—(C₁-C₈)alkyl, —(CH₂)$_m$—N-di-((C₁-C₈)alkyl) and —(CH₂)$_m$-phenyl;

X⁷ is —NH—C(=NH.HI)—X⁶, wherein X⁶ is thiophene, (C₁-C₁)alkyl or phenyl;

m for each occurrence is independently 0 or an integer from 1 to 6; and n for each occurrence is independently an integer from 1 to 5;

provided that:

(a) when R⁵ is (C₁-C₁₂)alkyl, or —C(O)—O-Z⁵ and Z⁵ is (C₁-C₁₂)alkyl or optionally substituted aryl; R⁶ is H or (C₁-C₈)alkyl; R⁷ is (C₁-C₁₂)alkyl or Z⁴ and Z⁴ is thiophene or optionally substituted phenyl, then R³ is not —C(O)—O—(CH₂)$_m$-Z where m is 0 and Z is H or (C₁-C₁₂)alkyl or where m is 1 to 6 and Z is H;

(b) when R⁵ is (C₁-C₁₂)alkyl or optionally substituted phenyl; R⁴ is H or (C₁-C₆)alkyl; R⁷ is (C₁-C₁₂)alkyl and R³ is —O—(CH₂)-Z², then Z² is not an optionally substituted moiety selected from the group consisting of phenyl, indolyl, imidazolyl, thiophene, benzothiophene, pyridinyl, and naphthyl; and (c) when $R^5$ is H or $(C_1-C_{12})$alkyl; $R^6$ is $(C_1-C_6)$alkyl; $R^7$ is $(C_1-C_{12})$alkyl; and $R^3$ is —O-$Z^2$ or —S-$Z^2$, then $Z^2$ is not an optionally substituted moiety selected from the group consisting of phenyl, naphthyl, thiophene, benzothienyl and indolyl.

A preferred group of compounds of formula (II), have the following formula:

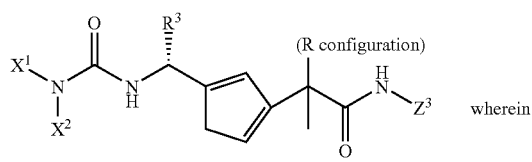

wherein $Z^3$ is —CH$_2$—NH$_2$, —(CH$_2$)$_2$—NH$_2$, —(CH$_2$)$_3$—NH$_2$ or

 ; and $Z^3$ is —CH$_2$—NH$_2$, —(CH$_2$)$_2$—NH$_2$, —(CH$_2$)$_3$—NH$_2$ or $X^1$ is —(CH$_2$)$_2$—N(CH$_3$)$_2$ and $X^2$ is benzyl; or $X^1$ and $X^2$ are taken together with the nitrogen atom to which they are attached, to form

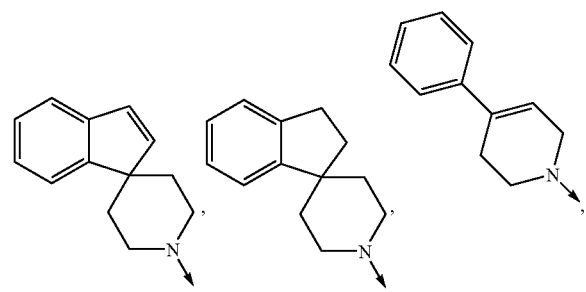

Another preferred group of compounds of formula (II) have the following formula:

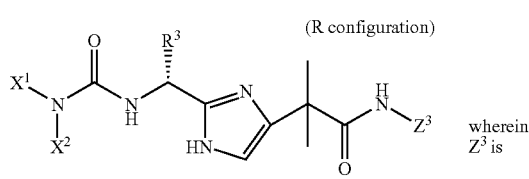

wherein $Z^3$ is

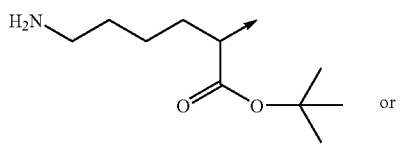

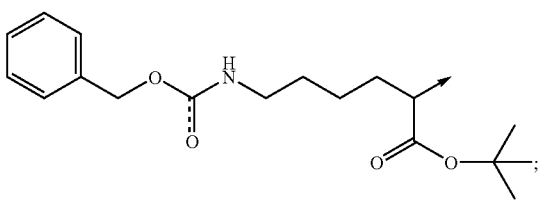

and $X^1$ is —(CH$_2$)$_2$—N(CH$_3$)$_2$ and $X^2$ is benzyl; or $X^1$ and $X^2$ are taken together with the nitrogen atom to which they are attached, to form

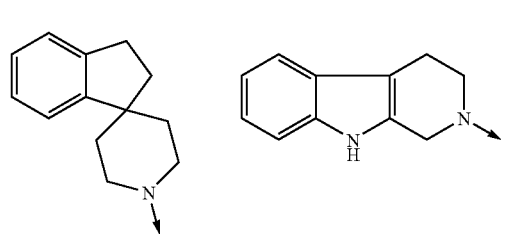

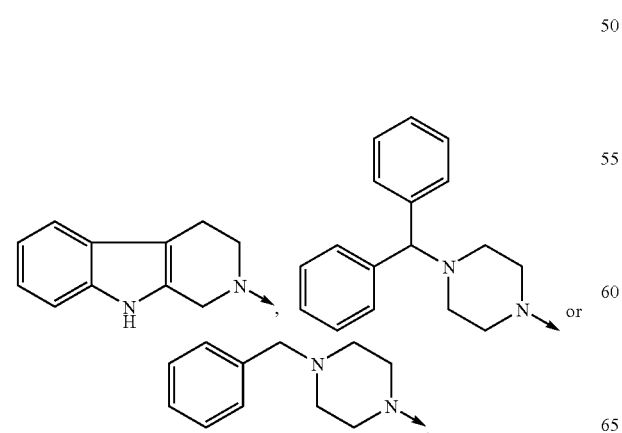

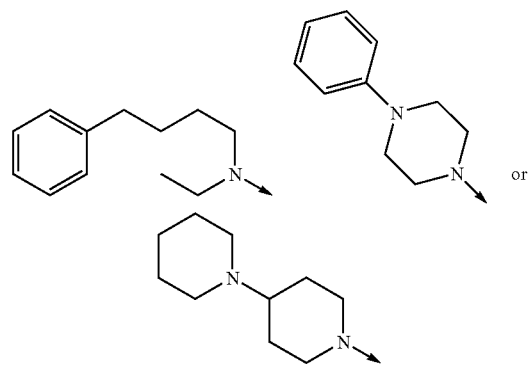

Yet another preferred group of compounds of formula (II) have the following formula:

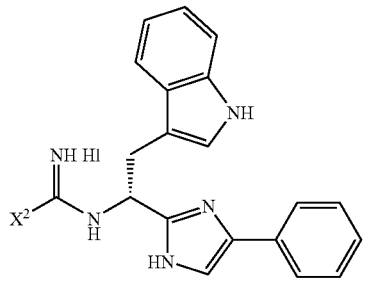

wherein $X^2$ is p-chloro-phenyl, p-methoxy-phenyl, 2,4-difluoro-phenyl or thienyl.

Still another preferred group of compounds of formula (II) have the following formula:

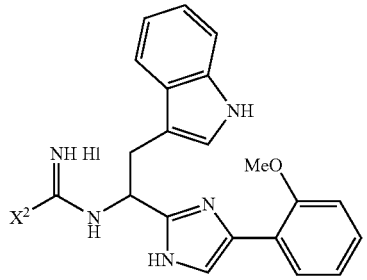

wherein $X^2$ is p-chloro phenyl, p-methoxy-phenyl, phenyl or thienyl.

Further still a preferred compound of formula (II) has the following formula:

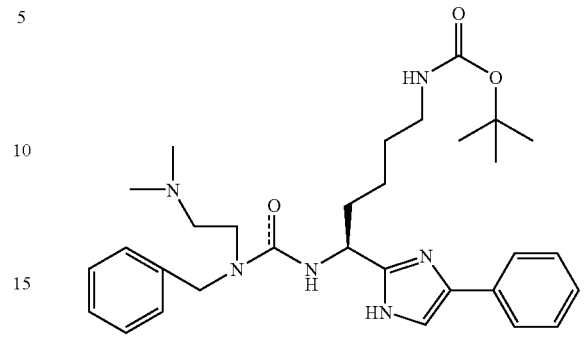

Further still another preferred compound of formula (II) has the following formula:

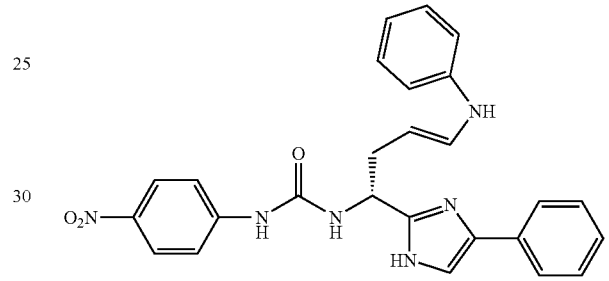

Further still another preferred group of compounds of formula (II) have the following formula:

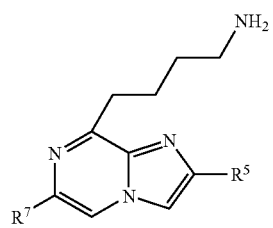

wherein:

$R^5$ is 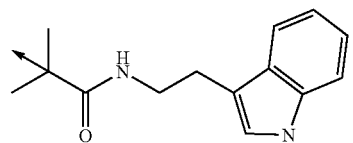 and $R^7$ is m-nitro-phenyl or 2-phenyl-ethyl; or $R^5$ is 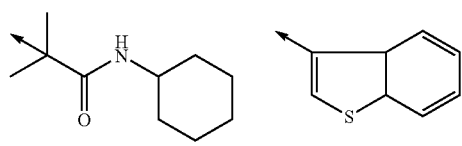 and $R^7$ is ; or -continued

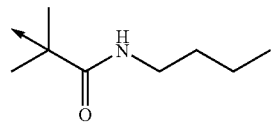

R⁵ is 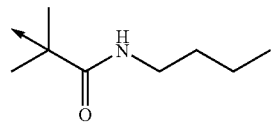 and R⁷ is 3,4-dichlorophenyl or 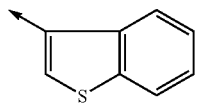 ; or

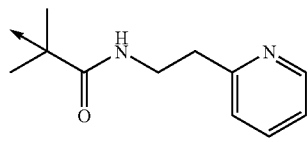

R⁵ is 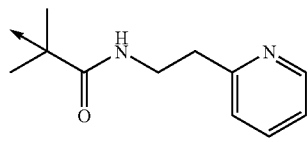 and R⁷ is 3,4-dichlorophenyl.

In another aspect, this invention is directed to a pharmaceutical composition comprising one or more of a compound of formula (I) or formula (II), as defined hereinabove, and a pharmaceutically acceptable carrier.

In another aspect, the present invention is directed to a method of eliciting an agonist effect from one or more of a somatostatin subtype receptor in a subject in need thereof, which comprises administering a compound of formula (I) or formula (II) or a pharmaceutically acceptable salt thereof to said subject.

In another aspect, the present invention is directed to a method of eliciting an antagonist effect from one or more of a somatostatin subtype receptor in a subject in need thereof, which comprises administering a compound of formula (I) or formula (II) or a pharmaceutically acceptable salt thereof to said subject.

In another aspect, the present invention is directed to a method of binding one or more of a somatostatin subtype receptor in a subject in need thereof, which comprises administering a compound of formula (I) or formula (II) or a pharmaceutically acceptable salt thereof to said subject.

In another aspect, the present invention is directed to a method of treating acromegaly, restenosis, Crohn's disease, systemic sclerosis, external and internal pancreatic pseudocysts and ascites, VIPoma, nesidoblastosis, hyperinsulinism, gastrinoma, Zollinger-Ellison syndrome, diarrhea, AIDS related diarrhea, chemotherapy related diarrhea, scleroderma, Irritable Bowel Syndrome, pancreatitis, small bowel obstruction, gastroesophageal reflux, duodenogastric reflux, Cushing's Syndrome, gonadotropinoma, hyperoparathyroidism, Graves' Disease, diabetic neuropathy, Paget's disease, polycystic ovary disease, cancer, cancer cachexia, hypotension, postprandial hypotension, panic attacks, GH secreting adenomas or TSH secreting adenomas, in a subject in need thereof, which comprises administering a compound of formula (I) or formula (II) or a pharmaceutically acceptable salt thereof to said subject.

In another aspect, the present invention is directed to a method of treating diabetes mellitus, hyperlipidemia, insulin insensitivity, Syndrome X, angiopathy, proliferative retinopathy, dawn phenomenon, Nephropathy, peptic ulcers, enterocutaneous and pancreaticocutaneous fistula, Dumping syndrome, watery diarrhea syndrome, acute or chronic pancreatitis, gastrointestinal hormone secreting tumors, angiogenesis, inflammatory disorders, chronic allograft rejection, angioplasty, graft vessel bleeding or gastrointestinal bleeding in a subject in need thereof, which comprises administering a compound of formula (I) or formula (II) or a pharmaceutically acceptable salt thereof to said subject.

In another aspect, the present invention is directed to a method of inhibiting the proliferation of *helicobacter pylori* in a subject in need thereof, which comprises administering a compound of formula (I) or formula (II) or a pharmaceutically acceptable salt thereof, to said subject.

DETAILED DESCRIPTION OF THE INVENTION

One of ordinary skill will recognize that certain substituents listed in the invention may have reduced chemical stability when combined with one another or with heteroatoms in the compounds. Such compounds with reduced chemical stability are not preferred.

In general, the compounds of Formula I or II can be made by processes which include processes known in the chemical arts for the production of compounds. Certain processes for the manufacture of Formula I or II compounds are provided as further features of the invention and are illustrated by the following reaction schemes and examples.

In the above structural formulae and throughout the instant application, the following terms have the indicated meanings unless expressly stated otherwise.

The alkyl groups are intended to include those alkyl groups of the designated length in either a straight or branched configuration. Exemplary of such alkyl groups are methyl, ethyl, propyl, isopropyl, butyl, sec-butyl, tertiary butyl, pentyl, isopentyl, hexyl, isohexyl, and the like.

When the definition "$C_0$-alkyl" occurs in the definition, it means a single covalent bond.

The alkoxy groups specified above are intended to include those alkoxy groups of the designated length in either a straight or branched configuration. Exemplary of such alkoxy groups are methoxy, ethoxy, propoxy, isopropoxy, butoxy, isobutoxy, tertiary butoxy, pentoxy, isopentoxy, hexoxy, isohexoxy and the like.

The term halogen or halo is intended to include the halogen atoms fluorine, chlorine, bromine and iodine.

The term cycloalkyl is intended to include a mono-cycloalkyl group or a bi-cycloalkyl group of the indicated carbon number known to those of skill in the art.

The term aryl is intended to include aromatic rings known in the art, which can be mono-cyclic, bi-cyclic or tri-cyclic, such as phenyl, naphthyl and anthracene.

The term heterocycle includes mono-cyclic, bi-cyclic and tri-cyclic systems having one or more heteroatoms, such as oxygen, nitrogen and/or sulfur. The ring systems may be aromatic, for example pyridine, indole, quinoline, pyrimidine, thiophene (also known as thienyl), furan, benzothiophene, tetrazole, dihydroindole, indazolyl, N-formylindole, benzimidazole, thiazole, and thiadiazole.

The ring systems may be non-aromatic, for example pyrrolidine, piperidine, morpholine and the like.

The chemist of ordinary skill will recognize that certain combinations of heteroatom-containing substituents listed in this invention define compounds which will be less stable under physiological conditions. Accordingly, such compounds are less preferred.

When a chemical structure as used herein has an arrow emanating from it, the arrow indicates the point of attachment. For example, the structure

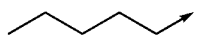

is a pentyl group. When an arrow is drawn through a cyclic moiety, the arrow indicates that the cyclic moiety can be attached at any of the available bonding points, for example

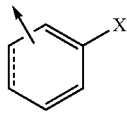

means that the phenyl can be bonded ortho, meta or para to the X group. When an arrow is drawn through a bi-cyclic or a tri-cyclic moiety, the arrow indicates that the bi-cyclic or tri-cyclic ring can be attached at any of the available bonding points in any of the rings, for example

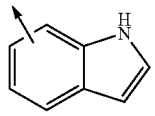

means that the indole is bonded either through the phenyl portion of the ring or the nitrogen containing ring portion.

The compounds of the instant invention have at least one asymmetric center as noted by the asterisk in the structural formula (I), (Ia) and (Ib), above. Additional asymmetric centers may be present on the molecule depending upon the nature of the various substituents on the molecule. Each such asymmetric center will produce two optical isomers and it is intended that all such optical isomers, as separated, pure or partially purified optical isomers, racemic mixtures or diastereomeric mixtures thereof, be included within the scope of the instant invention.

The instant compounds can be generally isolated in the form of their pharmaceutically acceptable acid addition salts, such as the salts derived from using inorganic and organic acids. Examples of such acids are hydrochloric, nitric, sulfuric, phosphoric, acetic, propionic, maleic, succinic, D-tartaric, L-tartaric, malonic, methane sulfonic and the like. In addition, certain compounds containing an acidic function such as a carboxy can be isolated in the form of their inorganic salt in which the counter-ion can be selected from sodium, potassium, lithium, calcium, magnesium and the like, as well as from organic bases.

The pharmaceutically acceptable salts are formed by taking about 1 equivalent of a compound of formula (I) or (II) and contacting with about 1 equivalent of the appropriate corresponding acid of the salt which is desired. Work-up and isolation of the resulting salt is well-known to those of ordinary skill in the art.

As is known in the art, agonists and antagonists of somatostatin are useful for treating a variety of medical conditions and diseases, such as inhibition of *H. pylori* proliferation, acromegaly, restenosis, Crohn's disease, systemic sclerosis, external and internal pancreatic pseudocysts and ascites, VIPoma, nesidoblastosis, hyperinsulinism, gastrinoma, Zollinger-Ellison Syndrome, diarrhea, AIDS related diarrhea, chemotherapy related diarrhea, scleroderma, Irritable Bowel Syndrome, pancreatitis, small bowel obstruction, gastroesophageal reflux, duodenogastric reflux and in treating endocrinological diseases and/or conditions, such as Cushing's Syndrome, gonadotropinoma, hyperparathyroidism, Graves' Disease, diabetic neuropathy, Paget's disease, and polycystic ovary disease; in treating various types of cancer such as thyroid cancer, hepatome, leukemia, meningioma and conditions associated with cancer such as cancer cachexia; in the treatment of such conditions as hypotension such as orthostatic hypotension and postprandial hypotension and panic attacks; GH secreting adenomas (Acromegaly) and TSH secreting adenomas. Activation of type 2 but not type 5 subtype receptor has been associated with treating prolactin secreting adenomas. Other indications associated with activation of the somatostatin subtypes are inhibition of insulin and/or glucagon and more particularly diabetes mellitus, hyperlipidemia, insulin insensitivity, Syndrome X, angiopathy, proliferative retinopathy, dawn phenomenon and Nephropathy; inhibition of gastric acid secretion and more particularly peptic ulcers, enterocutaneous and pancreaticocutaneous fistula, Dumping syndrome, watery diarrhea syndrome, acute or chronic pancreatitis and gastrointestinal hormone secreting tumors; inhibition of angiogenesis, treatment of inflammatory disorders such as arthritis; chronic allograft rejection; angioplasty; preventing graft vessel and gastrointestinal bleeding. Somatostatin agonists can also be used for decreasing body weight in a patient. Accordingly, the compounds of the instant invention are useful for the foregoing methods.

Accordingly, the present invention includes within its scope pharmaceutical compositions comprising, as an active ingredient at least one of the compounds of Formula (I) or (II) in association with a pharmaceutically acceptable carrier.

The compounds of this invention can be administered by oral, parenteral (e.g., intramuscular, intraperitoneal, intravenous or subcutaneous injection, or implant), nasal, vaginal, rectal, sublingual or topical routes of administration and can be formulated with pharmaceutically acceptable carriers to provide dosage forms appropriate for each route of administration.

Solid dosage forms for oral administration include capsules, tablets, pills, powders and granules. In such solid dosage forms, the active compound is admixed with at least one inert pharmaceutically acceptable carrier such as sucrose, lactose, or starch. Such dosage forms can also comprise, as is normal practice, additional substances other than such inert diluents, e.q., lubricating agent such as magnesium stearate. In the case of capsules, tablets and pills, the dosage forms may also comprise buffering agents. Tablets and pills can additionally be prepared with enteric coatings.

Liquid dosage forms for oral administration include pharmaceutically acceptable emulsions, solutions, suspensions, syrups, the elixirs containing inert diluents commonly used in the art, such as water. Besides such inert diluents, compositions can also include adjuvants, such as wetting agents, emulsifying and suspending agents, and sweetening, flavoring and perfuming agents.

Preparations according to this invention for parenteral administration include sterile aqueous or non-aqueous solutions, suspensions, or emulsions. Examples of non-aqueous solvents or vehicles are propylene glycol, polyethylene glycol, vegetable oils, such as olive oil and corn oil, gelatin, and injectable organic esters such as ethyl oleate. Such dosage forms may also contain adjuvants such as preserving, wetting, emulsifying, and dispersing agents. They may be sterilized by, for example, filtration through a bacteria-retaining filter, by incorporating sterilizing agents into the compositions, by irradiating the compositions, or by heating the compositions. They can also be manufactured in the form_of sterile solid compositions which can be dissolved in sterile water, or some other sterile injectable medium immediately before use.

Compositions for rectal or vaginal administration are preferably suppositories which may contain, in addition to the active substance, excipients such as coca butter or a suppository wax.

Compositions for nasal or sublingual administration are also prepared with standard excipients well known in the art.

Further, a compound of this invention can be administered in a sustained release composition such as he described in the following patents. U.S. Pat. No. 5,672,659 teaches sustained release compositions comprising a bioactive agent and a polyester. U.S. Pat. No 5,595,760 teaches sustained release compositions comprising a bioactive agent in a gelable form. U.S. application Ser. No. 08/929,363 filed Sep. 9, 1997, teaches polymeric sustained release compositions comprising a bioactive agent and chitosan. U.S. application Ser. No. 08/740,778 filed Nov. 1, 1996, teaches sustained release compositions comprising a bioactive agent and cyclodextrin. U.S. application Ser. No. 09/015,394 filed Jan. 29, 1998, teaches a absorbable sustained release compositions of a bioactive agent. The teachings of the foregoing patents and applications are incorporated herein by reference.

In general, an effective dosage of active ingredient in the compositions of this invention may be varied; it is necessary that the amount of the active ingredient be such that a suitable dosage form is obtained. The selected dosage depends upon the desired therapeutic effect, on the route of administration, and on the duration of the treatment, all of which are within the realm of knowledge of one of ordinary skill in the art. Generally, dosage levels of between 0.0001 to 100 mg/kg of body weight daily are administered to humans and other animals, e.g., mammals.

A preferred dosage range is 0.01 to 10.0 mg/kg of body weight daily, which can be administered as a single dose or divided into multiple doses.

Compounds of the instant invention can be and were assessed for its ability to bind to a somatostatin subtype receptor according to the following assays.

Human Somatostatin Subtype Receptor Binding Studies:

The affinity of a compound for human somatostatin subtype receptors 1 to 5 ($sst_1$, $sst_2$, $sst_3$, $sst_4$ and $sst_5$, respectively) is determined by measuring the inhibition of $[^{125}I\text{-}Tyr^{11}]$ SRIF-14 binding to CHO-K1 transfected cells.

The human $sst_1$ receptor gene was cloned as a genomic fragment. A 1.5 Kb PstI-XmnI segment containing 100 bp of the 5'-untranslated region, 1.17 Kb of the entire coding region, and 230 bp of the 3'-untranslated region was modified by the BglII linker addition. The resulting DNA fragment was subcloned into the BamHI site of a pCMV-81 to produce the mammalian expression plasmid (provided by Dr. Graeme Bell, Univ. Chicago). A clonal cell line stably expressing the $sst_1$ receptor was obtained by transfection into CHO-K1 cells (ATCC) using the calcium phosphate co-precipitation method (1). The plasmid pRSV-neo (ATCC) was included as a selectable marker. Clonal cell lines were selected in RPMI 1640 media containing 0.5 mg/ml of G418 (Gibco), ring cloned, and expanded into culture.

The human $sst_2$ somatostatin receptor gene, isolated as a 1.7 Kb BamHI-HindIII genomic DNA fragment and subcloned into the plasmid vector pGEM3Z (Promega), was kindly by Dr. G. Bell (Univ. of Chicago). The mammalian cell expression vector is constructed by inserting the 1.7 Kb BamH1-HindII fragment into compatible restriction endonuclease sites in the plasmid pCMV5. A clonal cell line is obtained by transfection into CHO-K1 cells using the calcium phosphate co-precipitation method. The plasmid pRSV-neo is included as a selectable marker.

The human $sst_3$ was isolated at genomic fragment, and the complete coding sequence was within a 2.4 Kb BamHI/HindIII fragment. The mammalian expression plasmid, pCMV-h3 was constructed by inserting the a 2.0 Kb NcoI-HindIII fragment into the EcoR1 site of the pCMV vector after modification of the ends and addition of EcoR1 linkers. A clonal cell line stably expressing the $sst_3$ receptor was obtained by transfection into CHO-K1 cells (ATCC) using the calcium phosphate co-precipitation method. The plasmid pRSV-neo (ATCC) was included as a selectable marker. Clonal cell lines were selected in RPMI 1640 media containing 0.5 mg/ml of G418 (Gibco), ring cloned, and expanded into culture.

The human $sst_4$ receptor or expression plasmid, pCMV-HX was provided by Dr. Graeme Bell (Univ. Chicago). The vector contains the 1.4 Kb NheI-NheI genomic fragment encoding the human $sst_4$, 456 bp of the 5'-untranslated region and 200 bp of the 3'-untranslated region, clone into the XbaI/EcoR1 sites of PCMV-HX. A clonal cell line stably expressing the $sst_4$ receptor was obtained by transfection into CHO-K1 cells (ATCC) using the calcium phosphate co-precipitation method. The plasmid pRSV-neo (ATCC) was included as a selectable marker. Clonal cell lines were selected in RPMI 1640 media containing 0.5 mg/ml of G418 (Gibco), ring cloned, and expanded into culture.

The human $sst_5$ gene was obtained by PCR using a λ genomic clone as a template, and kindly provided by Dr. Graeme Bell (Univ. Chicago). The resulting 1.2 Kb PCR fragment contained 21 base pairs of the 5'-untranslated region, the full coding region, and 55 bp of the 3'-untranslated region. The clone was inserted into EcoR1 site of the plasmid pBSSK(+). The insert was recovered as a 1.2 Kb HindIII-XbaI fragment for subcloning into pCVM5 mammalian expression vector. A clonal cell line stably expressing the $sst_5$ receptor was obtained by transfection into CHO-K1 cells (ATCC) using the calcium phosphate co-precipitation method. The plasmid pRSV-neo (ATCC) was included as a selectable marker. Clonal cell lines were selected in RPMI 1640 media containing 0.5 mg/ml of G418 (Gibco), ring cloned, and expanded into culture. CHO-K1 cells stablie expressing one of the human sst receptor are grown in RPMI 1640 containing 10% fetal calf serum and 0.4 mg/ml geneticin. Cells are collected with 0.5 mM EDTA, and centrifuged at 500 g for about 5 min. at about 4° C. The pellet is resuspended in 50 mM Tris, pH 7.4 and centrifuged twice at 500 g for about 5 min. at about 4° C. The cells are lysed by sonication and centrifuged at 39000 g for about 10 min. at about 4° C. The pellet is resuspended in the same buffer and centrifuged at 50000 g for about 10 min. at about 4° C. and membranes in resulting pellet are stored at −80° C.

Competitive inhibition experiments of [$^{125}$I-Tyr$^{11}$]SRIF-14 binding are run in duplicate in polypropylene 96 well plates. Cell membranes (10 μg protein/well) are incubated with [$^{125}$I-Tyr$^{11}$]SRIF-14 (0.05 nM) for about 60 min. at about 37° C. in 50 mM HEPES (pH 7.4), 0.2% BSA, 5 mM MgCl$_2$, 200 KIU/ml Trasylol, 0.02 mg/ml bacitracin and 0.02 mg/ml phenylmethylsulphonylfluoride.

Bound from free [$^{125}$I-Tyr$^{11}$]SRIF-14 is separated by immediate filtration through GF/C glass fiber filter plate (Unifilter, Packard) presoaked with 0.1% polyethylenimine (P.E.I.). using Filtermate 196 (Packard) cell harvester. Filters are washed with 50 mM HEPES at about 0-4° C. for about 4 sec. and assayed for radioactivity using Packard Top Count.

Specific binding is obtained by subtracting nonspecific binding (determined in the presence of 0.1 μM SRIF-14) from total binding. Binding data are analyzed by computer-assisted nonlinear regression analysis (MDL) and inhibition constant (Ki) values are determined.

The determination of whether a compound of the instant invention is an agonist or an antagonist is determined by the following assay.

Functional Assay: Inhibition of cAMP Intracellular Production:

CHO-K1 Cells expressing human somatostatin (SRIF-14) subtype receptors are seeded in 24-well tissue culture multidishes in RPMI 1640 media with 10% FCS and 0.4 mg/ml geneticin. The medium is changed the day before the experiment.

Cells at 10$^5$ cells/well are washed 2 times by 0.5 ml and fresh RPMI with 0.2% BSA supplemented with 0.5 mM (1) 3-isobutyl-1-methylxanthine (IBMX) and incubated for about 5 min at about 37° C.

Cyclic AMP production is stimulated by the addition of 1 mM forskolin (FSK) for about 15-30 minutes at about 37° C.

The agonist effect of a compound is measured by the simultaneous addition of FSK (1 μM), SRIF-14 (10$^{-12}$ M to 10$^{-6}$ M) and a test compound (10$^{-10}$ M to 10$^{-5}$ M).

The antagonist effect of a compound is measured by the simultaneous addition of FSK (1 μM), SRIF-14 (1 to 10 nM) and a test compound (10$^{-10}$ M to 10$^{-5}$ M).

The reaction medium is removed and 200 ml 0.1 N HCl is added. cAMP is measured using radioimmunoassay method (Kit FlashPlate SMP001A, New England Nuclear).

The compounds of the instant invention are synthesized according to the following procedures and examples.

Synthesis of Bromoketones

Gene Procedure: Two different methods can be applied; starting either from a carboxylic acid or an arylketone.

First method: Starting from a carboxylic acid (Macholan, L.; Skursky, L., *Chem listy,* 1955, 49, 1385-1388. Bestman, H. J., Seng, F., *Chem. Ber.,* 1963, 96, 465-469).

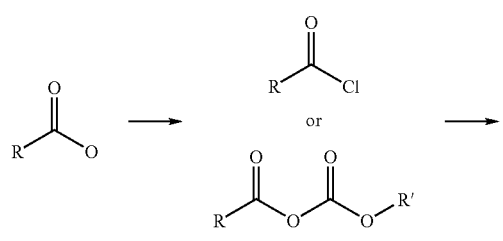

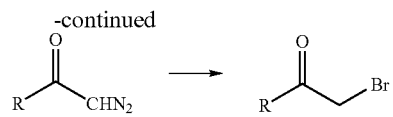

A carboxylic acid is first converted into an acyl chloride using oxalyl chloride or thionyl chloride or activated as a mixed anhydride with an alkylchloroformate (isobutylchloroformate (Krantz, A., Copp, L. J., *Biochemistry,* 1991, 30, 4678-4687) or ethylchloroformate (Podlech, J., Seebach, D., *Liebigs Ann.,* 1995, 1217-1228)) in the presence of a base (triethylamine or N-methyl morpholine).

The activated carboxyl group is then transformed into a diazoketone using ethereal diazomethane or trimethylsilyldiazomethane (Aoyama. T., Shiori. T., *Chem. Pharm. Bull.,* 1981, 29, 3249-3255) in an aprotic solvent such as dietyl ether, tetrahydrofuran or acetonitrile.

The bromination is then carried out using a brominating agent such as HBr in acetic acid, hydrobromic acid in water or in diethyl ether.

Preparation 1

1-Bromo-3-(4-chloro-phenoxy)-3-methyl-butan-2-one

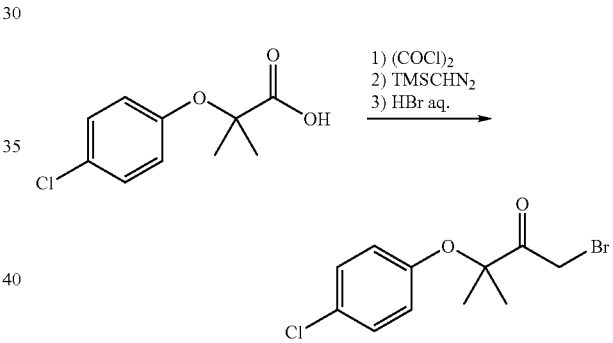

To a solution of chloro-4-phenoxy-2-isobutyric acid (2.15 g, 10 mmol) in 10 ml of anhydrous dichloromethane at about 0° C. were added oxalyl chloride (5.5 ml, 11 mmol of a 2M solution in dichloromethane) and DMF (2 drops, catalytic amount) via a septum under nitrogen atmosphere. The solution was stirred and allowed to warm up to room temperature over about 3 hrs. Concentration under reduced pressure afforded the crude acid chloride which was used directly without further purification.

The acylchloride was added dropwise at about 0° C. to a solution of TMSCHN$_2$ (11 ml, 22 mmol) in THF-acetonitrile (1:1, 10 ml). The mixture was stirred at about 25° C. for about 1 hour and then evaporated in vacuo.

A solution of the diazoketone in dichloromethane (10 ml) was added dropwise during about 10 minutes to a vigorously stirred mixture of concentrated hydrobromic acid (5 ml) in dichloromethane (20 ml). Nitrogen was evolved and a slight temperature rise occurred. After stirring for about a further 10 min., the mixture was diluted and the organic layer was washed with water (3 times 20 ml), dried over magnesium sulfate and evaporated. Flash chromatography of the residue eluting with AcOEt/Heptane (1:4) afforded the desired product with a yield of 79% (2.3 g).

$^1$H-NMR in CDCl$_3$ (100 MHz) δ: 7.05 (m, 4H, arom, H), 4.41 (s, 2H, CH$_2$) 1.53 (s, 6H, 2 CH$_3$).

Preparations 2-6

The following compounds were prepared analogously to the procedure described for Preparation 1:

| Prep. # | R | Yield |
|---|---|---|
| 2 | (benzyl) * | 78% |
| 3 | (phenethyl) * | 60% |
| 4 | (tert-butyl-CH) * | 10% |
| 5 | (4-chlorophenoxy-dimethyl) * | 79% |
| 6 | (indol-3-yl-methyl) | 41% |

\* Compounds already described in literature.

Second method: Starting from a methyl ketone

A methyl ketone is converted to a bromoketone by using different brominating agents:
- CuBr$_2$ (King, L. C., Ostrum, G. K. *J. Org. Chem.*, 1964, 29, 3459-3461) heated in AcOEt or dioxane.
- N-bromosuccinimide in CCl$_4$.
- Bromine in glacial acetic acid or sulfuric acid.
- Phenyltrimethylammonium tribromide (Sanchez, J. P., Parcell, R. P., *J. Heterocyclic Chem.*, 1988, 25, 469-474) at 20-80° C. in an aprotic solvent such as THF.
- Use of a polymer supported brominating agent such as perbromide on Ambertyst A-26, poly(vinylpyridinium hydrobromide perbromide) resin (Frechet, J. M. J., Farrall, M. J., *J. Macromol. Sci. Chem.*, 1977, 507-514) in a protic solvent such as methanol at about 20-35° C. for about 2-100 h.

Preparation 7

1-Bromo-2-(3,4,5-trimethoxy-phenyl)-ethanone

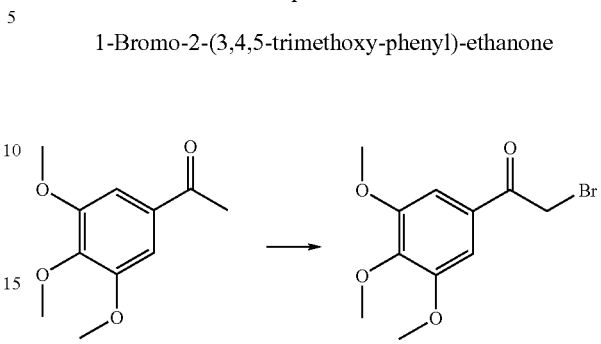

To a solution of 3,4,5-trimethoxyacetophenone (2.1 g, 10 mmol) in methanol (30 ml) was added pyridine hydrobromide perbromide polymer (1.4 eq). The resulting mixture was shaken at room temperature for about 2 hours and the reaction was stopped by filtration. The polymer was washed with methanol and the filtrate was evaporated in vacuo. The product was then purified by flash chromatography (AcOEt/Heptane, 1:4) affording 1.5 g (53% ) of a white solid.

$^1$H-NMR in CDCl$_3$ (100 MHz) δ: 7.2 (s, 2H, H arom.), 4.4 (s, 2H, CH$_2$) 3.9 (m, 9H, 3 OCH$_3$).

Preparations 8-17

The following compounds were prepared analogously to the procedure described for Preparation 7:

| Prep. # | R | Reaction time (h) | Yield |
|---|---|---|---|
| 8 | (benzothiophen-3-yl) * | 8 | 78 |
| 9 | (benzofuran-2-yl) * | 7 | 72 |
| 10 | (2-chloro-5-nitrophenyl) * | 85 | 62 |
| 11 | (4-butylphenyl) * | 2 | 62 |
| 12 | (5-bromothiophen-2-yl) * | 10 | 56 |

-continued

| Prep. # | R | Reaction time (h) | Yield |
|---|---|---|---|
| 13 | 3,4,5-trimethoxyphenyl * | 2 | 53 |
| 14 | 3,4-difluorophenyl * | 8.5 | 27 |
| 15 | 1H-indol-3-yl * | 3 | 43 |
| 16 | methyl 2,2-dimethylpropanoate * | 3 | 77 |
| 17 | 4-(benzyloxy)phenyl * | 3 | 95 |

* Compound already described in literature.

Synthesis of Imidazoyl Compounds

General Procedure: An amino acid is transformed to its cesium salt using cesium carbonate in a polar solvent such as DMF/H$_2$O (1:1) or EtOH/H$_2$O (1:1). An ester is then obtained using an appropriate bromoketone in a polar aprotic solvent such as dry DMF. The cesium bromide formed is filtered off and ammonium acetate is added in an aprotic solvent having a high boiling point such as xylene or toluene or in a protic acidic solvent such as acetic acid. The mixture is refluxed using a Dean-Stark trap for about 0.5-10 hours. In the scheme immediately below, PG is a protecting group, preferably a carbamate, such as t-Boc or benzyl carbamate.

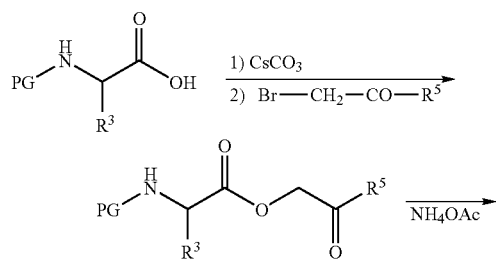

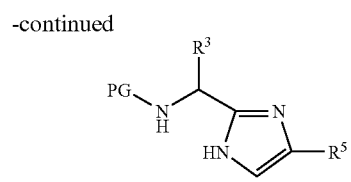

EXAMPLE 1

2-{(1S)-1-[-tertbutoxycarbonylamino]-2-[(1H-indol-3-yl]ethyl}-4-(2-methoxyphenyl)-1H-imidazole

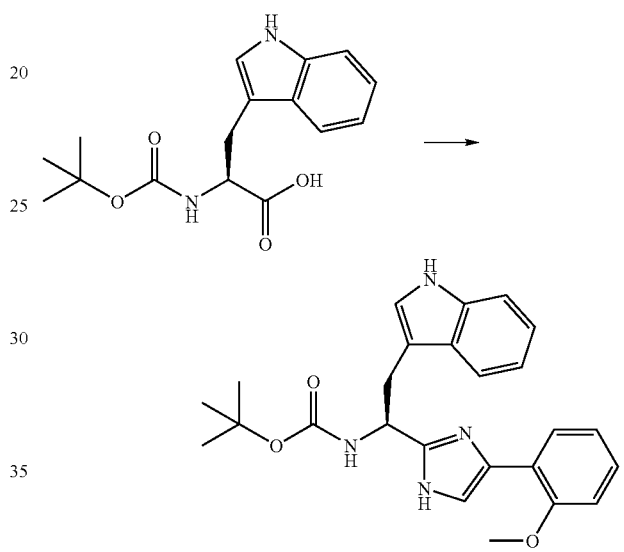

A solution of Boc-(D,L)-Trp-OH (10 g, 32.8 mmol) and cesium carbonate (0.5 eq., 5.34 g) in EtOH/H$_2$O (1:1, 70 ml) was shaken for about 30 minutes at room temperature, and then concentrated in vacuo about 40° C.

To the resulting salt in 40 mL of dry DMF was added 40 ml of a solution of 2-bromo-2'-methoxyacetophenone (7.66 g, 1 eq.) in dry DMF. The mixture was stirred for about 1 hr at room temperature under argon and then concentrated under reduced pressure. Ethyl acetate was added (100 ml), the mixture filtered, and the CsBr washed with ethyl acetate. The filtrate was then concentrated under reduced pressure.

A solution of the foregoing filtrate and ammonium acetate (50.5 g, 20 eq.) in xylene (240 ml) was refluxed for about 3 hours at about 150° C. Excess NH$_4$OAc and H$_2$O were removed using a Dean-Stark trap. The progress of the reaction was monitored by t.l.c. (eluent: CH$_2$Cl$_2$:MeOH, 95:5). The mixture was then concentrated under reduced pressure. The resulting residue was dissolved in ethyl acetate (100 ml) and washed with saturated aqueous NaHCO$_3$ solution until basic pH, and with brine until neutral pH. The organic layer was then dried over MgSO$_4$, and concentrated under reduced pressure.

Purification of the resulting residue by flash chromatography (eluent: CH$_2$Cl$_2$:MeOH, 95:5) afforded the desired compound (8.7 g, yield: 61%).

$^1$H-NMR (CDCl$_3$, 100 MHz) δ: 8.00 (s, 1H, NH), 7.80 (m, 2H, arom, H), 7.20 (m, 9H, arom, H, NH), 5.40 (m, 1H, NH), 5.10 (m, 1H, CH), 3.80 (s, 3H, OCH$_3$), 3.50 (m, 2H, CH$_2$), 1.50 (s, 9H, 6 CH$_3$). LC/MS: m/z=433.3 (M+H).

EXAMPLE 2

N-[2-tertbutoxycarbonylamino ethyl]-2-{2-[(1S)-1-(tertbutoxycarbonylamino)-2-(1H)-indol-3-yl)ethyl]-1H-imidazol-4-yl}-isobutyramide

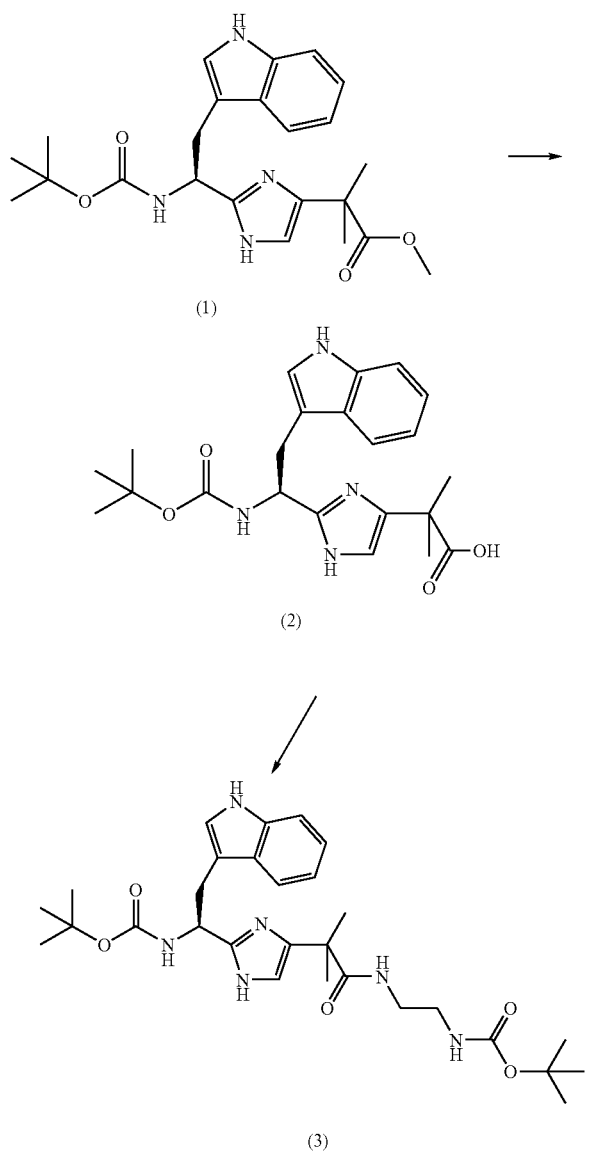

A solution of the 2-{2-[(1S)-1-(tertbutoxycarbonylamino)-2-(indol-3-yl)ethyl]-1H-imidazol-4-yl}-2-methyl-propionic acid-methyl ester 1 (2.6 g, 6 mmol), (prepared according to the procedure described in Example 1) and LiOH.H$_2$O (1.7 g, 6.6 eq.) in THF (50 ml) were stirred at about 80° C. for about 3 hours. The progress of the reaction was monitored by t.l.c (CH$_2$Cl$_2$:MeOH, 95:5). The resulting mixture was then concentrated in vacuo. About 50 ml of water was added to the residue which was then acidified with glacial acetic acid until about pH 5. The product of the reaction was then extracted with ethyl acetate (3×50 ml) and washed with brine until neutral pH. The organic layer was dried with MgSO$_4$, and concentrated under reduced pressure. The resulting intermediate 2 was obtained after crystallization in diethyl ether with a yield of 80% (2 g). $^1$H-NMR (400 MHz, DMSO) δ: 10.9 (s, 1H, NH), 7.1 (m, 7H, arom, H, NH), 5.00 (m, 1H, CH), 3.3 (m, 2H, CH$_2$), 1.3 (m, 15H, 5 CH$_3$). LC/MS: m/z=525.1 (M+TFA), m/z=413.2 (M+H).

The 2-{2-[(1S)-1-(tertbutoxycarbonylamino)-2-[(1H)-indol-3-yl]ethyl]-1H-imidazol-4-yl}-2-methyl-propionic acid 2 can be activated preferentially by carbonyldiimidazole in an aprotic solvent such as THF or DMF at about 20-100° C. for about 1-4 hours.

A solution of the acid 2 (1 g, 2.4 mmol) and carbonyldiimidazole (0.39 g, 2.4 mmol) in dry THF (20 ml) was shaken for about 1 hour at room temperature (25° C.).

N-Boc-ethylene-diamine (0.43 g, 2.7 mmol) was added and the mixture was shaken for about 1 hour at about 25° C.

The mixture was diluted in ethyl acetate (100 ml) and washed with saturated aqueous NaHCO$_3$ solution (2×50 ml) and brine until neutral pH. The organic layer was then dried over MgSO$_4$, and concentrated in vacuo.

Purification of the resulting residue by flash-chromatography (in CH$_2$Cl$_2$:MeOH, 95:5) afforded the desired product 3 with a yield of 77% (1 g).

$^1$H-NMR (400 MHz, DMSO) δ: 11.6 (s, 1H, NH), 10.7 (s, 1H, NH), 7.00 (m, 9H, arom, H, NH), 4.8 (m, 1H, CH), 3.00 (m, 6H, 3 CH$_2$), 1.3 (m, 24H, 8 CH$_3$). LC/MS: m/z=667.3 (M+TFA), 555.3 (M+H).

EXAMPLES 3-1178

The following compounds were prepared analogously to the procedure described for Example 1 or 2 using the appropriate starting materials, which can be obtained from commercial sources or synthesized according to methods known to those skilled in the art or as enabled by the teachings herein. Each combination of R$^3$, R$^5$ shown below, were or can be synthesized, therefore, the number of Examples are calculated by multiplying (PG (2 substituents)R$^3$ (12 substituents) (R$^5$ (49 substituents))=1176.

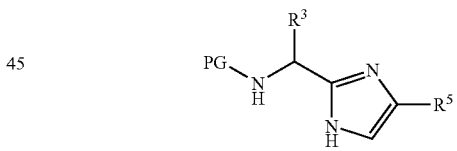

PG can also be hydrogen in the foregoing formula,

R$^3$:

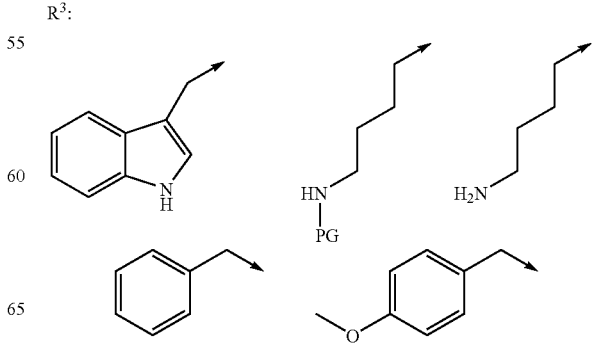

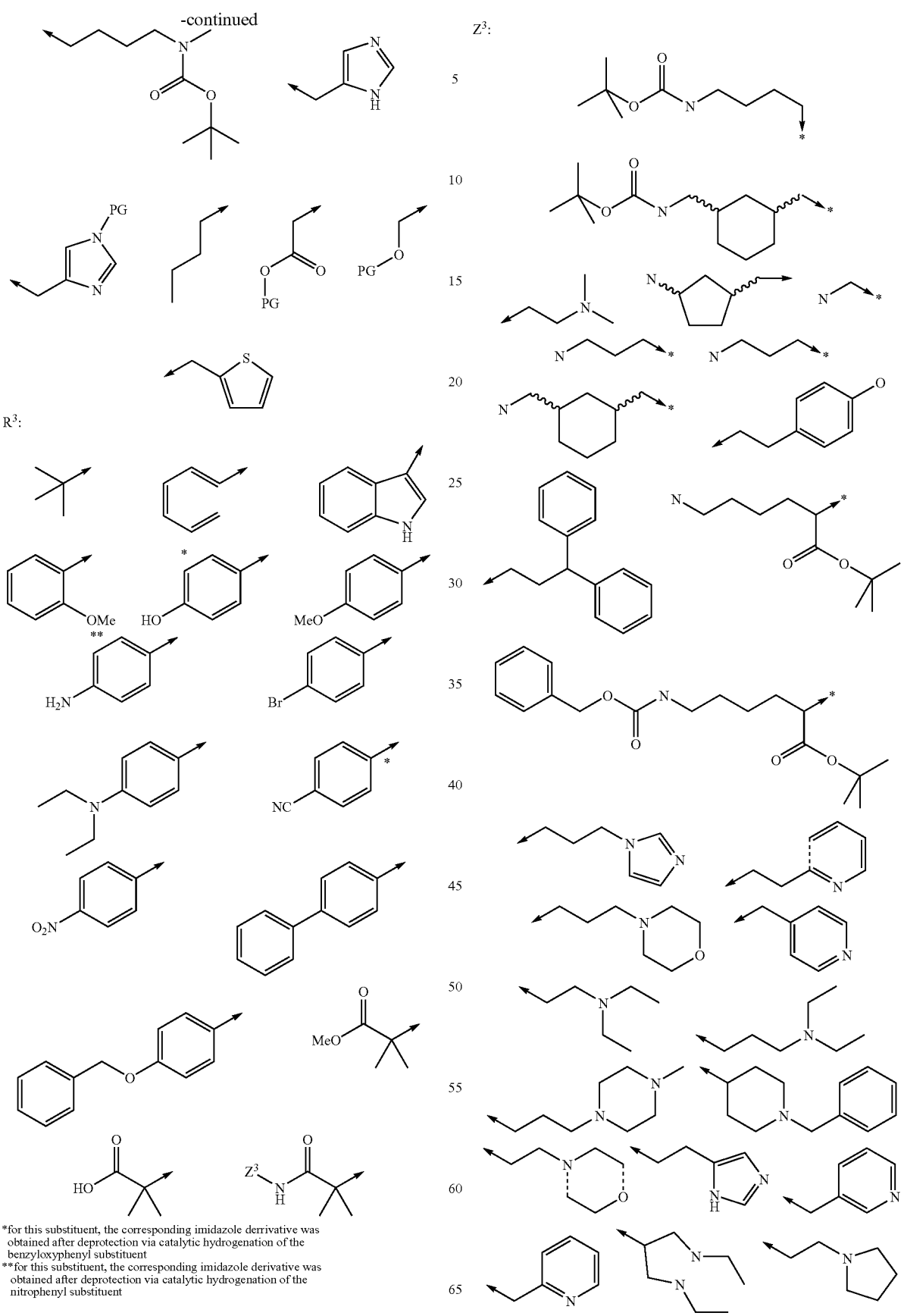
*for this substituent, the corresponding imidazole derivative was obtained after deprotection via catalytic hydrogenation of the benzyloxyphenyl substituent
**for this substituent, the corresponding imidazole derivative was obtained after deprotection via catalytic hydrogenation of the nitrophenyl substituent -continued

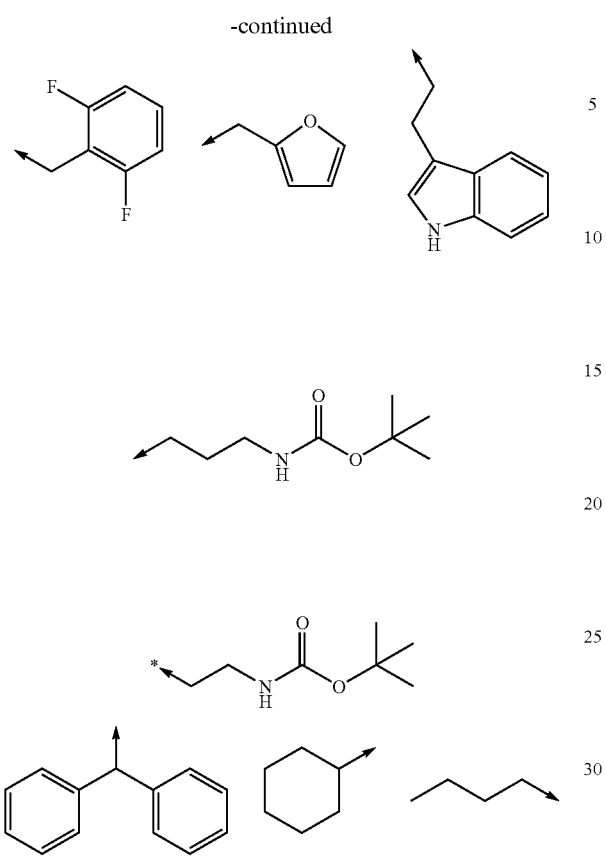

Synthesis of Amides from Imidazoyl Intermediates

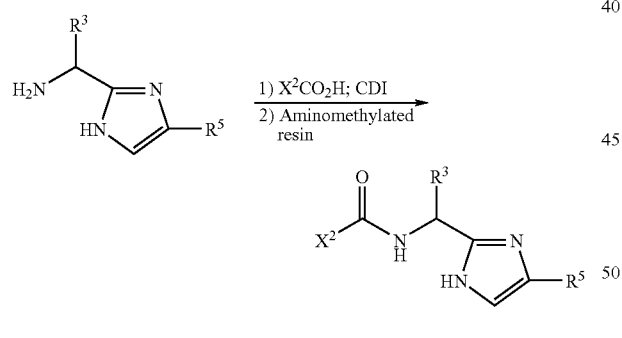

General procedure: Carboxylic acids are activated overnight at room temperature with carbonyldiimidazole in an aprotic solvent such as chloroform, THF or THF/DMF before addition of an amino starting material as shown above followed by a further 12-15 hours of stirring. The excess acylating agent is quenched with aminomethylated resin for about 12-15 hours and then purified on silica gel pad with dichloromethane or ethyl acetate as eluent.

For protected basic derivatives ($R^3$=(CH$_2$)$_4$NHBoc and/or $X^2$ containing NHBoc group), the corresponding deprotected compounds were obtained after treatment under acidic condition (DCM/TFA 10%) to remove the Boc group.

EXAMPLE 1179

2-{(1S)-1-[(2-Furanyl)carbonylamino]-2-[indol-3-yl]ethyl}-4-phenyl-1H-imidazole ($C_{24}H_{20}N_4O_2$, MW=396.45)

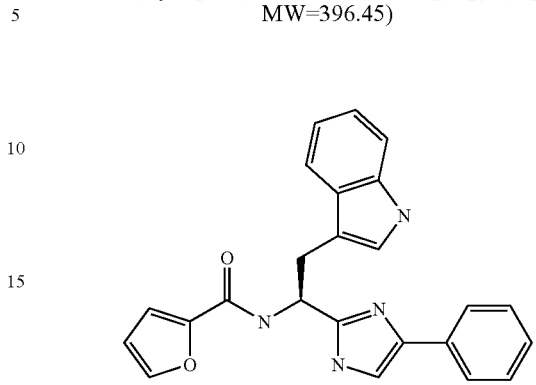

2-Furancarboxylic acid (12.6 mg, 0.11 mmol) was activated overnight at about 22° C. with carbonyldiimidazole (0.11 mmol, 0.2M in chloroform). 2-{(1S)-1-Amino-2-[indol-3-yl]ethyl}-4-phenyl-1H-imidazole (0.1 mmol, 0.5M in chloroform) was added to the media and the mixture was stirred for about 12 hours at about 22° C. Aminomethylated resin was then added (50-60 mg, 1.2 mmol/g, Novabiochem) in order to quench the excess of acylating agent for about 12 hours. Purification on silica gel pad (200 mg, Alltech) with ethyl acetate as eluent gave the expected product (37.2 mg, 94%). $^1$H-NMR (CDCl$_3$, 100 MHz) δ: 8.36 (br s, 1H); 7.67-6.4 (m, 16H); 5.48 (qd, J=7.1 Hz, 1H); 3.6 (ABX system, 2H). LC/MS: m/z=397 (M+H).

EXAMPLES 1180-3615

The following compounds were prepared analogously to the procedure described for Example 1179 using the appropriate starting materials, which can be obtained from commercial sources or synthesized according to methods known to those skilled in the art or as enabled by the teachings herein. Each combination of $R^3$, $R^5$ and $X^2$, shown below were or can be synthesized, therefore, the number of Examples are calculated by multiplying ($R^3$ (4 substituents))($R^5$ (7 substituents)) ($X^2$ (87 substituents))=2436.

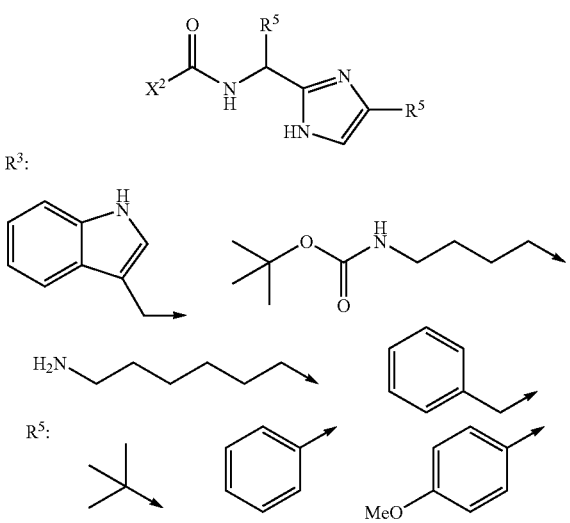

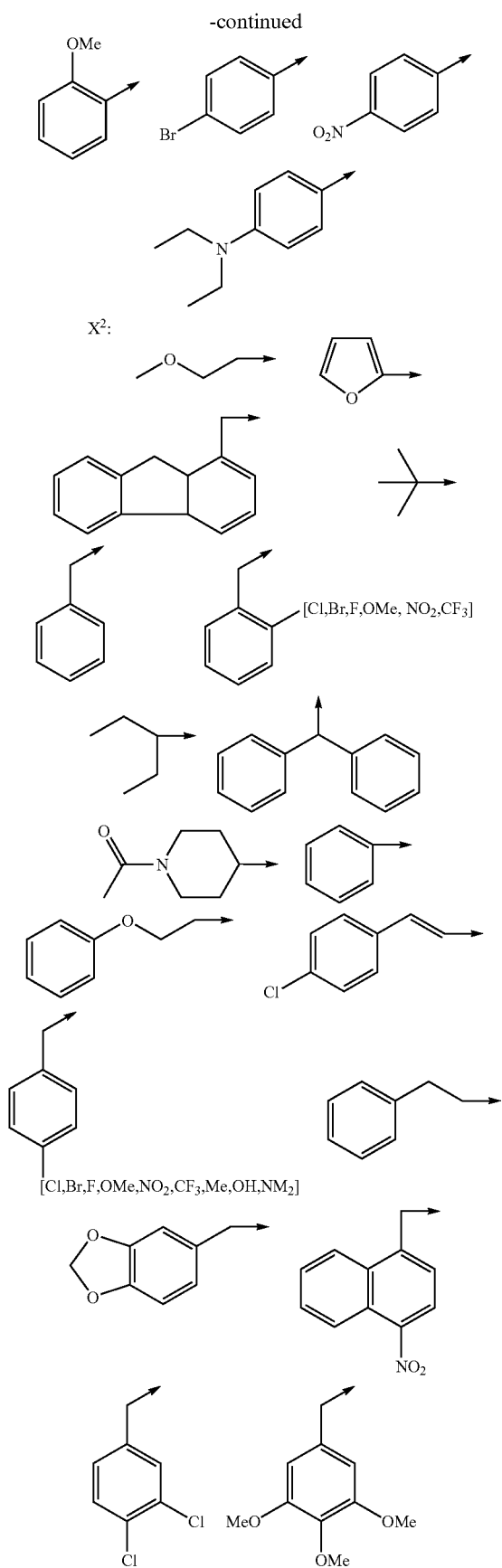
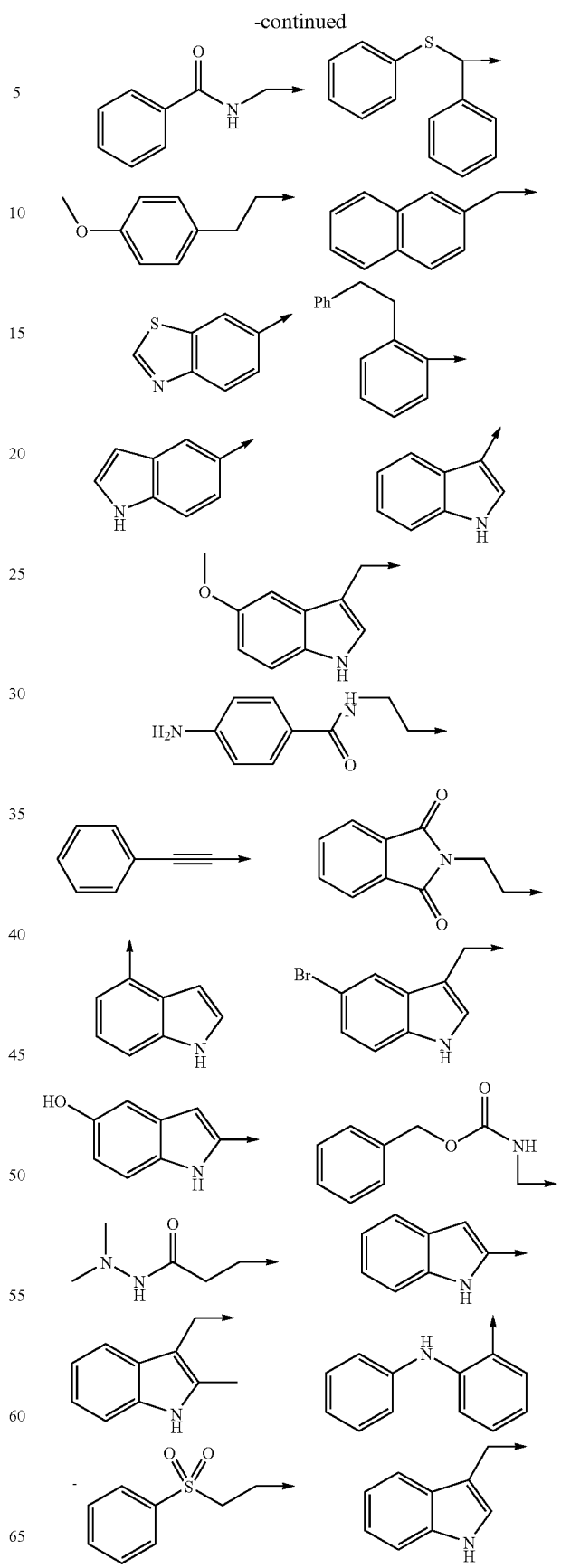

-continued

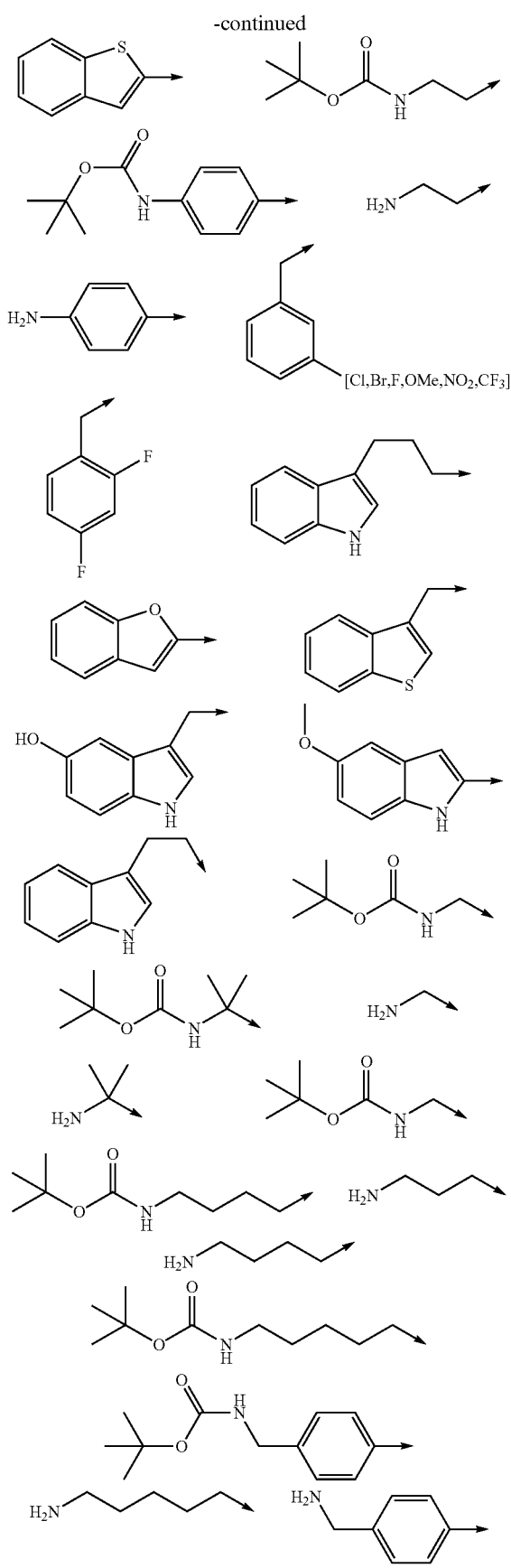
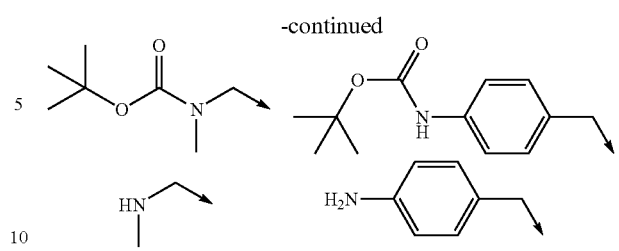

Synthesis of Ureas and Thioureas from Imidazolyl Intermediates

From Isocyanates and Isothiocyanates:

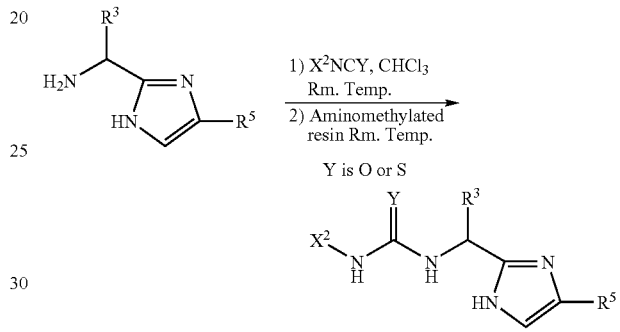

General procedure: Isocyanates or isothiocyanates are shaken overnight at room temperature with an imidazoyl intermediate in a aprotic solvent like dichloromethane, chloroform or chloroform/DMF. The reaction is quenched by addition of aminomethylated for about 12-15 hours and purified on silica gel pad with ethyl acetate as eluent.

For protected basic derivatives ($R^3=(CN_2)_4NHBoc$), the corresponding deprotected compounds were obtained after treatment under acidic condition (DCM/TFA 10%) to remove the Boc group.

EXAMPLE 3616

2-{(1R)-1-[(2,4-Difluorophenyl)aminocarbonylamino]-2-[indol-3-yl]-ethyl}-4-phenyl-1H-imidazole ($C_{24}H_{21}F_2N_5O$, MW=457.49)

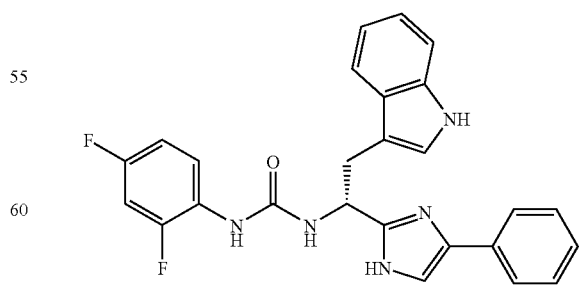

2,6-Difluorophenylisocyanate (36 µl, 0.3 mmol) and 2-{(1R)-1-amino-2-[indol-3-yl]ethyl}-4-phenyl-1H-imidazole (60.4 mg, 0.2 mmol) were stirred overnight in 2 mL of anhydrous dichloromethane. Filtration and purification by flash chromatography on silica gel (ethyl acetate/heptane 1:1 as eluent) afforded the expected product as a white powder (27 mg, 30%). $^1$H-NMR (DMSO D$_6$, 400 MHz) δ: 12.03 (s, 1H); 10.77 (s, 1H); 8.47 (s, 1H); 8.1 (dd, 1H); 7.8-6.92 (m, 14H); 5.11 (dd, J=7 and 14 Hz, 1H); 3.3 (m, 2H). LC/MS: m/z=458 (M+H).

EXAMPLES 3617-4435

The following compounds were prepared analogously to the procedure described for Example 3616, using the appropriate starting materials, which can be obtained from commercial sources or synthesized according to methods known to those skilled in the art or as enabled by the teachings herein. Each combination of R$^3$, R$^5$, and X$^2$ with Y is O or X$^2$ with Y is S, shown below, were or can be synthesized, therefore, the number of Examples are calculated by multiplying (R$^3$ (3 substituents))(R$^5$ (7 substituents))(X$^2$ (39 substituents))= 819.

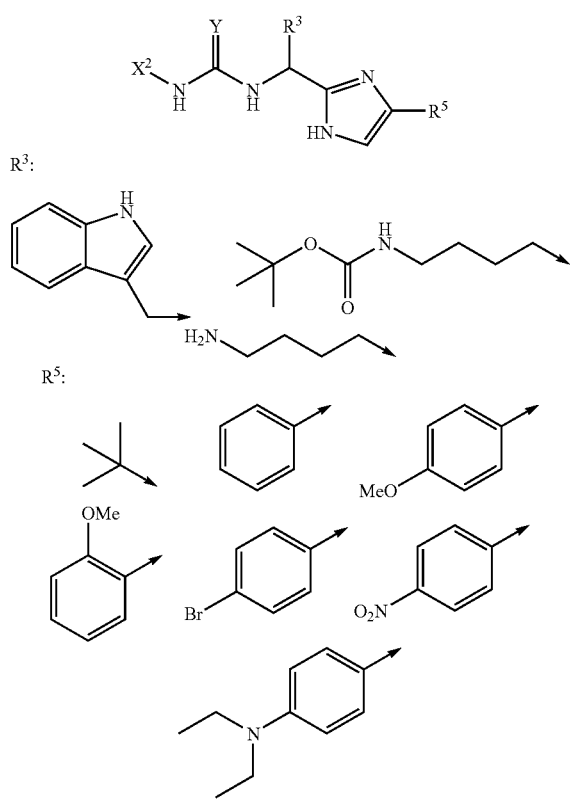

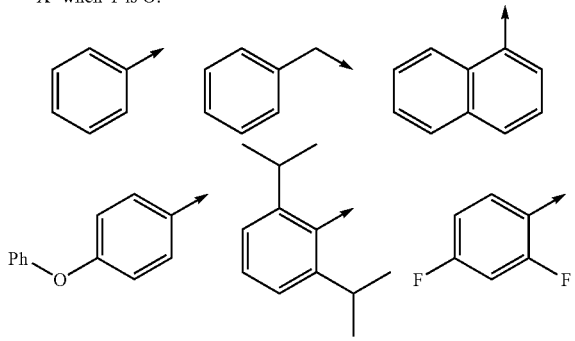

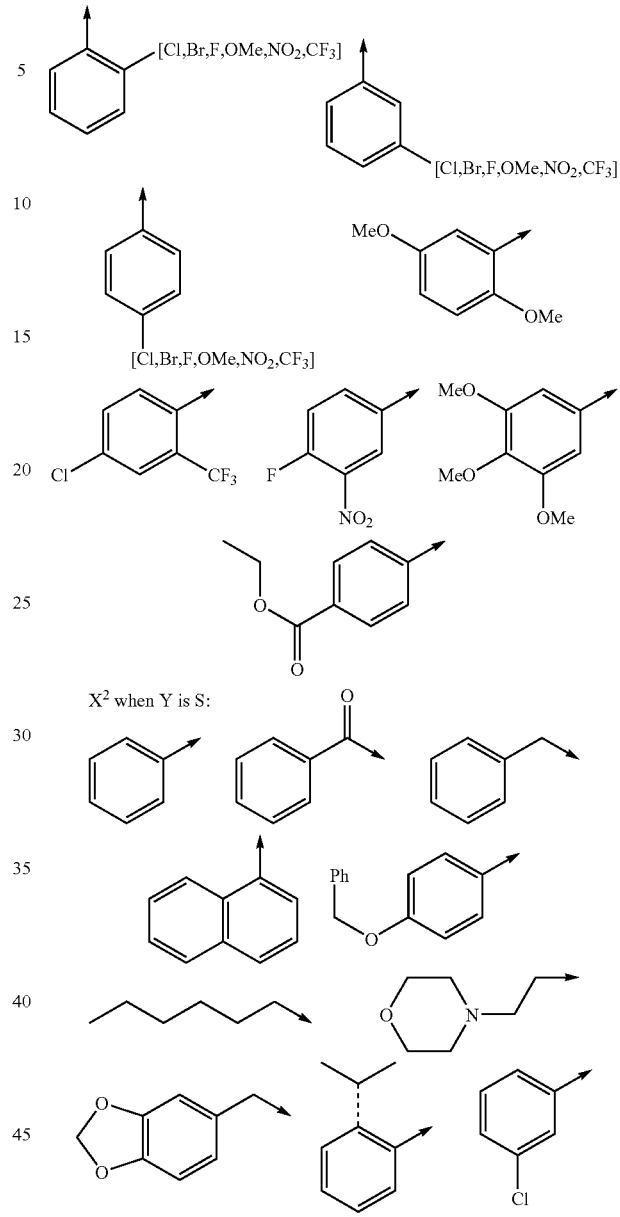

From Carbamate Intermediates and Primary and Secondary Amines:

General Procedure: The preparation of carbamate intermediates is described in the literature (Takeda. K. et al., *Tetrahedron Letters* 1983, 24, 4569-4572; Nimura, N. et al., *Anal. Chem.* 1986, 58, 2372-2375) from amino derivatives and N,N'-disuccinimidylcarbonate in acetonitrile at room temperature.

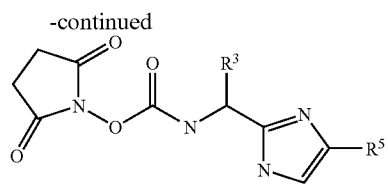

EXAMPLE 4436

2-{(1R)-1-[(2,5-Dioxo-1-pyrrolidinyloxy)carbonylamino]-2-[indol-3-yl]ethyl}-4-phenyl-1H-imidazole ($C_{24}H_{21}N_5O_4$, MW=443.46)

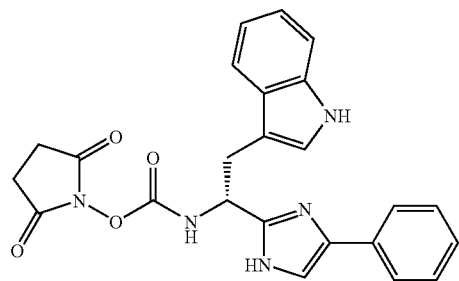

302.4 mg (1 mmol) of 2-{(1R)-1-amino-2-[indol-3-yl]ethyl}-4-phenyl-1H-imidazole previously dissolved in 20 mL of anhydrous acetonitrile was added dropwise to a solution of N,N'-disuccinimidylcarbonate (528 mg, 2 mmol, DSC) in 20 mL of anhydrous acetonitrile during 1.5 hour. After a further 4 hours of stirring at room temperature, the solvent was evaporated in vacuo and the residue redissolved in 30 mL of chloroform. Excess DSC was then discarded and the organic layer washed with water (4×30 mL), dried over $MgSO_4$ and concentrated to obtain a brown solid (215 mg, 49%). $^1$H-NMR ($CDCl_3$, 100 MHz) δ: 8.22 (brs, 1H); 8.1-7.08 (m, 12H); 5.9 (br s, 1H); 4.97 (dd, J=3.6 and 9.3 Hz, 1H); 3.75 (dd, J=3.6 and 14.8 Hz, 1H), 3.06 (dd, J=9.7 and 14.6 Hz, 1H); 2.96 (s, 2H); 2.89 (s, 2H). LC/MS: m/z=329 ((M+H)−SuOH.

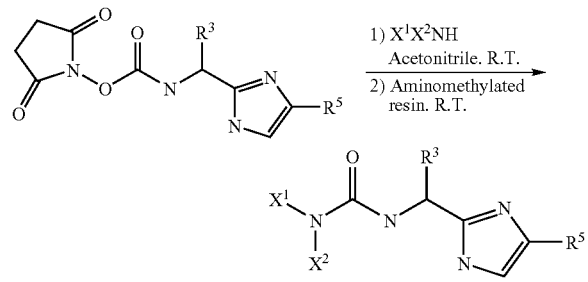

General procedure: A primary or secondary amine is stirred for about 2-15 hours at room temperature with a carbamate intermediate in an aprotic solvent like acetonitrile. Tetrahydrofuran and aminomethylated resin are then added and the reaction is then stirred for about 12-15 hours. Ureas are isolated after filtration, rinsed with ethyl acetate and evaporated in vacuo.

For protected basic derivatives ($R^3$=$(CH_2)_4$NHBoc), the corresponding deprotected compounds were obtained after treatment under acidic condition (DCM/TFA 10%) to remove the Boc group.

EXAMPLE 4437

2-{(1R)-1-[(Benzylamino)carbonylamino]-2-[indol-3-yl]ethyl}-4-phenyl-1H-imidazole ($C_{27}H_{25}N_5O$, MW=435.53)

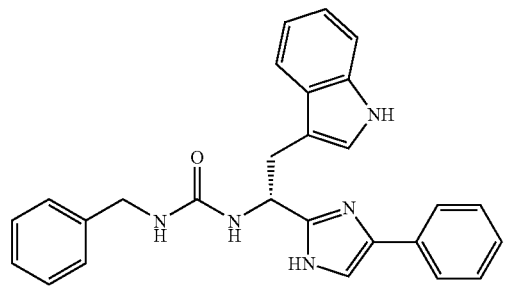

Benzylamine (5 μL, 50 mmol) and 2-{(1R)-1-amino-2-[indol-3-yl]ethyl}-4-phenyl-1H-imidazole (24 mg, 54 mmol) were stirred for about 2 hours at room temperature in anhydrous acetonitrile. Aminomethylated resin (50 mg, 0.75 mmol/g, Novabiochem) was then added and after further stirring overnight, the title product was obtained by filtration on silica gel pad (200 mg) and evaporated in vacuo as a brown powder (20 mg, 92%). $^1$H-NMR (DMSO $D_6$, 100 MHz) δ: 10.6 (br s, 1H); 7.9-6.88 (m, 17H); 6.53 (m, 2H); 5.12 (dd, J=6 and 14.6 Hz, 1H); 4.28 (m, 2H); 3.25 (m, 2H). LC/MS: m/z=436 (M+H).

EXAMPLES 4438-8469

The following compounds were prepared analogously to the procedure described for Example 4437, using the appropriate starting materials, which can be obtained from commercial sources or synthesized according to methods known to those skilled in the art or as enabled by the teachings herein. Each combination of $R^3$, $R^5$ and $NX^1X^2$, shown below, were or can be synthesized, therefore, the number of Examples are calculated by multiplying ($R^3$ (3 substituents))($R^5$ (12 substituents))($NX^1X^2$ (112 substituents))=4032.

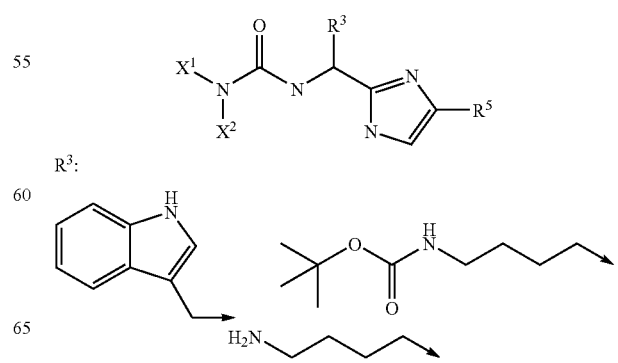

-continued
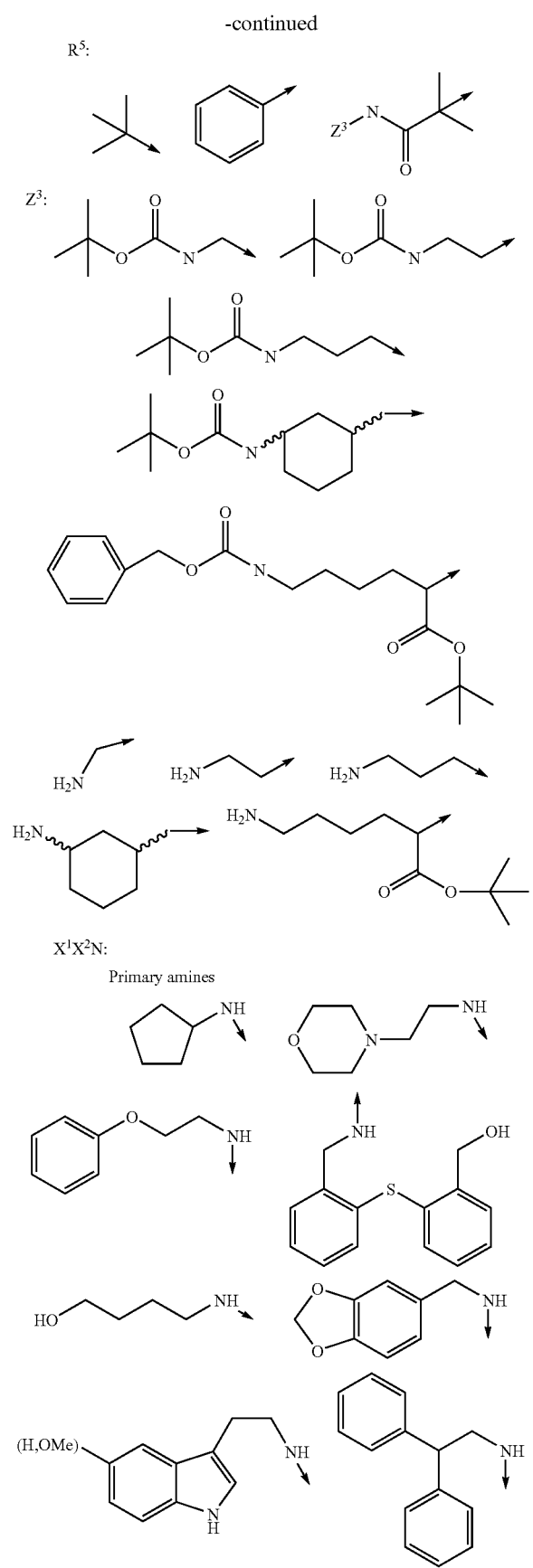
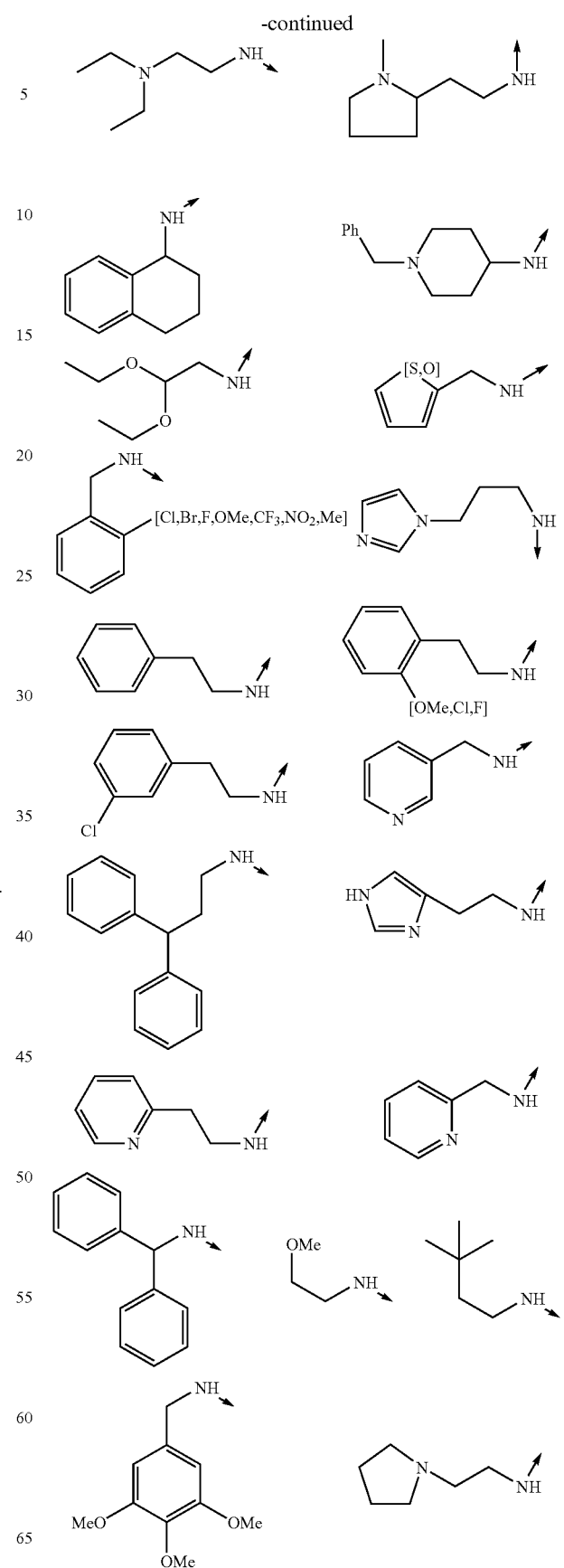

-continued
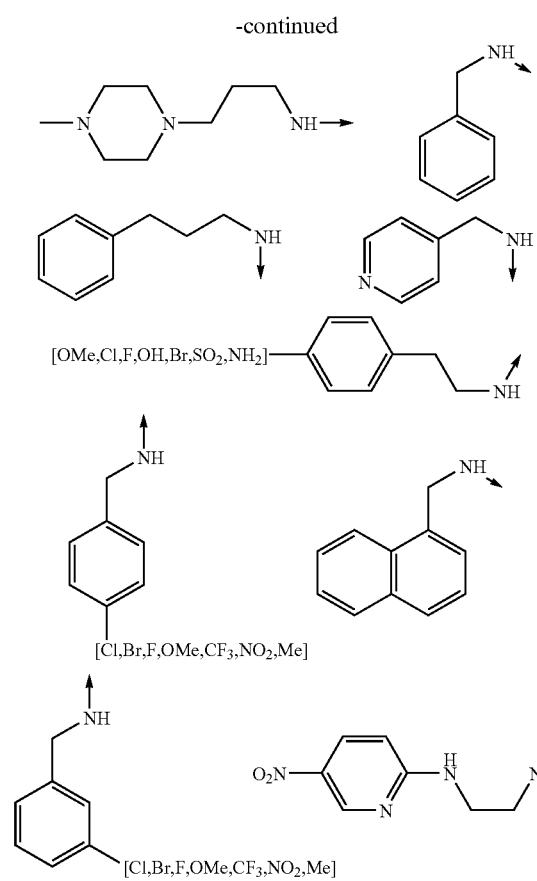
Secondary amines:
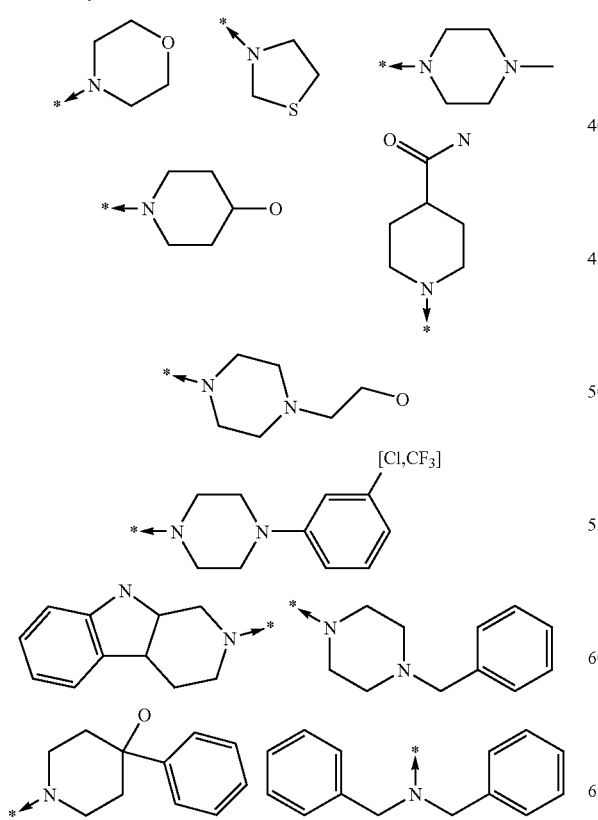
-continued
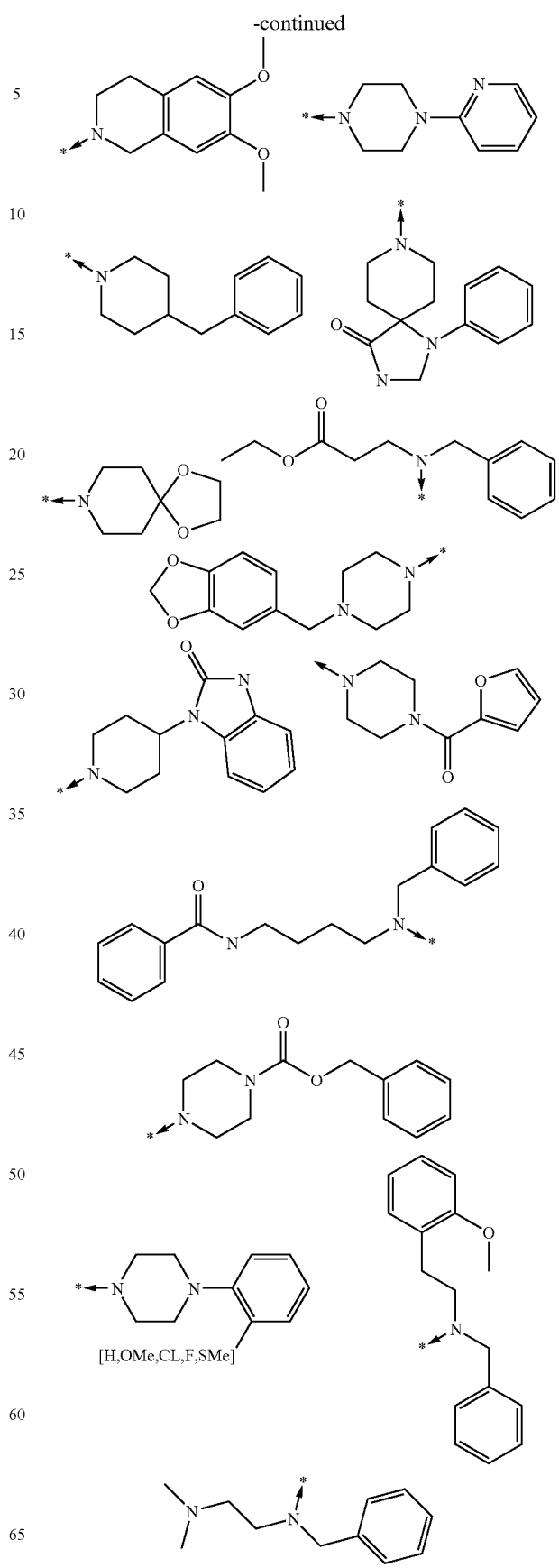

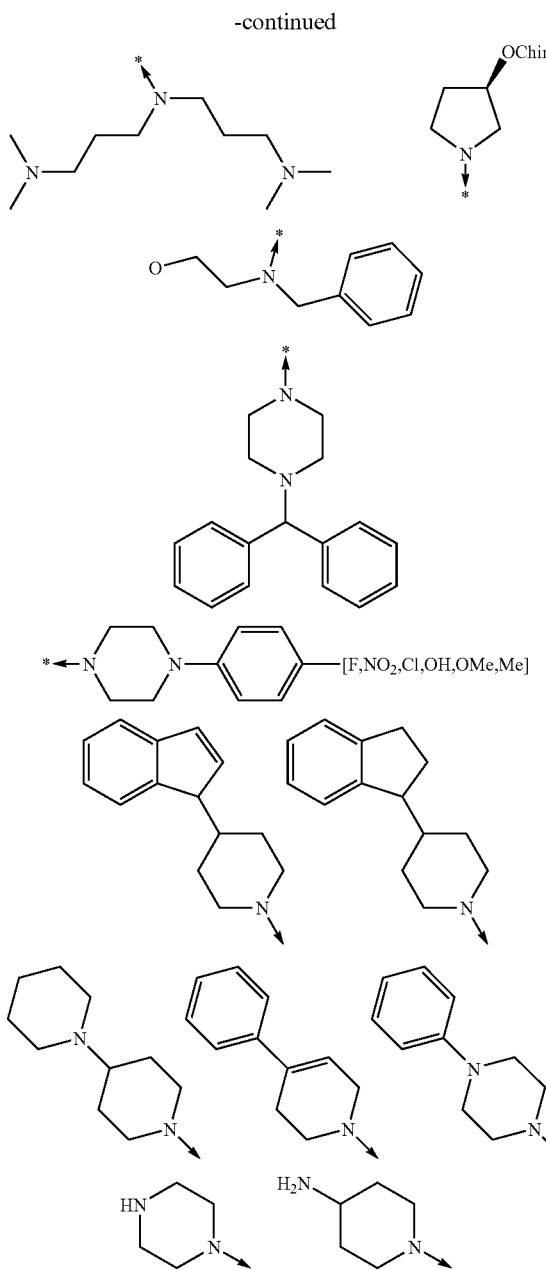

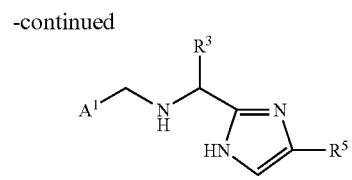

Synthesis of Secondary Amines by Reductive Aminations of Imidazolyl Intermediates (Kaldor, S. W.; Siegel, M. G.; Fritz, J. E.; Dressman, B. A.; Hahn., P. J. *Tetrahedron Letters* 1996, 37, 7193-7196)

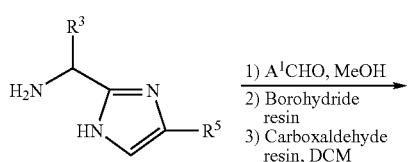

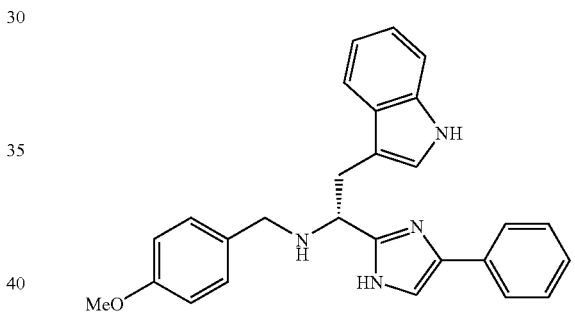

General procedure: Condensation of aldehydes with an imidazolyl intermediate in a protic solvent like methanol yields imines which are reduced in presence of AMBERLITE® IRA-400 borohydride. The slurry is then shaken overnight and the excess amino intermediate is quenched by addition of dichloromethane and aldehyde Wang resin. After further overnight stirring, the mixture is filtered, evaporated and purified on silica gel pad with ethyl acetate as eluent.

For protected basic derivatives ($R^3=(CH_2)_4NHBoc$), the corresponding deprotected compounds were obtained after treatment under acidic condition (DCM/TFA 10%) to remove the Boc group.

EXAMPLE 8470

2-{(1R)-1-[(4-Methoxybenzyl)amino]-2-[indol-3-yl]ethyl}-4-phenyl-1H-imidazole ($C_{27}H_{26}N_4O$, MW=422.42)

2-{(1R)-1-Amino-2-[indol-3-yl]ethyl}-4-phenyl-1H-imidazole (36.3 mg, 0.12 mmol) and p-anisaldehyde (12 µl, 0.1 mmol) in 1 mL of methanol were shaken for about 2 hours at about 22° C. Borohydride resin (76 mg, 2.5 mmol/g, AMBERLITE® IRA-400) was then added and the slurry was stirred overnight before addition of dichloromethane (1 mL) and aldehyde Wang resin (31 mg, 3.22 mmol/g, Novabiochem). After about 8 hours of stirring, the slurry was then filtered and evaporated in vacuo to give a yellow solid (32.2 mg. 76%). $^1$H-NMR (CDCl$_3$, 100 MHz) δ: 8.88 (br s, 1H); 7.73-6.68 (m, 15H); 4.62 (s, 1H); 4.33 (dd, J=4.7 and 8.5 Hz, 1H); 3.81 (s, 2H); 3.74 (s, 3H); 3.27 (ABX system, 2H)); 2.26 (s, 1H). LC/MS: m/z=423 (M+H).

EXAMPLE 8471-9331

The following compounds were prepared analogously to the procedure described for Example 8470, using the appropriate starting materials, which can be obtained from commercial sources or synthesized according to methods known to those skilled in the art or as enabled by the teachings herein. Each combination of $R^3$, $R^5$ and $A^1$, shown below, were or can be synthesized, therefore, the number of Examples are calculated by multiplying ($R^3$ (3 substituents))($R^5$ (7 substituents))($X^2$ (41 substituents))=861.

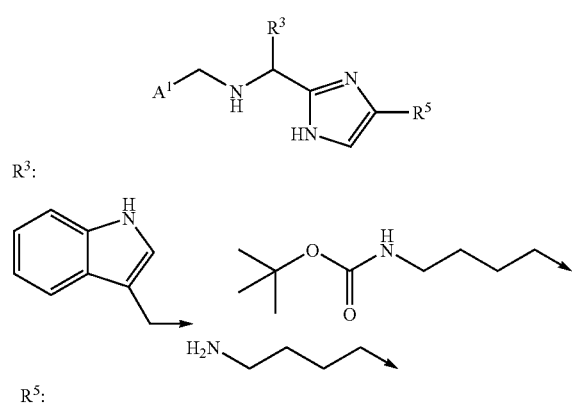
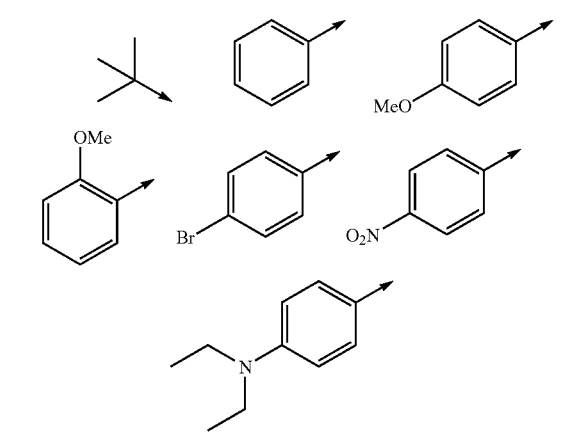
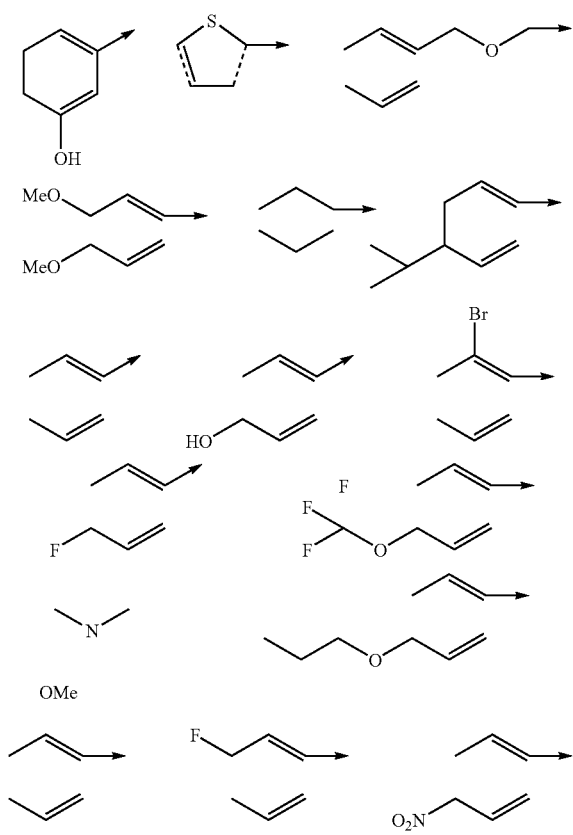
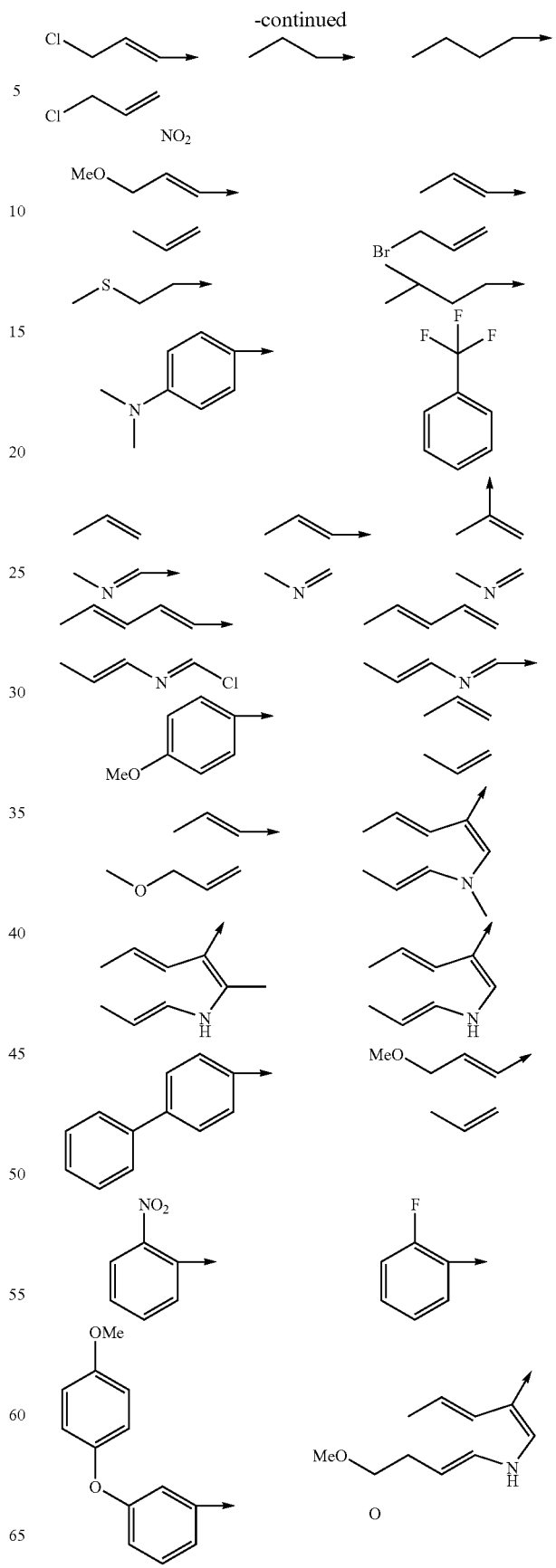

-continued

Synthesis of Amidines by Condensation of an Imidazolyl with Thioimidates

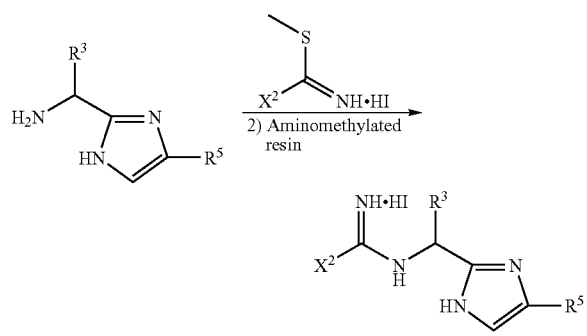

A series of thioimidates were previously synthesized by condensation of thioamides and iodomethane in acetone at room temperature. The precipitate was collected and then rinsed with acetone. Thioimidates so formed were used without further purification.

General procedure: Thioimidates are stirred overnight at room temperature with an amino intermediate in 2-propanol or 2-propanol/DMF before addition of tetrahydrofuran and aminomethylated resin. Further stirring overnight followed by filtration and washing with ethyl acetate yields an iodohydrate amidine after evaporation in vacuo.

For protected basic derivatives ($R^3=(CH_2)_4NHBoc$), the corresponding deprotected compounds were obtained after treatment under acidic condition (DCM/TFA 10%) to remove the Boc group.

EXAMPLE 9332

2-{(1R)-1-[2-Thienyl(imino)methyl)amino]-2-[indol-3-yl]ethyl}-4-phenyl-1H-imidazole hydroiodide ($C_{24}H_{21}N_5S$·HI, MW=539.43)

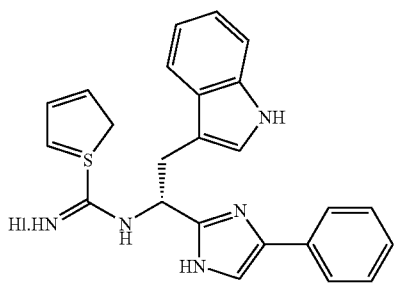

2-{(1R)-1-Amino-2-[indol-3-yl]ethyl}-4-phenyl-1H-imidazole (15.1 mg, 0.05 mmol) and S-methyl-2-thiophenethiocarboximide hydroiodide (13 mg, 0.06 mmol) were shaken in 1 mL of 2-propanol for about 16 hours. Aminomethylated resin (50 mg, 1.31 mmol/g, Novabiochem) was then added and after further stirring overnight a brown solid (19.8 mg, 84%) was isolated by filtration and evaporation in vacuo.

$^1$H-NMR (MeOD, 100 MHz) δ: 8.15 (m, 1H); 7.84-6.96 (m, 13H); 5.3 (m, 1H); 3.61 (m, 2H). LC/MS: m/z=412 (M+H).

EXAMPLES 9333-9920

The following compounds were prepared analogously to the procedure described for Example 9332, using the appropriate starting materials, which can be obtained from commercial sources or synthesized according to methods known to those skilled in the art or as enabled by the teachings herein. Each combination of $R^3$, $R^5$ and $X^2$, shown below, were or can be synthesized, therefore, the number of Examples are calculated by multiplying ($R^3$ (7 substituents))($R^5$ (7 substituents)) ($X^2$ (12 substituents))=588.

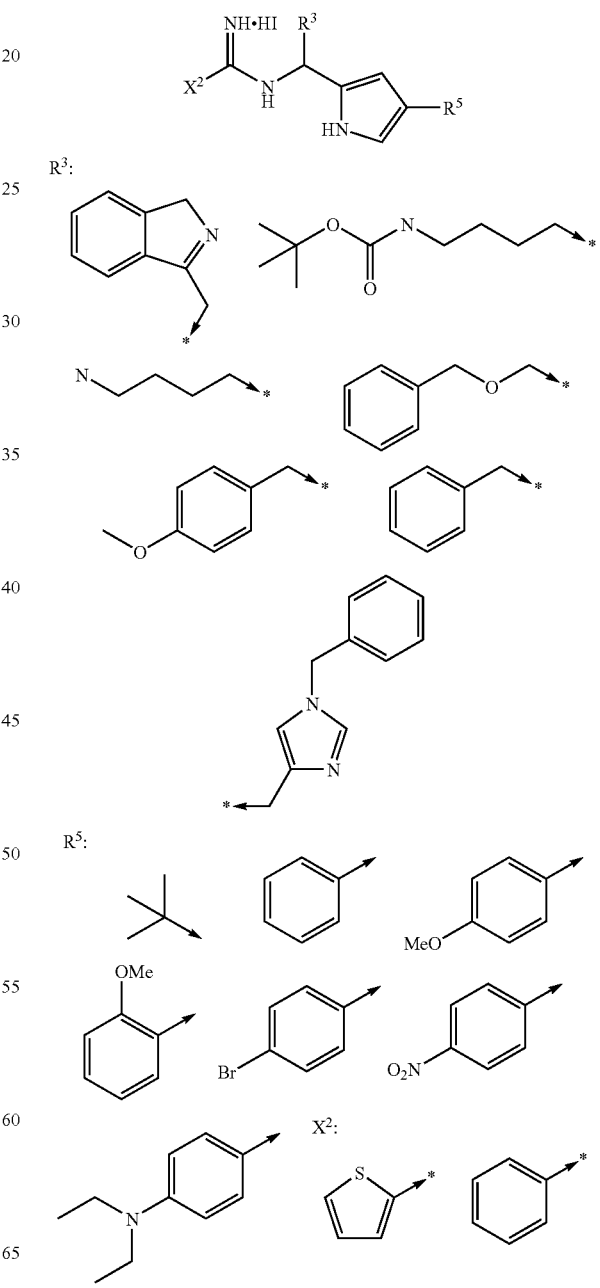

-continued

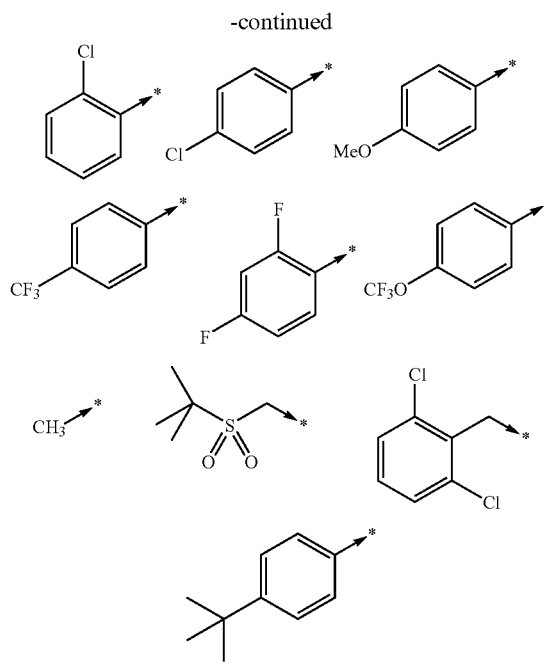

Synthesis of Amidines by Condensation of an Aniline with Thioimidates

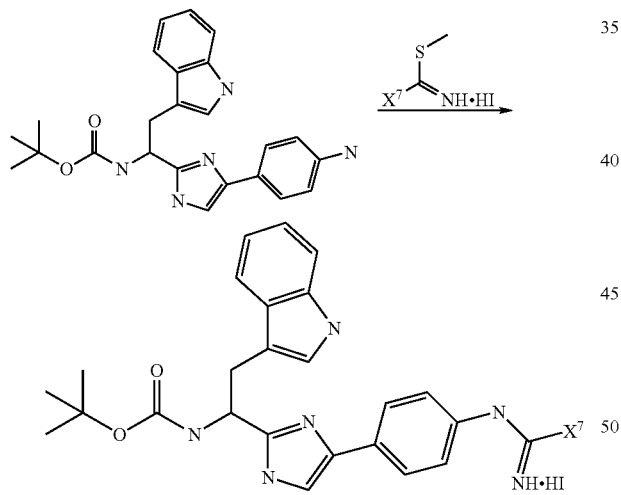

EXAMPLES 9921-9926

The following compounds were prepared analogously to the procedure described for Example 9332, using the appropriate starting materials, which can be obtained from commercial sources or synthesized according to known to those skilled in the art or as enabled by the teachings herein. Each combination of $R^4$ and $X^7$, shown below, were or can be synthesized, therefore, the number of Examples are calculated by multiplying ($R^4$ (2 substituents))($X^7$ (3 substituents)) =6.

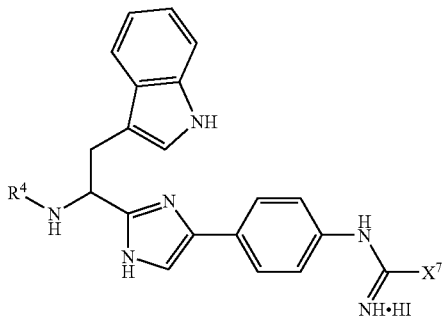

IMIDAZOLE DERIVATIVES N-ALKYLATION

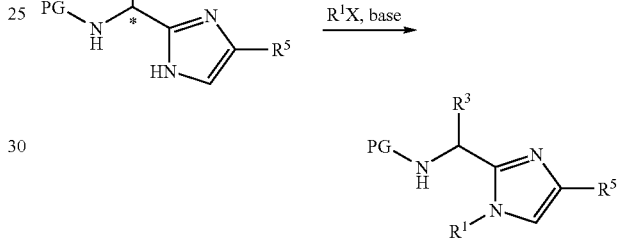

General procedure: A solution of an imidazole intermediate, and alkylating agent such as an α-bromoketone, an α-bromoester, an aryl or alkyl bromide or a sulfonyl chloride, in the presence of an organic or non-organic base which can be or not be supported on a resin such as polystyrene resin, in an aprotic solvent like THF, CH$_3$CN, DMF is heated at 20-80° C. for 2-48 hours. The resulting N-alkylated compound can be isolated either by aqueous work-up followed by flash chromatography on silica gel, or by addition to the reaction mixture of a nucleophile supported on polymer (to trap the excess of electrophile) such as aminomethyl or thiomethyl polystyrene resin followed by filtration and then rapid purification of the resulting residue on a silica gel pad (using Alltech silica cartridge and Alltech manifold).

EXAMPLE 9927

2-[1(S)-{1,2-Dimethylethoxy)carbonylamino}-2-phenylethyl]-1-(2-oxo-butyl)-4-phenyl-1H-imidazole

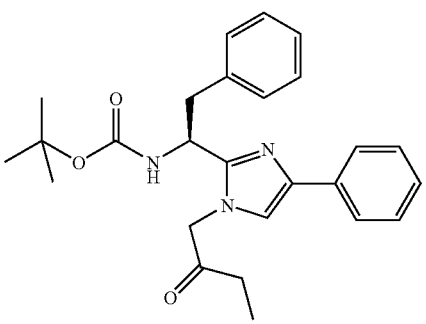

To a solution of 2-[1(S)-{(1,1-dimethylethoxy)carbonylamino}-2-phenylethyl]-4-phenyl-1H-imidazole (100 mg, 1 eq) in DMF (2 mL) were successively added morpholinomethyl polystyrene resin (Novabiochem, loading: 3.51 mmol/g, 159 mg, 2 eq) and 1-bromo-2-butanone (28 mL, 2 eq). After about 18 hours of stirring at about 20° C., 2 mL DMF were added to the reaction mixture followed by aminomethylpolystyrene resin (Novabiochem, loading: 1.73 mmol/g, 319 mg). The mixture was stirred overnight at 20° C. and filtered. The filtrate was concentrated under reduced pressure and then purified by a rapid filtration on a silica gel pad (Alltech silica cartridges) with ethylacetate as eluent to yield 107 mg (90% yield) of the title compound. NMR ($^1$H, 400 MHz, CDCl$_3$) δ: 7.80-6.98 (m, 11H, arom, H), 5.45 (d, 1H, NH), 4.80 (m, 1H, CH), 4.40 (AB, J=18 Hz, NCH$_2$CO), 3.33 (m, 2H, CH$_2$Ph), 2.25 (m, 2H, CH$_2$CH$_3$), 1.0 (t, 3H, CH$_3$). LC/MS: calculated MW=433.5, m/z=434.2 (M+H), m/z=432.2 (M−H).

EXAMPLES 9928-12307

The following compounds were prepared analogously to the procedure described for Example 9927, using the appropriate starting materials, which can be obtained from commercial sources or synthesized according to methods known to those skilled in the art or as enabled by the teachings herein. Each combination of $R^3$, $R^5$ and $R^1$, shown below, were or can be synthesized, therefore, the number of Examples are calculated by multiplying ($R^1$ (34 substituents {see definitions of $Z^1$}))$R^3$ (5 substituents))($R^5$ (14 substituents))=2380.

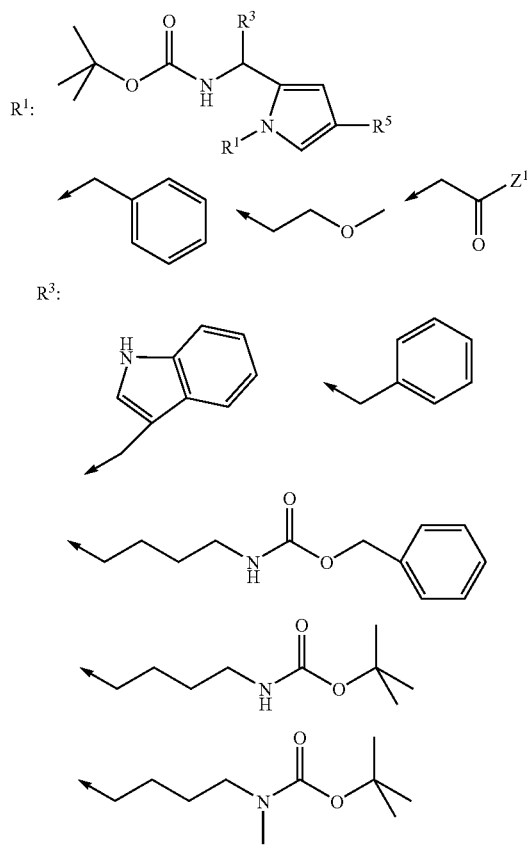

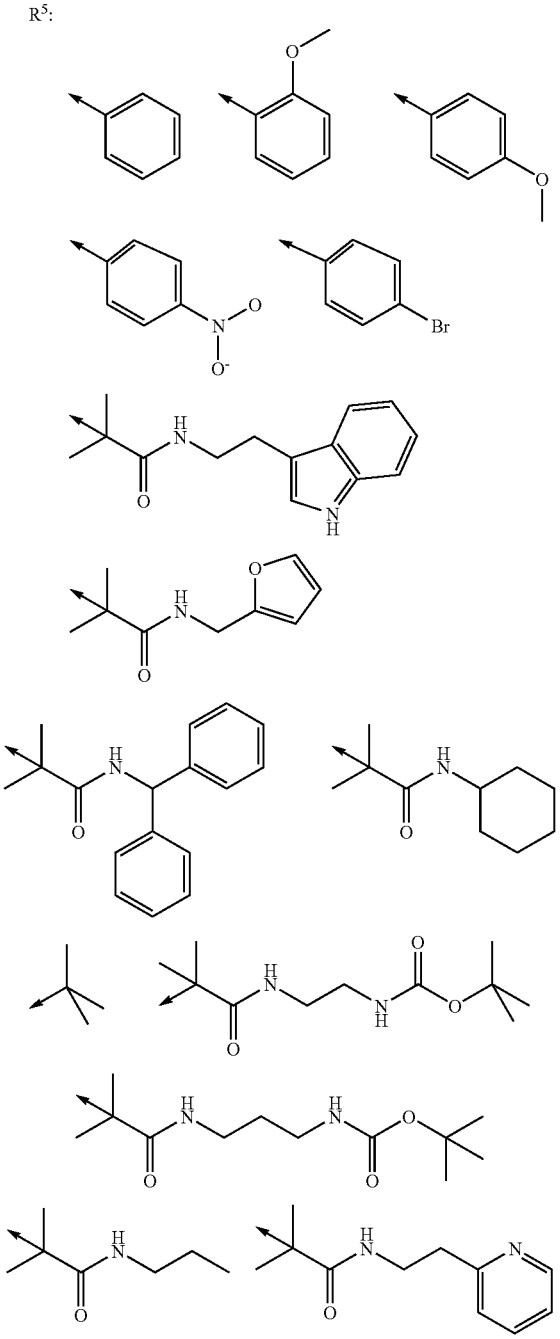

*In case of bromide derivatives, cesium carbonate was used instead of morpholinomethylpolystyrene resin and thiomethyl resin was used instead of aminomethylresin.

$Z^1$

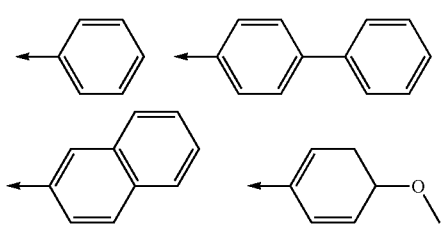

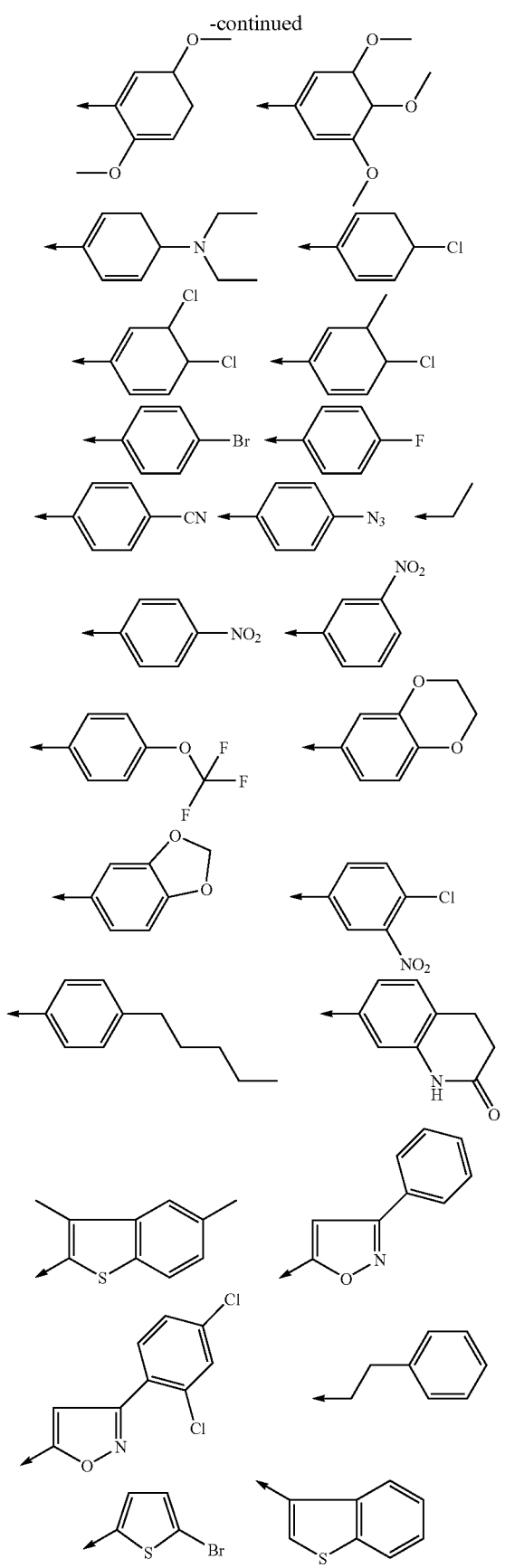

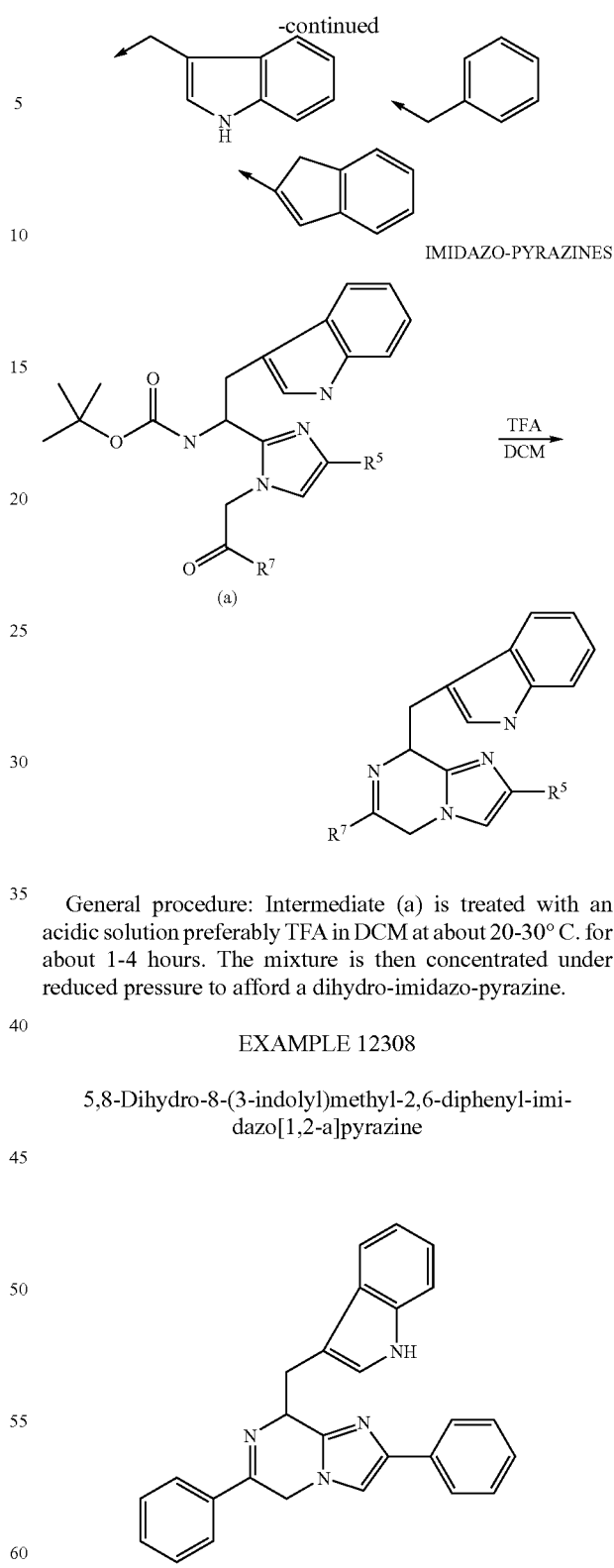

General procedure: Intermediate (a) is treated with an acidic solution preferably TFA in DCM at about 20-30° C. for about 1-4 hours. The mixture is then concentrated under reduced pressure to afford a dihydro-imidazo-pyrazine.

EXAMPLE 12308

5,8-Dihydro-8-(3-indolyl)methyl-2,6-diphenyl-imidazo[1,2-a]pyrazine

A solution of 2-[1(S)-{1,1-dimethylethoxy)carbonylamino}-2-(3-indolyl)ethyl]-1-(benzoylmethyl)-4-phenyl-1H-imidazole (prepared as described previously) (100 mg) in a mixture of 10% TFA in DCM (1.3 mL) was stirred for about 3 hours at about 20° C. and concentrated under reduced pressure to yield the expected dihydro-imidazo-pyrazine (yield=95%). LC/MS: calculated MW: 402.19, m/z=403.2 (M+H).

EXAMPLES 12309-12532

The following compounds were prepared analogously to the procedure described for Example 12308, using the appropriate starting materials, which can be obtained from commercial sources or synthesized according to methods known to those skilled in the art or as enabled by the teachings herein. Each combination of $R^5$ and $R^7$, shown below, were or can be synthesized, therefore, the number of Examples are calculated by multiplying ($R^5$ (7 substituents))($R^7$ (32 substituents))=224.

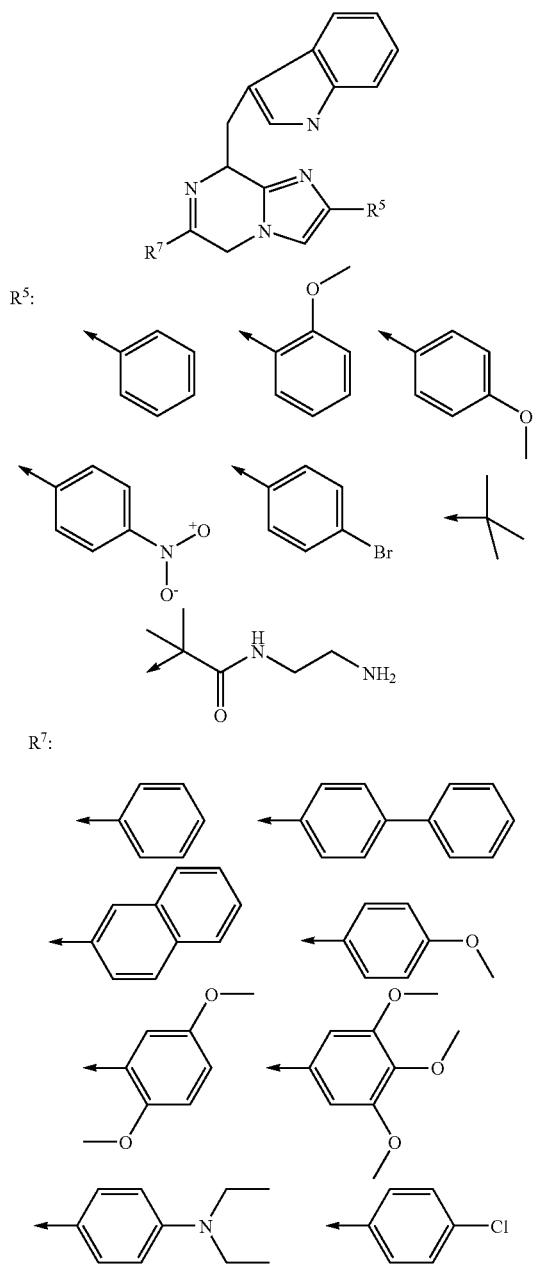
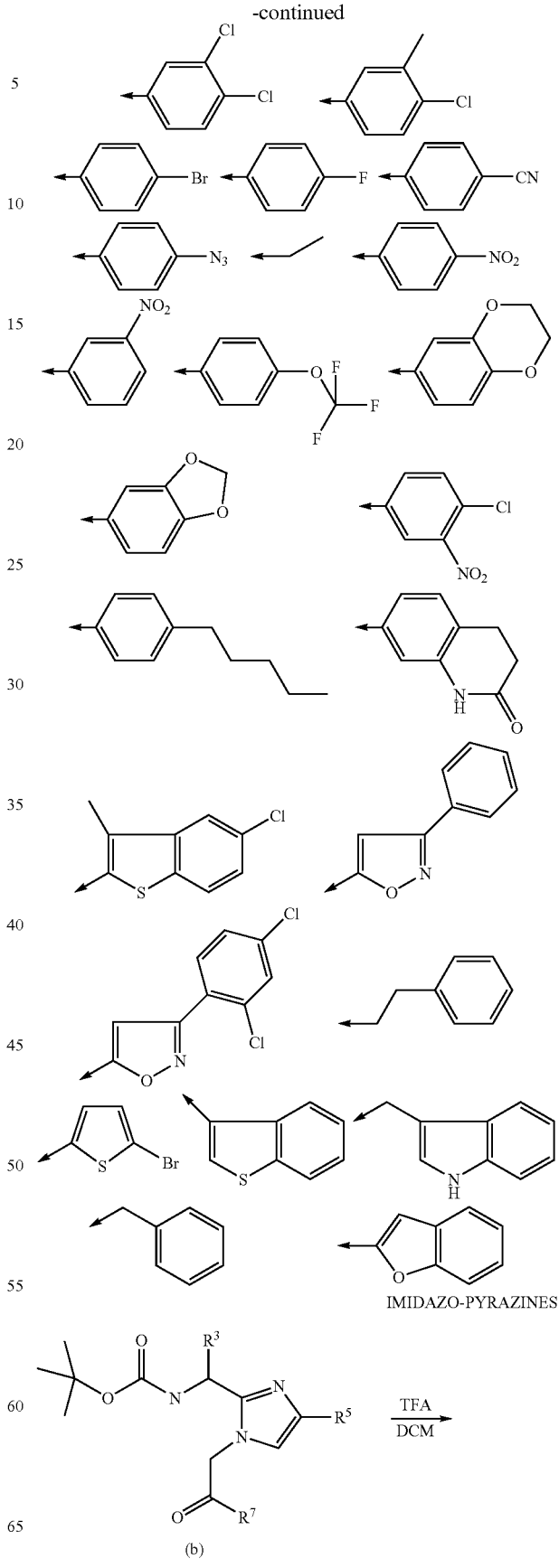

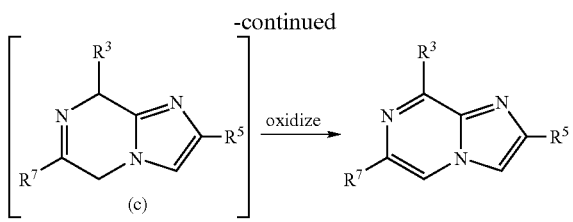

General procedure: Intermediate (b) is treated with an acidic solution preferably TFA in DCM at 20-30° C. for 14 hours. The mixture is then concentrated under reduced pressure to afford compound (c) which is oxidized to the corresponding fully aromatized imidazopyrazine either by keeping it in solution in methanol or DMSO for 5 hours-3 days at about 20° C. or by using an oxidative reagent such as manganese dioxide in a protic or aprotic solvent such as MeOH, toluene or chloroform at 20-70° C. for 2-10 hours or chromic acid supported or not on a resin in a protic solvent like methanol at 40-70° C. for 3-15 hours.

EXAMPLE 12533

2,6-Diphenyl-imidazo[1,2-a]pyrazine-8-butanamine

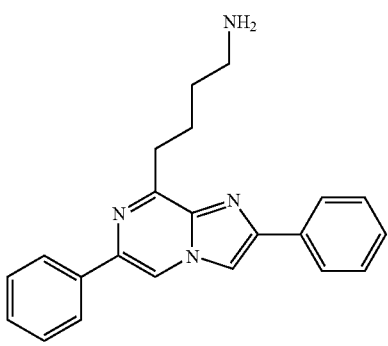

A solution of 2-[1,5-bis{(1,1-dimethylethoxy)carbonylamino}pentyl]-4-phenyl-1H-imidazole (50 mg) in a mixture of TFA/DCM 10% (700 mL) was stirred at about 20° C. for about 3 hours and then concentrated under reduced pressure to yield the intermediate dihydro-imidazo-pyrazine as its trifloroacetate salt. This salt was dissolved in MeOH (1 mL) and manganese dioxide (30 mg) was added. After about 3 hours of stirring at about 20° C., the mixture was filtered on a CELITE® pad and the filtrate concentrated under reduced pressure to afford the fully aromatized imidazo-pyrazine (78% yield). NMR ($^1$H, 400 MHz CD$_3$OD): 8.75-7.34 (m, 12H, arom, H), 3.32 (m, 4H, CH$_2$), 2.10 (m, 2H, CH$_2$), 1.90 (m, 2H, CH$_2$). LC/MS: calculated MW=342.4, m/z=343.2 (M+H).

EXAMPLES 12534-13773

The following compounds were prepared analogously to the procedure described for Example 12533, using the appropriate starting materials, which can be obtained from commercial sources or synthesized according to methods known to those skilled in the art or as enabled by the teachings herein. Each combination of R$^3$ and R$^7$, shown below, were or can be synthesized, therefore, the number of Examples are calculated by multiplying (R$^3$ (5 substituents))R$^5$ (8 substituents)) R$^7$ (31 substituents))=1240.

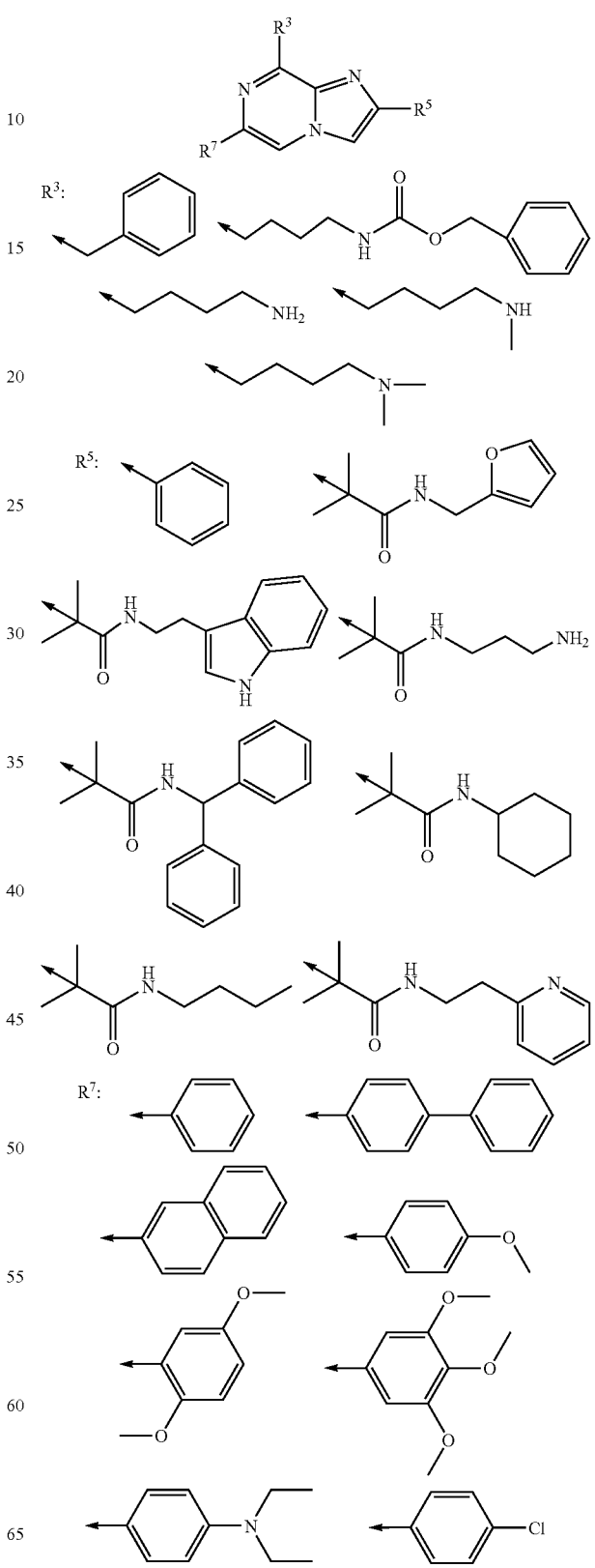

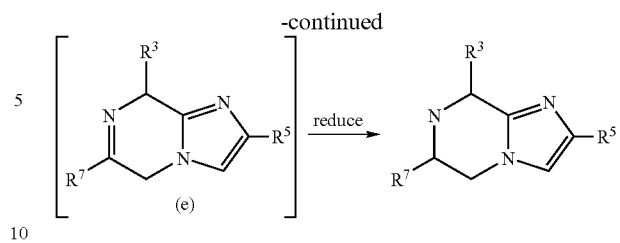

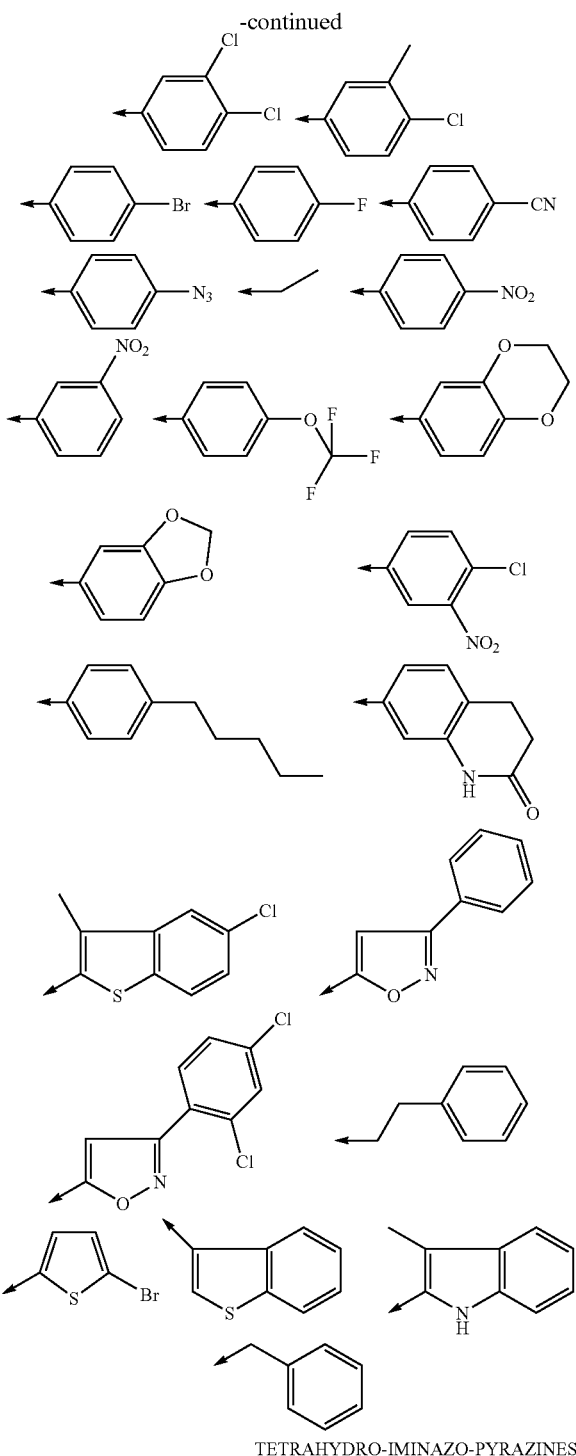

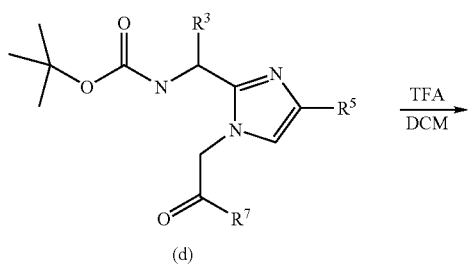

TETRAHYDRO-IMINAZO-PYRAZINES

General procedure: Intermediate (d) is treated with an acidic solution preferably TFA in DCM at 20-30° C. for 14 hours. The mixture is then concentrated under reduced pressure to afford the intermediate dihydro-imidazopyrazine (e). Reduction of (e) to the corresponding tetrahydro-imidazopyrazine is achieved by catalytic hydrogenation or by using any reducing agent such as $NaBH_4$ (which can be supported on a resin), $NaBH(OAc)_3$, $NaBH_3CN$ in a protic solvent such as MeOH at pH maintained weakly acidic (around pH 5) by addition of acetic acid or TFA.

EXAMPLE 13774

6-Ethyl-5,6,7,8-tetrahydro-2-phenyl-8(S)-phenylmethyl-imidazol[1,2-a]pyrazine

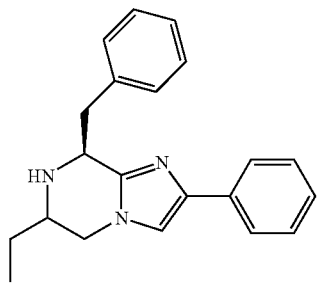

2-[1(S)-{(1,1-Dimethylethoxy)carbonylamino}-2-phenylethyl]-1-(2-oxo-butyl)-4-phenyl-1H-imidazole (60 mg) in a mixture of 10% TFA in DCM was stirred at about 20° C. for about 3 hours and then concentrated under reduced pressure. The resulting intermediate dihydro-imidazo-pyrazine was dissolved in methanol and borohydride supported on resin (AMBERLITE® IRA 400, Aldrich, 2.5 mmol $BH_4^-$/g; 4 eq) was added. The pH was maintained at about 5 by addition of drops of TFA. After about 2 hours of stirring at about 20° C., the mixture was filtered and the filtrate concentrated under reduced pressure. The residue was purified by flash chromatography (ethyl acetate/Heptane 7:3; Rf=0.30). The tetrahydro-imidazo-pyrazine was obtained as a single diastereoisomer in 86% yield (38 mg) NMR ($^1$H, 400 MHz, $CDCl_3$) δ: 7.87-7.10 (m, 11H, arom, H), 4.28 (dd, 1H, $^3J=10$ Hz, $^3J=3$ Hz, H8), 3.95 (dd, 1H, $^2J=11.5$ Hz, $^3J=3.6$ Hz), 3.85 (dd, 1H, $^2J=13.6$ Hz, $^3J=3.0$ Hz), 3.60 (t, 1H, $^2J=^3J=11.5$ Hz), 3.85 (dd, 1H, $^2J=13.6$ Hz, $^3J=10$, Hz), 2.98 (m, 2H), 1.85 (s, 1H, NH), 1.55 (m, 2H, $CH_2$), 0.95 (t, 3H, $CN_3$). NMR ($^{13}$C, 100 MHz $CDCl_3$): 146.3, 140.9, 138.0, 134.4, 129.4, 128.6, 128.5, 126.6, 126.5, 124.8, 113.8, 55.9, 54.4, 50.2, 40.0, 26.6, 10.0. LC/MS: calculated MW=317.43, m/z=318.20 (M+H).

EXAMPLE 13775

The following compound was prepared analogously to the procedure described for Example 13774 using the appropriate starting materials, which can be obtained from commercial sources or synthesized according to methods known to those skilled in the art or as enabled by the teachings herein.

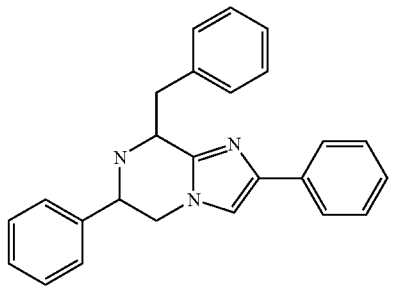

Example 13775

N-SUBSTITUTED TETRAHYDRO-IMIDAZO-PYRAZINES

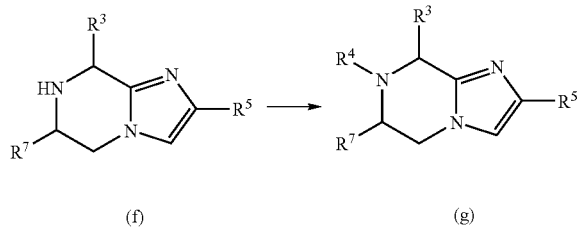

(f)   (g)

General procedure: A compound of formula (f) can react with isocyanates, isothiocyanates, N-succinimidyl carbamates, acyl chlorides or activated carboxylic acids in an aprotic solvent at 20-70° C. for 2-18 hours. The resulting derivative can be isolated by evaporation of the mixture followed by flash chromatography on silica gel or by addition to the mixture of a nucleophile supported on polymer such as aminomethyl or thiomethyl polystyrene resin followed by a filtration.

EXAMPLE 13776

5,6,7,8-Tetrahydro-7-(methoxymethylcarbonyl)-2,6-diphenyl-8(S)-phenylmethyl-imidazo[1,2-a]pyrazine

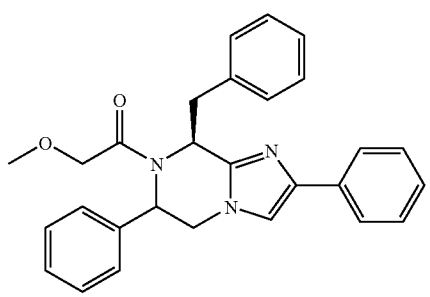

To a solution of 5,6,7,8-tetrahydro-2,6-diphenyl-8(S)-phenylmethyl-imidazo[1,2-a]pyrazine (29 mg) in chloroform were successively added morpholinomethylpolystyrene resin (Novabiochem, loading=3.51 mmol/g, 50 mg, 2 eq) and methoxyacetylchloride (10 mL, 1.3 eq). After about 3 hours of stirring at about 20° C. chloroform was added to the mixture followed by aminomethylpolystyrene resin (Novabiochem, loading=1.2 mmol/g, 132 mg, 2 eq). The reaction mixture was stirred for another 2 hours and then filtered. The filtrate was concentrated under reduced pressure to afford 23 mg of the title compound (yield=68%). NMR ($^1$H, 100 MHz, $CDCl_3$): 7.9-7.0 (m, 16H, arom, H), 6.6 (m, 1H, $H_1$), 5.3 (m, 1H, $H_1$), 4.6 (dd, 1H, $^2J$=13 Hz, H5), 4.35 (dd, 1H, $^2J$=13 Hz, $^3J$=5 Hz, H5'), 3.7-2.9 (m, 5H, $CH_2Ph$, $OCH_3$).

The following tables of compounds illustrate some of the compounds of the present invention that were synthesized and provide the hplc retention time (denoted Rt or Tr) in minutes and mass spectra results of each compound.

Mass spectra were acquired on a single quadrupole electrospray mass spectrometer (Micromass, Platform model), 0.8 Da resolution. A monthly calibration, between 80 and 1000 Da, is performed with sodium and rubidium iodide solution isopropanol/water (1/1 Vol.).

HPLC retention times were acquired on an HPLC system: HP1100 (Hewlett-Packard) equipped with a photodiode array UV detector.

The HPLC conditions are as follows and the conditions used for each of the following tables of compounds are noted below, the wavelength of the UV detector is noted in parenthesis after the formula number.

Condition A:
Solvent:
A: Water + 0.4% Formic acid
B: Acetonitrile + 0.4% Formic acid

| T(min) | A% | B% |
|---|---|---|
| 0 | 90 | 10 |
| 5 | 90 | 10 |
| 16 | 40 | 60 |
| 17 | 10 | 90 |
| 20 | 10 | 90 |

Flow rate: 1 ml/min
Injection volume volume: 20 µL
Column: Kromasil ODS 5 µm 150* 4.6 mm i.d.
Temp.: 40° C.

Condition $A_2$:
Solvent:
A: Water + 0.4% Formic acid
B: Acetonitrile + 0.4% Formic acid

| T(min) | A% | B% |
|---|---|---|
| 0 | 90 | 10 |
| 2 | 90 | 10 |
| 14 | 10 | 90 |
| 20 | 10 | 90 |

Flow rate: 1 ml/min
Injection volume: 20 µL
Column: Kromasil ODS 5 µm 150* 4.6 mm i.d.
Temp.: 40° C.

Condition $A_3$:
Solvent:
A: Water + 0.4% Formic acid
B: Acetonitrile + 0.4% Formic acid

| T(min) | A% | B% |
|---|---|---|
| 0 | 90 | 10 |
| 5 | 90 | 10 |
| 16 | 46 | 54 |
| 17.5 | 10 | 90 |
| 22 | 10 | 90 |

Flow rate: 1 ml/min
Injection volume: 20 µL
Column: Kromasil ODS 5 µm 150* 4.6 mm i.d.
Temp.: 40° C.

Condition A₄:
Solvent:
A: Water + 0.4% Formic acid
B: Acetonitrile + 0.4% Formic acid

| T(min) | A% | B% |
|---|---|---|
| 0 | 90 | 10 |
| 5 | 90 | 10 |
| 20 | 10 | 90 |
| 25 | 10 | 90 |

Flow rate: 1 ml/min
Injection volume: 20 μL
Column: Kromasil ODS 5 μm 150* 4.6 mm i.d.
Temp.: 40° C.

Condition A₅:
Solvent:
A: Water + 0.4% Formic acid
B: Acetonitrile + 0.4% Formic acid

| T(min) | A% | B% |
|---|---|---|
| 0 | 90 | 10 |
| 5 | 90 | 10 |
| 25 | 10 | 90 |
| 30 | 10 | 90 |

Flow rate: 1 ml/min
Injection volume: 20 μL
Column: Kromasil ODS 5 μm 150* 4.6 mm i.d.
Temp.: 40° C.

Condition B:
Solvent:
A: Water + 0.02% Trifluoroacetic acid
B: Acetonitrile

| T(min) | A% | B% |
|---|---|---|
| 0 | 100 | 0 |
| 1 | 100 | 0 |
| 8 | 30 | 70 |
| 10 | 30 | 70 |

Flow rate: 1.1 ml/min
Injection volume: 5 μL
Column: Uptisphere ODS 3 μm 33* 4.6 mm i.d.
Temp.: 40° C.

Condition C:
Solvent:
A: Water + 0.02% Trifluoroacetic acid
B: Acetonitrile

| T(min) | A% | B% |
|---|---|---|
| 0 | 100 | 0 |
| 1 | 100 | 0 |
| 10 | 85 | 25 |
| 12 | 85 | 25 |

Flow rate: 1.1 ml/min
Injection volume: 5 μL
Column: Uptisphere ODS 3 μm 33* 4.6 mm i.d.
Temp.: 40° C.

Condition D:
Solvent:
A: Water + 0.04% Trifluoroacetic acid
B: Acetonitrile

| T(min) | A% | B% |
|---|---|---|
| 0 | 100 | 0 |
| 1 | 100 | 0 |
| 8 | 30 | 70 |
| 10 | 30 | 70 |

Flow rate: 1.1 ml/min
Injection volume: 5 μL
Column: Uptisphere ODS 3 μm 33* 4.8 mm i.d.
Temp.: 40° C.

Condition E:
Solvent:
A: Water + 0.04% Trifluoroacetic acid
B: Acetonitrile

| T(min) | A% | B% |
|---|---|---|
| 0 | 90 | 10 |
| 1 | 90 | 10 |
| 8 | 0 | 100 |
| 10 | 0 | 100 |

Flow rate: 1.1 ml/min
Injection volume: 5 μL
Column: Uptisphere ODS 3 μm 33* 4.6 mm i.d.
Temp.: 40° C.

In the following description Formula numbers are noted in bold and the wavelength is in parenthesis.

Method A=Used for Tables of compounds of Formulas: 17 (250), 18 (250) and 57 (220).

Method A₄=Used for Tables of compounds of Formulas: 58 (210).

Method B=Used for Tables of compounds of Formulas: 7 (220), 8 (220), 9 (220), 10 (220), 11 (220), 12 (250), 19 (220), 20 (260), 21 (250), 25 (240), 26 (220), 27 (220), 28 (220), 29 (220), 37 (220), 38 (220), 39 (220), 40 (240), 44 (220), 45 (220), 46 (220), 47 (220), 48 (220), 49 (250), 55 (260), and 56 (220).

Method C=Used for Tables of compounds of Formulas: 1 (220), 2 (220), 3 (220), 4 (260), 5 (220), 6 (220), 13 (220), 14 (220), 16 (260), 23 (250), 24 (250), 30 (220), 31 (254), 32 (250), 33 (250), 34 (250), 35 (250), and 36 (254).

Method D=Used for Tables of compounds of Formulas: 15 (220), 51 (220), 52 (220), 53 (220), and 54 (220).

Method E=Used for Tables of compounds of Formulas: 22 (250), 41 (220), 42 (250), 43 (220), and 50 (250).

FORMULA 1
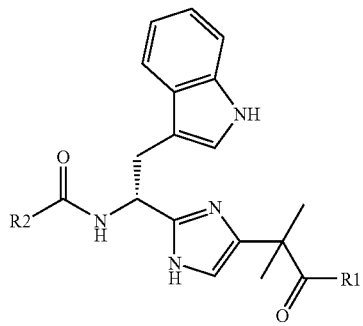
| | R1 | R2 | Analysis | |
|---|---|---|---|---|
| | | | Rt (min) | [M + H]+ |
| 1 | tert-butyl N-(2-aminoethyl)carbamate-* | spiro[indene-1,4'-piperidine]-N-* | 7.0 | 666.5 |
| 2 | tert-butyl N-(2-aminoethyl)carbamate-* | spiro[indane-1,4'-piperidine]-N-* | 7.1 | 668.5 |
| 3 | tert-butyl N-(2-aminoethyl)carbamate-* | 1-(piperidin-4-yl)-1,3-dihydro-2H-benzimidazol-2-one-N'-* | 6.2 | 712.5 |
| 4 | tert-butyl N-(2-aminoethyl)carbamate-* | 4-piperidin-1-yl-piperidin-N-* | 6.1 | 698.5 |
| 5 | tert-butyl N-(2-aminoethyl)carbamate-* | 4-piperidin-1-yl-piperidin-N-* | 5.0 | 649.5 |

-continued
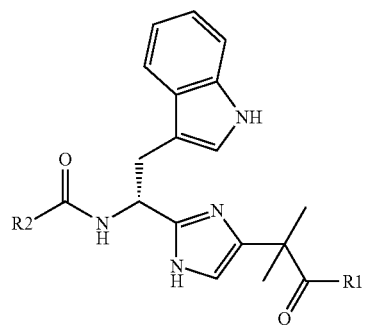
FORMULA 1
| | R1 | R2 | Rt (min) | [M + H]+ |
|---|---|---|---|---|
| 6 | Boc-NH-CH2CH2-NH-* | 4-benzylpiperidin-1-yl-* | 7.2 | 656.5 |
| 7 | Boc-NH-CH2CH2-NH-* | 4-hydroxy-4-phenylpiperidin-1-yl-* | 6.2 | 658.5 |
| 8 | Boc-NH-CH2CH2-NH-* | 4-phenylpiperazin-1-yl-* | 6.4 | 543.5 |
| 9 | Boc-NH-CH2CH2-NH-* | 4-(2-fluorophenyl)piperazin-1-yl-* | 6.7 | 661.5 |
| 10 | Boc-NH-CH2CH2-NH-* | 4-(2-methylthiophenyl)piperazin-1-yl-* | 7.0 | 689.5 |
| 11 | Boc-NH-CH2CH2-NH-* | 4-(furan-2-carbonyl)piperazin-1-yl-* | 5.8 | 661.4 |
| 12 | Boc-NH-CH2CH2-NH-* | 4-benzylpiperazin-1-yl-* | 5.3 | 657.5 |

-continued
FORMULA 1
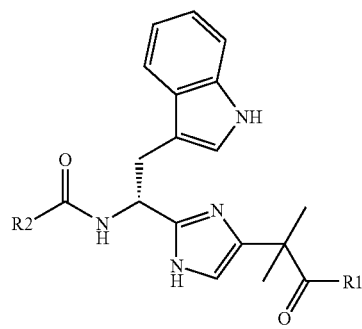
| | R1 | R2 | Analysis Rt (min) | [M + H]+ |
|---|---|---|---|---|
| 13 | Boc-NH-CH2CH2-NH-* | piperonyl-piperazinyl-* | 5.4 | 701.5 |
| 14 | Boc-NH-CH2CH2-NH-* | benzhydryl-piperazinyl-* | 6.2 | 733.5 |
| 15 | Boc-NH-CH2CH2-NH-* | tetrahydro-β-carbolinyl-* | 6.7 | 653.5 |
| 16 | Boc-NH-CH2CH2-NH-* | PhCH2-N(*)-CH2CH2-N(CH3)2 | 5.5 | 659.5 |
| 17 | Boc-NH-CH2CH2-NH-* | *-N-piperazinyl-N-CH2CH2OH | 4.8 | 611.4 |
| 18 | Boc-NH-CH2CH2-NH-* | Boc-NH-piperazinyl-* | 6.4 | 581.5 |
| 19 | Boc-NH-CH2CH2-NH-* | Boc-piperazinyl-* | 5.4 | 667.5 |

-continued
FORMULA 1
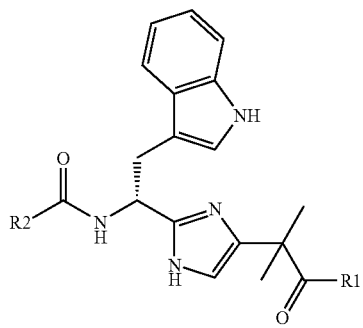
| | R1 | R2 | Analysis Rt (min) | [M + H]+ |
|---|---|---|---|---|
| 20 | tert-butyl (2-aminoethyl)carbamate-* | 1-benzylpiperidin-4-ylamino-* | 5.4 | 671.5 |
| 21 | tert-butyl (3-aminopropyl)carbamate-* | spiro[indene-1,4'-piperidine]-N-* | 7.2 | 680.5 |
| 22 | tert-butyl (3-aminopropyl)carbamate-* | spiro[indane-1,4'-piperidine]-N-* | 7.2 | 682.5 |
| 23 | tert-butyl (3-aminopropyl)carbamate-* | 1-phenyl-1,3,8-triazaspiro[4.5]decan-4-one-N8-* | 5.4 | 726.5 |

-continued

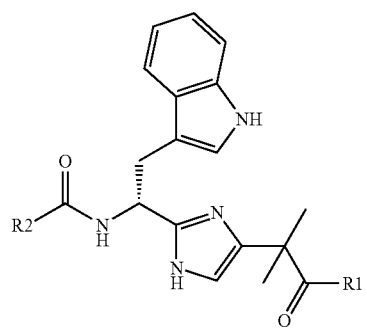

FORMULA 1

| | R1 | R2 | Rt (min) | [M + H]+ |
|---|---|---|---|---|
| 24 | tert-butyl 3-aminopropylcarbamate | 1-(piperidin-4-yl)-1,3-dihydro-2H-benzimidazol-2-one | 5.2 | 712.5 |
| 25 | tert-butyl 3-aminopropylcarbamate | 4-piperidinopiperidine | 5.1 | 663.5 |
| 26 | tert-butyl 3-aminopropylcarbamate | 4-benzylpiperidine | 7.2 | 670.5 |
| 27 | tert-butyl 3-aminopropylcarbamate | 4-hydroxy-4-phenylpiperidine | 6.3 | 672.5 |
| 28 | tert-butyl 3-aminopropylcarbamate | 1-phenylpiperazine | 6.6 | 657.5 |
| 29 | tert-butyl 3-aminopropylcarbamate | 1-(2-fluorophenyl)piperazine | 6.8 | 675.5 |

-continued

FORMULA 1

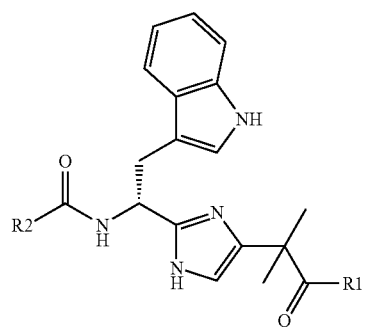

| | R1 | R2 | Analysis Rt (min) | [M + H]+ |
|---|---|---|---|---|
| 30 | tert-butyl (3-aminopropyl)carbamate-* | 2-(methylthio)phenyl piperazine-* | 7.1 | 703.5 |
| 31 | tert-butyl (3-aminopropyl)carbamate-* | furan-2-carbonyl piperazine-* | 5.9 | 675.4 |
| 32 | tert-butyl (3-aminopropyl)carbamate-* | benzyl piperazine-* | 5.4 | 671.5 |
| 33 | tert-butyl (3-aminopropyl)carbamate-* | benzo[d][1,3]dioxol-5-ylmethyl piperazine-* | 5.5 | 715.5 |
| 34 | tert-butyl (3-aminopropyl)carbamate-* | diphenylmethyl piperazine-* | 6.3 | 747.5 |
| 35 | tert-butyl (3-aminopropyl)carbamate-* | 3,4-dihydro-1H-β-carboline-2(9H)-yl-* | 6.8 | 667.5 |

-continued

FORMULA 1

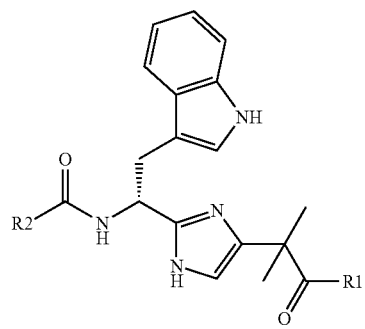

| | R1 | R2 | Rt (min) | [M + H]+ |
|---|---|---|---|---|
| 36 | tert-butyl (3-aminopropyl)carbamate linker | N-benzyl-N'-(2-(dimethylamino)ethyl)amine | 5.6 | 673.5 |
| 37 | tert-butyl (3-aminopropyl)carbamate linker | 4-(2-hydroxyethyl)piperazine | 4.9 | 625.5 |
| 38 | tert-butyl (3-aminopropyl)carbamate linker | tert-butyl 4-aminopiperidine-1-carboxylate | 6.5 | 681.5 |
| 39 | tert-butyl (3-aminopropyl)carbamate linker | tert-butyl piperazine-1-carboxylate | 6.5 | 695.5 |
| 40 | tert-butyl (3-aminopropyl)carbamate linker | 1-benzyl-4-aminopiperidine | 5.5 | 685.5 |

-continued
FORMULA 1
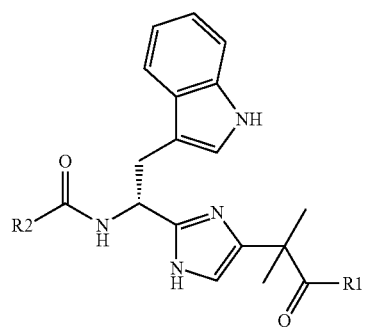
| | R1 | R2 | Analysis Rt (min) | [M + H]+ |
|---|---|---|---|---|
| 41 | | | 7.2 | 694.5 |
| 42 | | | 7.3 | 596.5 |
| 43 | | | 6.4 | 740.5 |
| 44 | | | 6.3 | 726.5 |
| 45 | | | 5.2 | 677.5 |

-continued

FORMULA 1

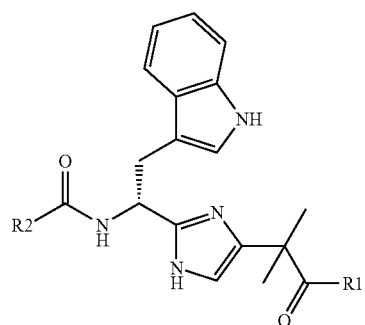

| | R1 | R2 | Rt (min) | [M + H]+ |
|---|---|---|---|---|
| 46 | tert-butyl carbamate-(CH2)4-NH-* | 4-benzylpiperidine-N-* | 7.3 | 684.5 |
| 47 | tert-butyl carbamate-(CH2)4-NH-* | 4-hydroxy-4-phenylpiperidine-N-* | 6.4 | 686.5 |
| 48 | tert-butyl carbamate-(CH2)4-NH-* | 4-phenylpiperazine-N-* | 6.6 | 671.5 |
| 49 | tert-butyl carbamate-(CH2)4-NH-* | 4-(2-fluorophenyl)piperazine-N-* | 5.8 | 589.5 |
| 50 | tert-butyl carbamate-(CH2)4-NH-* | 4-(2-methylthiophenyl)piperazine-N-* | 7.1 | 717.5 |
| 51 | tert-butyl carbamate-(CH2)4-NH-* | 4-(furan-2-carbonyl)piperazine-N-* | 6.0 | 689.5 |
| 52 | tert-butyl carbamate-(CH2)4-NH-* | 4-benzylpiperazine-N-* | 5.5 | 685.5 |

-continued

FORMULA 1

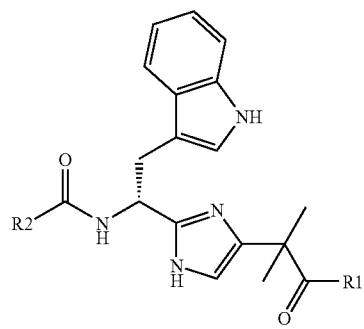

| | R1 | R2 | Rt (min) | [M + H]+ |
|---|---|---|---|---|
| 53 | tert-butyl carbamate-butyl-NH-* | benzodioxole-CH2-piperazine-* | 5.5 | 729.5 |
| 54 | tert-butyl carbamate-butyl-NH-* | diphenylmethyl-piperazine-* | 6.4 | 761.5 |
| 55 | tert-butyl carbamate-butyl-NH-* | tetrahydro-β-carboline-* | 6.9 | 681.4 |
| 56 | tert-butyl carbamate-butyl-NH-* | benzyl-N(CH2CH2NMe2)-* | 5.6 | 687.5 |
| 57 | tert-butyl carbamate-butyl-NH-* | hydroxyethyl-piperazine-* | 5.0 | 639.5 |
| 58 | tert-butyl carbamate-butyl-NH-* | Boc-NH-piperidine-* | 6.6 | 709.5 |
| 59 | tert-butyl carbamate-butyl-NH-* | Boc-piperazine-* | 6.6 | 695.5 |

-continued
FORMULA 1
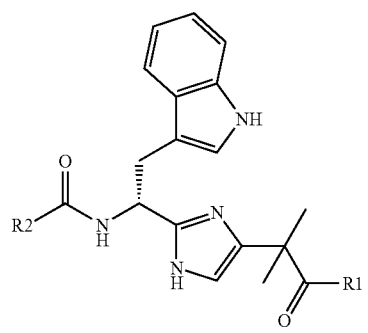
| | R1 | R2 | Analysis Rt (min) | [M + H]+ |
|---|---|---|---|---|
| 60 | | | 5.5 | 699.5 |
| 61 | | | 7.58+ 7.8 | 748.5 |
| 62 | | | 7.7 | 750.5 |
| 63 | | | 7.0 | 794.5 |

-continued
FORMULA 1
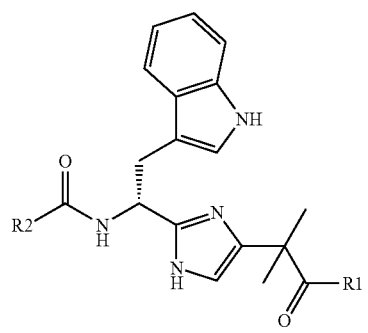
| | R1 | R2 | Analysis Rt (min) | [M + H]+ |
|---|---|---|---|---|
| 64 | | | 6.8 | 780.5 |
| 65 | | | 5.8 | 731.6 |
| 66 | | | 7.8 | 738.5 |
| 67 | | | 6.9 | 740.5 |
| 68 | | | 7.2 | 725.5 |
| 69 | | | 7.3 | 743.5 |

-continued
FORMULA 1
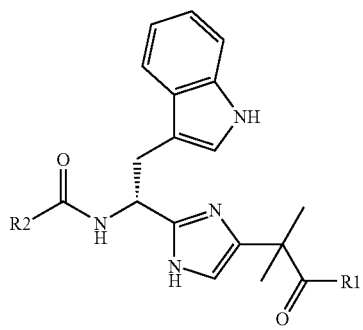
| | R1 | R2 | Analysis | |
|---|---|---|---|---|
| | | | Rt (min) | [M + H]+ |
| 70 | | | 7.6 | 771.5 |
| 71 | | | 6.5 | 743.5 |
| 72 | | | 6.0 | 739.5 |
| 73 | | | 6.0 | 783.5 |
| 74 | | | 6.8 | 815.6 |
| 75 | | | 7.4 | 735.5 |

-continued
FORMULA 1
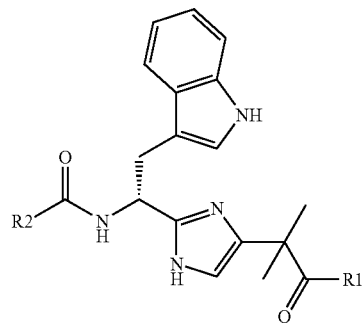
| | R1 | R2 | Analysis Rt (min) | [M + H]+ |
|---|---|---|---|---|
| 76 | tert-butyl carbamate-CH2-cyclohexyl-CH2-NH-* | benzyl-N(CH2CH2N(CH3)2)-* | 6.1 | 741.5 |
| 77 | tert-butyl carbamate-CH2-cyclohexyl-CH2-NH-* | *-N-piperazine-N-CH2CH2OH | 5.6 | 693.5 |
| 78 | tert-butyl carbamate-CH2-cyclohexyl-CH2-NH-* | Boc-NH-piperidine-N-* | 7.1+ 7.2 | 749.5 |
| 79 | tert-butyl carbamate-CH2-cyclohexyl-CH2-NH-* | Boc-piperazine-N-* | 7.1+ 7.2 | 753.5 |
| 80 | tert-butyl carbamate-CH2-cyclohexyl-CH2-NH-* | benzyl-piperidine-NH-* | 6.0 | 753.5 |

FORMULA 2
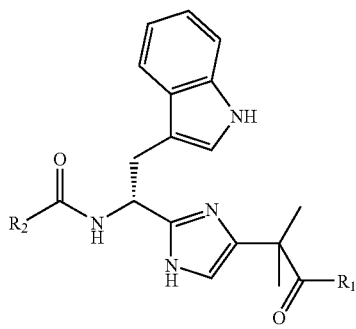
| | R1 | R2 | Rt (min.) | [M + H]+ |
|---|---|---|---|---|
| 1 | H₂N-CH₂CH₂-NH-* | spiro[indene-1,4'-piperidine]-N-* | 5.5 | 566.3 |
| 2 | H₂N-CH₂CH₂-NH-* | spiro[indane-1,4'-piperidine]-N-* | 5.6 | 568.3 |
| 3 | H₂N-CH₂CH₂-NH-* | 1-phenyl-1,3,8-triazaspiro[4.5]decan-4-one-N-* | 4.9 | 612.3 |
| 4 | H₂N-CH₂CH₂-NH-* | 1-(benzimidazol-2-one-1-yl)piperidin-4-yl-N-* | 4.8 | 598.3 |
| 5 | H₂N-CH₂CH₂-NH-* | 4-piperidinopiperidin-N-* | 3.8 | 549.4 |

-continued
| | | | | |
|---|---|---|---|---|
| 6 | 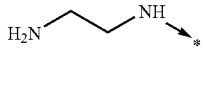 | 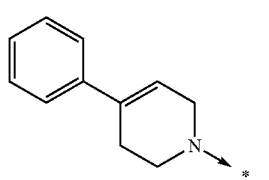 | 5.6 | 556.3 |
| 7 | 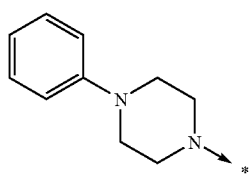 |  | 5.3 | 540.3 |
| 8 | 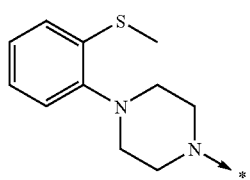 | 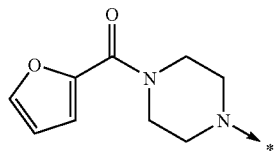 | 4.9 | 543.3 |
| 9 | 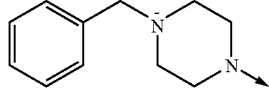 | 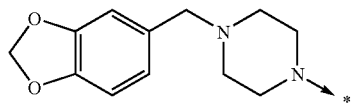 | 5.1 | 561.3 |
| 10 | 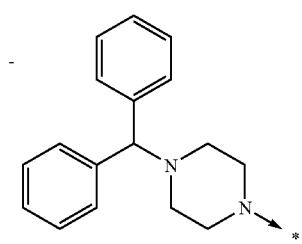 | | 5.4 | 589.3 |
| 11 | | | 4.3 | 561.3 |
| 12 | | | 4.1 | 557.3 |
| 13 | | | 4.1 | 601.3 |
| 14 | | | 4.9 | 633.4 |

-continued
| 15 |  | 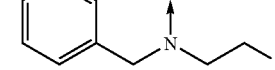 | 5.3 | 533.3 |
| 16 |  | 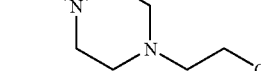 | 4.2 | 559.3 |
| 17 | 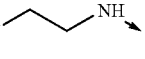 | 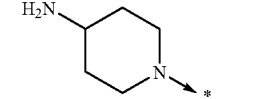 | 3.5 | 511.3 |
| 18 |  |  | 3.5 | 481.3 |
| 19 | 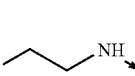 |  | 3.5 | 467.3 |
| 20 |  | 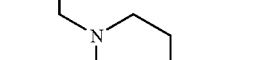 | 4.1 | 571.3 |
| 21 |  |  | 5.6 | 580.4 |
| 22 |  |  | 5.6 | 582.4 |

-continued

| | | | | |
|---|---|---|---|---|
| 23 | H₂N~~~NH-* | 1-phenyl-1,3,8-triazaspiro[4.5]decan-4-one (N-linked) | | 4.9 | 626.4 |
| 24 | H₂N~~~NH-* | 1-(piperidin-4-yl)-1,3-dihydro-2H-benzimidazol-2-one (N-linked) | | 4.8 | 612.4 |
| 25 | H₂N~~~NH-* | 4-(piperidin-1-yl)piperidine (N-linked) | | 3.8 | 563.4 |
| 26 | H₂N~~~NH-* | 4-benzylpiperidine (N-linked) | | 5.6 | 570.4 |
| 27 | H₂N~~~NH-* | 4-phenyl-1,2,3,6-tetrahydropyridine (N-linked) | | 5.4 | 554.3 |
| 28 | H₂N~~~NH-* | 1-phenylpiperazine (N-linked) | | 4.9 | 557.3 |
| 29 | H₂N~~~NH-* | 1-(2-fluorophenyl)piperazine (N-linked) | | 5.1 | 575.3 |
| 30 | H₂N~~~NH-* | 1-(2-methylthiophenyl)piperazine (N-linked) | | 5.4 | 603.3 |

-continued
| | | | |
|---|---|---|---|
| 31 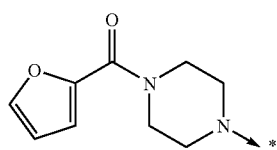 | 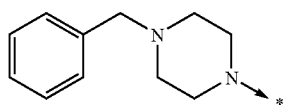 | 4.4 | 575.3 |
| 32 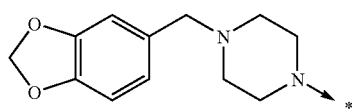 | 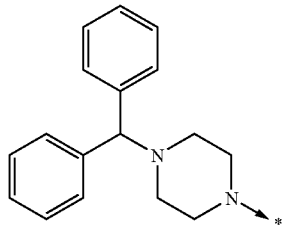 | 4.1 | 571.3 |
| 33 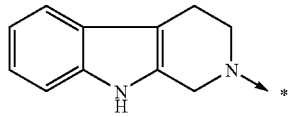 | 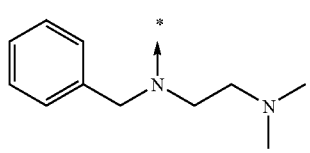 | 4.1 | 615.4 |
| 34 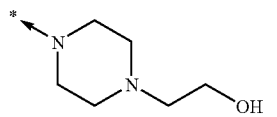 | 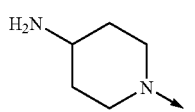 | 4.9 | 647.4 |
| 35 | | 5.3 | 567.3 |
| 36 | | 4.2 | 573.3 |
| 37 | | 3.5 | 525.3 |
| 38 | | 3.5 | 495.3 |
| 39 | 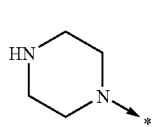 | 3.5 | 481.3 |

-continued
| | | | | |
|---|---|---|---|---|
| 40 | 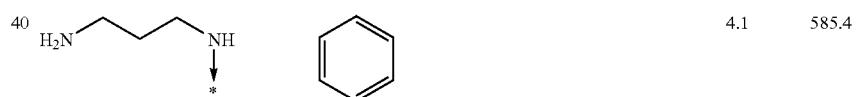 | | 4.1 | 585.4 |
| | 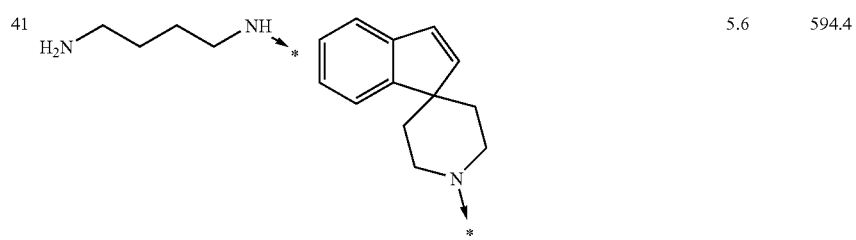 | | | |
| 41 | | | 5.6 | 594.4 |
| 42 | 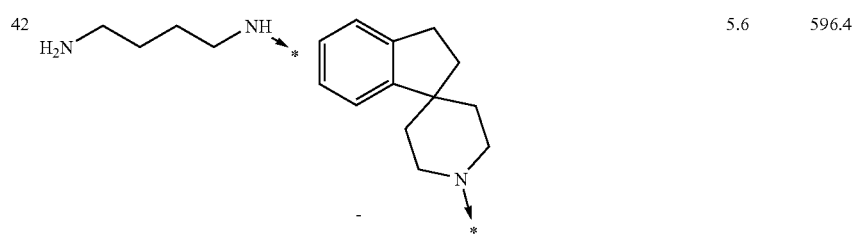 | | 5.6 | 596.4 |
| 43 | 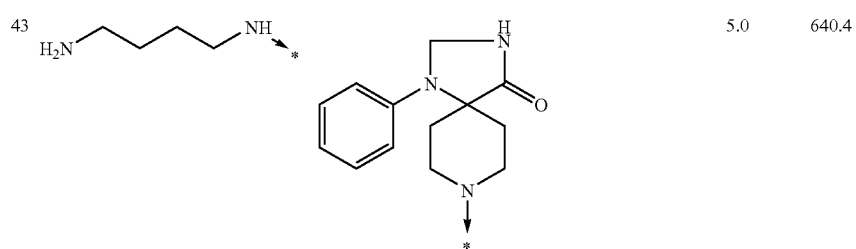 | | 5.0 | 640.4 |
| 44 | 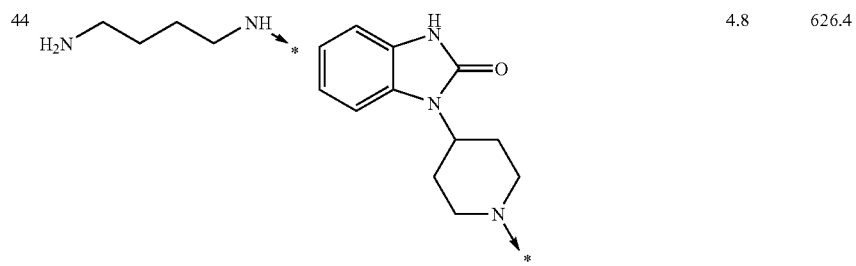 | | 4.8 | 626.4 |
| 45 | 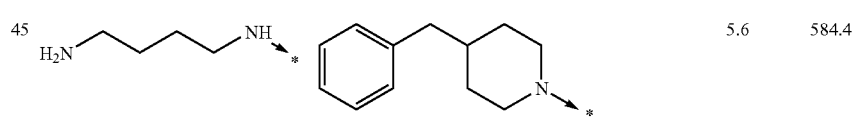 | | 5.6 | 584.4 |

-continued
| | | | | |
|---|---|---|---|---|
| 46 | 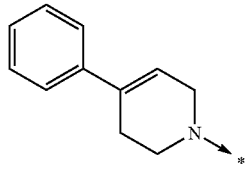 | | 5.7 | 568.3 |
| 47 | 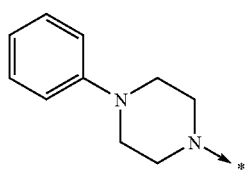 | | 5 | 571.3 |
| 48 | 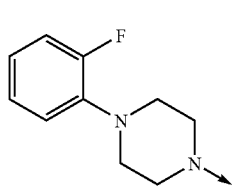 | | 5.1 | 589.4 |
| 49 | 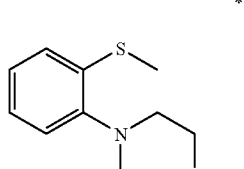 | | 5.5 | 617.4 |
| 50 | 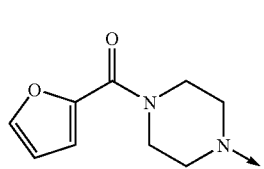 | | 4.4 | 589.3 |
| 51 | 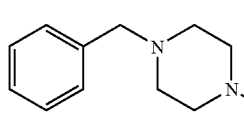 | | 4.1 | 585.4 |
| 52 | 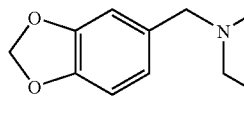 | | 4.2 | 629.4 |
| 53 | 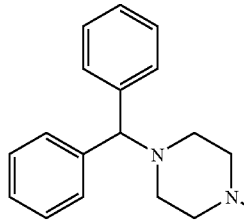 | | 4.9 | 661.5 |
| 54 | 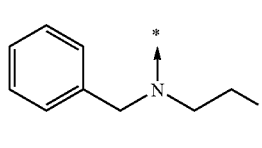 | | 4.3 | 587.4 |

-continued
| | | | | |
|---|---|---|---|---|
| 55 | 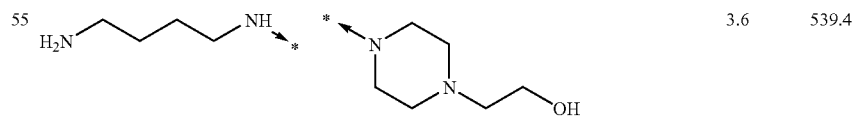 | | 3.6 | 539.4 |
| 56 |  | | 3.6 | 509.4 |
| 57 | 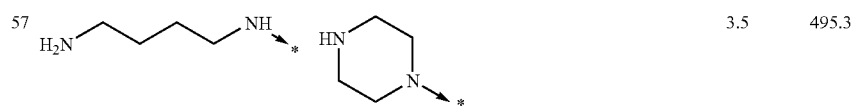 | | 3.5 | 495.3 |
| 58 | 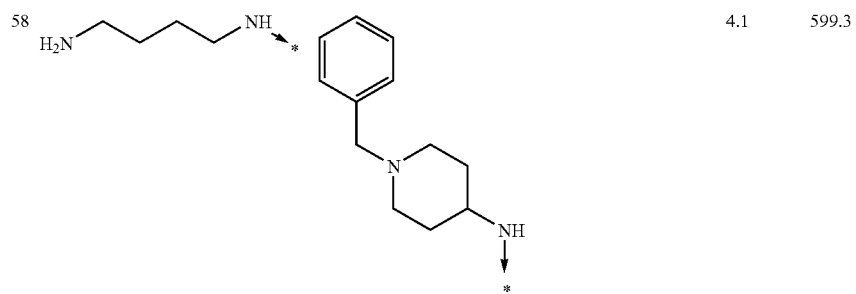 | | 4.1 | 599.3 |
| 59 | 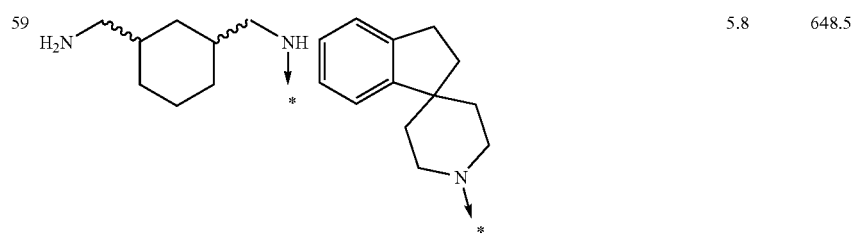 | | 5.8 | 648.5 |

-continued
| | R1 | R2 | Tr | [M + H]+ |
|---|---|---|---|---|
| 60 | 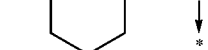 | 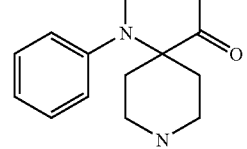 | 5.9 | 650.5 |
FORMULA 2
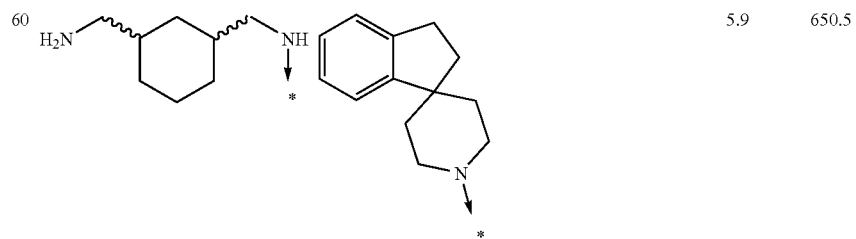
| | R1 | R2 | Tr | [M + H]+ |
|---|---|---|---|---|
| 61 | 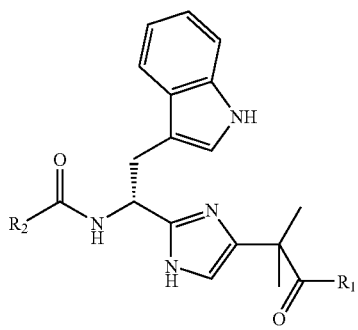 |  | 5.2 | 694.5 |
| 62 | 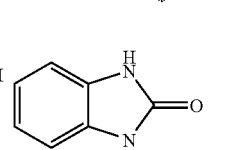 |  | 5 | 680.5 |
| 63 | 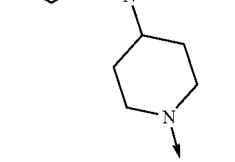 |  | 5.9 | 638.5 |
| 64 | 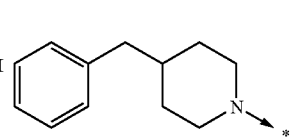 | | 5.2 | 625.5 |

-continued
| | | | |
|---|---|---|---|
| 65 | 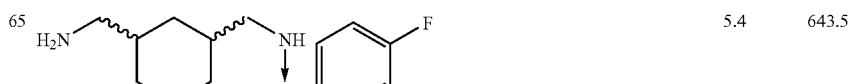 | 5.4 | 643.5 |
| 66 | 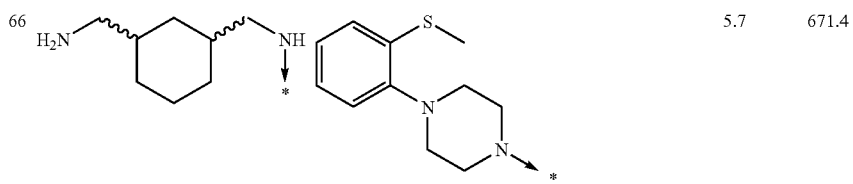 | 5.7 | 671.4 |
| 67 | 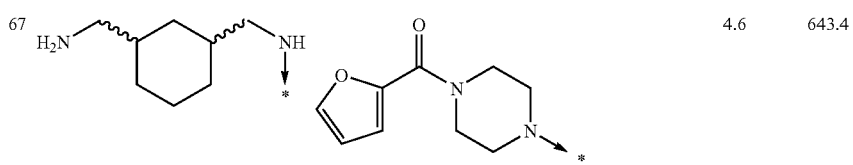 | 4.6 | 643.4 |
| 68 | 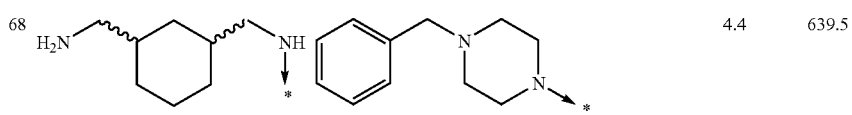 | 4.4 | 639.5 |
| 69 | 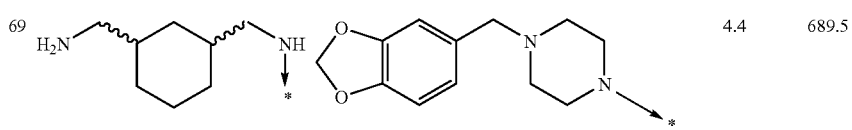 | 4.4 | 689.5 |
| 70 | 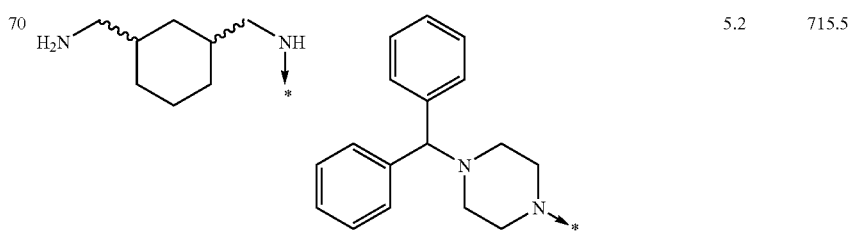 | 5.2 | 715.5 |
| 71 | 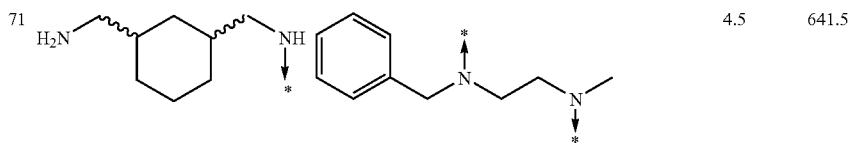 | 4.5 | 641.5 |
| 72 | 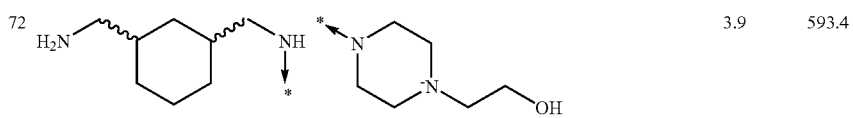 | 3.9 | 593.4 |

FORMULA 3
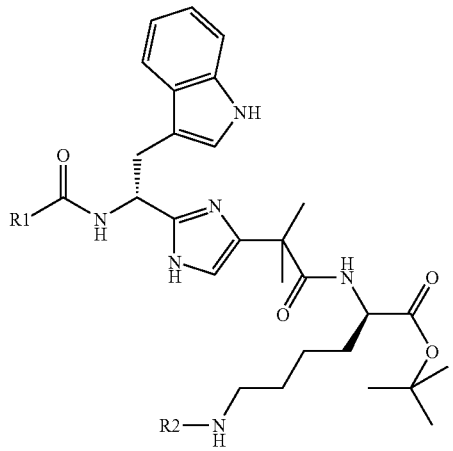
| Structure | Analysis | |
|---|---|---|
| | Rt (min) | [M + H]+ |
| 1 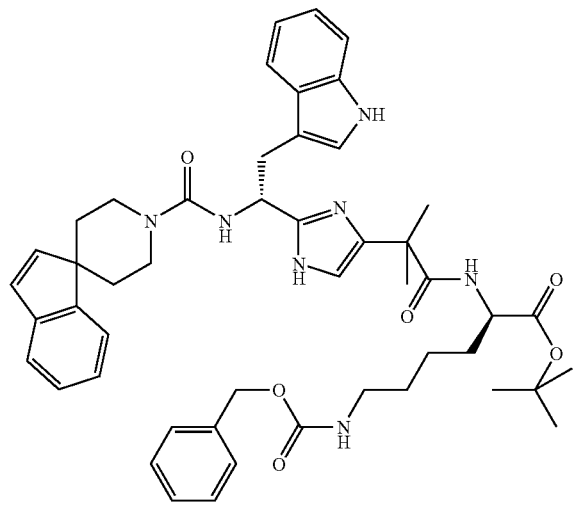 | 9.1 | 842.5 |
| 2 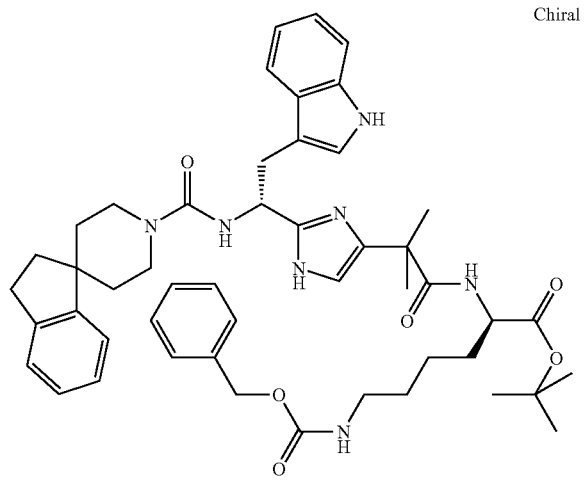 Chiral | 9.2 | 844.5 |

FORMULA 3
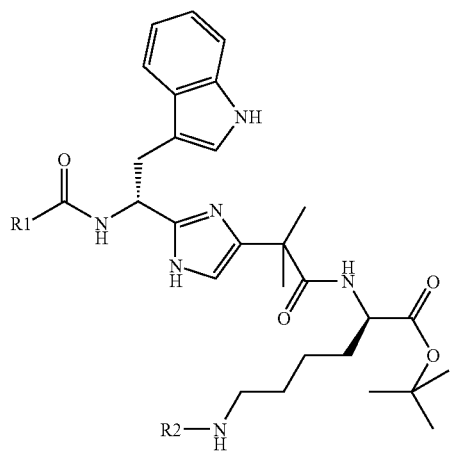
| Structure | | Analysis | |
|---|---|---|---|
| | | Rt (min) | [M + H]+ |
| 3 | Chiral | 8.3 | 888.5 |
| 4 | Chiral | 8.1 | 874.5 |

-continued
FORMULA 3
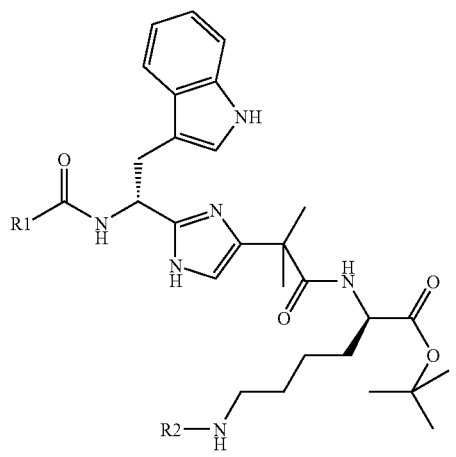
| Structure | | Analysis | |
|---|---|---|---|
| | | Rt (min) | [M + H]+ |
| 5 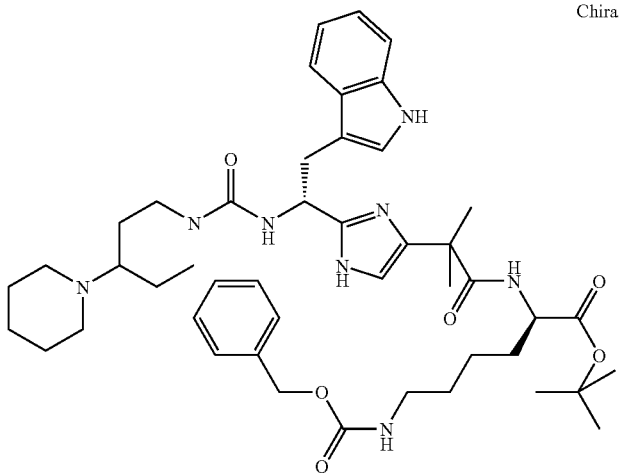 | Chiral | 6.9 | 825.5 |
| 6 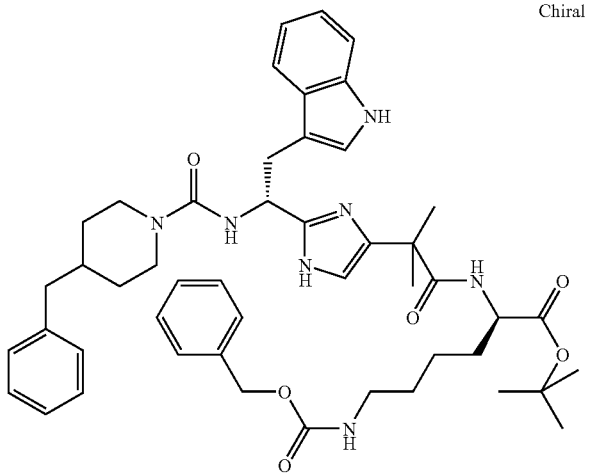 | Chiral | 9.2 | 832.5 |

-continued
FORMULA 3
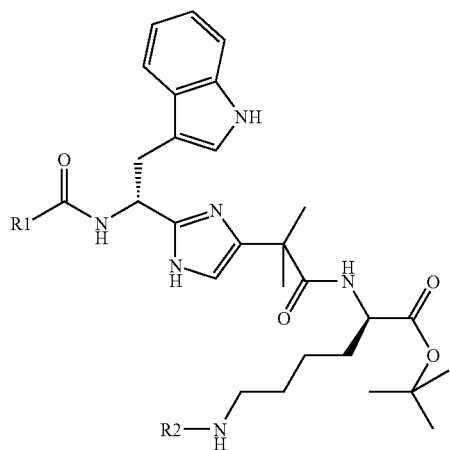
| Structure | | Analysis | |
|---|---|---|---|
| | | Rt (min) | [M + H]+ |
| 7 | Chiral | 8.2 | 834.5 |
| 8 | Chiral | 8.6 | 819.4 |

-continued
FORMULA 3
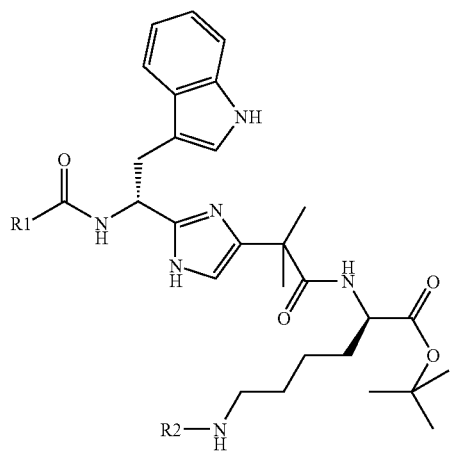
| Structure | | Analysis | |
|---|---|---|---|
| | | Rt (min) | [M + H]+ |
| 9 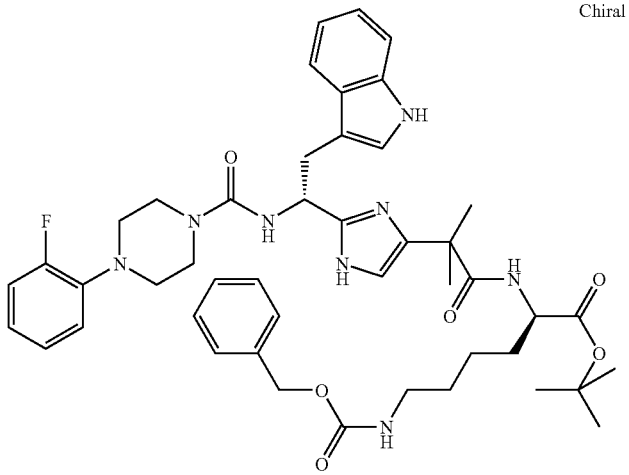 | Chiral | 8.7 | 837.5 |
| 10 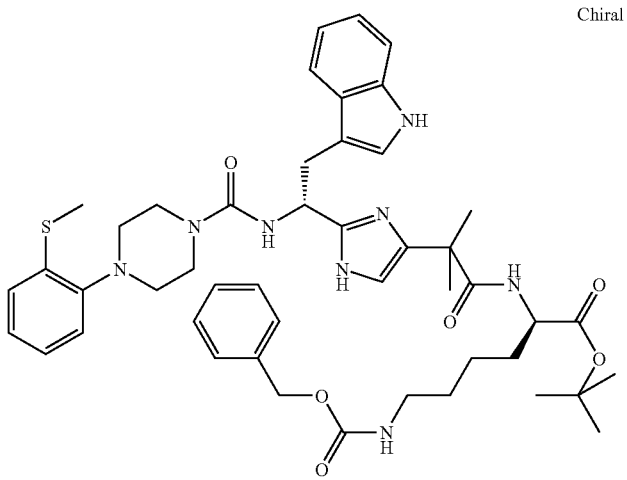 | Chiral | 9 | 865.5 |

FORMULA 3
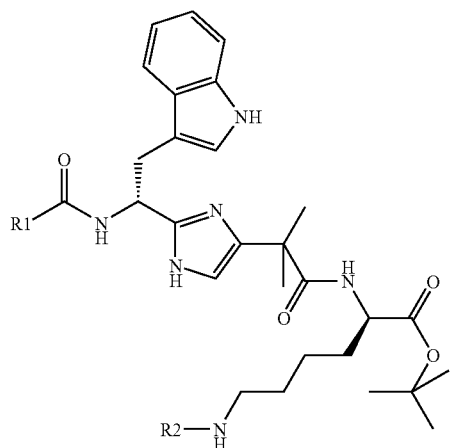
| Structure | | Analysis | |
|---|---|---|---|
| | | Rt (min) | [M + H]+ |
| 11 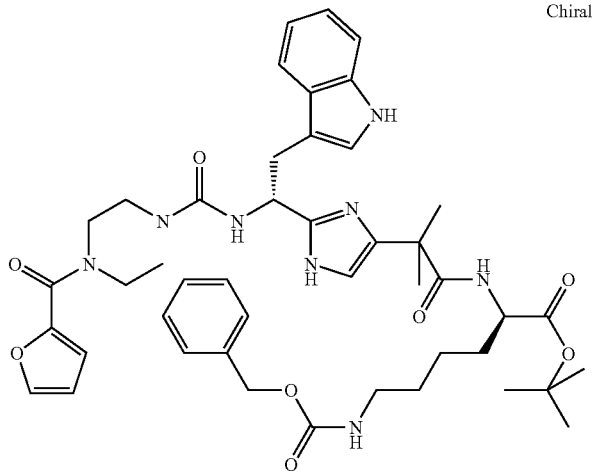 | Chiral | 7.8 | 837.4 |
| 12 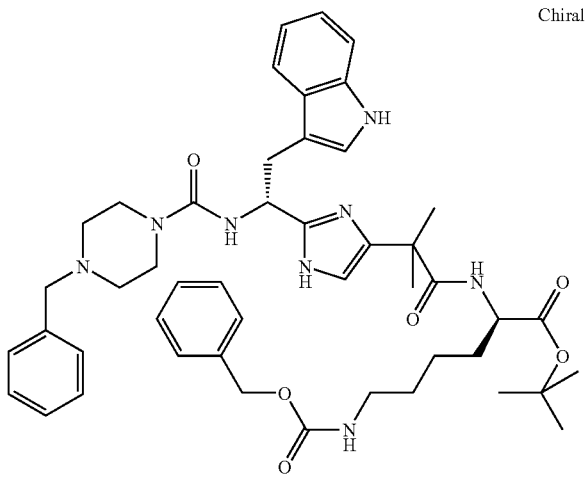 | Chiral | 7.1 | 833.5 |

FORMULA 3
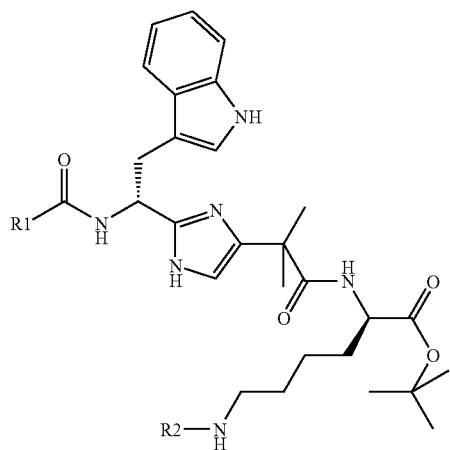
| Structure | | Analysis | |
|---|---|---|---|
| | | Rt (min) | [M + H]+ |
| 13 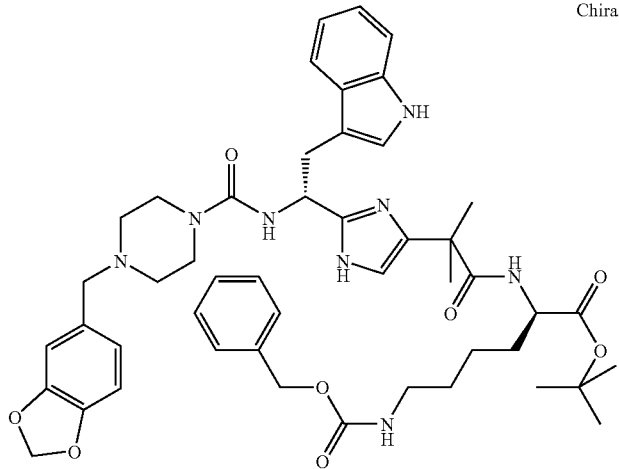 | Chiral | 7.1 | 877.5 |
| 14 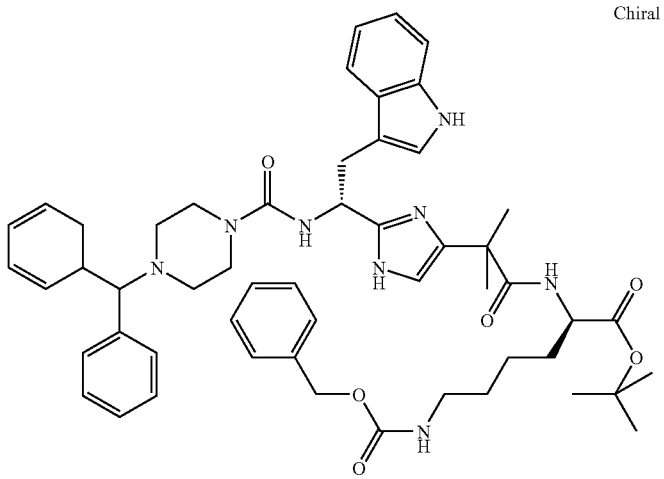 | Chiral | 8.1 | 909.5 |

FORMULA 3
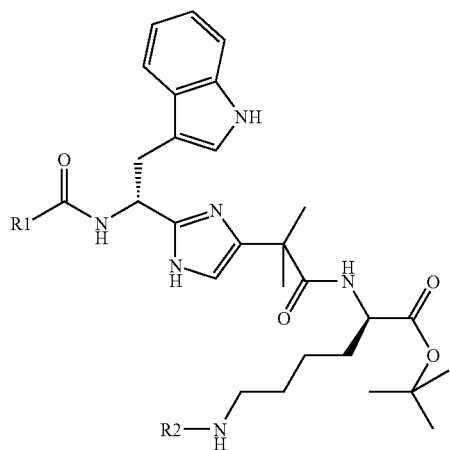
| Structure | Analysis | |
|---|---|---|
| | Rt (min) | [M + H]+ |
| 15 *(Chiral structure)* | 8.7 | 829.5 |
| 16 *(Chiral structure)* | 7.2 | 835.5 |

FORMULA 3
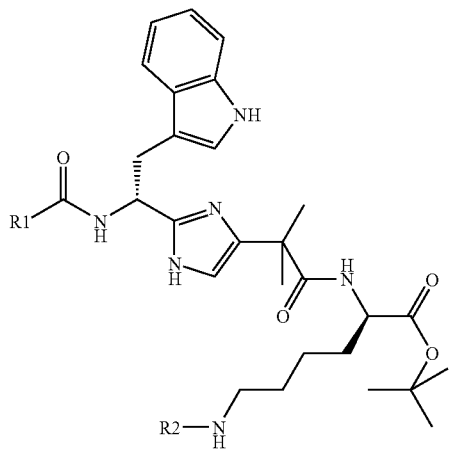
| Structure | Analysis | |
|---|---|---|
| | Rt (min) | [M + H]+ |
| 17 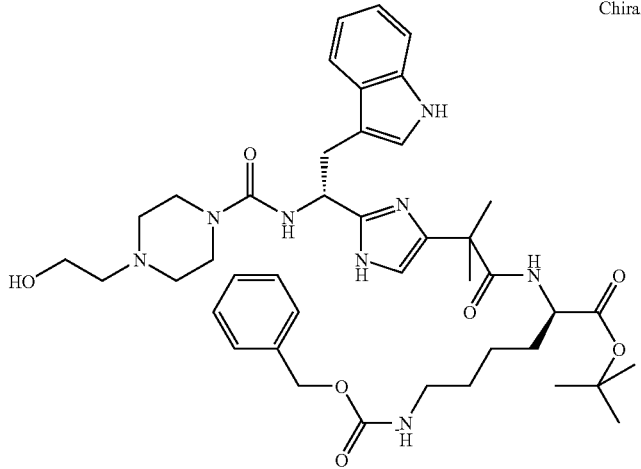 Chiral | 5.7 | 787.4 |
| 18 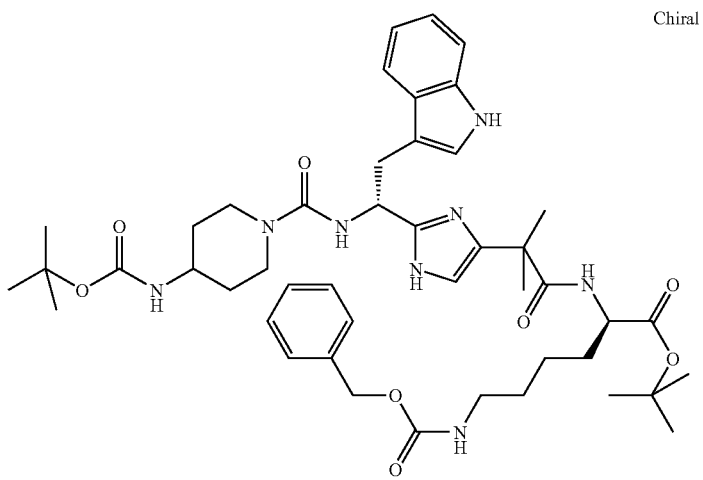 Chiral | 8.5 | 843.5 |

-continued
FORMULA 3
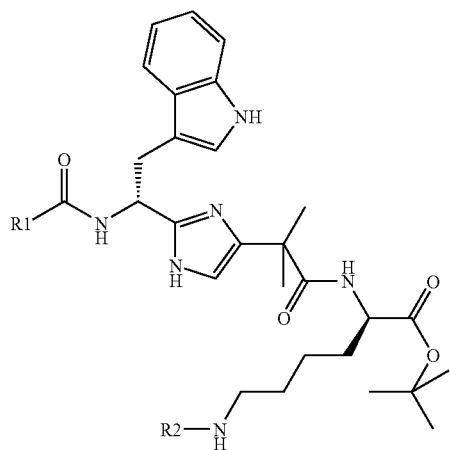
| Structure | | Analysis | |
|---|---|---|---|
| | | Rt (min) | [M + H]+ |
| 19 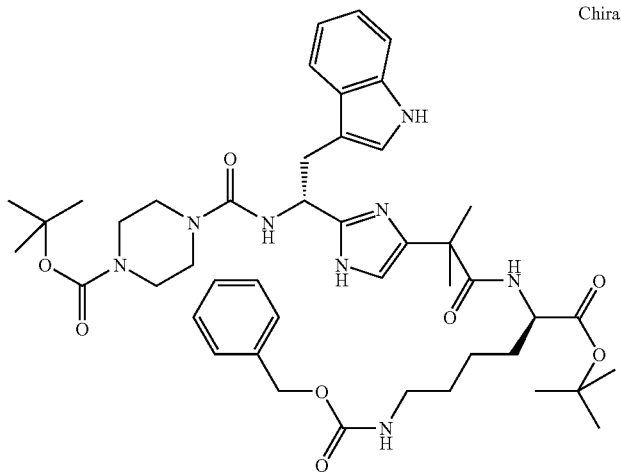 | Chiral | 8.5 | 857.5 |
| 20 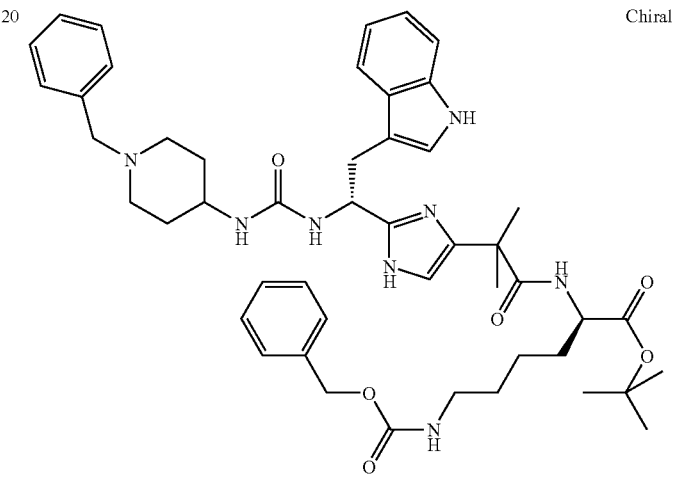 | Chiral | 7.1 | 847.5 |

-continued
FORMULA 3
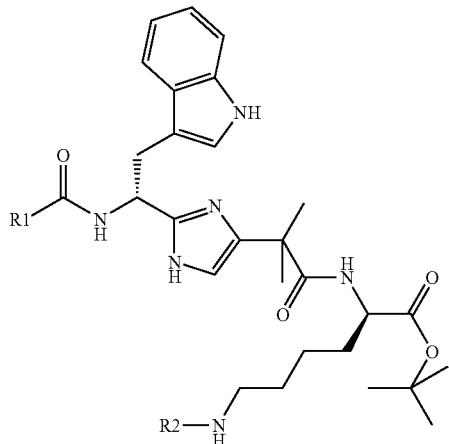
| Structure | | Analysis | |
|---|---|---|---|
| | | Rt (min) | [M + H]+ |
| 21 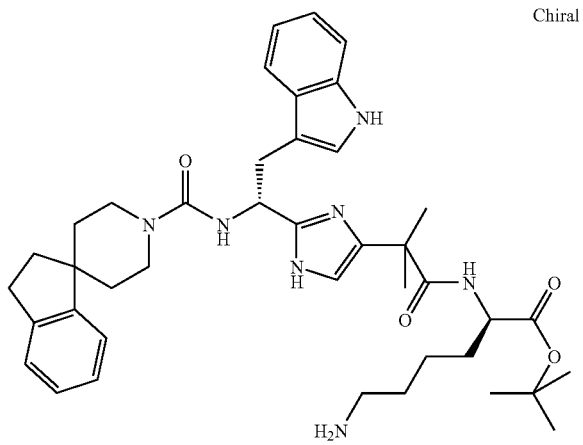 | Chiral | 4.5 | 710.5 |
| 22 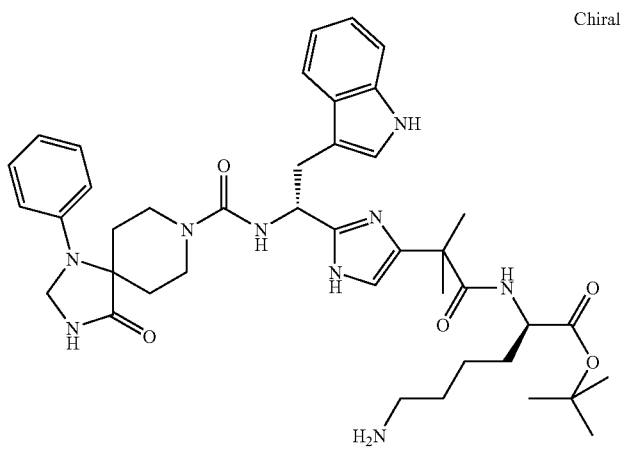 | Chiral | 4.1 | 754.5 |

-continued
FORMULA 3
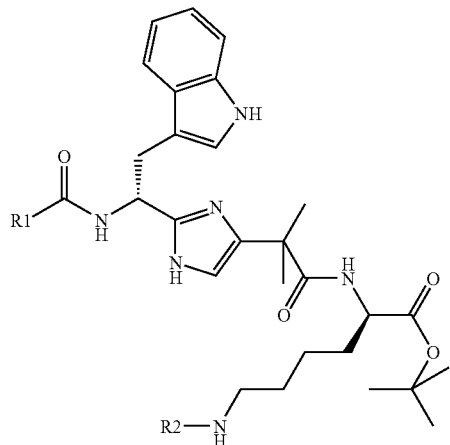
| Structure | | Analysis | |
|---|---|---|---|
| | | Rt (min) | [M + H]+ |
| 23 | Chiral | 4 | 740.5 |
| 24 | Chiral | 3.1 | 591.5 |

FORMULA 3
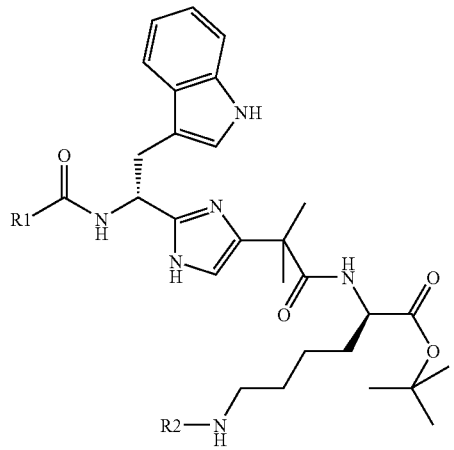
| Structure | | Analysis | |
|---|---|---|---|
| | | Rt (min) | [M + H]+ |
| 25 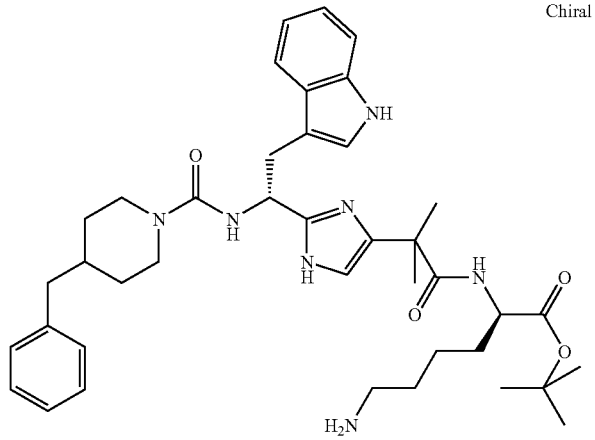 | Chiral | 4.5 | 698.5 |
| 26 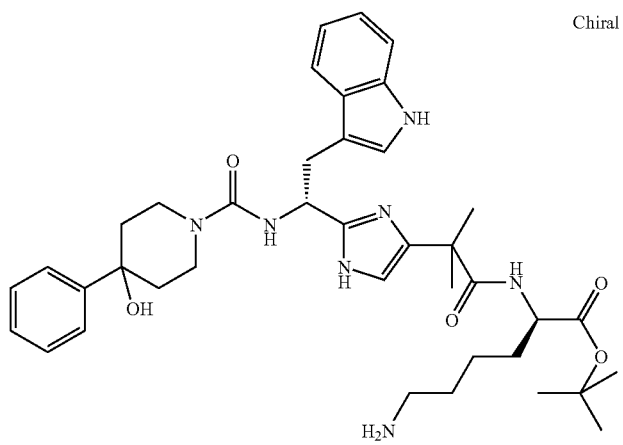 | Chiral | 3.9 | 700.5 |

-continued
FORMULA 3
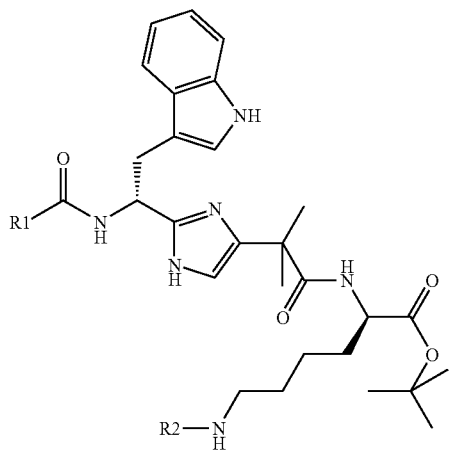
| Structure | Analysis | |
|---|---|---|
| | Rt (min) | [M + H]+ |
| 27 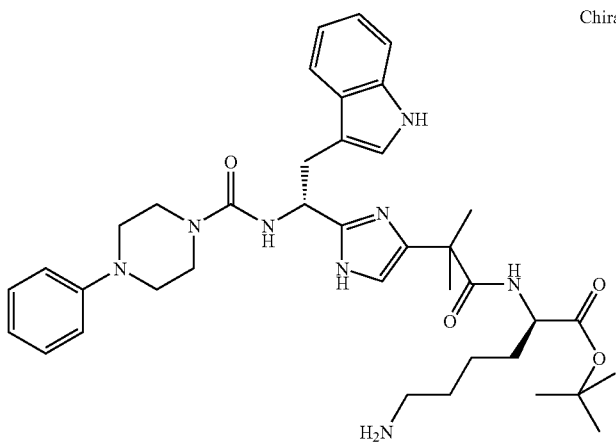 Chiral | 4.1 | 585.5 |
| 28 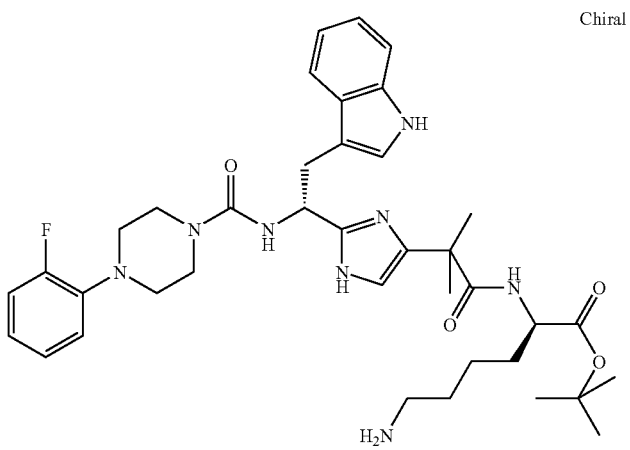 Chiral | 4.2 | 703.5 |

-continued
FORMULA 3
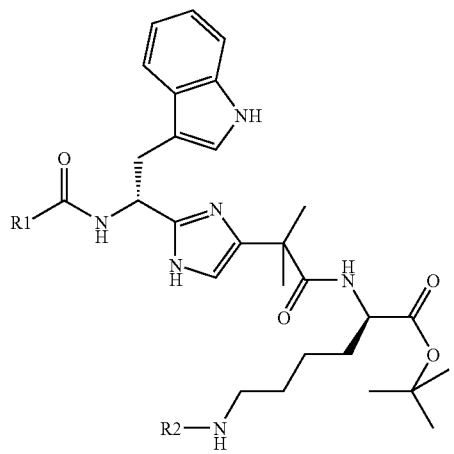
| Structure | Analysis | |
|---|---|---|
| | Rt (min) | [M + H]+ |
| 29 Chiral 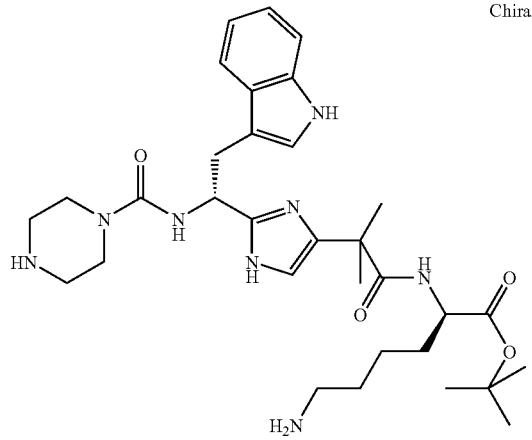 | 3.1 | 721.4 |
| 30 Chiral 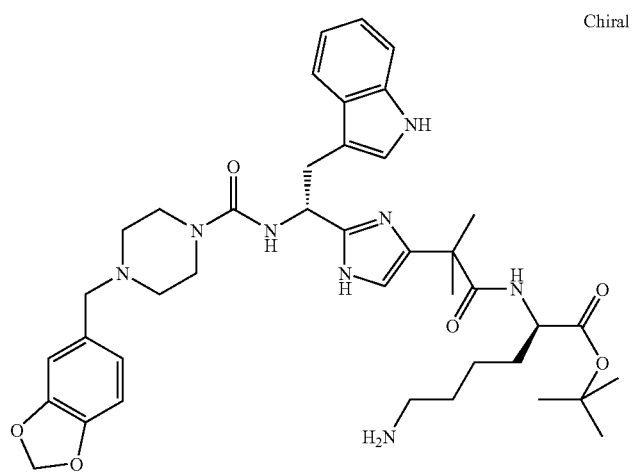 | 3.3 | 743.5 |

-continued
FORMULA 3
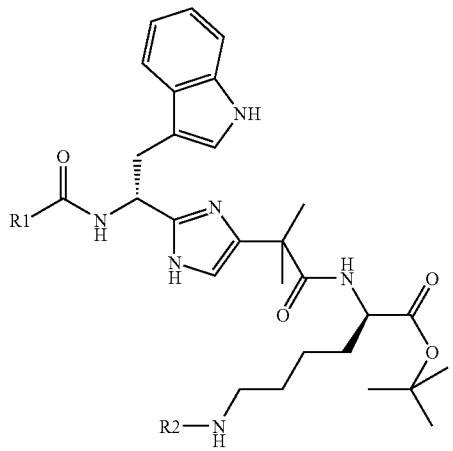
| Structure | Analysis | |
|---|---|---|
| | Rt (min) | [M + H]+ |
| 31 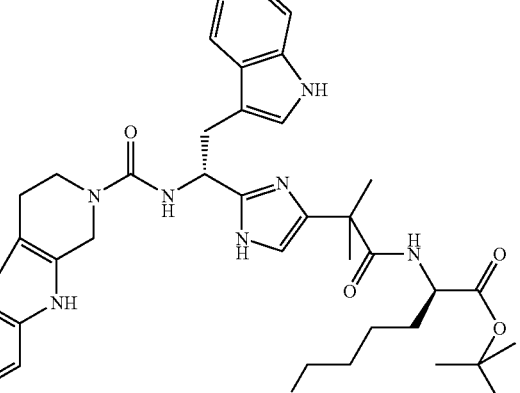 Chiral | 4.2 | 695.5 |
| 32 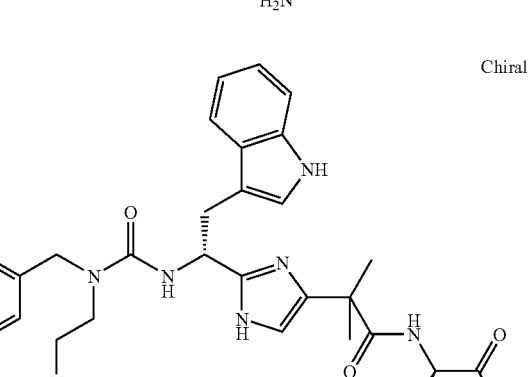 Chiral | 3.4 | 701.5 |

-continued
FORMULA 3
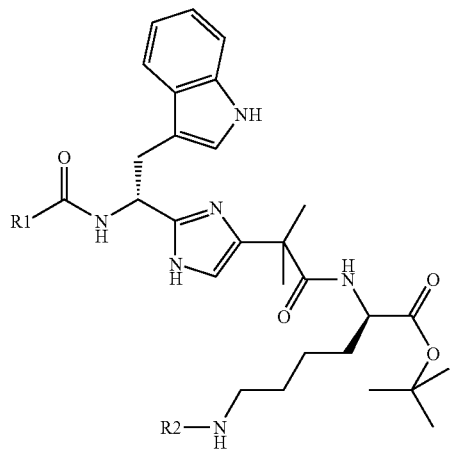
| Structure | Analysis | | |
|---|---|---|---|
| | | Rt (min) | [M + H]+ |
| 33 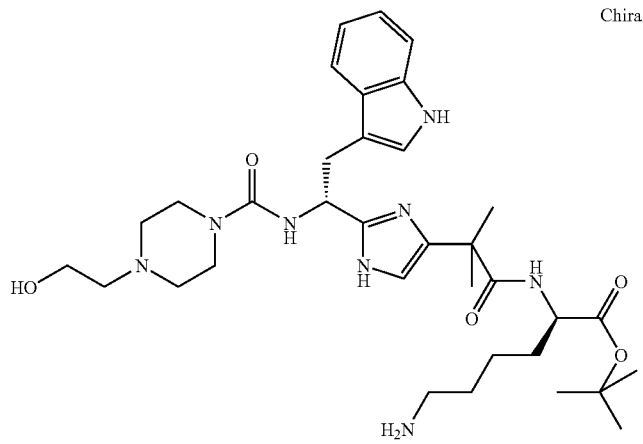 | Chiral | 3 | 653.4 |
| 34 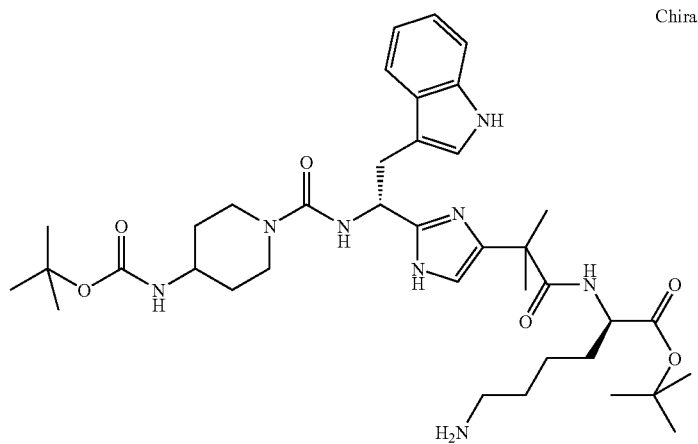 | Chiral | 4.1 | 709.5 |

-continued
FORMULA 3
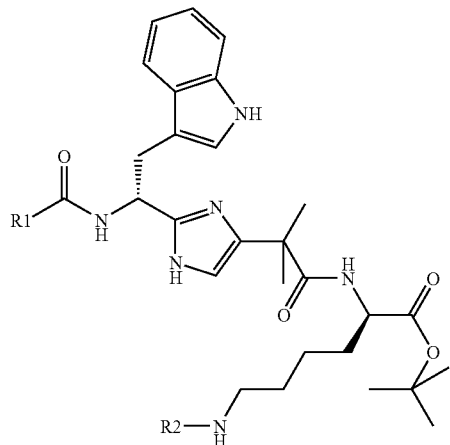
| Structure | Analysis | |
|---|---|---|
| | Rt (min) | [M + H]+ |
| 35 Chiral | 4 | 723.5 |
| 36 Chiral | 3.2 | 623.4 |

FORMULA 4
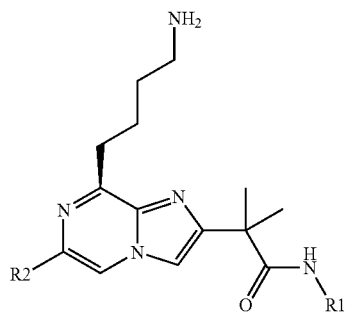
| | R1 | R2 | Tr (min) | (M + H)+ |
|---|---|---|---|---|
| 1 | *∽N∼∼∼N | 3-nitrophenyl | 4.53 | 454.24 |
| 2 | *∽N∼∼∼N | 4-chloro-3-nitrophenyl | 4.87 | 488.21 |
| 3 | *∽N∼∼∼N | benzo[b]thiophen-3-yl | 4.79 | 465.24 |
| 4 | *∽N∼∼∼N | 4-nitrophenyl | 4.53 | 454.25 |
FORMULA 5
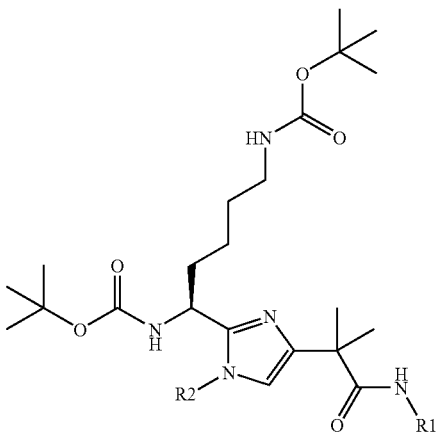
| | R1 | R2 | Tr (min) | [M + H]+ |
|---|---|---|---|---|
| 1 | N-cyclohexyl | 4-bromophenyl | 8.0 | 732.2 |

-continued

FORMULA 5

| | R1 | R2 | Tr (min) | [M + H]+ |
|---|---|---|---|---|
| 2 | *–N–butyl | 4-Br-phenyl–* | 7.7 | 706.2 |
| 3 | *–N–CH2CH2-(2-pyridyl) | 4-Br-phenyl–* | 6.4 | 755.2 |
| 4 | furan-2-yl-CH2–N–* | *–3-NO2-phenyl | 7.3 | 697.2 |
| 5 | furan-2-yl-CH2–N–* | *–4-Cl-3-NO2-phenyl | 7.6 | 731.2 |
| 6 | indol-3-yl-CH2CH2–N–* | *–3-NO2-phenyl | 7.6 | 760.3 |
| 7 | indol-3-yl-CH2CH2–N–* | *–4-Cl-3-NO2-phenyl | 7.9 | 794.3 |
| 8 | indol-3-yl-CH2CH2–N–* | *–CH2CH2-phenyl | 7.8 | 743.4 |

-continued
FORMULA 5
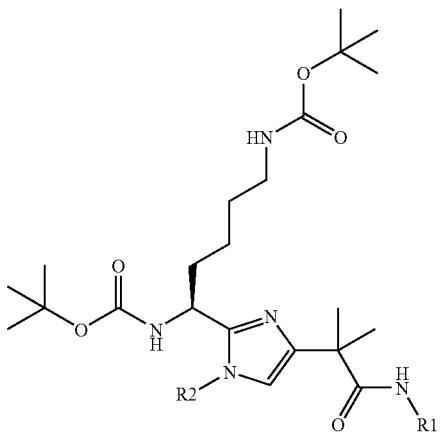
| | R1 | R2 | Tr (min) | [M + H]+ |
|---|---|---|---|---|
| 9 | *–N–(CH2)3–N(H)–C(O)–O–tBu | 3-nitrophenyl | 7.5 | 774.4 |
| 10 | *–N–(CH2)3–N(H)–C(O)–O–tBu | 4-chloro-3-nitrophenyl | 7.5 | 808.3 |
| 11 | *–N–(CH2)3–N(H)–C(O)–O–tBu | phenethyl | 7.8 | 757.4 |
| 12 | *–N–(CH2)3–N(H)–C(O)–O–tBu | benzyl | 7.6 | 743.4 |
| 13 | *–N–(CH2)3–N(H)–C(O)–O–tBu | benzothiophen-3-yl | 7.8 | 785.4 |
| 14 | *–N–(CH2)3–N(H)–C(O)–O–tBu | 4-nitrophenyl | 7.6 | 774.4 |
| 15 | *–N–(CH2)3–N(H)–C(O)–O–tBu | 4-chlorophenyl | 7.8 | 763.4 |

-continued
FORMULA 5
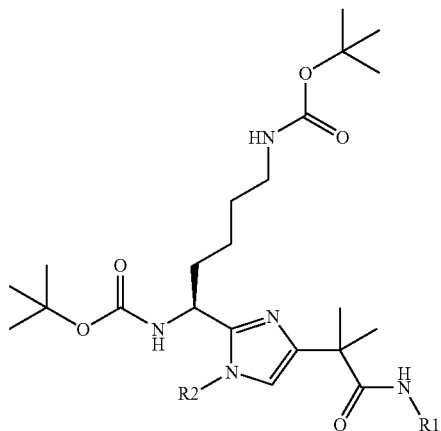
| R1 | R2 | Tr (min) | [M + H]+ |
|---|---|---|---|
| 16 ![diphenylmethyl-N] | ![3-nitrophenyl] | 8.5 | 783.3 |
| 17 ![diphenylmethyl-N] | ![4-chloro-3-nitrophenyl] | 8.9 | 817.3 |
FORMULA 6
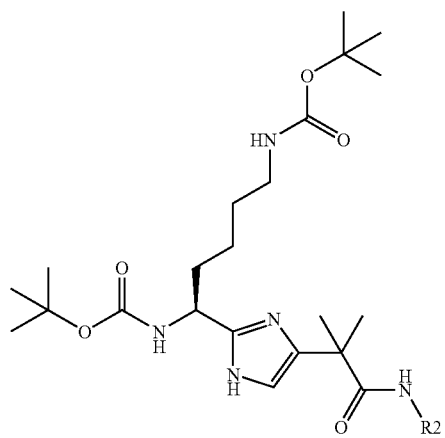
| R2 | Tr (min) | [M + H]+ |
|---|---|---|
| 1 ![dimethylaminoethylamine] | 4.7 | 525.3 |
-continued
FORMULA 6
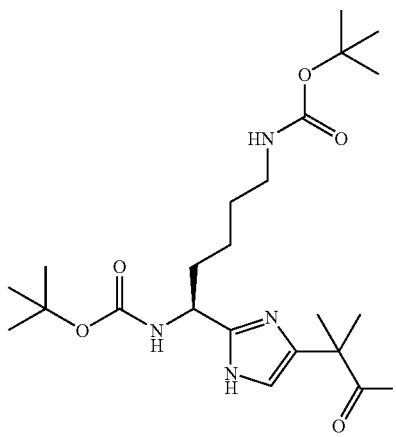
| R2 | Tr (min) | [M + H]+ |
|---|---|---|
| 2 ![furfurylamine] | 6.0 | 534.3 |

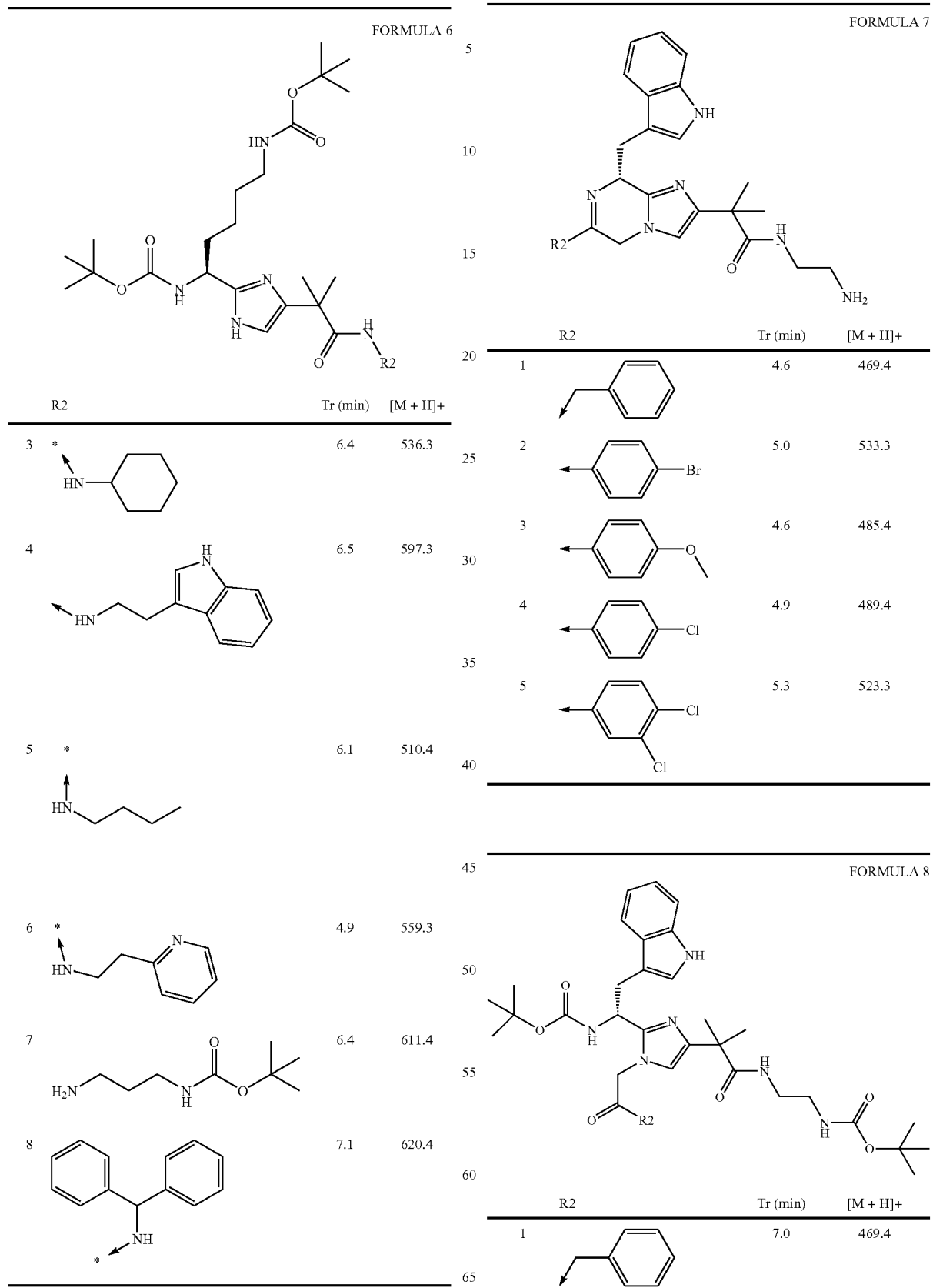

-continued
FORMULA 8
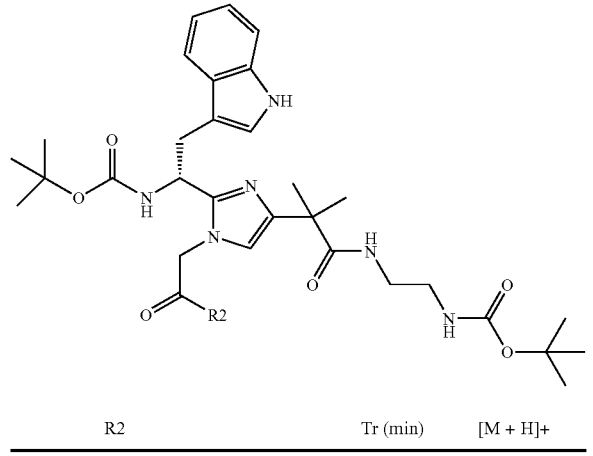
| | R2 | Tr (min) | [M + H]+ |
|---|---|---|---|
| 2 | 4-Br-phenyl | 7.3 | 657.5 |
| 3 | 4-OMe-phenyl | 6.9 | 751.3 |
| 4 | 4-Cl-phenyl | 7.2 | 707.4 |
| 5 | 3,4-diCl-phenyl | 7.5 | 741.3 |
FORMULA 9
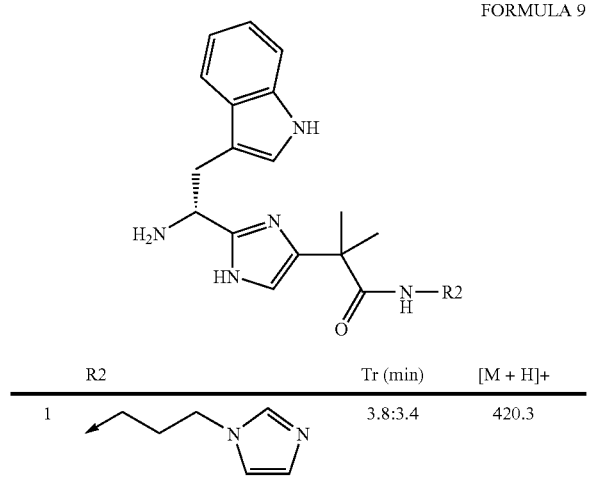
| | R2 | Tr (min) | [M + H]+ |
|---|---|---|---|
| 1 | propyl-imidazole | 3.8:3.4 | 420.3 |
| 2 | ethyl-2-pyridyl | 3.8:3.6 | 417.3 |
-continued
FORMULA 9
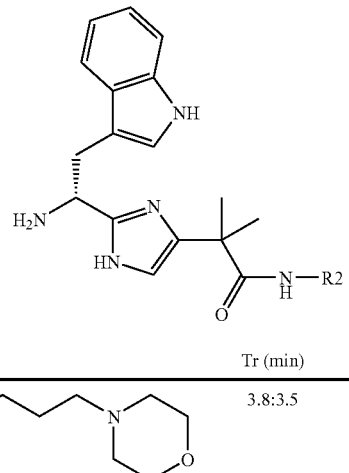
| | R2 | Tr (min) | [M + H]+ |
|---|---|---|---|
| 3 | propyl-morpholine | 3.8:3.5 | 439.3 |
| 4 | methyl-4-pyridyl | 3.7:3.4 | 403.3 |
| 5 | ethyl-NEt2 | 3.9:3.6 | 411.4 |
FORMULA 10
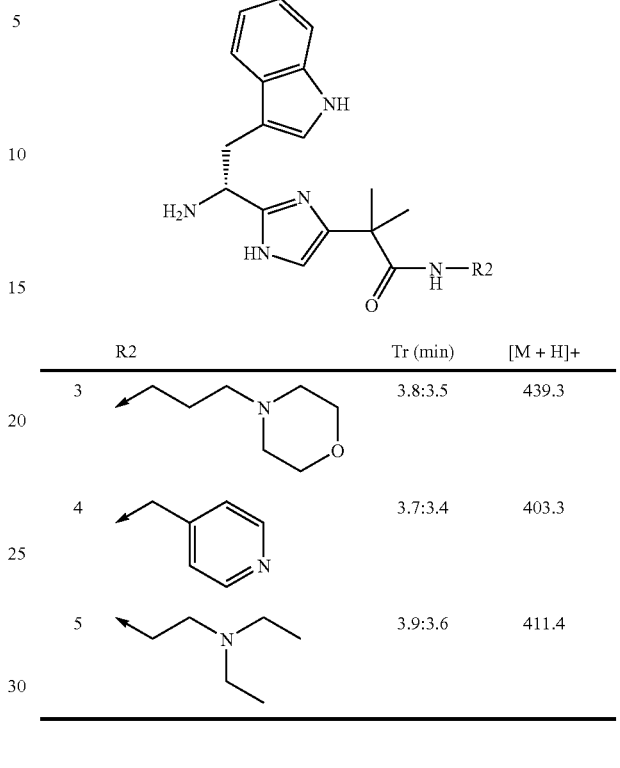
| | R2 | Tr (min) | [M + H]+ |
|---|---|---|---|
| 1 | propyl-imidazole | 4.4 | 520.2 |
| 2 | propyl-2-pyridyl | 4.5 | 517.2 |
| 3 | propyl-morpholine | 4.4 | 539.3 |
| 4 | methyl-4-pyridyl | 4.4 | 503.2 |

-continued
FORMULA 10
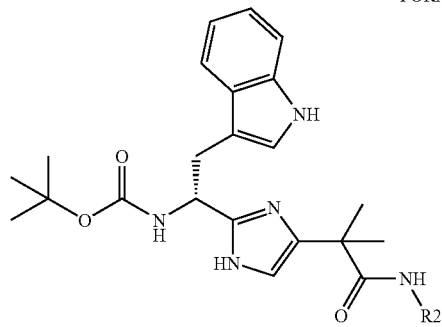
| R2 | | Tr (min) | [M + H]+ |
|---|---|---|---|
| 5 | (diethylaminoethyl) | 4.5 | 511.3 |
| 6 | (4-carbamoylcyclohexyl) | 5.1 | 523.3 |
| 7 | (1-(pyrimidin-2-yl)piperidin-4-yl) | 5.5 | 559.2 |
FORMULA 11
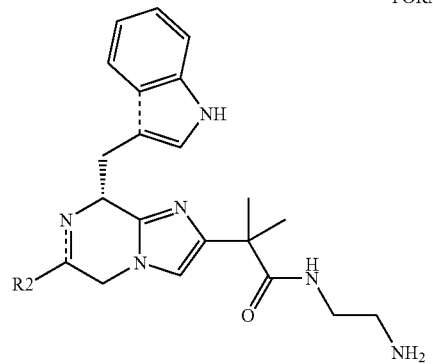
Analyses
* = (M + TFA − H)+
| R2 | | Tr (min) | [M + H]+ |
|---|---|---|---|
| 1 | phenyl | 4.6 | 455.2 |
| 2 | 2,5-dimethoxyphenyl | 4.9 | 515.2 |
-continued
FORMULA 11
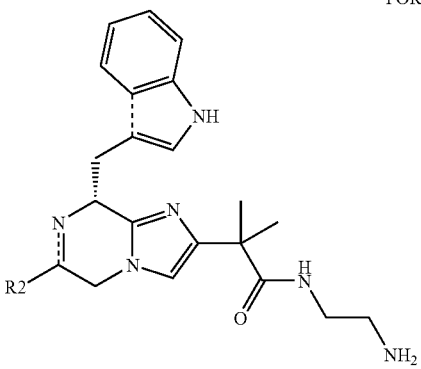
Analyses
* = (M + TFA − H)+
| R2 | | Tr (min) | [M + H]+ |
|---|---|---|---|
| 3 | 4-F-phenyl | 4.8 | 473.2 |
| 4 | 4-NO2-phenyl | 4.9 | 612.2* |
| 5 | 3-NO2-phenyl | 4.8 | 500.2 |
| 6 | 4-(diethylamino)phenyl | 4.2 | 526.3 |
| 7 | 4-OCF3-phenyl | 5.4 | 539.2 |
| 8 | 5-bromothiophen-2-yl | 5.1 | 539.1 |
| 9 | phenethyl | 5.1 | 583.3 |
| 10 | furo[3,2-b]pyridin-2-yl | 5.0 | 495.2 |
| 11 | (alkyl) | 4.1 | 519.2* |
| 12 | 2-oxo-1,2,3,4-tetrahydroquinolin-7-yl | 4.4 | 524.3 |

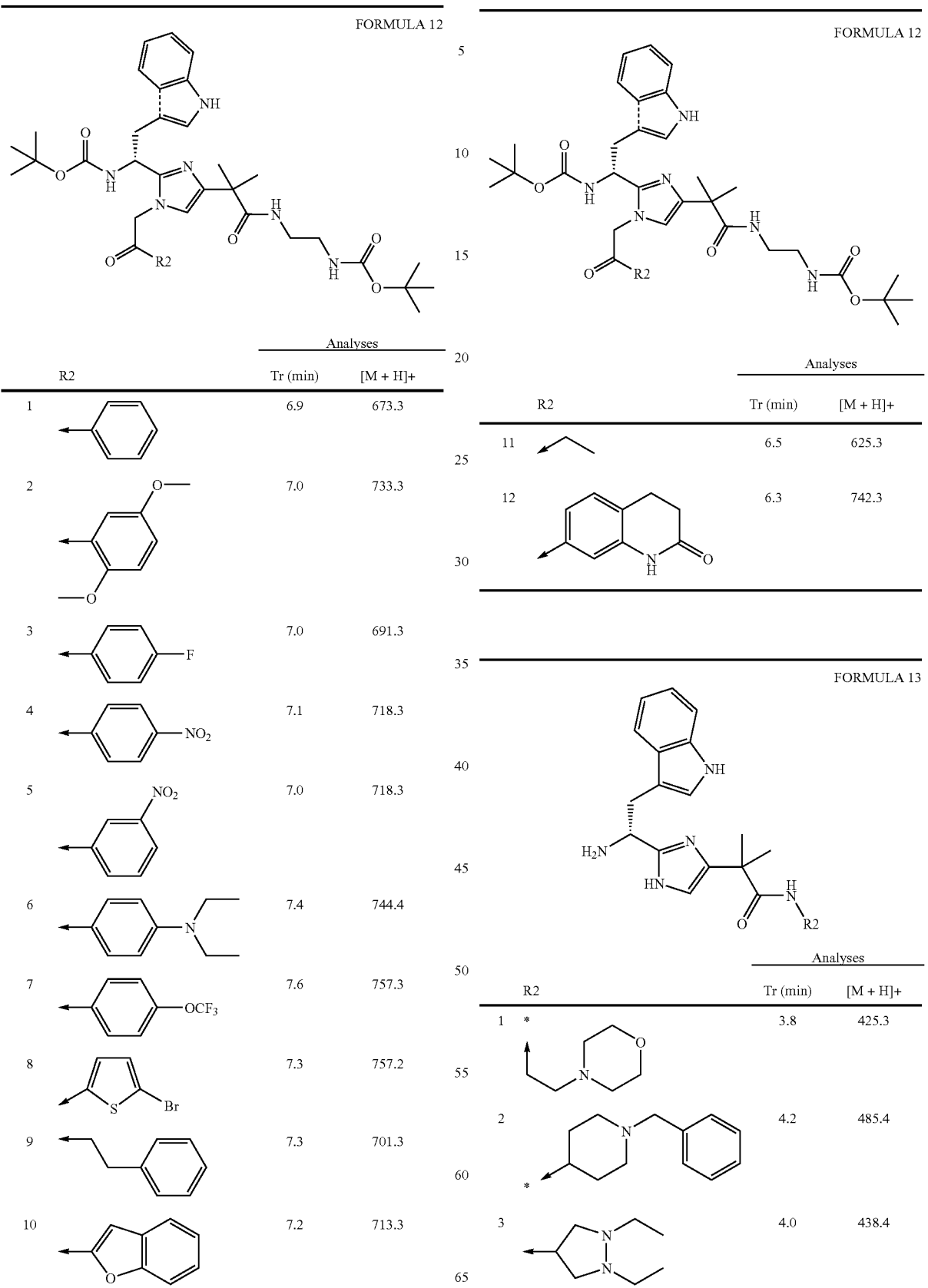

171
-continued
FORMULA 13
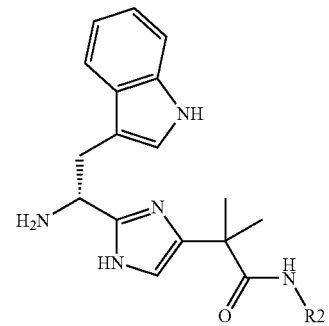
| R2 | Analyses Tr (min) | [M + H]+ |
|---|---|---|
| 4 (2-pyridylmethyl) | 4.0 | 403.3 |
| 5 (diethylaminobutyl) | 3.9 | 425.4 |
| 6 (4-methylpiperazinylbutyl) | 3.6 | 452.4 |
| 7 (3-pyridylmethyl) | 3.8 | 403.3 |
| 8 (2,6-difluorobenzyl) | 5.1 | 438.3 |
| 9 (4-hydroxyphenethyl) | 4.6 | 432.3 |
| 10 (3,3-diphenylpropyl) | 6.2 | 506.4 |
172
-continued
FORMULA 13
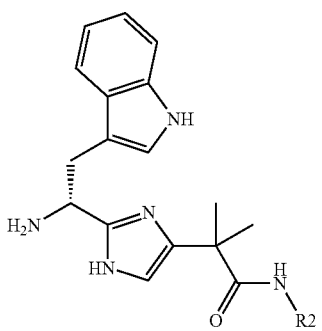
| R2 | Analyses Tr (min) | [M + H]+ |
|---|---|---|
| 11 (pyrrolidinylethyl) | 3.8 | 409.3 |
FORMULA 14
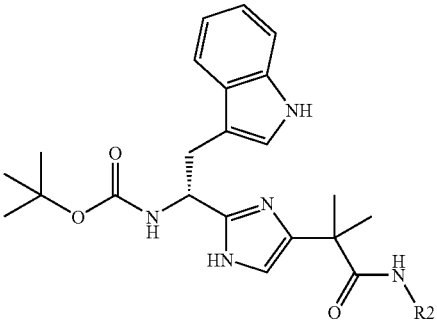
| R2 | Analyses Tr (min) | [M + H]+ |
|---|---|---|
| 1 (morpholinoethyl) | 4.5 | 525.3 |
| 2 (1-benzylpiperidin-4-yl) | 5.0 | 585.3 |
| 3 (1,2-diethylpyrazolidin-4-yl) | 4.8 | 538.4 |

-continued
FORMULA 14
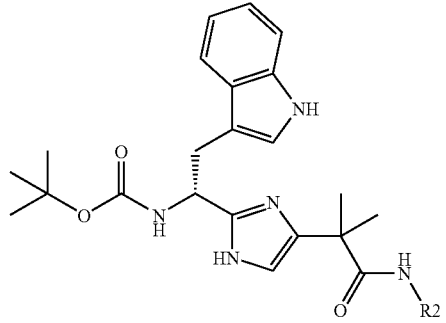
| R2 | Analyses Tr (min) | [M + H]+ |
|---|---|---|
| 4 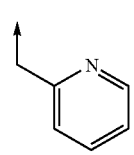 | 4.9 | 503.3 |
| 5 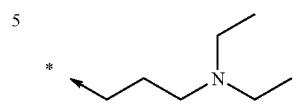 | 4.5 | 525.4 |
-continued
FORMULA 14
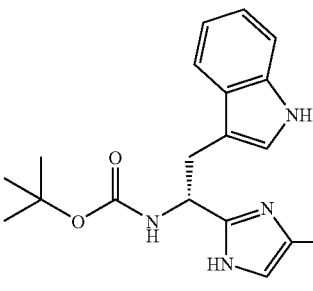
| R2 | Analyses Tr (min) | [M + H]+ |
|---|---|---|
| 6 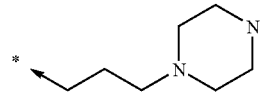 | 4.3 | 552.4 |
| 7 * | 4.5 | 503.3 |
FORMULA 15
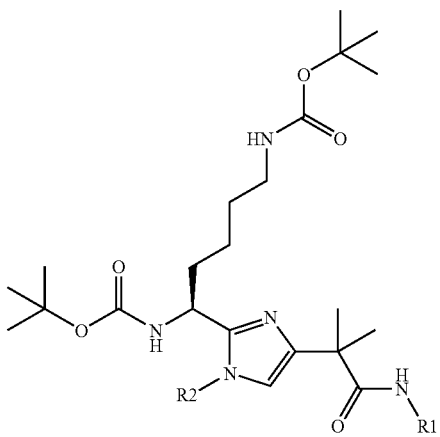
| R1 | R2 | Analyses Tr (min) | [M + H]+ |
|---|---|---|---|
| 1 | 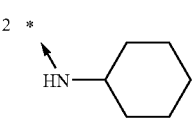 | 5.9 | 623.4 |
| 2 | 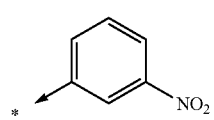 | 7.6 | 699.4 |

-continued
FORMULA 15
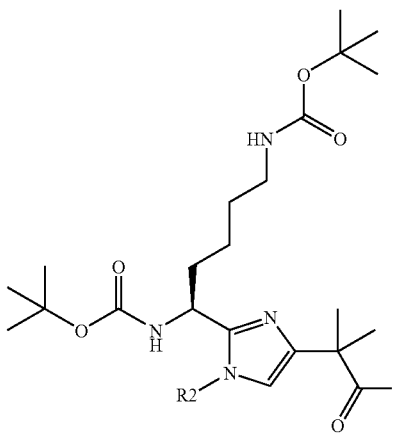
| | R1 | R2 | Tr (min) | [M + H]+ |
|---|---|---|---|---|
| 3 | *-HN-cyclohexyl | 4-Cl-3-NO2-phenyl | 7.9 | 582.4 |
| 4 | *-HN-cyclohexyl | *-CH2CH2-phenyl | 7.9 | 582.4 |
| 5 | *-HN-cyclohexyl | *-CH2-phenyl | 7.7 | 668.4 |
| 6 | *-HN-cyclohexyl | benzothiophen-3-yl | 7.9 | 710.3 |
| 7 | *-HN-cyclohexyl | 4-NO2-phenyl | 7.7 | 699.4 |
| 8 | *-HN-cyclohexyl | 4-Cl-phenyl | 7.9 | 688.3 |
| 9 | *-HN-cyclohexyl | 3,4-diCl-phenyl | 8.2 | 722.3 |

-continued
FORMULA 15
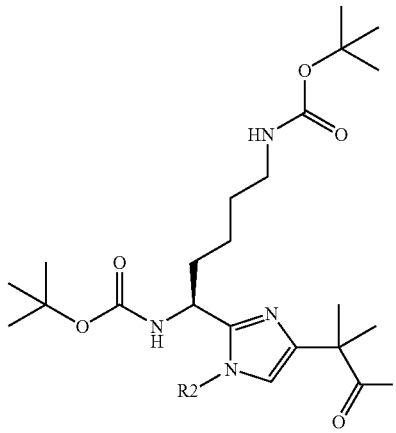
| | R1 | R2 | Analyses Tr (min) | [M + H]+ |
|---|---|---|---|---|
| 10 | HN-cyclohexyl | 2,3-dihydrobenzo[1,4]dioxine | 7.5 | 712.4 |
| 11 | HN-cyclohexyl | tert-butyl | 7.5 | 634.4 |
| 12 | HN-butyl | 3-nitrophenyl | 7.3 | 673.3 |
| 13 | HN-butyl | 4-chloro-3-nitrophenyl | 7.6 | 707.3 |
| 14 | HN-butyl | phenethyl | 7.6 | 556.4 |
| 15 | HN-butyl | benzyl | 7.4 | 642.4 |
| 16 | HN-butyl | benzo[b]thiophen-3-yl | 7.6 | 684.3 |

-continued
FORMULA 15
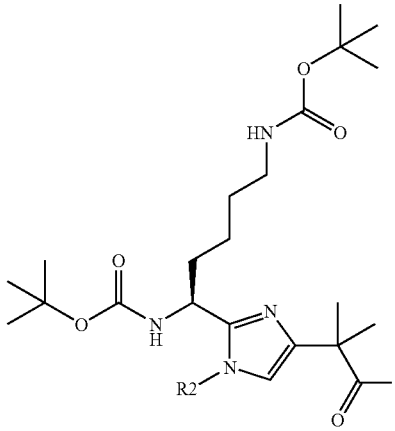
| | R1 | R2 | Tr (min) | [M + H]+ |
|---|---|---|---|---|
| 17 | *HN-butyl | 4-NO2-phenyl | 7.4 | 673.3 |
| 18 | *HN-butyl | 4-Cl-phenyl | 7.6 | 662.3 |
| 19 | *HN-butyl | 3,4-diCl-phenyl | 7.9 | 696.3 |
| 20 | *HN-butyl | 3,4-dimethoxy-phenyl | 7.2 | 686.4 |
| 21 | *HN-butyl | isopropyl | 7.3 | 608.4 |
| 22 | *HN-CH2CH2-(2-pyridyl) | 3-NO2-phenyl | 6.0 | 722.3 |
| 23 | *HN-CH2CH2-(2-pyridyl) | 4-Cl-3-NO2-phenyl | 6.4 | 756.3 |
| 24 | *HN-CH2CH2-(2-pyridyl) | CH2CH2-phenyl | 6.3 | 705.4 |

-continued
FORMULA 15
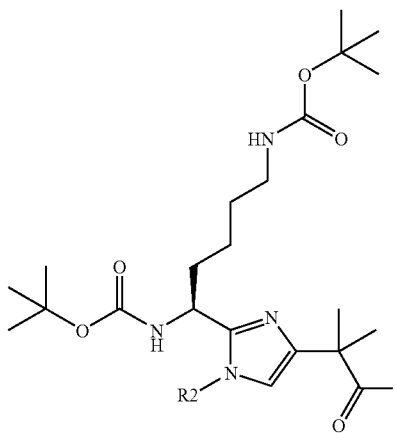
| | R1 | R2 | Tr (min) | [M + H]+ |
|---|---|---|---|---|
| | | | Analyses | |
| 25 | *HN-CH₂CH₂-(2-pyridyl) | *-CH₂-phenyl | 6.1 | 691.4 |
| 26 | *HN-CH₂CH₂-(2-pyridyl) | benzothiophen-3-yl* | 6.4 | 733.3 |
| 27 | *HN-CH₂CH₂-(2-pyridyl) | 4-NO₂-phenyl* | 6.1 | 722.3 |
| 28 | *HN-CH₂CH₂-(2-pyridyl) | 4-Cl-phenyl-* | 6.3 | 711.3 |
| 29 | *HN-CH₂CH₂-(2-pyridyl) | 3,4-diCl-phenyl-* | 6.7 | 745.2 |
| 30 | *HN-CH₂CH₂-(2-pyridyl) | 2,3-dihydrobenzo[1,4]dioxin-6-yl* | 5.9 | 735.3 |
| 31 | *HN-CH₂CH₂-(2-pyridyl) | *-C(CH₃)₃ | 6.0 | 657.4 |

FORMULA 16
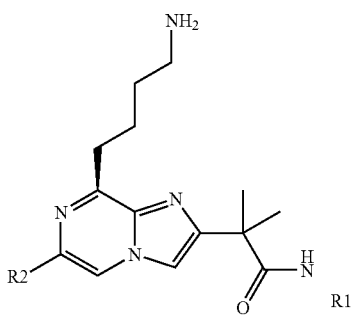
| | R1 | R2 | Tr (min) | [M + H]+ |
|---|---|---|---|---|
| 1 | cyclopentadienyl-CH2-NH-* | *-C6H4-3-NO2 | 5.7 | 477.2 |
| 2 | cyclopentadienyl-CH2-NH-* | *-C6H3-4-Cl-3-NO2 | 6.0 | 511.1 |
| 3 | indol-3-yl-CH2CH2-NH-* | *-C6H4-3-NO2 | 6.1 | 540.2 |
| 4 | indol-3-yl-CH2CH2-NH-* | *-C6H3-4-Cl-3-NO2 | 6.3 | 574.1 |
| 5 | indol-3-yl-CH2CH2-NH-* | *-CH2CH2-C6H5 | 6.0 | 523.3 |
| 6 | *-HN-(CH2)4-NH2 | *-CH2CH2-C6H5 | 4.4 | 437.3 |
| 7 | *-HN-(CH2)4-NH2 | *-CH2-C6H5 | 4.2 | 423.3 |

-continued
FORMULA 16
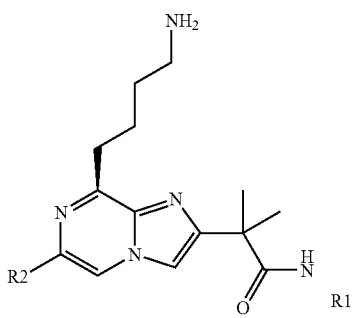
| R1 | R2 | Tr (min) | [M + H]+ |
|---|---|---|---|
| 8 * HN-(CH2)4-NH2 | 4-Cl-C6H4-* | 4.8 | 443.3 |
| 9 *NH-CH(C6H5)2 | 3-NO2-C6H4-* | 6.8 | 563.2 |
| 10 *NH-CH(C6H5)2 | 4-Cl-3-NO2-C6H3-* | 7.0 | 597.2 |
| 11 * HN-cyclohexyl | 3-NO2-C6H4-* | 6.1 | 479.3 |
| 12 * HN-cyclohexyl | 4-Cl-3-NO2-C6H3-* | 6.5 | 513.2 |
| 13 * HN-cyclohexyl | *-CH2CH2-C6H5 | 6.0 | 462.3 |
| 14 * HN-cyclohexyl | *-CH2-C6H5 | 5.8/5.9 | 448.3 |
| 15 * HN-cyclohexyl | benzo[b]thiophen-3-yl-* | 6.4 | 490.2 |

-continued
FORMULA 16
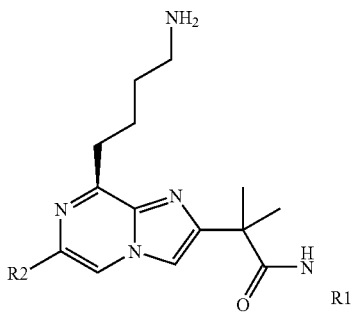
| | R1 | R2 | Tr (min) | [M + H]+ |
|---|---|---|---|---|
| 16 | *-NH-cyclohexyl | 4-NO$_2$-phenyl-* | 6.1 | 479.3 |
| 17 | *-NH-cyclohexyl | 4-Cl-phenyl-* | 6.4 | 468.2 |
| 18 | *-NH-cyclohexyl | 3,4-diCl-phenyl-* | 6.8 | 502.2 |
| 19 | *-NH-cyclohexyl | 2,3-dihydro-1,4-benzodioxin-6-yl-* | 6.0 | 492.3 |
| 20 | *-NH-cyclohexyl | 4-Br-phenyl-* | 6.5 | 512.2 |
| 21 | *-NH-butyl | 3-NO$_2$-phenyl-* | 5.9 | 453.3 |
| 22 | *-NH-butyl | 4-Cl-3-NO$_2$-phenyl-* | 6.2 | 487.2 |
| 23 | *-NH-butyl | phenethyl-* | 5.7 | 436.3 |

-continued
FORMULA 16
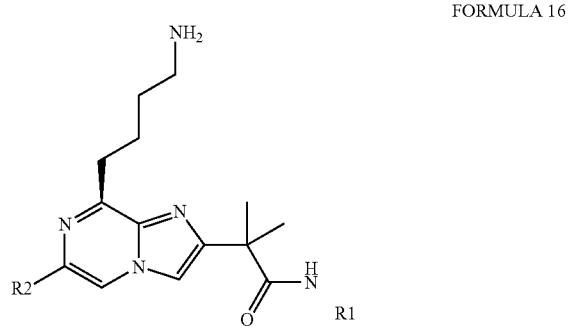
| | R1 | R2 | Tr (min) | [M + H]+ |
|---|---|---|---|---|
| 24 | *–NH–butyl | *–CH2–phenyl | 5.5/5.6 | 422.3 |
| 25 | *–NH–butyl | benzothiophen-3-yl–* | 6.2 | 464.2 |
| 26 | *–NH–butyl | 4-NO2–phenyl–* | 5.9/6.0 | 453.3 |
| 27 | *–NH–butyl | 4-Cl–phenyl–* | 6.1 | 442.2 |
| 28 | *–NH–butyl | 3,4-diCl–phenyl–* | 6.5 | 476.2 |
| 29 | *–NH–butyl | 2,3-dihydro-1,4-benzodioxin-6-yl–* | 5.7 | 466.3 |
| 30 | *–NH–butyl | 4-Br–phenyl–* | 6.2 | 486.2 |
| 31 | *–NH–CH2CH2–(pyridin-2-yl) | 3-NO2–phenyl–* | 4.7 | 502.2 |

-continued
FORMULA 16
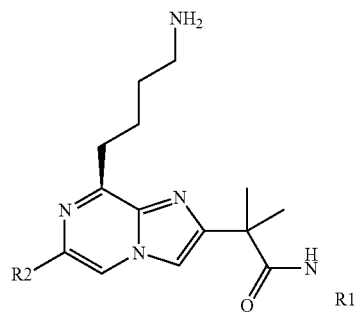
| | R1 | R2 | Tr (min) | [M + H]+ |
|---|---|---|---|---|
| 32 | *HN-CH2CH2-(2-pyridyl) | *-CH=C(-CH=CH-Cl)(-CH=CH-NO2) | 5.0 | 536.2 |
| 33 | *HN-CH2CH2-(2-pyridyl) | *-CH2CH2-phenyl | 4.6 | 485.3 |
| 34 | *HN-CH2CH2-(2-pyridyl) | *-CH2-phenyl | 4.5 | 471.3 |
| 35 | *HN-CH2CH2-(2-pyridyl) | benzothiophen-3-yl* | 5.0 | 513.2 |
| 36 | *HN-CH2CH2-(2-pyridyl) | O2N-C6H4-* | 4.7 | 502.2 |
| 37 | *HN-CH2CH2-(2-pyridyl) | Cl-C6H4-* | 4.9 | 491.2 |
| 38 | *HN-CH2CH2-(2-pyridyl) | 3,4-di-Cl-C6H3-* | 5.3 | 525.2 |
| 39 | *HN-CH2CH2-(2-pyridyl) | 2,3-dihydro-1,4-benzodioxin-6-yl* | 4.6 | 515.2 |

-continued
FORMULA 16
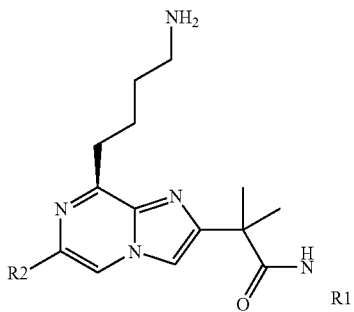
| | | Analyses | |
|---|---|---|---|
| R1 | R2 | Tr (min) | [M + H]+ |
| 40 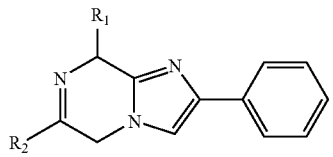 | Br— ⌬ —* | 5.0 | 535.1 |
FORMULA 17
[Structure of imidazopyrazine with R1, R2, and 2-phenyl substituents]
| | | Analyses | |
|---|---|---|---|
| R1 | R2 | Tr (min) | [M + H]+ |
| 1 (S) [indol-3-ylmethyl] | [phenyl] | 14.3 | 403.2 |
| 2 (S) [indol-3-ylmethyl] | [biphenyl] | 15.0 | 479.2 |
| 3 (S) [indol-3-ylmethyl] | [naphthyl] | 14.8 | 453.2 |
| 4 (S) [indol-3-ylmethyl] | [2,5-dimethoxyphenyl] | 14.4 | 463.2 |

-continued
FORMULA 17
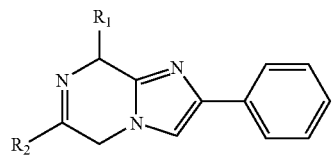
| | R1 | R2 | Analyses | |
|---|---|---|---|---|
| | | | Tr (min) | [M + H]+ |
| 5 (S) | 1H-indol-3-ylmethyl | 4-Cl-phenyl | 14.5 | 437.1 |
| 6 (S) | 1H-indol-3-ylmethyl | 3,4-diCl-phenyl | 15.0 | 471.1 |
| 7 (S) | 1H-indol-3-ylmethyl | 3-Me-4-Cl-phenyl | 14.8 | 451.1 |
| 8 (S) | 1H-indol-3-ylmethyl | 4-Br-phenyl | 14.8 | 481.0 |
| 9 (S) | 1H-indol-3-ylmethyl | 4-F-phenyl | 14.5 | 421.2 |
| 10 (S) | 1H-indol-3-ylmethyl | 4-CN-phenyl | 15.0 | 479.2 |
| 11 (S) | 1H-indol-3-ylmethyl | 4-N$_3$-phenyl | 14.5 | 444.2 |
| 12 (S) | 1H-indol-3-ylmethyl | 4-NO$_2$-phenyl | 14.5 | 448.1 |

-continued
FORMULA 17
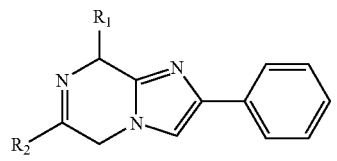
| | R1 | R2 | Analyses Tr (min) | [M + H]+ |
|---|---|---|---|---|
| 13 (S) | 1H-indol-3-ylmethyl | 3-nitrophenyl | 14.5 | 448.1 |
| 14 (S) | 1H-indol-3-ylmethyl | propyl | 14.0 | 355.2 |
| 15 (R) | 1H-indol-3-ylmethyl | phenyl | 14.3 | 403.2 |
| 16 (R) | 1H-indol-3-ylmethyl | 4-biphenyl | 15.2 | 479.2 |
| 17 (R) | 1H-indol-3-ylmethyl | 2-naphthyl | 14.9 | 453.2 |
| 18 (R) | 1H-indol-3-ylmethyl | 4-methoxyphenyl | 14.4 | 433.2 |
| 19 (R) | 1H-indol-3-ylmethyl | 2,5-dimethoxyphenyl | 14.5 | 483.2 |
| 20 (R) | 1H-indol-3-ylmethyl | 4-chlorophenyl | 14.8 | 437.1 |

-continued
FORMULA 17
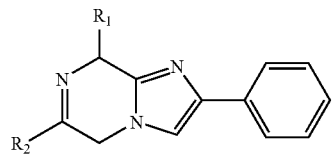
| R1 | R2 | Analyses | |
|---|---|---|---|
| | | Tr (min) | [M + H]+ |
| 21 (R) indol-3-yl-methyl | 3,4-dichlorophenyl | 15.1 | 474.1 |
| 22 (R) indol-3-yl-methyl | 3-methyl-4-chlorophenyl | 15.0 | 451.1 |
| 23 (R) indol-3-yl-methyl | 4-bromophenyl | 14.8 | 481.0 |
| 24 (R) indol-3-yl-methyl | 4-fluorophenyl | 14.5 | 421.2 |
| 25 (R) indol-3-yl-methyl | 4-cyanophenyl | 14.4 | 428.1 |
| 26 (R) indol-3-yl-methyl | 4-azidophenyl | 14.7 | 444.1 |
| 27 (R) indol-3-yl-methyl | 4-nitrophenyl | 14.6 | 448.1 |

-continued
FORMULA 17
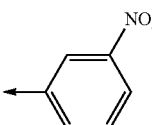
| | R1 | R2 | Tr (min) | [M + H]+ |
|---|---|---|---|---|
| 28 | indol-3-ylmethyl (R) | 3-nitrophenyl | 14.5 | 448.1 |
| 29 | indol-3-ylmethyl (R) | propyl | 13.9 | 355.2 |
| 30 | benzyl | phenyl | 15.2 | 364.2 |
| 31 | benzyl | 4-biphenyl | 15.2 | 479.2 |
| 32 | benzyl | 2-naphthyl | 15.9 | 414.2 |
| 33 | benzyl | 4-methoxyphenyl | 15.1 | 394.2 |
| 34 | benzyl | 2,5-dimethoxyphenyl | 15.1 | 424.2 |
| 35 | benzyl | 4-(diethylamino)phenyl | 15.1 | 435.2 |
| 36 | benzyl | 4-chlorophenyl | 15.8 | 398.1 |
| 37 | benzyl | 3,4-dichlorophenyl | 16.8 | 432.1 |

-continued
FORMULA 17
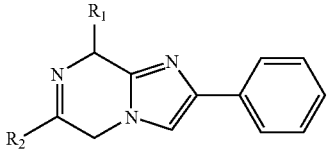
| | R1 | R2 | Tr (min) | [M + H]+ |
|---|---|---|---|---|
| 38 | 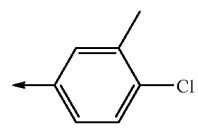 | 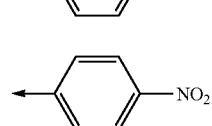 | 16.3 | 412.1 |
| 39 | 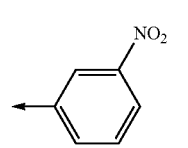 | 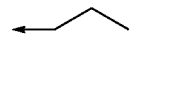 | 16.1 | 442.0 |
| 40 | 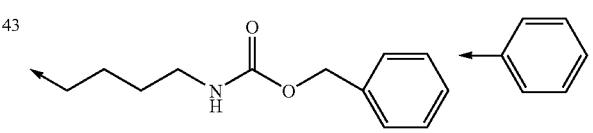 | 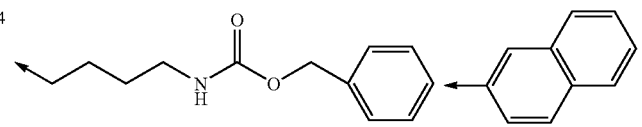 | 15.6 | 409.1 |
| 41 | 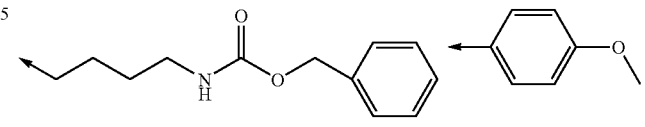 | 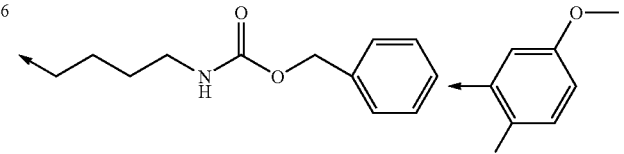 | 15.6 | 409.1 |
| 42 | 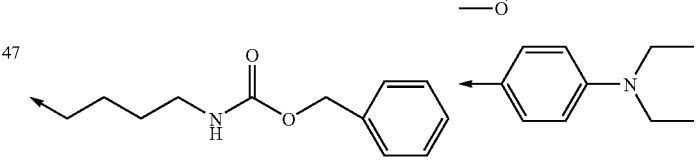 | | 14.4 | 316.2 |
| 43 | | | 15.1 | 479.2 |
| 44 | | | 15.6 | 529.2 |
| 45 | | | 15.0 | 509.2 |
| 46 | | | 15.2 | 539.2 |
| 47 | | | 15.2 | 550.2 |

-continued

FORMULA 17

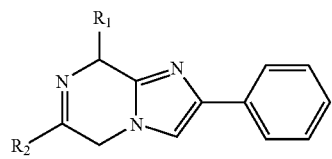

|  | R1 | R2 | Tr (min) | [M + H]+ |
|---|---|---|---|---|
| 48 | benzyl (4-aminobutyl)carbamate chain | 4-Cl-phenyl | 15.6 | 513.1 |
| 49 | benzyl (4-aminobutyl)carbamate chain | 3,4-diCl-phenyl | 16.0 | 547.1 |
| 50 | benzyl (4-aminobutyl)carbamate chain | 3-methyl-4-Cl-phenyl | 15.8 | 527.2 |
| 51 | benzyl (4-aminobutyl)carbamate chain | 4-Br-phenyl | 15.6 | 557.0 |
| 52 | benzyl (4-aminobutyl)carbamate chain | 4-F-phenyl | 15.2 | 497.2 |
| 53 | benzyl (4-aminobutyl)carbamate chain | 4-N₂-phenyl | 15.7 | 520.2 |
| 54 | benzyl (4-aminobutyl)carbamate chain | 3-NO₂-phenyl | 15.4 | 524.2 |
| 55 | benzyl (4-aminobutyl)carbamate chain | propyl | 14.5 | 431.2 |

Analyses header above Tr (min) and [M + H]+ columns.

FORMULA 18
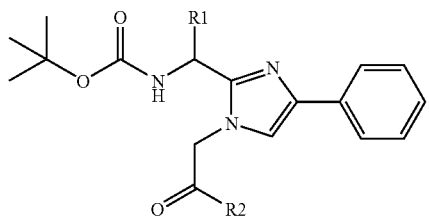
| R1 | R2 | Tr (min) | [M + H]+ |
|---|---|---|---|
| 1 indol-3-ylmethyl (S) | phenyl | 15.4 | 521.2 |
| 2 indol-3-ylmethyl (S) | biphenyl-4-yl | 16.5 | 597.1 |
| 3 indol-3-ylmethyl (S) | naphth-2-yl | 16.1 | 571.2 |
| 4 indol-3-ylmethyl (S) | 4-methoxyphenyl | 15.3 | 551.2 |
| 5 indol-3-ylmethyl (S) | 2,5-dimethoxyphenyl | 15.3 | 581.2 |
| 6 indol-3-ylmethyl (S) | 4-(diethylamino)phenyl | 15.8 | 592.2 |

-continued
FORMULA 18
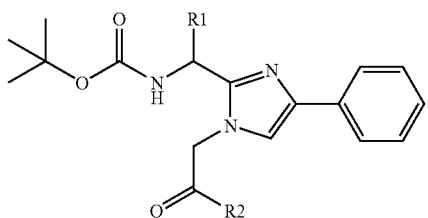
| R1 | R2 | Analysis | |
|---|---|---|---|
| | | Tr (min) | [M + H]+ |
| 7 (S) 1H-indol-3-ylmethyl | 4-Cl-phenyl | 16.1 | 555.1 |
| 8 (S) 1H-indol-3-ylmethyl | 3,4-diCl-phenyl | 16.7 | 589.0 |
| 9 (S) 1H-indol-3-ylmethyl | 3-methyl-4-Cl-phenyl | 16.4 | 569.1 |
| 10 (S) 1H-indol-3-ylmethyl | 4-Br-phenyl | 16.1 | 599.0 |
| 11 (S) 1H-indol-3-ylmethyl | 4-F-phenyl | 15.6 | 539.1 |
| 12 (S) 1H-indol-3-ylmethyl | 4-CN-phenyl | 15.4 | 546.2 |

-continued
FORMULA 18
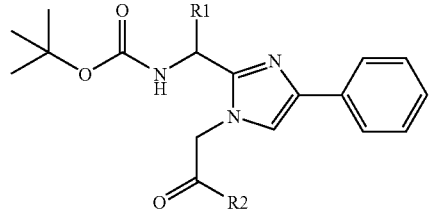
| R1 | R2 | Analysis | |
|---|---|---|---|
| | | Tr (min) | [M + H]+ |
| 13 1H-indol-3-ylmethyl (S) | 4-azidophenyl | 15.8 | 562.1 |
| 14 1H-indol-3-ylmethyl (S) | 4-nitrophenyl | 15.8 | 566.1 |
| 15 1H-indol-3-ylmethyl (S) | 3-nitrophenyl | 15.7 | 566.1 |
| 16 1H-indol-3-ylmethyl (S) | propyl | 14.8 | 473.2 |
| 17 1H-indol-3-ylmethyl (S) | phenyl | 15.5 | 521.2 |
| 18 1H-indol-3-ylmethyl (R) | 4-biphenyl | 16.5 | 597.1 |
| 19 1H-indol-3-ylmethyl (R) | 2-naphthyl | 16.1 | 571.1 |

-continued
FORMULA 18
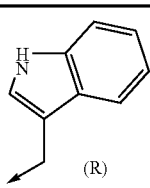
| | R1 | R2 | Tr (min) | [M + H]+ |
|---|---|---|---|---|
| 20 | 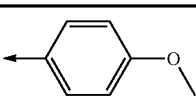 (R) | 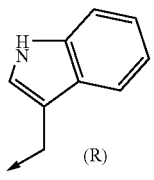 | 15.4 | 551.2 |
| 21 | 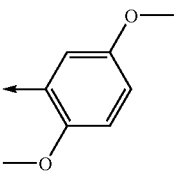 (R) | 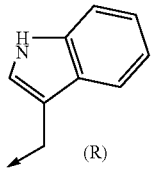 | 15.4 | 581.1 |
| 22 | 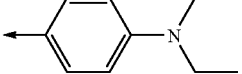 (R) | 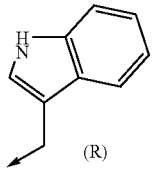 | 15.9 | 592.2 |
| 23 |  (R) | 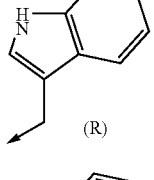 | 16.3 | 555.1 |
| 24 | 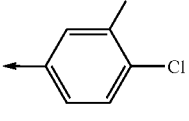 (R) | 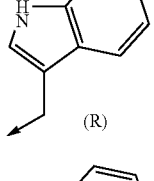 | 16.8 | 589.0 |
| 25 | 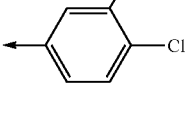 (R) | 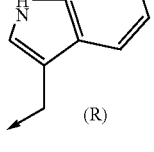 | 16.7 | 569.1 |
| 26 | 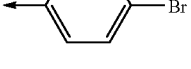 (R) | | 16.4 | 599.0 |

-continued
FORMULA 18
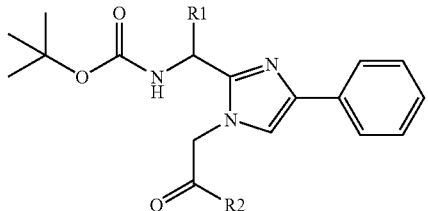
| R1 | R2 | Analysis | |
|---|---|---|---|
| | | Tr (min) | [M + H]+ |
| 27 indol-3-ylmethyl (R) | 4-F-phenyl | 15.8 | 539.1 |
| 28 indol-3-ylmethyl (R) | 4-CN-phenyl | 15.6 | 546.1 |
| 29 indol-3-ylmethyl (R) | 4-N₂-phenyl | 16.0 | 562.1 |
| 30 indol-3-ylmethyl (R) | 4-NO₂-phenyl | 15.9 | 566.1 |
| 31 indol-3-ylmethyl (R) | 3-NO₂-phenyl | 15.8 | 566.1 |
| 32 indol-3-ylmethyl (R) | propyl | 15.0 | 473.2 |
| 33 benzyl | phenyl | 16.7 | 482.2 |

-continued
FORMULA 18
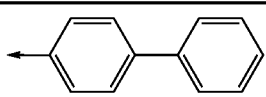
| | R1 | R2 | Tr (min) | [M + H]+ |
|---|---|---|---|---|
| 34 | benzyl | 4-biphenyl | 18.0 | 588.2 |
| 35 | benzyl | 4-methoxyphenyl | 16.4 | 512.2 |
| 36 | benzyl | 2,5-dimethoxyphenyl | 16.5 | 542.2 |
| 37 | benzyl | 4-(diethylamino)phenyl | 17.0 | 553.2 |
| 38 | benzyl | 4-chlorophenyl | 17.8 | 516.1 |
| 39 | benzyl | 3,4-dichlorophenyl | 18.2 | 550.1 |
| 40 | benzyl | 4-chloro-3-methylpyridyl | 18.0 | 530.1 |
| 41 | benzyl | 4-bromophenyl | 17.7 | 560.0 |
| 42 | benzyl | 4-fluorophenyl | 16.9 | 500.2 |
| 43 | benzyl | 4-cyanophenyl | 16.7 | 507.2 |

-continued
FORMULA 18
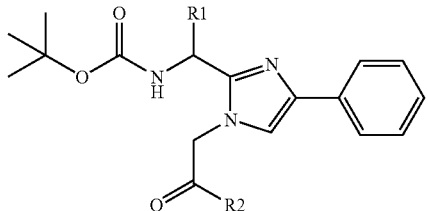
| | R1 | R2 | Tr (min) | [M + H]+ |
|---|---|---|---|---|
| 44 | benzyl | 4-N₃-phenyl | 17.2 | 523.2 |
| 45 | benzyl | 4-NO₂-phenyl | 16.9 | 527.2 |
| 46 | benzyl | 3-NO₂-phenyl | 16.8 | 527.2 |
| 47 | benzyl | isopropyl | 15.8 | 434.2 |
| 48 | (Cbz-NH-butyl) | phenyl | 15.8 | 597.2 |
| 49 | (Cbz-NH-butyl) | 4-biphenyl | 16.6 | 673.2 |
| 50 | (Cbz-NH-butyl) | isoquinolinyl | 16.5 | 647.2 |
| 51 | (Cbz-NH-butyl) | 4-methoxyphenyl | 15.8 | 627.2 |
| 52 | (Cbz-NH-butyl) | 2,5-dimethoxyphenyl | 15.8 | 657.2 |

-continued
FORMULA 18
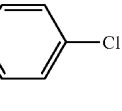
| | R1 | R2 | Tr (min) | [M + H]+ |
|---|---|---|---|---|
| 53 | 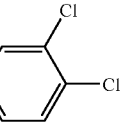 | 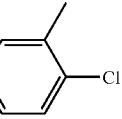 4-Cl | 16.5 | 631.1 |
| 54 | | 3,4-diCl | 17.2 | 665.1 |
| 55 | | 3-Me, 4-Cl | 16.7 | 645.1 |
| 56 | | 4-Br | 16.5 | 675.1 |
| 57 | | 4-F | 16.0 | 615.1 |
| 58 | | 4-CN | 15.9 | 622.1 |
| 59 | | 4-N₃ | 15.1 | 638.2 |
| 60 | | 4-NO₂ | 16.1 | 642.1 |
| 61 | | 3-NO₂ | 16.2 | 642.1 |

-continued
FORMULA 18
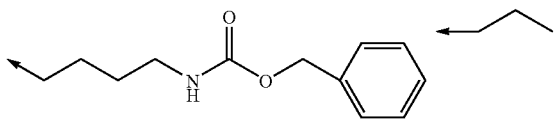
| | R1 | R2 | Analysis | |
|---|---|---|---|---|
| | | | Tr (min) | [M + H]+ |
| 62 | 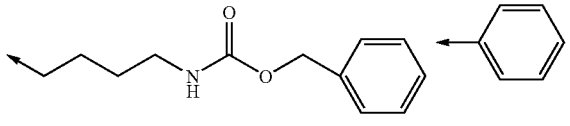 | 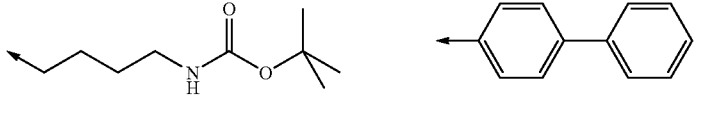 | 15.4 | 549.2 |
| 63 | 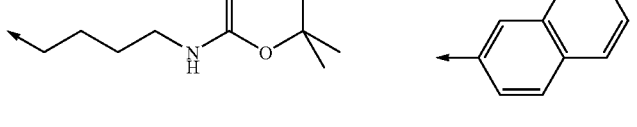 | 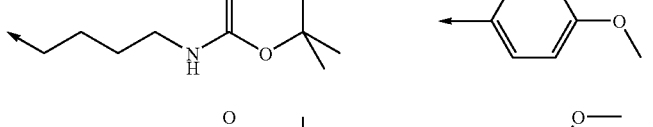 | 15.9 | 563.2 |
| 64 | 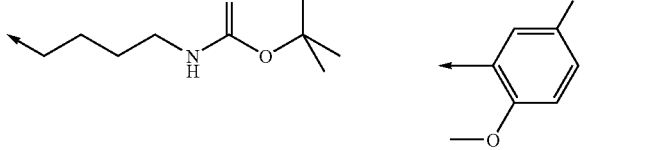 | 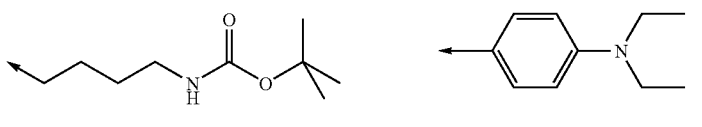 | 17.0 | 639.2 |
| 65 | 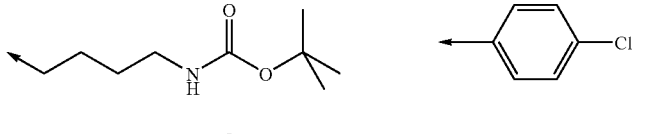 | 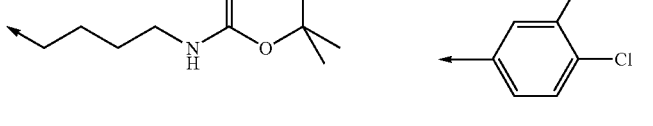 | 16.5 | 613.2 |
| 66 | | | 15.7 | 593.2 |
| 67 | | | 15.8 | 623.2 |
| 68 | | | 16.2 | 634.2 |
| 69 | | | 16.6 | 597.1 |
| 70 | | | 17.4 | 631.1 |

-continued
FORMULA 18
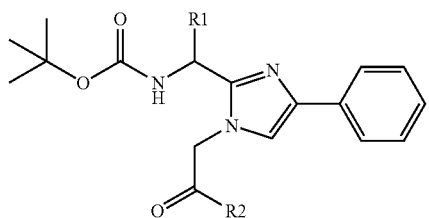
| | R1 | R2 | Tr (min) | [M + H]+ |
|---|---|---|---|---|
| 71 | ←~~~NHBoc | ←C6H3(Cl)(CH3) | 17.0 | 611.1 |
| 72 | ←~~~NHBoc | ←C6H4-Br | 16.7 | 641.1 |
| 73 | ←~~~NHBoc | ←C6H4-F | 16.1 | 581.2 |
| 74 | ←~~~NHBoc | ←C6H4-CN | 15.9 | 588.2 |
| 75 | ←~~~NHBoc | ←C6H4-N2 | 16.2 | 604.2 |
| 76 | ←~~~NHBoc | ←pyridyl-NO2 | 16.2 | 608.2 |
| 77 | ←~~~NHBoc | ←C6H4-NO2 (meta) | 16.1 | 506.2 |
| 78 | ←~~~NHBoc | ←propyl | 15.3 | 515.3 |

FORMULA 19
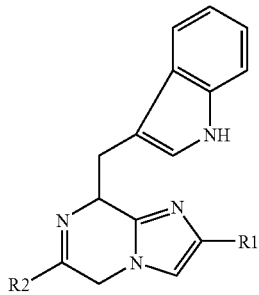
| | R1 | R2 | Tr | [M + H]+ | Analyses * = [M + TFA − H]− |
|---|---|---|---|---|---|
| 1 | o-OMe-phenyl | phenyl | 6.2 | 433.2 | |
| 2 | o-OMe-phenyl | biphenyl | 7.0 | 509.2 | |
| 3 | o-OMe-phenyl | 2-naphthyl | 6.8 | 483.2 | |
| 4 | o-OMe-phenyl | 4-OMe-phenyl | 6.2 | 483.2 | |
| 5 | o-OMe-phenyl | 3,5-diOMe-phenyl | 6.5 | 493.2 | |
| 6 | o-OMe-phenyl | 4-NEt2-phenyl | 5.4 | 504.3 | |

-continued
FORMULA 19
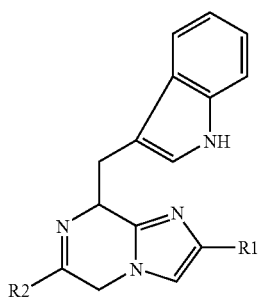
| | R1 | R2 | Tr | [M + H]+ Analyses * = [M + TFA − H]− |
|---|---|---|---|---|
| 7 | 2-methoxyphenyl | 4-Cl-phenyl | 6.5 | 457.2 |
| 8 | 2-methoxyphenyl | 3,4-diCl-phenyl | 6.9 | 501.1 |
| 9 | 2-methoxyphenyl | 3-methyl-4-Cl-phenyl | 6.8 | 481.2 |
| 10 | 2-methoxyphenyl | 4-Br-phenyl | 6.5 | 511.1 |
| 11 | 2-methoxyphenyl | 4-F-phenyl | 6.3 | 451.2 |
| 12 | 2-methoxyphenyl | 4-CN-phenyl | 6.2 | 458.2 |

-continued
FORMULA 19
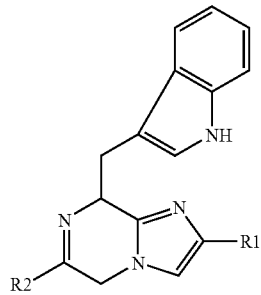
| R1 | R2 | Tr | [M + H]+ Analyses * = [M + TFA − H]− |
|---|---|---|---|
| 13 ⟵–⌬–O⟋ (2-OMe-Ph) | ⟵–⌬–N₃ (4-N₃-Ph) | 6.5 | 474.2 |
| 14 ⟵–⌬–O⟋ (2-OMe-Ph) | ⟵–⌬–NO₂ (4-NO₂-Ph) | 6.3 | 476.2 |
| 15 ⟵–⌬–O⟋ (2-OMe-Ph) | ⟵–⌬–NO₂ (3-NO₂-Ph) | 6.3 | 476.2 |
| 16 ⟵–⌬–O⟋ (2-OMe-Ph) | ⟵–Et | 5.7 | 385.2 |
| 17 ⟵–⌬–O⟋ (4-OMe-Ph) (S) | ⟵–⌬ (Ph) | 6.9 | 433.2 |
| 18 ⟵–⌬–O⟋ (4-OMe-Ph) (S) | ⟵–pyridyl–Ph | 7.0 | 509.2 |
| 19 ⟵–⌬–O⟋ (4-OMe-Ph) (S) | ⟵–naphthyl | 6.7 | 483.2 |

-continued
FORMULA 19
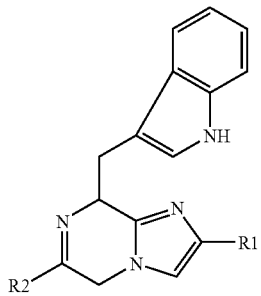
| | R1 | R2 | Tr | [M + H]+ Analyses * = [M + TFA − H]− |
|---|---|---|---|---|
| 20 | 4-methoxyphenyl (S) | 4-methoxyphenyl | 6.2 | 453.2 |
| 21 | 4-methoxyphenyl (S) | 2,5-dimethoxyphenyl | 6.3 | 493.2 |
| 22 | 4-methoxyphenyl (S) | 4-(N,N-diethylamino)phenyl | 5.3 | 504.3 |
| 23 | 4-methoxyphenyl (S) | 4-chlorophenyl | 6.5 | 457.2 |
| 24 | 4-methoxyphenyl (S) | 3,4-dichlorophenyl | 6.8 | 501.1 |
| 25 | 4-methoxyphenyl (S) | 3-methyl-4-chlorophenyl | 6.7 | 481.2 |
| 26 | 4-methoxyphenyl (S) | 4-bromophenyl | 6.5 | 511.1 |
| 27 | 4-methoxyphenyl (S) | 4-fluorophenyl | 6.2 | 451.2 |

-continued
FORMULA 19
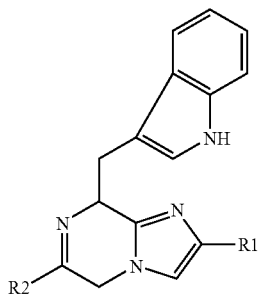
| | R1 | R2 | Tr | [M + H]+ Analyses * = [M + TFA − H]− |
|---|---|---|---|---|
| 28 | 4-methoxyphenyl (S) | 4-cyanophenyl | 6.1 | 458.2 |
| 29 | 4-methoxyphenyl (S) | 4-azidophenyl | 6.4 | 474.2 |
| 30 | 4-methoxyphenyl (S) | 4-nitrophenyl | 6.3 | 478.2 |
| 31 | 4-methoxyphenyl (S) | 3-nitrophenyl | 6.3 | 478.2 |
| 32 | 4-methoxyphenyl (S) | ethyl | 5.6 | 385.2 |
| 33 | 4-bromophenyl | phenyl | 6.5 | 481.1 |
| 34 | 4-bromophenyl | 4-biphenyl | 7.4 | 557.1 |
| 35 | 4-bromophenyl | 2-naphthyl | 7.1 | 531.1 |
| 36 | 4-bromophenyl | 4-methoxyphenyl | 6.6 | 511.1 |

-continued
FORMULA 19
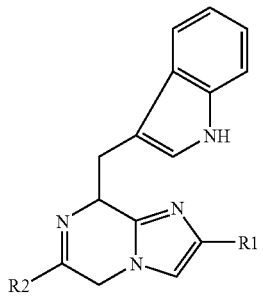
| | R1 | R2 | Tr | Analyses<br>* =<br>[M + TFA − H]−<br>[M + H]+ |
|---|---|---|---|---|
| 37 | ⟵⟨ ⟩—Br | 2,5-dimethoxyphenyl | 6.8 | 541.1 |
| 38 | ⟵⟨ ⟩—Br | ⟵⟨ ⟩—N(Et)₂ | 5.7 | 552.2 |
| 39 | ⟵⟨ ⟩—Br | ⟵⟨ ⟩—Cl | 6.9 | 515.0 |
| 40 | ⟵⟨ ⟩—Br | 3,4-dichlorophenyl | 7.3 | 549.0 |
| 41 | ⟵⟨ ⟩—Br | 4-chloro-3-methylphenyl | 7.1 | 529.1 |
| 42 | ⟵⟨ ⟩—Br | ⟵⟨ ⟩—Br | 7.0 | 670.1* |
| 43 | ⟵⟨ ⟩—Br | ⟵⟨ ⟩—F | 6.6 | 499.1 |
| 44 | ⟵⟨ ⟩—Br | ⟵⟨ ⟩—CN | 6.6 | 506.1 |
| 45 | ⟵⟨ ⟩—Br | ⟵⟨ ⟩—N₃ | 6.8 | 522.1 |
| 46 | ⟵⟨ ⟩—Br | ⟵⟨ ⟩—NO₂ | 6.8 | 528.1 |

-continued
FORMULA 19
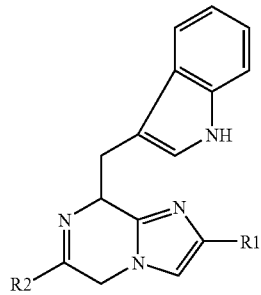
| | R1 | R2 | Tr | [M + H]+ |
|---|---|---|---|---|
| | | | Analyses * = [M + TFA − H]− | |
| 47 | 4-Br-phenyl | 3-NO₂-phenyl | 6.7 | 526.1 |
| 48 | 4-Br-phenyl | ethyl | 6.0 | 433.1 |
| 49 | 4-NO₂-phenyl | phenyl | 6.5 | 448.2 |
| 50 | 4-NO₂-phenyl | 4-biphenyl | 7.7 | 524.2 |
| 51 | 4-NO₂-phenyl | 2-naphthyl | 7.4 | 496.2 |
| 52 | 4-NO₂-phenyl | 4-methoxyphenyl | 6.6 | 478.2 |
| 53 | 4-NO₂-phenyl | 2,5-dimethoxyphenyl | 6.7 | 508.2 |
| 54 | 4-NO₂-phenyl | 4-(diethylamino)phenyl | 5.8 | 519.2 |
| 55 | 4-NO₂-phenyl | 4-Cl-phenyl | 7.2 | 482.1 |

-continued
FORMULA 19
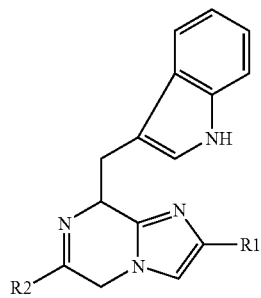
| | R1 | R2 | Tr | [M + H]+ Analyses * = [M + TFA − H]− |
|---|---|---|---|---|
| 56 | —⟨⟩—NO₂ | —⟨⟩(Cl)(Cl) | 7.7 | 516.1 |
| 57 | —⟨⟩—NO₂ | —⟨⟩(CH₃)(Cl) | 7.5 | 496.2 |
| 58 | —⟨⟩—NO₂ | —⟨⟩—Br | 7.3 | 526.1 |
| 59 | —⟨⟩—NO₂ | —⟨⟩—F | 6.8 | 466.2 |
| 60 | —⟨⟩—NO₂ | —⟨⟩—CN | 6.8 | 473.2 |
| 61 | —⟨⟩—NO₂ | —⟨⟩—N₃ | 7.1 | 489.2 |
| 62 | —⟨⟩—NO₂ | —⟨⟩—NO₂ | 7.1 | 493.1 |
| 63 | —⟨⟩—NO₂ | —⟨pyridyl⟩—NO₂ | 7.0 | 493.2 |
| 64 | —⟨⟩—NO₂ | —Et | 5.8 | 400.2 |
| 65 | —C(CH₃)₃ | —⟨⟩ | 5.8 | 383.2 |

-continued
FORMULA 19
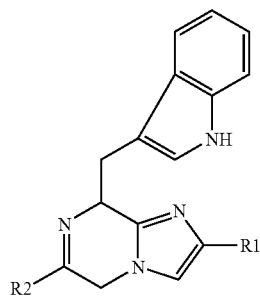
| | R1 | R2 | Tr | [M + H]+ |
|---|---|---|---|---|
| | | | | Analyses *= [M + TFA − H]− |
| 66 | t-Bu | biphenyl-4-yl | 6.8 | 459.2 |
| 67 | t-Bu | naphthalen-2-yl | 6.5 | 433.2 |
| 68 | t-Bu | 4-methoxyphenyl | 5.9 | 413.2 |
| 69 | t-Bu | 2,5-dimethoxyphenyl | 6.2 | 443.3 |
| 70 | t-Bu | 4-(diethylamino)phenyl | 5.0 | 454.3 |
| 71 | t-Bu | 4-chlorophenyl | 6.3 | 417.2 |
| 72 | t-Bu | 3,4-dichlorophenyl | 6.6 | 451.1 |
| 73 | t-Bu | 4-chloro-3-methylphenyl | 6.5 | 431.2 |

-continued
FORMULA 19
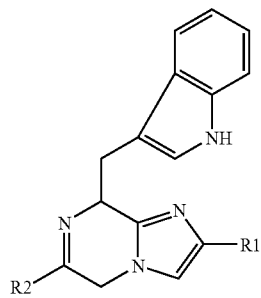
| | R1 | R2 | Tr | [M + H]+ Analyses *= [M + TFA − H]− |
|---|---|---|---|---|
| 74 | *tBu* | 4-Br-C6H4 | 6.3 | 461.1 |
| 75 | *tBu* | 4-F-C6H4 | 6.0 | 401.2 |
| 76 | *tBu* | 4-CN-C6H4 | 5.8 | 408.2 |
| 77 | *tBu* | 4-N3-C6H4 | 6.2 | 424.2 |
| 78 | *tBu* | 4-NO2-C6H4 | 6.0 | 428.2 |
| 79 | *tBu* | 3-NO2-C6H4 | 6.0 | 428.2 |
| 80 | *tBu* | Et | 5.3 | 335.3 |

FORMULA 20
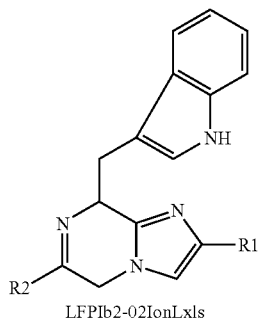
LFPIb2-02IonLxls
| | R1 | R2 | Tr (min) | [M + H]+ |
|---|---|---|---|---|
| 1 | phenyl (R) | 4-(trifluoromethoxy)phenyl | 5.9 | 487.2 |
| 2 | phenyl (R) | 2,3-dihydro-1,4-benzodioxin-6-yl | 6.3 | 461.3 |
| 3 | phenyl (R) | 1,3-benzodioxol-5-yl | 6.3 | 447.3 |
| 4 | phenyl (R) | 3,4,5-trimethoxyphenyl | 6.2 | 493.3 |
| 5 | phenyl (R) | 4-chloro-3-nitrophenyl | 6.7 | 482.2 |
| 6 | phenyl (R) | 4-(benzyloxy)phenyl | 7.2 | 509.3 |
| 7 | phenyl (R) | 4-pentylphenyl | 7.7 | 473.4 |

-continued
FORMULA 20
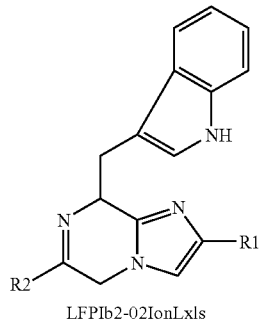
LFPIb2-02IonLxls
| | R1 | R2 | Tr (min) | [M + H]+ |
|---|---|---|---|---|
| 8 | phenyl (R) | 3,4-dihydroquinolin-2(1H)-one-7-yl | 5.8 | 472.3 |
| 9 | phenyl (R) | 5-chloro-3-methylbenzo[b]thiophen-2-yl | 7.3 | 507.2 |
| 10 | phenyl (R) | benzo[b]thiophen-3-yl | 6.6 | 459.3 |
| 11 | phenyl (R) | 5-bromothiophen-2-yl | 6.6 | 487.2 |
| 12 | phenyl (R) | 3-phenylisoxazol-5-yl | 6.7 | 470.3 |
| 13 | phenyl (R) | 3-(2,4-dichlorophenyl)isoxazol-5-yl | 7.2 | 538.2 |

-continued
FORMULA 20
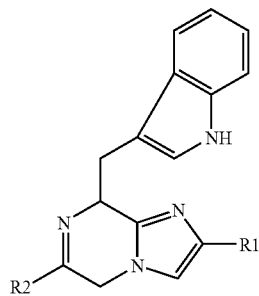
LFPIb2-02IonLxls
| | R1 | R2 | Tr (min) | [M + H]+ |
|---|---|---|---|---|
| 14 | phenyl (R) | 1H-indol-3-ylmethyl | 6.6 | 456.3 |
| 15 | phenyl (R) | 2-phenylethyl | 6.6 | 431.3 |
| 16 | phenyl (R) | 3,4-difluorophenyl | 6.5 | 439.3 |
| 17 | 2-methoxyphenyl | 4-(trifluoromethoxy)phenyl | 7.1 | 517.3 |
| 18 | 2-methoxyphenyl | 2,3-dihydro-1,4-benzodioxin-6-yl | 6.5 | 491.3 |
| 19 | 2-methoxyphenyl | 1,3-benzodioxol-5-yl | 6.4 | 477.3 |

-continued
FORMULA 20
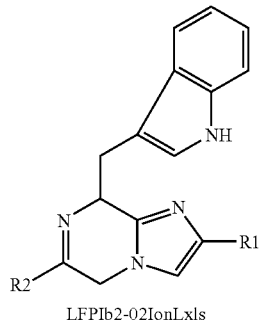
LFPIb2-02IonLxls
| | R1 | R2 | Analyses | |
|---|---|---|---|---|
| | | | Tr (min) | [M + H]+ |
| 20 | 2-methoxyphenyl | 3,4,5-trimethoxyphenyl | 6.4 | 523.3 |
| 21 | 2-methoxyphenyl | 4-chloro-3-nitrophenyl | 6.9 | 512.3 |
| 22 | 2-methoxyphenyl | 4-benzyloxyphenyl | 7.3 | 538.3 |
| 23 | 2-methoxyphenyl | 4-pentylphenyl | 7.8 | 503.4 |
| 24 | 2-methoxyphenyl | 2-oxo-1,2,3,4-tetrahydroquinolin-7-yl | 6.0 | 502.3 |
| 25 | 2-methoxyphenyl | 5-chloro-3-methylbenzo[b]thiophen-2-yl | 7.4 | 537.3 |

-continued
FORMULA 20
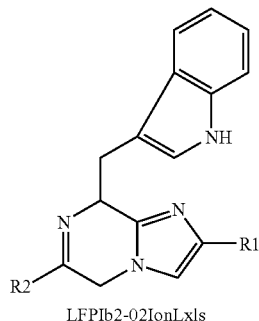
LFPIb2-02IonLxls
| | R1 | R2 | Tr (min) | [M + H]+ |
|---|---|---|---|---|
| 26 | 2-methoxyphenyl | benzothiophen-3-yl | 6.8 | 489.3 |
| 27 | 2-methoxyphenyl | 5-bromothiophen-2-yl | 6.8 | 517.2 |
| 28 | 2-methoxyphenyl | 3-phenylisoxazol-5-yl | 6.8 | 500.3 |
| 29 | 2-methoxyphenyl | 3-(2,4-dichlorophenyl)isoxazol-5-yl | 7.4 | 562.2 |
| 30 | 2-methoxyphenyl | 1H-indol-3-ylmethyl | 6.7 | 486.4 |
| 31 | 2-methoxyphenyl | 2-phenylethyl | 6.8 | 461.3 |

-continued
FORMULA 20
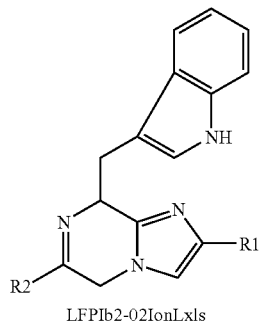
LFPIb2-02IonLxls
| | R1 | R2 | Analyses | |
|---|---|---|---|---|
| | | | Tr (min) | [M + H]+ |
| 32 | 2-methoxyphenyl | 3,4-difluorophenyl | 6.7 | 469.3 |
| 33 | 4-nitrophenyl | 4-(trifluoromethoxy)phenyl | 7.4 | 532.3 |
| 34 | 4-nitrophenyl | 2,3-dihydro-1,4-benzodioxin-6-yl | 6.6 | 506.3 |
| 35 | 4-nitrophenyl | 1,3-benzodioxol-5-yl | 6.6 | 492.3 |
| 36 | 4-nitrophenyl | 3,4,5-trimethoxyphenyl | 6.6 | 538.3 |
| 37 | 4-nitrophenyl | 4-chloro-3-nitrophenyl | 7.3 | 527.2 |
| 38 | 4-nitrophenyl | 4-(benzyloxy)phenyl | 7.5 | 554.3 |

-continued
FORMULA 20
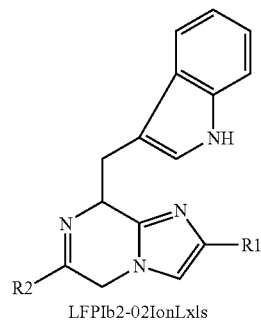
LFPIb2-02IonLxls
| | R1 | R2 | Tr (min) | [M + H]+ |
|---|---|---|---|---|
| 39 | —⟨⟩—NO₂ | —⟨⟩—(pentyl) | 8.1 | 518.3 |
| 40 | —⟨⟩—NO₂ | 3,4-dihydroquinolin-2(1H)-one-7-yl | 6.1 | 517.3 |
| 41 | —⟨⟩—NO₂ | 5-chloro-3-methylbenzo[b]thiophen-2-yl | 8.1 | 552.2 |
| 42 | —⟨⟩—NO₂ | benzo[b]thiophen-3-yl | 7.0 | 504.3 |
| 43 | —⟨⟩—NO₂ | 5-bromothiophen-2-yl | 7.2 | 532.1 |
| 44 | —⟨⟩—NO₂ | 3-phenylisoxazol-5-yl | 7.4 | 515.3 |
| 45 | —⟨⟩—NO₂ | 3-(2,4-dichlorophenyl)isoxazol-5-yl | 8.1 | 583.2 |
| 46 | —⟨⟩—NO₂ | (1H-indol-3-yl)methyl | 6.8 | 501.3 |

-continued
FORMULA 20
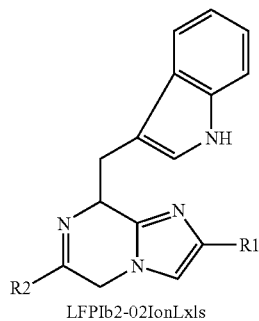
LFPIb2-02IonLxls
| R1 | R2 | Tr (min) | [M + H]+ |
|---|---|---|---|
| 47 ←⟨⟩—NO₂ | ←CH₂CH₂—⟨⟩ | 6.9 | 476.3 |
| 48 ←⟨⟩—NO₂ | ←⟨⟩—F, F | 7.0 | 484.3 |
| 49 ←⟨⟩—Br | ←⟨⟩—O—CF₃ | 7.3 | 565.2 |
| 50 ←⟨⟩—Br | ←benzodioxine | 6.7 | 539.2 |
| 51 ←⟨⟩—Br | ←methylenedioxyphenyl | 6.7 | 525.2 |
| 52 ←⟨⟩—Br | ←3,4,5-trimethoxyphenyl | 6.7 | 571.2 |
| 53 ←⟨⟩—Br | ←⟨⟩—Cl, NO₂ | 7.1 | 560.1 |
| 54 ←⟨⟩—Br | ←⟨⟩—O—CH₂—⟨⟩ | 7.6 | 587.2 |

-continued
FORMULA 20
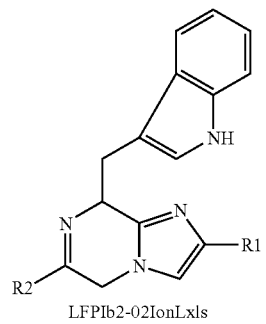
LFPIb2-02IonLxls
| | R1 | R2 | Tr (min) | [M + H]+ |
|---|---|---|---|---|
| 55 | 4-Br-phenyl | 4-pentyl-phenyl | 8.0 | 551.3 |
| 56 | 4-Br-phenyl | 3,4-dihydroquinolin-2(1H)-one-7-yl | 6.3 | 550.2 |
| 57 | 4-Br-phenyl | 5-chloro-3-methylbenzo[b]thiophen-2-yl | 7.7 | 585.1 |
| 58 | 4-Br-phenyl | benzo[b]thiophen-3-yl | 7.0 | 537.2 |
| 59 | 4-Br-phenyl | 5-bromothiophen-2-yl | 7.0 | 565.0 |
| 60 | 4-Br-phenyl | 3-phenylisoxazol-5-yl | 7.2 | 548.2 |
| 61 | 4-Br-phenyl | 3-(2,4-dichlorophenyl)isoxazol-5-yl | 7.7 | 616.1 |
| 62 | 4-Br-phenyl | (1H-indol-3-yl)methyl | 7.0 | 534.2 |

-continued
FORMULA 20
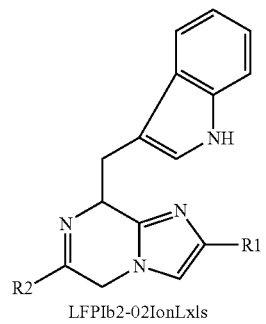
LFPIb2-02IonLxls
| | R1 | R2 | Tr (min) | [M + H]+ |
|---|---|---|---|---|
| 63 | 4-Br-phenyl | phenethyl | 7.0 | 509.2 |
| 64 | 4-Br-phenyl | 3,4-difluorophenyl | 6.9 | 517.2 |
| 65 | t-Bu | 4-(OCF₃)-phenyl | 6.8 | 467.3 |
| 66 | t-Bu | 2,3-dihydro-1,4-benzodioxin-6-yl | 6.1 | 444.3 |
| 67 | t-Bu | 1,3-benzodioxol-5-yl | 6.1 | 427.3 |
| 68 | t-Bu | 3,4,5-trimethoxyphenyl | 6.1 | 473.4 |
| 69 | t-Bu | 4-chloro-3-nitrophenyl | 6.6 | 462.3 |
| 70 | t-Bu | 4-benzyloxyphenyl | 7.1 | 489.4 |

-continued
FORMULA 20
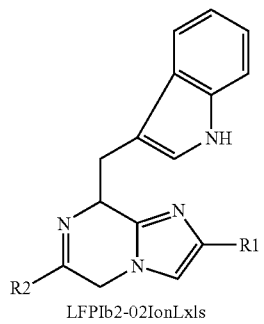
LFPIb2-02IonLxls
| | R1 | R2 | Tr (min) | [M + H]+ |
|---|---|---|---|---|
| 71 | tBu | 4-pentylphenyl | 7.5 | 453.4 |
| 72 | tBu | 3,4-dihydro-2(1H)-quinolinon-7-yl | 5.6 | 452.3 |
| 73 | tBu | 5-chloro-3-methylbenzothiophen-2-yl | 7.2 | 487.3 |
| 74 | tBu | benzothiophen-3-yl | 6.5 | 439.3 |
| 75 | tBu | 5-bromothiophen-2-yl | 6.5 | 467.2 |
| 76 | tBu | 3-phenylisoxazol-5-yl | 6.5 | 450.3 |
| 77 | tBu | 3-(2,4-dichlorophenyl)isoxazol-5-yl | 7.1 | 518.2 |
| 78 | tBu | (1H-indol-3-yl)methyl | 6.3 | 436.3 |

-continued
FORMULA 20
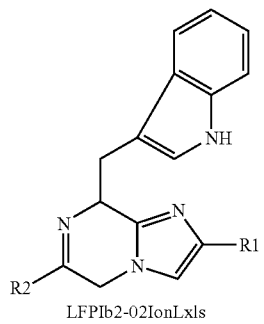
LFPIb2-02IonLxls
| | | | Analyses | |
|---|---|---|---|---|
| | R1 | R2 | Tr (min) | [M + H]+ |
| 79 | ![tBu] | ![phenethyl] | 6.5 | 411.3 |
| 80 | ![tBu] | ![3,4-diF-phenyl] | 6.4 | 419.3 |
FORMULA 21
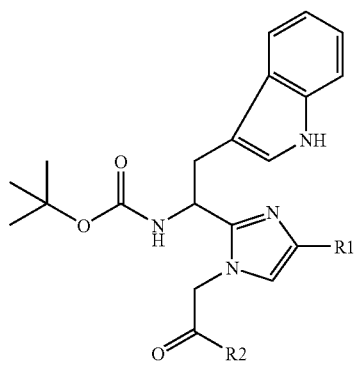
| | | | Analyses * = [M + TFA − H] | |
|---|---|---|---|---|
| | R1 | R2 | Tr (min) | [M + H]+ |
| 1 | ![2-OMe-phenyl] | ![phenyl] | 7.0 | 551.2 |
| 2 | ![2-OMe-phenyl] | ![biphenyl] | 7.8 | 627.2 |

-continued
FORMULA 21
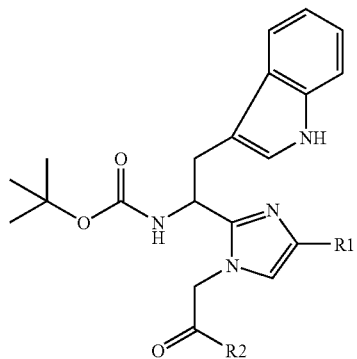
| | R1 | R2 | Tr (min) | [M + H]+ Analyses * = [M + TFA − H] |
|---|---|---|---|---|
| 3 | 2-methoxyphenyl | 2-naphthyl | 7.5 | 501.2 |
| 4 | 2-methoxyphenyl | 4-methoxyphenyl | 7.1 | 581.2 |
| 5 | 2-methoxyphenyl | 2,4-dimethoxyphenyl | 7.1 | 611.2 |
| 6 | 2-methoxyphenyl | 4-(diethylamino)phenyl | 7.5 | 622.3 |
| 7 | 2-methoxyphenyl | 4-chlorophenyl | 7.4 | 585.2 |
| 8 | 2-methoxyphenyl | 3,4-dichlorophenyl | 7.7 | 619.1 |

-continued
FORMULA 21
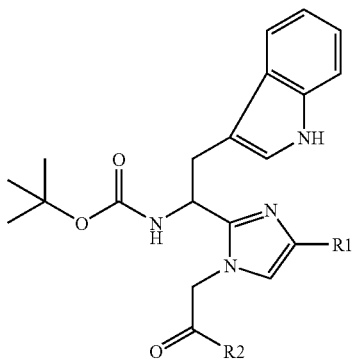
| | R1 | R2 | Tr (min) | [M + H]+ |
|---|---|---|---|---|
| | | | Analyses * = [M + TFA − H] | |
| 9 | 2-OMe-phenyl | 4-Cl-3-Me-phenyl | 7.7 | 599.2 |
| 10 | 2-OMe-phenyl | 4-Br-phenyl | 7.4 | 629.1 |
| 11 | 2-OMe-phenyl | 4-F-phenyl | 7.1 | 569.2 |
| 12 | 2-OMe-phenyl | 4-CN-phenyl | 7.0 | 576.2 |
| 13 | 2-OMe-phenyl | 4-N₃-phenyl | 7.3 | 592.2 |
| 14 | 2-OMe-phenyl | 4-NO₂-phenyl | 7.2 | 596.2 |

-continued
FORMULA 21
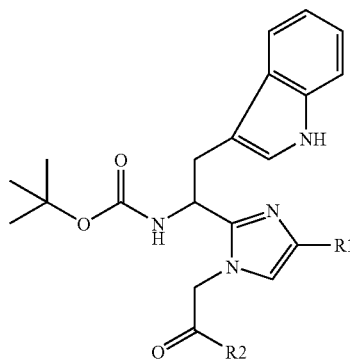
| | R1 | R2 | Tr (min) | [M + H]+ |
|---|---|---|---|---|
| | | | Analyses * = [M + TFA − H] | |
| 15 | 2-methoxyphenyl | 3-nitrophenyl | 7.1 | 596.2 |
| 16 | 2-methoxyphenyl | propyl | 6.5 | 503.3 |
| 17 (S) | 4-methoxyphenyl | phenyl | 7.0 | 551.2 |
| 18 (S) | 4-methoxyphenyl | biphenyl | 7.8 | 527.2 |
| 19 (S) | 4-methoxyphenyl | naphthyl | 7.5 | 601.2 |
| 20 (S) | 4-methoxyphenyl | 4-methoxyphenyl | 7.0 | 581.2 |
| 21 (S) | 4-methoxyphenyl | 2,?-dimethoxyphenyloxy | 7.1 | 611.2 |

-continued
FORMULA 21
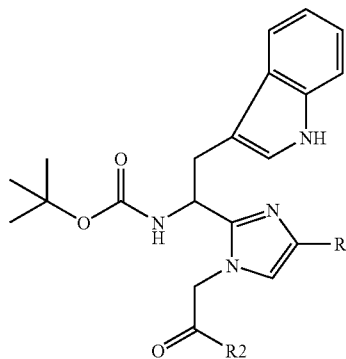
| | R1 | R2 | Tr (min) | [M + H]+ |
|---|---|---|---|---|
| | | | Analyses * = [M + TFA − H] | |
| 22 (S) | 4-methoxyphenyl | 4-(N,N-diethylamino)phenyl | 7.5 | 622.3 |
| 23 (S) | 4-methoxyphenyl | 4-chlorophenyl | 7.4 | 585.2 |
| 24 (S) | 4-methoxyphenyl | 3,4-dichlorophenyl | 7.7 | 619.1 |
| 25 (S) | 4-methoxyphenyl | 3-methyl-4-chlorophenyl | 7.6 | 599.2 |
| 26 (S) | 4-methoxyphenyl | 4-bromophenyl | 7.4 | 529.1 |
| 27 (S) | 4-methoxyphenyl | 4-fluorophenyl | 7.1 | 569.2 |
| 28 (S) | 4-methoxyphenyl | 4-cyanophenyl | 6.9 | 576.2 |
| 29 (S) | 4-methoxyphenyl | 4-azidophenyl | 7.3 | 704.2* |
| 30 (S) | 4-methoxyphenyl | 4-nitrophenyl | 7.1 | 596.2 |

-continued
FORMULA 21
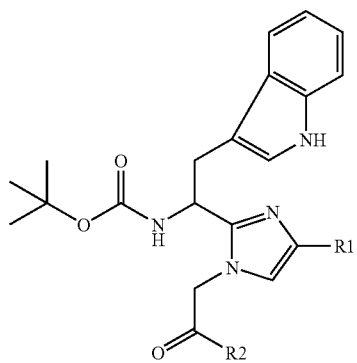
| | R1 | R2 | Tr (min) | [M + H]+ |
|---|---|---|---|---|
| | | | Analyses * = [M + TFA − H] | |
| 31 (S) | 4-methoxyphenyl | 3-nitrophenyl | 7.0 | 596.2 |
| 32 (S) | 4-methoxyphenyl | propyl | 6.5 | 503.2 |
| 33 | 4-bromophenyl | phenyl | 8.1 | 599.1 |
| 34 | 4-bromophenyl | biphenyl-4-yl | 9.0 | 675.1 |
| 35 | 4-bromophenyl | naphthalen-2-yl | 8.7 | 649.1 |
| 36 | 4-bromophenyl | 4-methoxyphenyl | 8.1 | 629.1 |
| 37 | 4-bromophenyl | 2,6-dimethoxyphenyl | 8.0 | 659.1 |
| 38 | 4-bromophenyl | 4-(diethylamino)phenyl | 8.4 | 670.2 |
| 39 | 4-bromophenyl | 4-chlorophenyl | 8.6 | 633.1 |

-continued
FORMULA 21
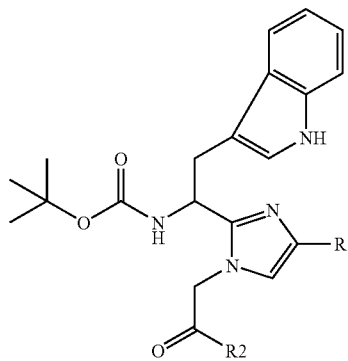
| | R1 | R2 | Analyses * = [M + TFA − H] Tr (min) | [M + H]+ |
|---|---|---|---|---|
| 40 | ←⟨⟩—Br | Cl ←⟨⟩—Cl | 9.0 | 667.0 |
| 41 | ←⟨⟩—Br | CH₃ ←⟨⟩—Cl | 8.8 | 547.1 |
| 42 | ←⟨⟩—Br | ←⟨⟩—Br | 8.6 | 677.0 |
| 43 | ←⟨⟩—Br | ←⟨⟩—F | 8.3 | 617.1 |
| 44 | ←⟨⟩—Br | ←⟨⟩—CN | 8.2 | 624.1 |
| 45 | ←⟨⟩—Br | ←⟨⟩—N₃ | 8.4 | 540.1 |
| 46 | ←⟨⟩—Br | ←⟨⟩—NO₂ | 8.4 | 644.1 |
| 47 | ←⟨⟩—Br | NO₂ ←⟨⟩ | 8.3 | 544.1 |
| 48 | ←⟨⟩—Br | ←CH₂CH₂CH₃ | 7.6 | 551.1 |
| 49 | ←⟨⟩—NO₂ | ←⟨⟩ | 8.7 | 566.2 |

-continued
FORMULA 21
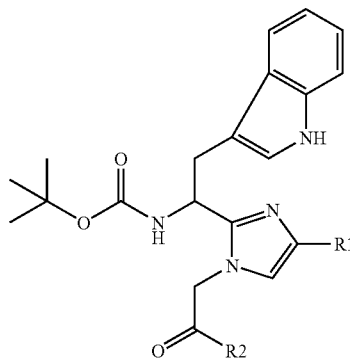
| R1 | R2 | Tr (min) | [M + H]+ |
|---|---|---|---|
| 50  4-NO2-C6H4- | biphenyl-4-yl | 9.7 | 642.2 |
| 51  4-NO2-C6H4- | naphthalen-2-yl | 9.3 | 616.2 |
| 52  4-NO2-C6H4- | 4-methoxyphenyl | 8.5 | 596.2 |
| 53  4-NO2-C6H4- | 2,3-dimethoxyphenyl | 8.7 | 626.2 |
| 54  4-NO2-C6H4- | 4-(diethylamino)phenyl | 9.1 | 637.2 |
| 55  4-NO2-C6H4- | 4-chlorophenyl | 9.2 | 600.1 |
| 56  4-NO2-C6H4- | 3,4-dichlorophenyl | 9.6 | 634.1 |
| 57  4-NO2-C6H4- | 4-chloro-3-methylphenyl | 9.5 | 614.1 |
| 58  4-NO2-C6H4- | 4-bromophenyl | 9.3 | 644.1 |
Analyses * = [M + TFA − H]

-continued
FORMULA 21
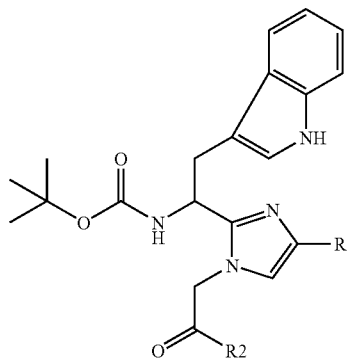
| | R1 | R2 | Tr (min) | [M + H]+ |
|---|---|---|---|---|
| | | | Analyses * = [M + TFA − H] | |
| 59 | 4-NO2-phenyl | 4-F-phenyl | 8.8 | 584.2 |
| 60 | 4-NO2-phenyl | 4-CN-phenyl | 8.7 | 591.2 |
| 61 | 4-NO2-phenyl | 4-N3-phenyl | 9.0 | 607.2 |
| 62 | 4-NO2-phenyl | 4-NO2-phenyl | 8.9 | 611.1 |
| 63 | 4-NO2-phenyl | 3-NO2-phenyl | 8.8 | 611.1 |
| 64 | 4-NO2-phenyl | n-propyl | 8.2 | 518.2 |
| 65 | tert-butyl | phenyl | 6.7 | 501.3 |
| 66 | 4-NO2-phenyl | 4-phenyl-phenyl | 7.5 | 577.2 |
| 67 | 4-NO2-phenyl | 2-naphthyl | 7.2 | 551.3 |
| 68 | 4-NO2-phenyl | 4-OMe-phenyl | 6.8 | 531.3 |

-continued
FORMULA 21
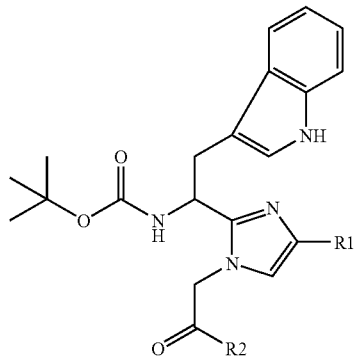
| | R1 | R2 | Tr (min) | [M + H]+ |
|---|---|---|---|---|
| | | | Analyses * = [M + TFA − H] | |
| 69 | 4-NO₂-phenyl | 2-methoxyphenoxy | 6.9 | 561.2 |
| 70 | 4-NO₂-phenyl | 4-(N,N-diethylamino)phenyl | 7.3 | 572.3 |
| 71 | 4-NO₂-phenyl | 4-Cl-phenyl | 7.0 | 535.2 |
| 72 | 4-NO₂-phenyl | 3,4-diCl-phenyl | 7.3 | 569.1 |
| 73 | 4-NO₂-phenyl | 3-methyl-4-Cl-phenyl | 7.3 | 549.2 |
| 74 | 4-NO₂-phenyl | 4-Br-phenyl | 7.1 | 579.1 |
| 75 | 4-NO₂-phenyl | 4-F-phenyl | 6.8 | 519.2 |
| 76 | 4-NO₂-phenyl | 4-CN-phenyl | 6.6 | 526.3 |
| 77 | 4-NO₂-phenyl | 4-N₃-phenyl | 7.0 | 542.2 |

-continued
FORMULA 21
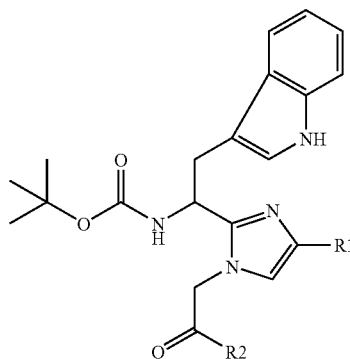
|   | R1 | R2 | Tr (min) | [M + H]+ Analyses * = [M + TFA − H] |
|---|---|---|---|---|
| 78 | —C₆H₄—NO₂ | —C₆H₄—NO₂ | 6.8 | 546.2 |
| 79 | —C₆H₄—NO₂ | —C₆H₄—NO₂ (3-NO₂) | 6.7 | 546.2 |
| 80 | —C₆H₄—NO₂ | propyl | 6.2 | 453.3 |
FORMULA 22
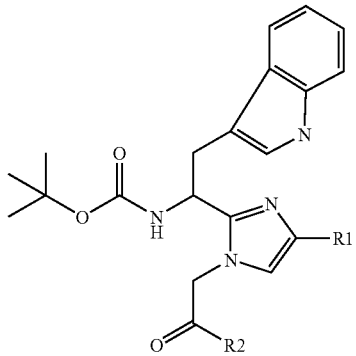
|   | R1 | R2 | Tr(min) | [M + H]+ Analysis |
|---|---|---|---|---|
| 1 (R) | phenyl | —C₆H₄—OCF₃ | 6.6 | 505.3 |

-continued
FORMULA 22
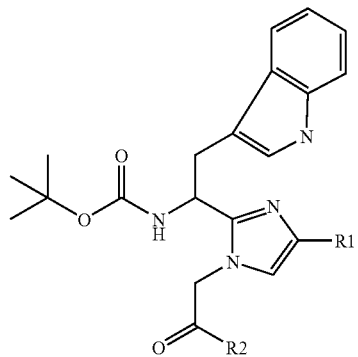
| | R1 | R2 | Analysis Tr(min) | [M + H]+ |
|---|---|---|---|---|
| 2 | (R) phenyl | 2,3-dihydrobenzo[1,4]dioxin-6-yl | 6.3 | 579.3 |
| 3 | (R) phenyl | 2,3-dihydrobenzo[1,4]dioxin-6-yl | 6.3 | 565.3 |
| 4 | (R) phenyl | 3,4,5-trimethoxyphenyl | 6.3 | 611.3 |
| 5 | (R) phenyl | 4-chloro-3-nitrophenyl | 6.5 | 600.2 |
| 6 | (R) phenyl | 4-benzyloxyphenyl | 6.6 | 627.3 |
| 7 | (R) phenyl | 4-pentylphenyl | 6.9 | |
| 8 | (R) phenyl | 2-oxo-1,2,3,4-tetrahydroquinolin-7-yl | 5.9 | 590.3 |

-continued
FORMULA 22
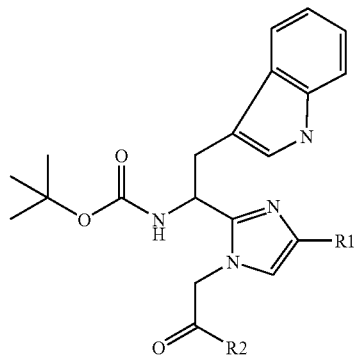
| | R1 | R2 | Tr(min) | [M + H]+ |
|---|---|---|---|---|
| 9 (R) | phenyl | 5-chloro-3-methylbenzo[b]thiophen-2-yl | 6.9 | 625.2 |
| 10 (R) | phenyl | 3-methylbenzo[b]thiophen-2-yl | 6.5 | 577.3 |
| 11 (R) | phenyl | 5-bromothiophen-2-yl | 6.6 | (605.12) THEO |
| 12 (R) | phenyl | 3-phenylisoxazol-5-yl | 6.6 | 588.3 |
| 13 (R) | phenyl | 3-(2,4-dichlorophenyl)isoxazol-5-yl | 7.0 | 656.2 |
| 14 (R) | phenyl | (1H-indol-3-yl)methyl | 6.4 | 574.3 |
| 15 (R) | phenyl | benzyl-CH2 | 6.5 | 549.3 |
| 16 (R) | phenyl | 3,4-difluorophenyl | 6.6 | 557.3 |

-continued
FORMULA 22
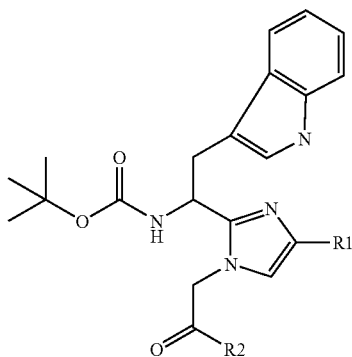
| | R1 | R2 | Tr(min) | [M + H]+ |
|---|---|---|---|---|
| 17 | 2-methoxyphenyl | 4-(trifluoromethoxy)phenyl | 6.5 | 635.3 |
| 18 | 2-methoxyphenyl | 2,3-dihydro-1,4-benzodioxin-6-yl | 6.2 | 609.3 |
| 19 | 2-methoxyphenyl | 2,3-dihydro-1,4-benzodioxin-6-yl | 6.2 | 595.3 |
| 20 | 2-methoxyphenyl | 3,4,5-trimethoxyphenyl | 6.2 | 641.3 |
| 21 | 2-methoxyphenyl | 4-chloro-3-nitrophenyl | 6.4 | 630.2 |
| 22 | 2-methoxyphenyl | 4-(benzyloxy)phenyl | 6.5 | 657.3 |

-continued
FORMULA 22
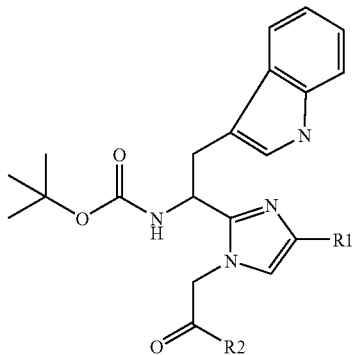
| | R1 | R2 | Tr(min) | [M + H]+ |
|---|---|---|---|---|
| 23 | 2-methoxyphenyl | 4-pentylphenyl | 6.8 | 621.4 |
| 24 | 2-methoxyphenyl | 3,4-dihydroquinolin-2(1H)-one-7-yl | 5.9 | |
| 25 | 2-methoxyphenyl | 5-chloro-3-methylbenzothiophen-2-yl | 6.7 | 655.2 |
| 26 | 2-methoxyphenyl | 3-methylbenzothiophen-2-yl | 6.4 | 607.2 |
| 27 | 2-methoxyphenyl | 5-bromothiophen-2-yl | 6.4 | 635.2 |
| 28 | 2-methoxyphenyl | 3-phenylisoxazol-5-yl | 6.5 | 618.3 |

-continued
FORMULA 22
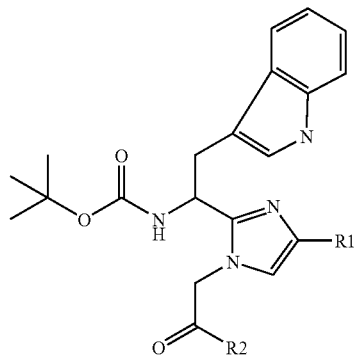
| | R1 | R2 | Tr(min) | [M + H]+ |
|---|---|---|---|---|
| 29 | 2-methoxyphenyl | 3-(2,4-dichlorophenyl)isoxazol-5-yl | 6.7 | 686.2 |
| 30 | 2-methoxyphenyl | indol-3-ylmethyl | 2 OU 6.3 | 504.3 |
| 31 | 2-methoxyphenyl | 2-phenylethyl | 6.4 | 579.3 |
| 32 | 2-methoxyphenyl | 3,4-difluorophenyl | 6.3 | 587.2 |
| 33 | 4-nitrophenyl | 4-(trifluoromethoxy)phenyl | 7.3 | 504.3 |
| 34 | 4-nitrophenyl | 2,3-dihydrobenzo[1,4]dioxin-6-yl | 7.0 | 624.2 |
| 35 | 4-nitrophenyl | 2,3-dihydrobenzo[1,4]dioxin-6-yl | 7.0 | 610.2 |

-continued
FORMULA 22
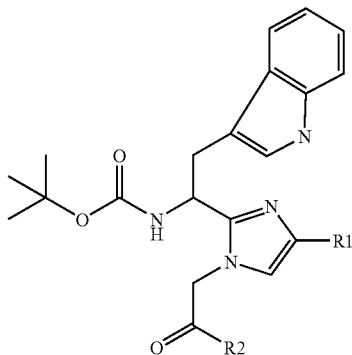
| | R1 | R2 | Tr(min) | [M + H]+ |
|---|---|---|---|---|
| 36 | -C6H4-NO2 (para) | 3,4,5-trimethoxyphenyl | 7.0 | 656.3 |
| 37 | -C6H4-NO2 (para) | 4-chloro-3-nitrophenyl | 7.0 | 645.1 |
| 38 | -C6H4-NO2 (para) | 4-benzyloxyphenyl | 7.3 | 672.3 |
| 39 | -C6H4-NO2 (para) | 4-pentylphenyl | 7.6 | 636.3 |
| 40 | -C6H4-NO2 (para) | 2-oxo-1,2,3,4-tetrahydroquinolin-7-yl | 7.8 | 635.2 |
| 41 | -C6H4-NO2 (para) | 5-chloro-3-methylbenzothiophen-2-yl | 7.5 ? | 670.2 ? |
| 42 | -C6H4-NO2 (para) | 3-methylbenzothiophen-2-yl | 7.3 ? | 622.2 ? |
| 43 | -C6H4-NO2 (para) | 5-bromothiophen-2-yl | 7.3 | 650.1 |

-continued
FORMULA 22
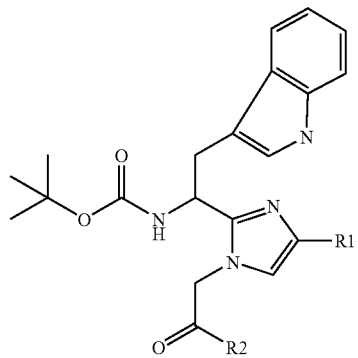
| | R1 | R2 | Tr(min) | [M + H]+ |
|---|---|---|---|---|
| 44 | 4-NO2-phenyl | 3-phenyl-isoxazol-5-yl | 7.3 | 633.2 |
| 45 | 4-NO2-phenyl | 3-(2,4-dichlorophenyl)-isoxazol-5-yl | 7.6 | 701.2 |
| 46 | 4-NO2-phenyl | 2-phenylethyl | 7.2 | 594.3 |
| 47 | 4-NO2-phenyl | 3,4-difluorophenyl | 7.2 | 602.2 |
| 48 | 4-Br-phenyl | 4-(OCF3)-phenyl | 7.3 | (683.14) THEO |
| 49 | 4-Br-phenyl | 2,3-dihydro-1,4-benzodioxin-6-yl | 6.7 | 657.2 |
| 50 | 4-Br-phenyl | 2,3-dihydro-1,4-benzodioxin-6-yl | 6.7 | 543.1 |

-continued
FORMULA 22
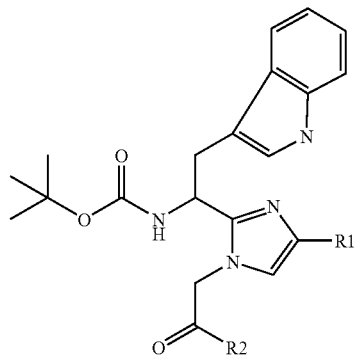
| | R1 | R2 | Tr(min) | [M + H]+ |
|---|---|---|---|---|
| 51 | 4-Br-phenyl | 3,4,5-trimethoxyphenyl | 6.7 | 589.2 |
| 52 | 4-Br-phenyl | 4-Cl-3-NO2-phenyl | 7.0 ? | 678.1 ? |
| 53 | 4-Br-phenyl | 4-benzyloxyphenyl | 7.0 | 705.2 |
| 54 | 4-Br-phenyl | 4-pentylphenyl | 7.2 | 699.3 |
| 55 | 4-Br-phenyl | 2-oxo-1,2,3,4-tetrahydroquinolin-7-yl | 7.3 | 668.1 |
| 56 | 4-Br-phenyl | 5-chloro-3-methylbenzothiophen-2-yl | 9.5 | 703.0 |
| 57 | 4-Br-phenyl | 3-methylbenzothiophen-2-yl | 8.6 | 655.0 |
| 58 | 4-Br-phenyl | 5-bromothiophen-2-yl | 8.7 | 683.0 |

-continued
FORMULA 22
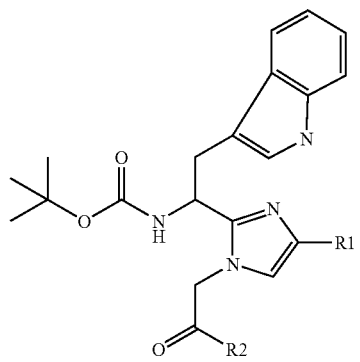
| | R1 | R2 | Tr(min) | [M + H]+ |
|---|---|---|---|---|
| 59 | 4-Br-phenyl | 3-phenyl-isoxazol-5-yl | 9.0 | 666.1 |
| 60 | 4-Br-phenyl | 3-(2,4-dichlorophenyl)-isoxazol-5-yl | 9.8 | 734.0 |
| 61 | 4-Br-phenyl | 1H-indol-3-ylmethyl | 8.0 | 652 |
| 62 | 4-Br-phenyl | 2-phenylethyl | 8.5 | 627.1 |
| 63 | 4-Br-phenyl | 3,4-difluorophenyl | 8.5 | 635.1 |
| 64 | tert-butyl | 4-(trifluoromethoxy)phenyl | 7.3 | 585.2 |
| 65 | tert-butyl | 2,3-dihydrobenzo[1,4]dioxin-6-yl | 6.7 | 559.2 |

-continued
FORMULA 22
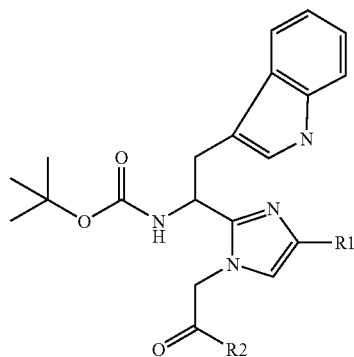
| | R1 | R2 | Tr(min) | [M + H]+ |
|---|---|---|---|---|
| 66 | t-Bu | 2,3-dihydrobenzo[1,4]dioxin-6-yl | 6.7 | 545.2 |
| 67 | t-Bu | 3,4,5-trimethoxyphenyl | 6.7 | 591.3 |
| 68 | t-Bu | 4-chloro-3-nitrophenyl | 7.0 | 580.2 |
| 69 | t-Bu | 4-benzyloxyphenyl | 7.6 | 607.3 |
| 70 | t-Bu | 4-pentylphenyl | 8.0 | 571.3 |
| 71 | t-Bu | 2-oxo-1,2,3,4-tetrahydroquinolin-7-yl | 6.1 | 570.3 |
| 72 | t-Bu | 5-chloro-3-methylbenzo[b]thiophen-2-yl | 7.3 | 605.2 |

-continued
FORMULA 22
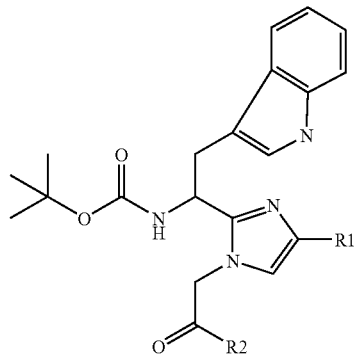
| | R1 | R2 | Analysis Tr(min) | [M + H]+ |
|---|---|---|---|---|
| 73 | tBu | 3-methylbenzothiophene | 7.1 | 585.2 |
| 74 | tBu | 5-bromothiophene | 7.0 | 585.1 |
| 75 | tBu | 3-phenylisoxazole | 7.1 | 568.2 |
| 76 | tBu | 3-(2,4-dichlorophenyl)isoxazole | 7.6 | 536.2 |
| 77 | tBu | 3-methylindole | 6.8 | 554.2 |
| 78 | tBu | phenethyl | 7.1 | 529.3 |
| 79 | tBu | 3,4-difluorophenyl | 6.9 | 537.2 |

313
FORMULA 23
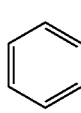
| | R1 | Analysis | |
|---|---|---|---|
| | | Tr | [M + H]+ |
| 1 | 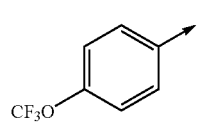 | 5.5 | 448.3 |
| 2 | 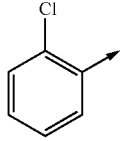 | 5.8 | 482.2 |
| 3 | 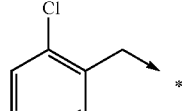 | 5.9 | 482.2 |
| 4 | 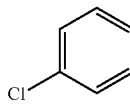 | 5.7 | 478.3 |
| 5 | 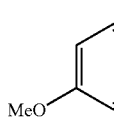 | 6.2 | 516.2 |
| 6 | 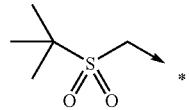 | 6.5 | 504.3 |
| 7 | 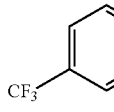 | 5.7 | 484.3 |
314
-continued
FORMULA 23
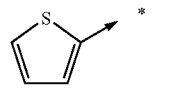
| | R1 | Analysis | |
|---|---|---|---|
| | | Tr | [M + H]+ |
| 8 | 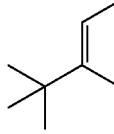 | 6.3 | 532.2 |
| 9 | 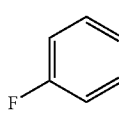 | 6.2 | 530.2 |
| 10 | 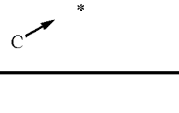 | 5.6 | 506.3 |
| 11 | | 5.5 | 454.2 |
| 12 | | 5.0 | 386.3 |

FORMULA 24
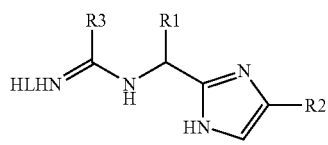
| | R1 | R2 | R3 | Analysis Tr | [M + H]+ |
|---|---|---|---|---|---|
| 1 (S) | BnOCH2-phenyl-* | phenyl-* | thiophene-* | 5.6 | 403.1 |
| 2 (S) | BnOCH2-phenyl-* | phenyl-* | C-* | 4.9 | 335.2 |
| 3 (S) | 4-MeO-benzyl-* | phenyl-* | thiophene-* | 5.3 | 403.2 |
| 4 (S) | 4-MeO-benzyl-* | phenyl-* | C-* | 4.8 | 335.3 |
| 5 (R) | indol-3-ylmethyl-* | 4-MeO-phenyl-* | thiophene-* | 5.1 | 442.2 |
| 6 (R) | indol-3-ylmethyl-* | 4-MeO-phenyl-* | C-* | 4.7 | 374.2 |
| 7 (R,S) | indol-3-ylmethyl-* | 2-MeO-phenyl-* | thiophene-* | 5.2 | 442.2 |

-continued
FORMULA 24
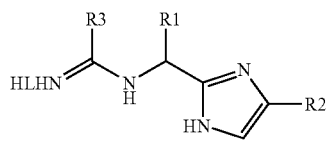
| | R1 | R2 | R3 | Tr | [M + H]+ |
|---|---|---|---|---|---|
| 8 (R,S) | indol-3-ylmethyl | 2-methoxyphenyl | C | 4.7 | 374.2 |
| 9 (R,S) | indol-3-ylmethyl | tert-butyl | 2-thienyl | 4.5 | 392.2 |
| 10 (R,S) | indol-3-ylmethyl | tert-butyl | C | 4.3 | 324.3 |
| 11 (S) | (1-benzylimidazol-4-yl)methyl | phenyl | 2-thienyl | 4.8 | 455.2 |
| 12 (S) | (1-benzylimidazol-4-yl)methyl | phenyl | C | 4.5 | 387.2 |
| 13 (S) | benzyl | phenyl | 2-thienyl | 5.3 | 373.2 |
| 14 (S) | benzyl | phenyl | C | 4.7 | 305.2 |

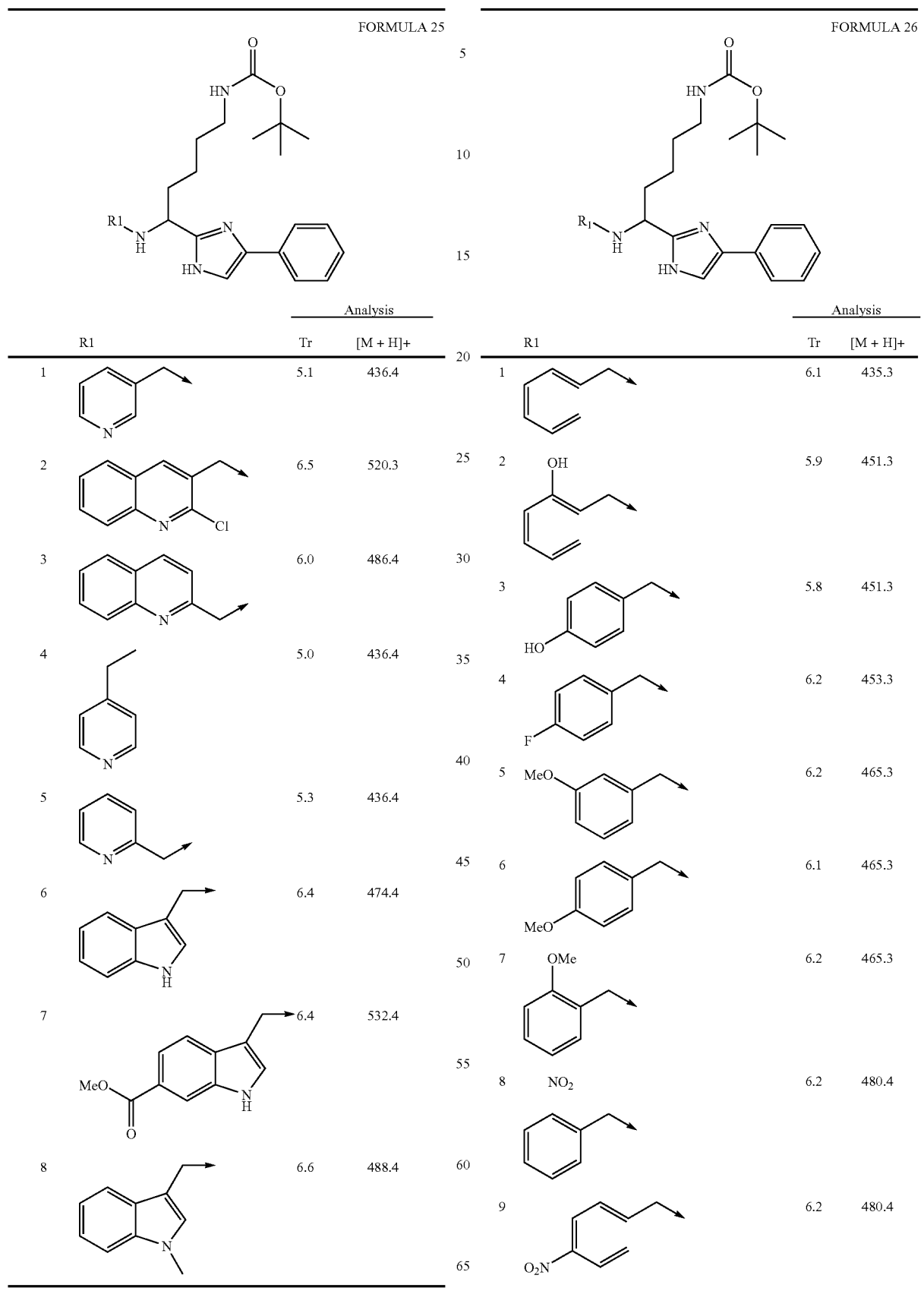
FORMULA 25
| | R1 | Tr | [M + H]+ |
|---|---|---|---|
| 1 | pyridin-3-ylmethyl | 5.1 | 436.4 |
| 2 | 2-chloroquinolin-3-ylmethyl | 6.5 | 520.3 |
| 3 | quinolin-2-ylmethyl | 6.0 | 486.4 |
| 4 | pyridin-4-ylmethyl | 5.0 | 436.4 |
| 5 | pyridin-2-ylmethyl | 5.3 | 436.4 |
| 6 | 1H-indol-3-ylmethyl | 6.4 | 474.4 |
| 7 | 6-(methoxycarbonyl)-1H-indol-3-ylmethyl | 6.4 | 532.4 |
| 8 | 1-methyl-1H-indol-3-ylmethyl | 6.6 | 488.4 |
FORMULA 26
| | R1 | Tr | [M + H]+ |
|---|---|---|---|
| 1 | phenyl-CH2 | 6.1 | 435.3 |
| 2 | 2-hydroxyphenyl-CH2 | 5.9 | 451.3 |
| 3 | 4-hydroxyphenyl-CH2 | 5.8 | 451.3 |
| 4 | 4-fluorophenyl-CH2 | 6.2 | 453.3 |
| 5 | 3-methoxyphenyl-CH2 | 6.2 | 465.3 |
| 6 | 4-methoxyphenyl-CH2 | 6.1 | 465.3 |
| 7 | 2-methoxyphenyl-CH2 | 6.2 | 465.3 |
| 8 | 2-nitrophenyl-CH2 | 6.2 | 480.4 |
| 9 | 3-nitrophenyl-CH2 | 6.2 | 480.4 |

-continued
FORMULA 26
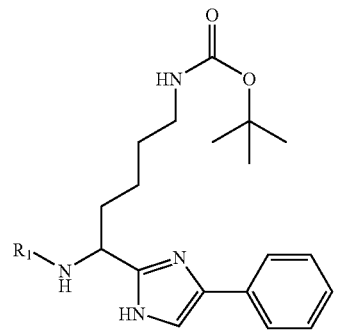
| | R1 | Analysis | |
|---|---|---|---|
| | | Tr | [M + H]+ |
| 10 | 3,4-diCl-benzyl | 6.7 | 503.3 |
| 11 | 2-NO2-3-MeO-benzyl | 6.4 | 510. |
| 12 | 4-Br-benzyl | 6.5 | 513.3 |
| 13 | thiophen-2-ylmethyl | 6.0 | 441.3 |
| 14 | 3,4,5-triMeO-benzyl | 6.1 | 525.4 |
| 15 | 4-benzyloxy-benzyl | 7.0 | 541.4 |
| 16 | 2-F-benzyl | 6.1 | 453.4 |
| 17 | 2-benzyloxy-ethyl | 6.5 | 479.4 |
-continued
FORMULA 26
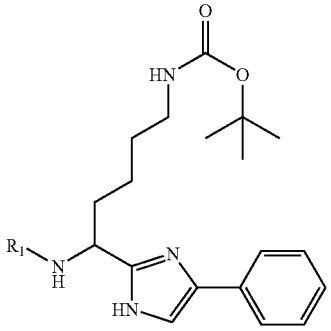
| | R1 | Analysis | |
|---|---|---|---|
| | | Tr | [M + H]+ |
| 18 | 2-CF3-benzyl | 6.6 | 503.4 |
| 19 | biphenyl-4-ylmethyl | 6.9 | 511.4 |
| 20 | 2-Br-benzyl | 6.4 | 513.3 |
| 21 | 4-NMe2-benzyl | 5.8 | 478.4 |
| 22 | 4-OCF3-benzyl | 6.8 | 519.3 |
| 23 | 4-(3-NMe2-propoxy)-benzyl | 5.1 | 536.5 |
| 24 | 3-F-4-MeO-benzyl | 6.2 | 483.4 |
| 25 | 4-tBu-benzyl | 7.0 | 491.4 |

-continued

FORMULA 26

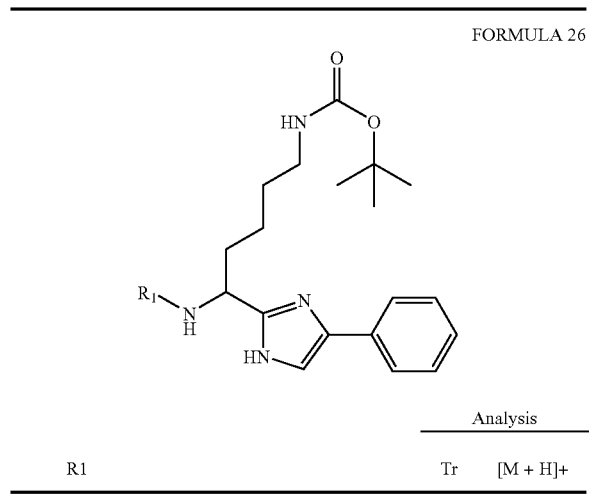

| | R1 | Analysis Tr | [M + H]+ |
|---|---|---|---|
| 26 | Br-phenyl-CH2 | 6.5 | 513.3 |
| 27 | 3-(4-OMe-phenoxy)phenyl-CH2 | 5.9 | 557.4 |

-continued

FORMULA 27

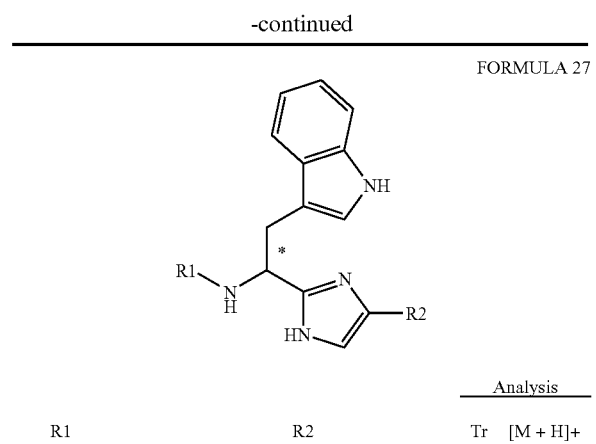

| | R1 | R2 | | Analysis Tr | [M + H]+ |
|---|---|---|---|---|---|
| 3 | 2-chloroquinolin-3-ylmethyl | phenyl | (R) | 4.8 | 394.3 |
| 4 | pyridin-2-ylmethyl | phenyl | (R) | 4.9 | 394.3 |
| 5 | pyridin-3-ylmethyl | phenyl | (S) | 4.8 | 394.3 |
| 6 | 2-chloroquinolin-3-ylmethyl | phenyl | (S) | 6.4 | 478.3 |
| 7 | quinolin-2-ylmethyl | phenyl | (S) | 5.6 | 444.3 |
| 8 | pyridin-4-ylmethyl | phenyl | (S) | 4.7 | 394.3 |
| 9 | pyridin-2-ylmethyl | phenyl | (S) | 4.9 | 394.3 |
| 10 | pyridin-3-ylmethyl | 2-OMe-phenyl | (R,S) | 4.9 | 424.3 |
| 11 | 2-chloroquinolin-3-ylmethyl | 2-OMe-phenyl | (R,S) | 6.6 | 508.3 |

FORMULA 27

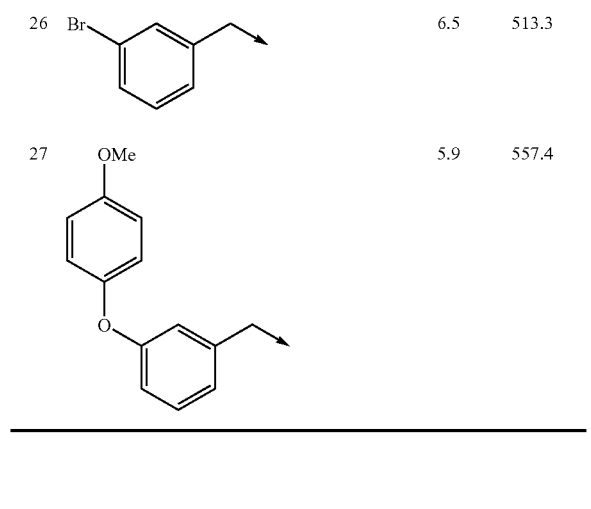

| | R1 | R2 | | Analysis Tr | [M + H]+ |
|---|---|---|---|---|---|
| 1 | 2-chloroquinolin-3-ylmethyl | phenyl | (R) | 6.4 | 478.3 |
| 2 | quinolin-2-ylmethyl | phenyl | (R) | 5.9 | 444.3 |

325

-continued

FORMULA 27

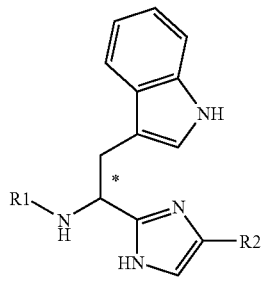

| R1 | R2 | Tr | [M + H]+ |
|---|---|---|---|
| 12 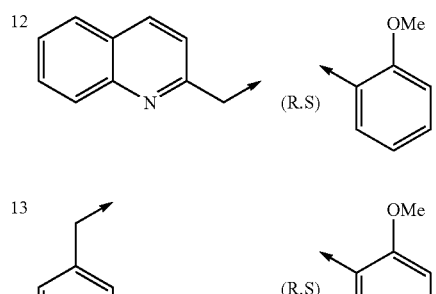 quinolin-2-ylmethyl | 2-OMe-phenyl (R,S) | 5.7 | 474.3 |
| 13 pyridin-4-ylmethyl | 2-OMe-phenyl (R,S) | 4.49 | 424.3 |
| 14 pyridin-2-ylmethyl | 2-OMe-phenyl (R,S) | 5.0 | 424.3 |
| 15 pyridin-3-ylmethyl | 4-OMe-phenyl (R) | 4.9 | 424.3 |
| 16 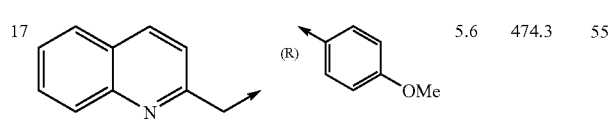 2-chloroquinolin-3-ylmethyl | 4-OMe-phenyl (R) | 6.5 | 508.3 |
| 17 quinolin-2-ylmethyl | 4-OMe-phenyl (R) | 5.6 | 474.3 |
| 18 pyridin-4-ylmethyl | 4-OMe-phenyl (R) | 4.9 | 424.3 |

326

-continued

FORMULA 27

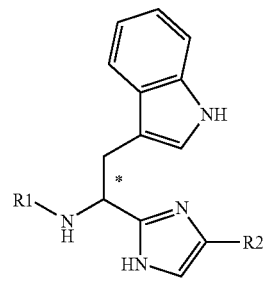

| R1 | R2 | Tr | [M + H]+ |
|---|---|---|---|
| 19 pyridin-2-ylmethyl | 4-OMe-phenyl (R) | 5.0 | 424.3 |
| 20 pyridin-3-ylmethyl | 4-OMe-phenyl (S) | 4.9 | 424.3 |
| 21 2-chloroquinolin-3-ylmethyl | 4-OMe-phenyl (S) | 6.5 | 508.3 |
| 22 quinolin-2-ylmethyl | 4-OMe-phenyl (S) | 5.6 | 474.3 |
| 23 pyridin-4-ylmethyl | 4-OMe-phenyl (S) | 4.9 | 424.3 |
| 24 pyridin-2-ylmethyl | 4-OMe-phenyl (S) | 5.0 | 424.3 |

FORMULA 28
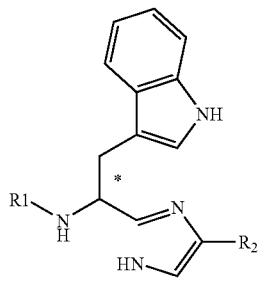
| | R1 | R2 | Tr | [M + H]+ |
|---|---|---|---|---|
| 1 | F, MeO-phenyl-CH2 | (S) phenyl | 6.1 | 441.2 |
| 2 | Br-phenyl-CH2 | (S) phenyl | 6.4 | 471.2 |
| 3 | n-butyl | (S) phenyl | 5.8 | 359.3 |
| 4 | n-pentyl | (S) phenyl | 6.1 | 373.3 |
| 5 | MeS-CH2CH2CH2 | (S) phenyl | 5.8 | 391.2 |
| 6 | neopentyl-CH2 | (S) phenyl | 6.2 | 387.3 |
| 7 | PhCH2O-CH2CH2 | (S) phenyl | 7.1 | 437.5 |
| 8 | cyclohexyl-CH2 | (S) phenyl | 6.3 | 399.3 |
| 9 | 4-tBu-phenyl-CH2 | (S) phenyl | 6.4 | 387.3 |
| 10 | n-hexyl | (S) phenyl | 6.4 | 387.3 |

-continued
FORMULA 28
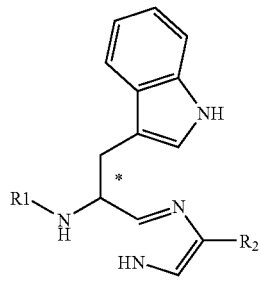
| | R1 | R2 | Tr | [M + H]+ |
|---|---|---|---|---|
| 11 | F, MeO-benzyl | OMe (R.S) | 6.1 | 471.2 |
| 12 | Br-benzyl | OMe (R.S) | 6.5 | 501.1 |
| 13 | propyl | OMe (R.S) | 5.8 | 389.3 |
| 14 | butyl | OMe (R.S) | 6.1 | 403.3 |
| 15 | MeS-propyl | OMe (R.S) | 5.8 | 421.2 |
| 16 | neopentyl | OMe (R.S) | 6.2 | 417.3 |
| 17 | PhCH2O-ethyl | OMe (R.S) | 7.0 | 467.2 |

-continued
FORMULA 28
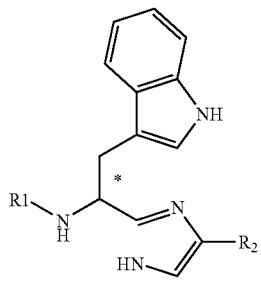
| R1 | R2 | Analysis Tr | [M + H]+ |
|---|---|---|---|
| 18 cyclohexylmethyl | 2-OMe-phenyl (R.S) | 6.3 | 429.3 |
| 19 4-tert-butylbenzyl | 2-OMe-phenyl (R.S) | 6.9 | 479.3 |
| 20 n-hexyl | 2-OMe-phenyl (R.S) | 6.4 | 417.3 |
| 21 3-F-4-MeO-benzyl | 4-OMe-phenyl (R) | 6.0 | 471.2 |
| 22 3-Br-benzyl | 4-OMe-phenyl (R) | 6.4 | 501.1 |
| 23 n-pentyl | 4-OMe-phenyl (R) | 6.0 | 403.3 |
| 24 3,3-dimethylbutyl | 4-OMe-phenyl (R) | 6.1 | 471.3 |
| 25 2-(benzyloxy)ethyl | 4-OMe-phenyl (R) | 6.9 | 467.1 |
| 26 cyclohexylmethyl | 4-OMe-phenyl (R) | 6.3 | 429.3 |

-continued

FORMULA 28

| | R1 | R2 | Analysis Tr | [M + H]+ |
|---|---|---|---|---|
| 27 | 4-tert-butylbenzyl | (R) 4-methoxyphenyl | 6.8 | 479.3 |
| 28 | n-heptyl | (R) 4-methoxyphenyl | 6.4 | 417.3 |
| 29 | 3-fluoro-4-methoxybenzyl | (S) 4-methoxyphenyl | 6.1 | 471.2 |
| 30 | 3-bromobenzyl | (S) 4-methoxyphenyl | 6.4 | 501.1 |
| 31 | n-pentyl | (S) 4-methoxyphenyl | 5.8 | 389.3 |
| 32 | 3,3-dimethylbutyl | (S) 4-methoxyphenyl | 6.2 | 417.3 |
| 33 | 2-(benzyloxy)ethyl | (S) 4-methoxyphenyl | 6.9 | 467.1 |
| 34 | cyclohexylmethyl | (S) 4-methoxyphenyl | 6.3 | 429.3 |
| 35 | 4-tert-butylbenzyl | (S) 4-methoxyphenyl | 6.8 | 479.3 |

-continued
FORMULA 28
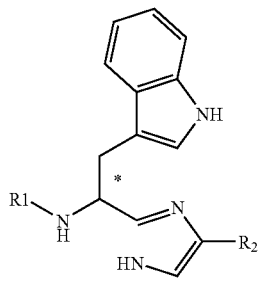
| R1 | R2 | Tr | [M + H]+ |
|---|---|---|---|
| 36 (hexyl) | (S) 4-OMe-phenyl | 6.4 | 417.3 |
FORMULA 29
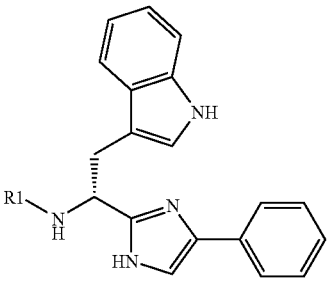
| | R1 | Tr | [M + H]+ |
|---|---|---|---|
| 1 | benzyl | 5.9 | 393.3 |
| 2 | 2-OH-benzyl | 5.7 | 409.3 |
| 3 | 4-OH-benzyl | 5.6 | 409.3 |
| 4 | 4-F-benzyl | 6.1 | 411.3 |
| 5 | 3-MeO-benzyl | 6.0 | 423.3 |
-continued
FORMULA 29
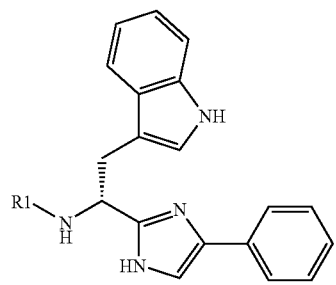
| | R1 | Tr | [M + H]+ |
|---|---|---|---|
| 6 | 2-OMe-benzyl | 6.1 | 423.3 |
| 7 | 4-NO2-benzyl | 6.1 | 438.3 |
| 8 | 3,4-diCl-benzyl | 6.6 | 461.2 |
| 9 | 2-NO2-3-MeO-benzyl | 6.2 | 393.3 |

-continued
FORMULA 29
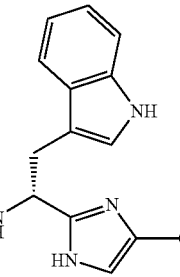
| R1 | Analysis Tr | [M + H]+ |
|---|---|---|
| 10 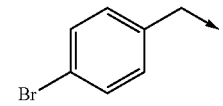 | 6.4 | 471.2 |
| 11 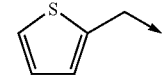 | 5.9 | 399.3 |
| 12 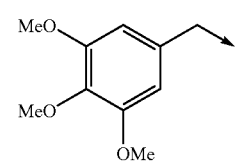 | 5.9 | 483.4 |
| 13 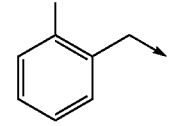 | 6.3 | 471.2 |
| 14 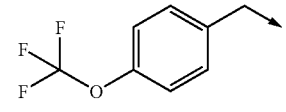 | 6.7 | 477.3 |
| 15 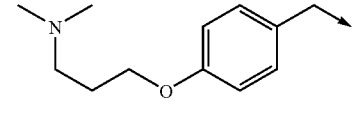 | 6.5 | 494.4 |
| 16 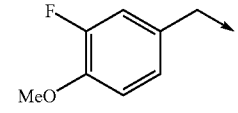 | 6.1 | 441.3 |
| 17 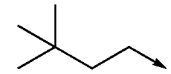 | 6.3 | 387.3 |
| 18 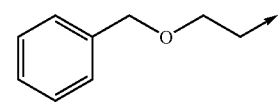 | 6.4 | 437.3 |
| 19 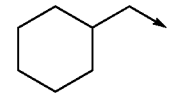 | 6.4 | 399.4 |
-continued
FORMULA 29
| R1 | Analysis Tr | [M + H]+ |
|---|---|---|
| 20 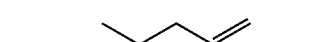 | 6.9 | 449.4 |
| 21 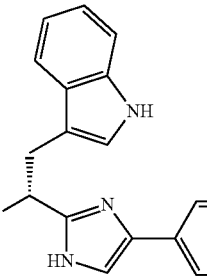 | 6.4 | 387.4 |
FORMULA 30
| R1 | Analysis Tr | [M + H]+ |
|---|---|---|
| 1 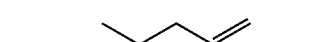 | 5.4 | 458.2 |
| 2 | 5.7 | 460.2 |
| 3 | 5.3 | 499.3 |
| 4 | 6.1 | 522.3 |

339

-continued

FORMULA 30

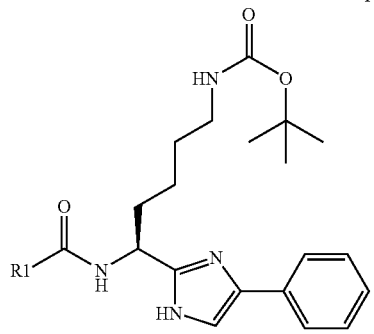

| R1 | Analysis Tr | [M + H]+ |
|---|---|---|
| 5 ![indole-ethylamine] | 6.3 | 531.3 |
| 6 ![N-phenylpiperazine] | 6.4 | 533.3 |
| 7 ![tetrahydro-β-carboline] | 5.6 | 543.3 |
| 8 ![benzylpiperazine] | 5.1 | 547.3 |
| 9 ![4-F-phenylpiperazine] | 6.5 | 551.3 |
| 10 ![2-OMe-phenylpiperazine] | 6.1 | 563.3 |
| 11 ![3-Cl-phenylpiperazine] | 6.9 | 567.2 |
| 12 ![dibenzylamine] | 7.2 | 568.2 |
| 13 ![nitro-piperazine] | 5.5 | 578.2 |

340

-continued

FORMULA 30

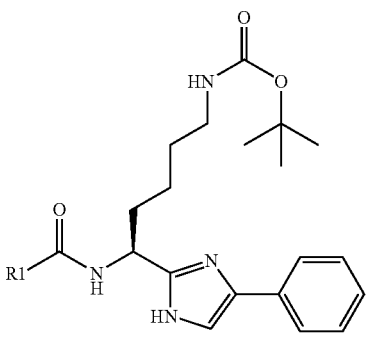

| R1 | Analysis Tr | [M + H]+ |
|---|---|---|
| 14 ![dimethoxy-tetrahydropyridine] | 5.1 | 564.3 |
| 15 ![4-Cl-phenylpiperazine] | 6.8 | 567.2 |
| 16 ![N-methylpiperazine] | 4.9 | 534.3 |
| 17 ![4-benzylpiperidine] | 7.0 | 546.3 |
| 18 ![ethyl ester benzylamino] | 6.8 | 578.3 |
| 19 ![methylenedioxybenzyl piperazine] | 5.1 | 591.3 |
| 20 ![3-CF3-phenylpiperazine] | 7.1 | 601.3 |

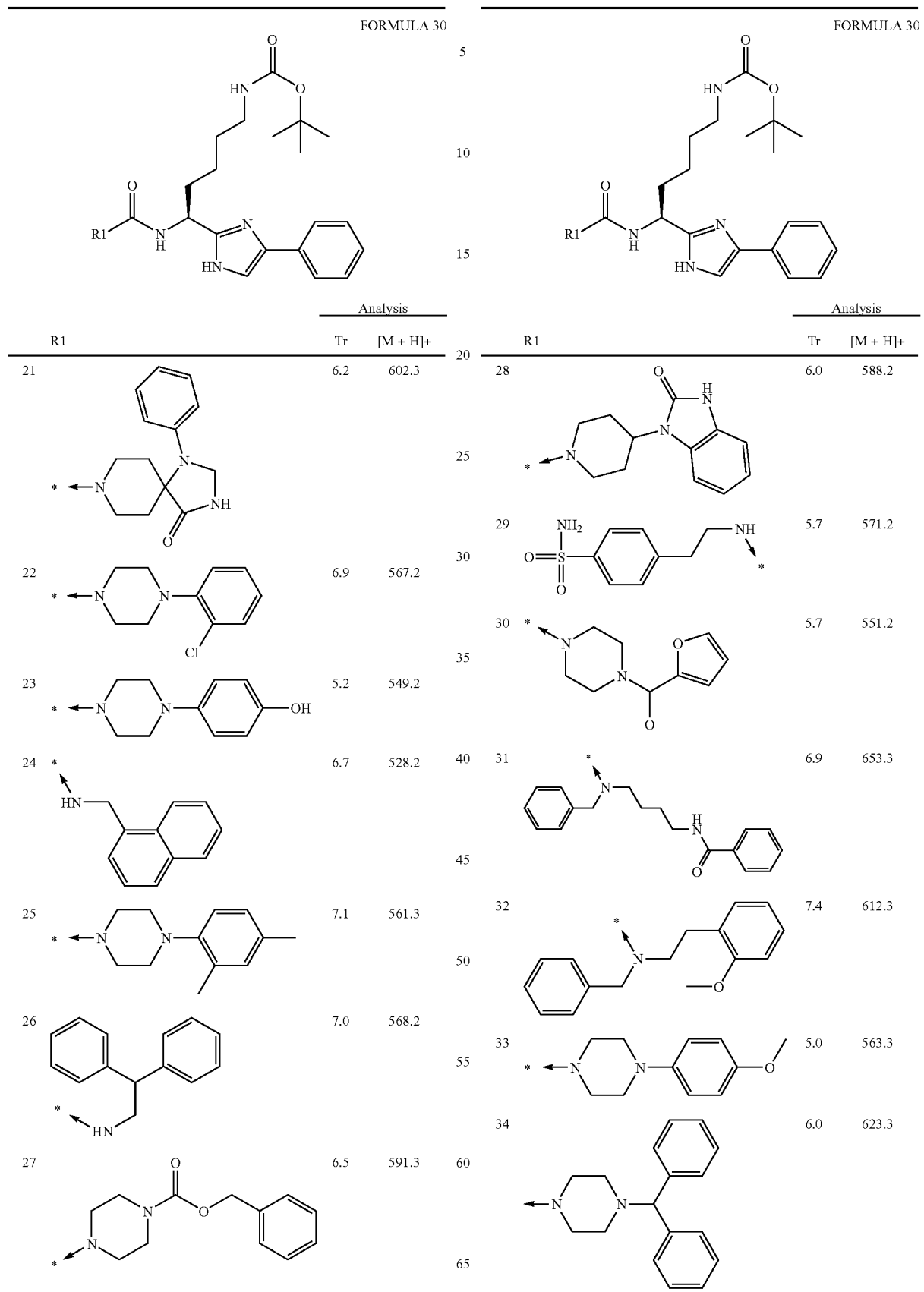

-continued
FORMULA 30
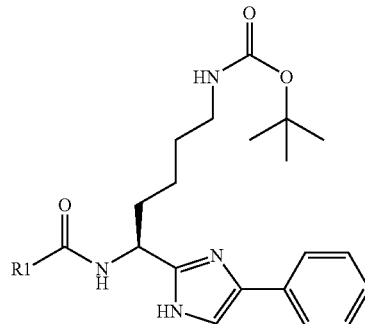
| R1 | Analysis Tr | [M + H]+ |
|---|---|---|
| 35 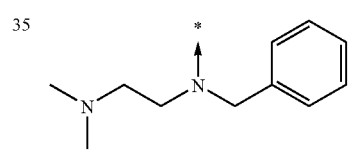 | 5.2 | 549.3 |
| 36 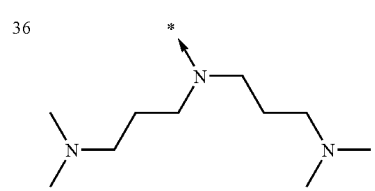 | 4.4 | 558.3 |
| 37 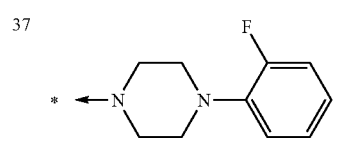 | 6.6 | 551.3 |
FORMULA 31
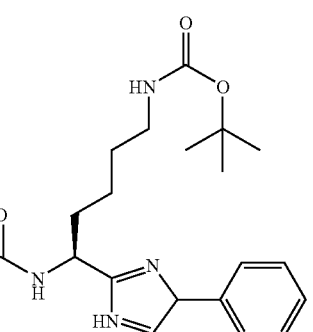
| R1 | Analysis Tr | [M + H]+ |
|---|---|---|
| 1 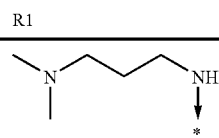 | 4.7 | 473.3 |
-continued
FORMULA 31
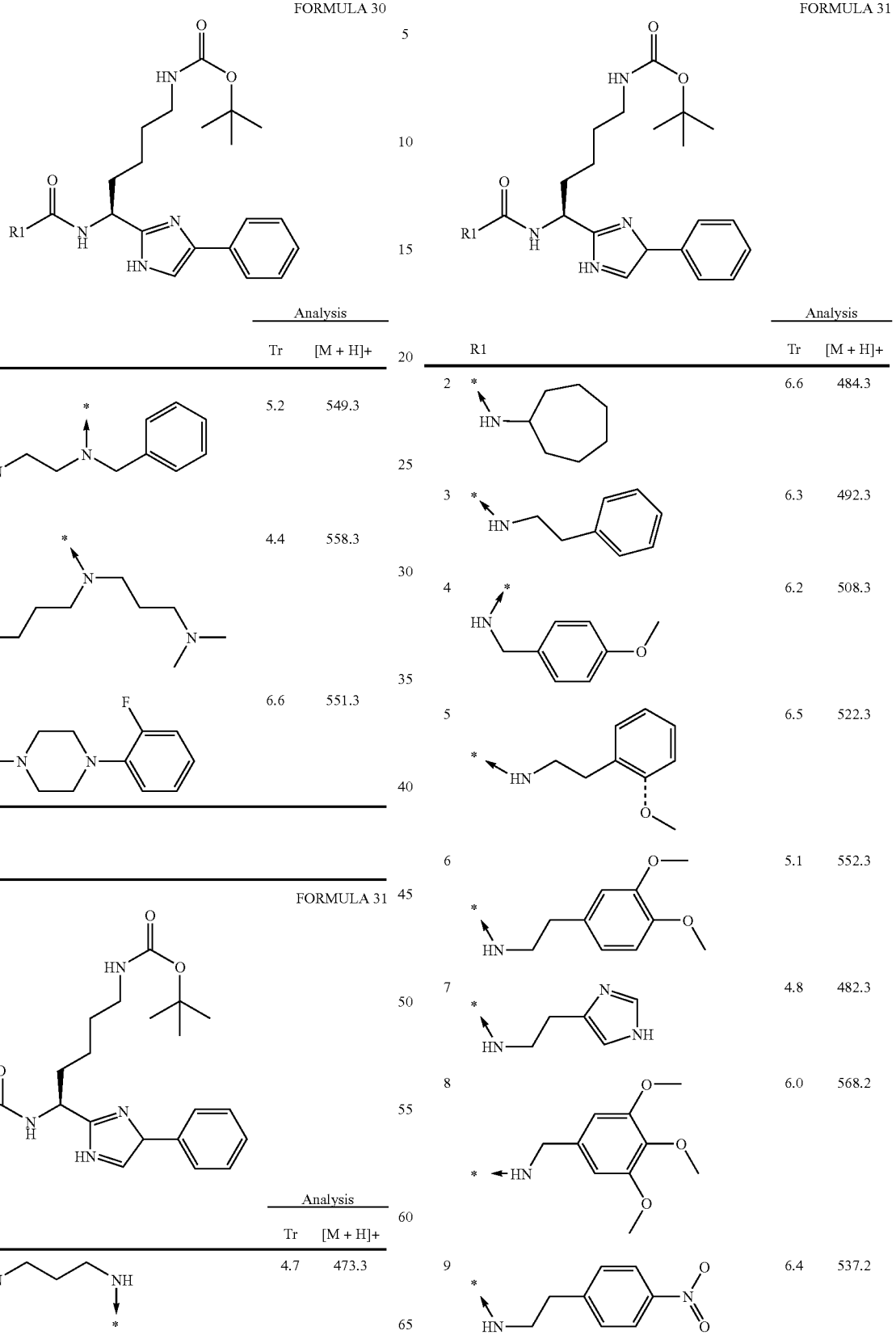
| | R1 | Analysis Tr | [M + H]+ |
|---|---|---|---|
| 2 | cycloheptyl-NH- | 6.6 | 484.3 |
| 3 | phenethyl-NH- | 6.3 | 492.3 |
| 4 | 4-methoxybenzyl-NH- | 6.2 | 508.3 |
| 5 | 2-methoxyphenethyl-NH- | 6.5 | 522.3 |
| 6 | 3,4-dimethoxyphenethyl-NH- | 5.1 | 552.3 |
| 7 | imidazolyl-ethyl-NH- | 4.8 | 482.3 |
| 8 | 3,4,5-trimethoxybenzyl-NH- | 6.0 | 568.2 |
| 9 | 4-nitrophenethyl-NH- | 6.4 | 537.2 |

-continued

FORMULA 31

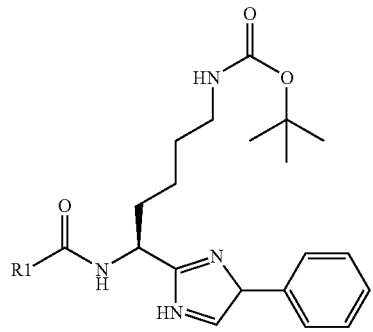

| R1 | Analysis Tr | [M + H]+ |
|---|---|---|
| 10 (neopentyl-NH) | 6.5 | 472.3 |
| 11 (4-pyridyl-CH2-NH) | 4.7 | 479.3 |
| 12 (2-pyridyl-ethyl-NH) | 4.8 | 493.3 |
| 13 (morpholinopropyl-NH) | 4.8 | 515.3 |
| 14 (N-ethoxycarbonyl-piperidin-4-yl-NH) | 5.9 | 543.3 |
| 15 (5-nitropyridin-2-yl-aminoethyl-NH) | 5.0 | 553.2 |
| 16 (benzylthio-ethyl-NH) | 6.6 | 538.2 |
| 17 (3,4-dihydroxybenzyl-NH) | 5.5 | 510.3 |

-continued

FORMULA 31

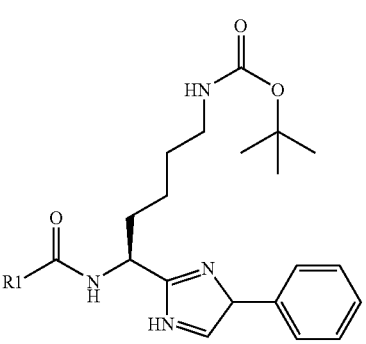

| R1 | Analysis Tr | [M + H]+ |
|---|---|---|
| 18 (1,2-diethylpyrazolidin-4-yl-NH) | 4.9 | 514.3 |
| 19 (tert-butyl-NH) | 6.1 | 444.3 |
| 20 (4-(3-chlorophenyl)piperazin-1-yl-ethyl-NH) | 5.8 | 610.3 |
| 21 (diphenylmethyl-NH) | 7.0 | 554.3 |
| 22 (2-pyridyl-CH2-NH) | 4.9 | 479.3 |
| 23 (3-chlorobenzyl-NH) | 6.5 | 512.2 |

-continued
FORMULA 31
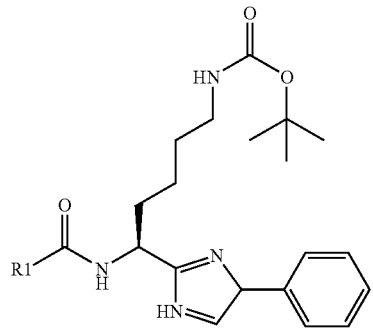
| R1 | | Analysis | |
|---|---|---|---|
| | | Tr | [M + H]+ |
| 24 | 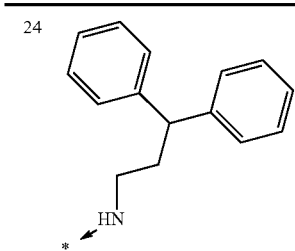 | 7.2 | 582.3 |
| 25 | 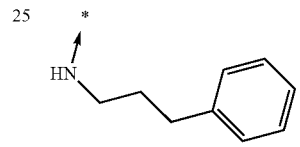 | 6.6 | 506.3 |
| 26 | 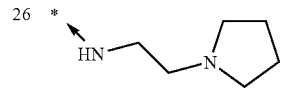 | 4.8 | 485.3 |
| 27 | 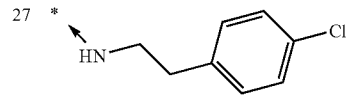 | 6.7 | 526.2 |
| 28 | 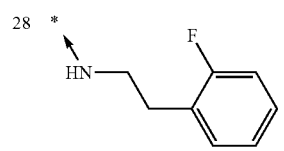 | 6.4 | 510.3 |
| 29 | 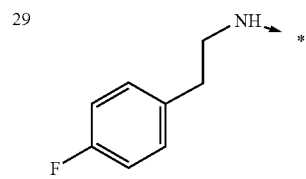 | 6.4 | 510.3 |
| 30 | 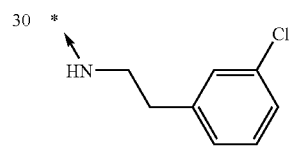 | 6.7 | 526.2 |
-continued
FORMULA 31
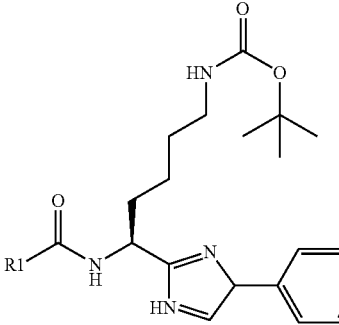
| R1 | Analysis | |
|---|---|---|
| | Tr | [M + H]+ |
| 31 (4-Br phenethyl) | 6.8 | 570.2 |
| 32 (3-CF₃ benzyl) | 6.7 | 546.2 |
| 33 (4-CF₃ benzyl) | 6.8 | 546.2 |
| 34 (3-pyridylmethyl) | 4.8 | 479.3 |
| 35 (2-methoxybenzyl) | 5.3 | 508.3 |
| 36 (2-Cl benzyl) | 5.4 | 512.2 |
| 37 (3-F benzyl) | 6.3 | 496.3 |
| 38 (2-F benzyl) | 6.2 | 496.3 |

-continued
FORMULA 31
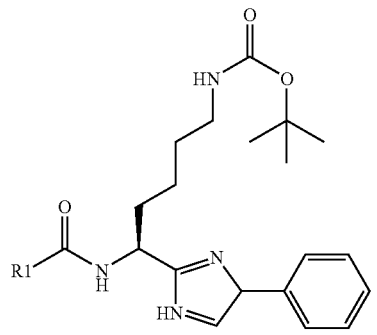
| R1 | | Analysis | |
|---|---|---|---|
| | | Tr | [M + H]+ |
| 39 | HN—CH2—C6H4—F (4-F) * | 6.3 | 496.3 |
| 40 | Me-N(piperazine)-N-(CH2)3-NH—* | 4.5 | 528.3 |
FORMULA 32
R1 structure with Boc-protected aminopentyl, urea linkage, imidazole-phenyl
| R1 | | Analysis | |
|---|---|---|---|
| | | Tr | [M + H]+ |
| 3 | 2-Cl-C6H4 | 5.4 | 498.2 |
| 2 | 3-Cl-C6H4 | 6.6 | 498.2 |
| 3 | 4-Cl-C6H4 | 6.6 | 498.2 |
-continued
FORMULA 32
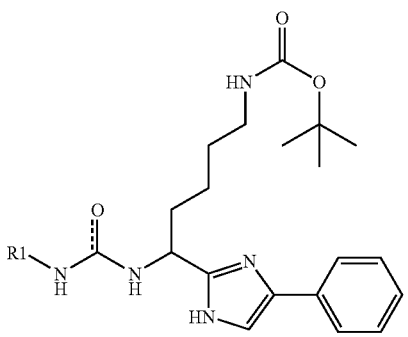
| R1 | | Analysis | |
|---|---|---|---|
| | | Tr | [M + H]+ |
| 4 | 2-Br-C6H4 | 6.4 | 542.1 |
| 5 | 3-Br-C6H4 | 6.6 | 542.1 |
| 6 | 4-Br-C6H4 | 6.7 | 542.1 |
| 7 | 3-F-C6H4 | 6.3 | 482.2 |
| 8 | 2,4-diF-C6H3 | 6.3 | 500.2 |
| 9 | 2,5-diF-C6H3 | 6.4 | 500.2 |
| 10 | 2-NO2-C6H4 | 6.3 | 509.2 |
| 11 | 3-NO2-C6H4 | 6.4 | 509.2 |

-continued
FORMULA 32
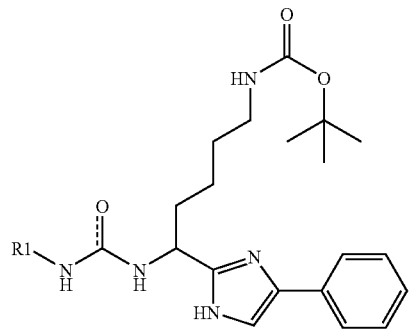
| | R1 | Analysis Tr | [M + H]+ |
|---|---|---|---|
| 12 | 4-O$_2$N-C$_6$H$_4$ | 6.4 | 509.2 |
| 13 | 2-CF$_3$-C$_6$H$_4$ | 6.5 | 532.2 |
| 14 | 3-CF$_3$-C$_6$H$_4$ | 6.8 | 532.2 |
| 15 | 4-CF$_3$-C$_6$H$_4$ | 6.8 | 532.2 |
| 16 | 2,5-(MeO)$_2$-C$_6$H$_3$ | 6.3 | 524.2 |
| 17 | 3-MeO-C$_6$H$_4$ | 6.2 | 494.2 |
| 18 | 4-MeO-C$_6$H$_4$ | 6.1 | 494.2 |
| 19 | 4-Cl-2-CF$_3$-C$_6$H$_3$ | 6.9 | 566.1 |
-continued
FORMULA 32
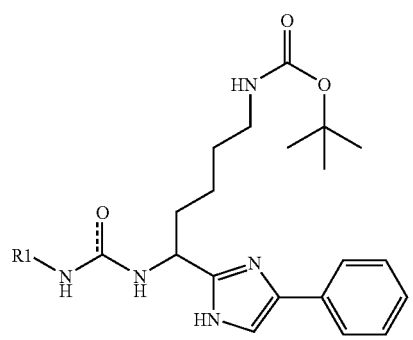
| | R1 | Analysis Tr | [M + H]+ |
|---|---|---|---|
| 20 | 4-F-3-NO$_2$-C$_6$H$_3$ | 6.4 | 527.2 |
FORMULA 33
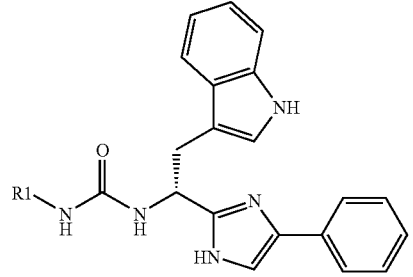
| | R1 | Analysis Tr | [M + H]+ |
|---|---|---|---|
| 1 | 3-Cl-C$_6$H$_4$ | 6.4 | 456.1 |
| 2 | 2-Br-C$_6$H$_4$ | 6.2 | 500.1 |
| 3 | 3-Br-C$_6$H$_4$ | 6.4 | 500.1 |

-continued
FORMULA 33
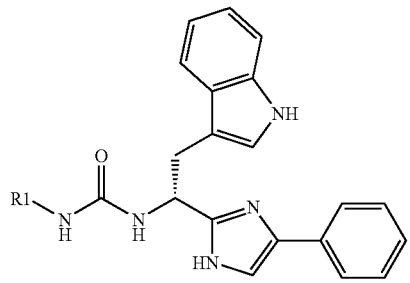
| | R1 | Analysis | |
|---|---|---|---|
| | | Tr | [M + H]+ |
| 4 | 4-Br-C6H4 | 6.4 | 500.1 |
| 5 | 3-F-C6H4 | 6.1 | 440.1 |
| 6 | 2,5-diF-C6H3 | 6.2 | 458.1 |
| 7 | 2-NO2-C6H4 | 5.1 | 467.1 |
| 8 | 4-NO2-C6H4 | 6.2 | 467.1 |
| 9 | 2-CF3-C6H4 | 6.2 | 490.1 |
| 10 | 4-CF3-C6H4 | 6.6 | 490.1 |
| 11 | 2,5-diMeO-C6H3 | 6.1 | 482.2 |
| 12 | 3-MeO-C6H4 | 6.0 | 452.2 |
-continued
FORMULA 33
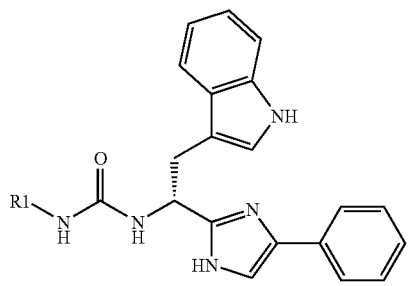
| | R1 | Analysis | |
|---|---|---|---|
| | | Tr | [M + H]+ |
| 13 | 4-MeO-C6H4 | 5.9 | 452.2 |
| 14 | 5-Cl-2-CF3-C6H3 | 6.7 | 524.1 |
| 15 | 4-F-3-NO2-C6H3 | 6.2 | 485.1 |
FORMULA 34
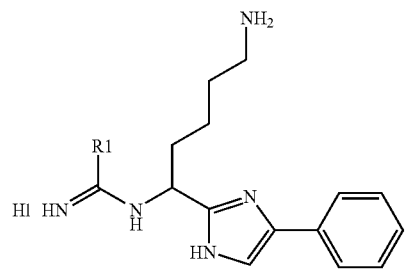
| | R1 | Analysis | |
|---|---|---|---|
| | | Tr | [M + H]+ |
| 1 | Ph* | 3.9 | 348.3 |
| 2 | 2-Cl-C6H4* | 4.0 | 382.2 |

-continued
FORMULA 34
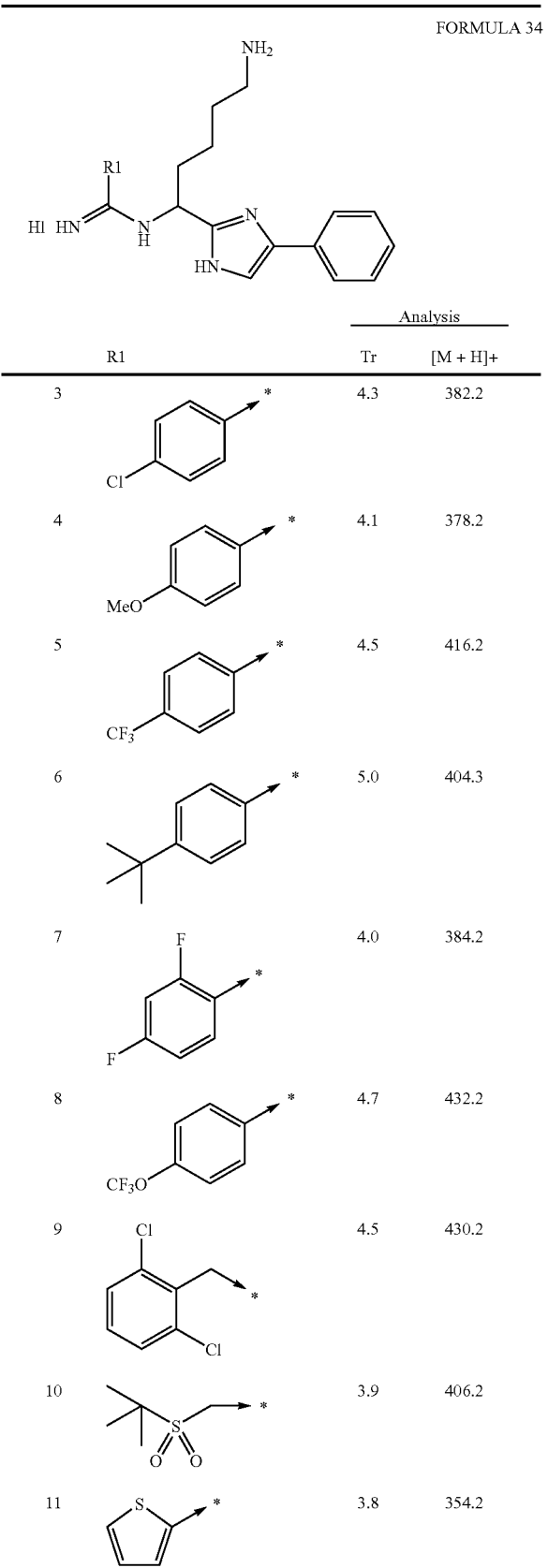
| R1 | | Analysis | |
|---|---|---|---|
| | | Tr | [M + H]+ |
| 3 | 4-Cl-C6H4 | 4.3 | 382.2 |
| 4 | 4-MeO-C6H4 | 4.1 | 378.2 |
| 5 | 4-CF3-C6H4 | 4.5 | 416.2 |
| 6 | 4-tBu-C6H4 | 5.0 | 404.3 |
| 7 | 2,4-F2-C6H3 | 4.0 | 384.2 |
| 8 | 4-CF3O-C6H4 | 4.7 | 432.2 |
| 9 | 2,6-Cl2-C6H3-CH2 | 4.5 | 430.2 |
| 10 | tBu-SO2-CH2 | 3.9 | 406.2 |
| 11 | thiophene-2-yl | 3.8 | 354.2 |
-continued
FORMULA 34
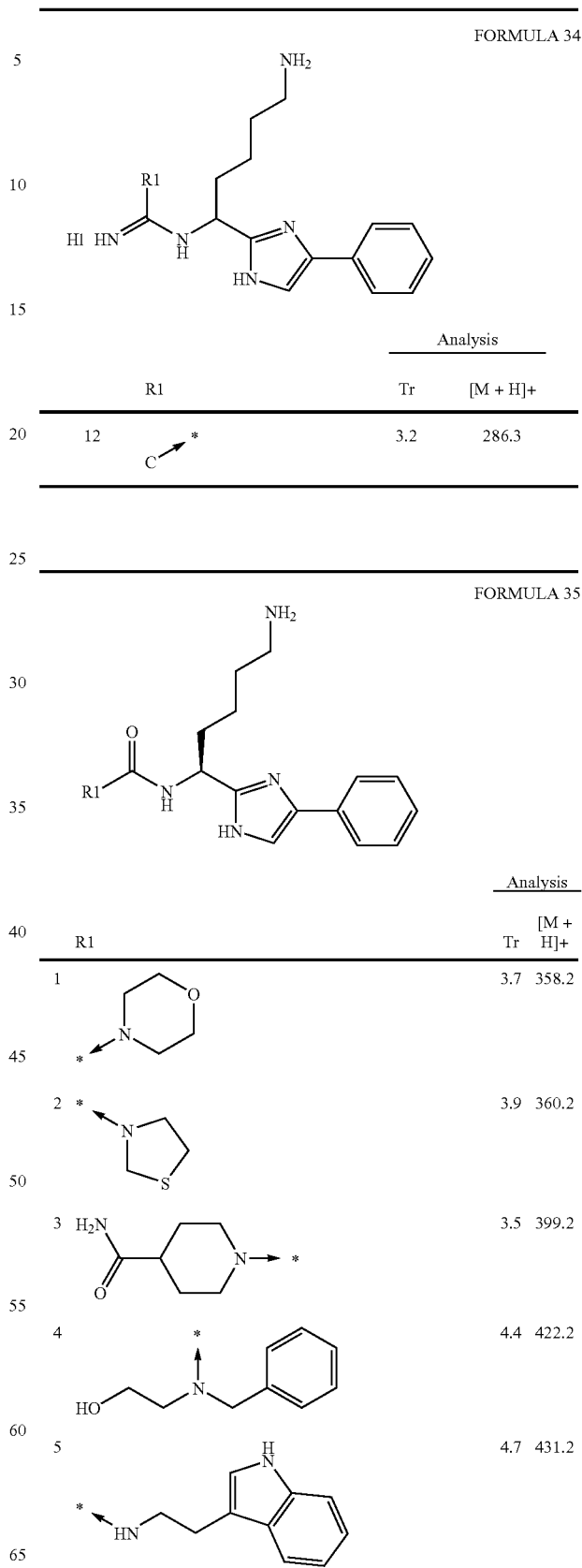
| R1 | | Analysis | |
|---|---|---|---|
| | | Tr | [M + H]+ |
| 12 | C-* | 3.2 | 286.3 |
FORMULA 35
| R1 | | Analysis | |
|---|---|---|---|
| | | Tr | [M + H]+ |
| 1 | morpholine | 3.7 | 358.2 |
| 2 | thiazolidine | 3.9 | 360.2 |
| 3 | 4-carbamoyl-piperidine | 3.5 | 399.2 |
| 4 | N-benzyl-N-(2-hydroxyethyl)amino | 4.4 | 422.2 |
| 5 | tryptamine | 4.7 | 431.2 |

-continued
FORMULA 35
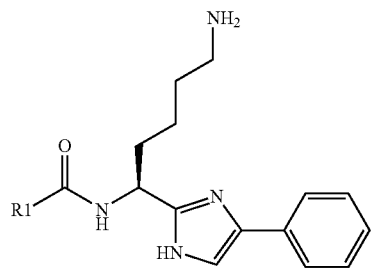
| R1 | Analysis Tr | [M+H]+ |
|---|---|---|
| 6 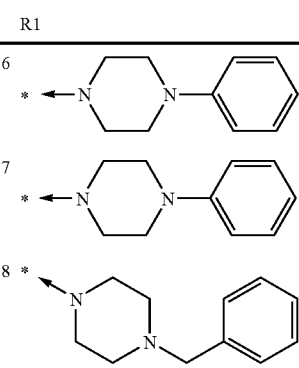 | 4.7 | 433.2 |
| 7 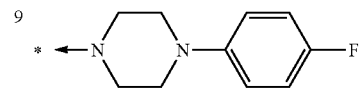 | 5.0 | 443.2 |
| 8 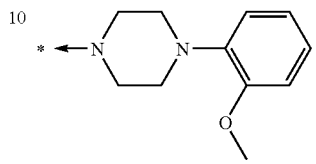 | 3.8 | 447.3 |
| 9 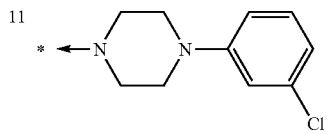 | 4.8 | 451.2 |
| 10 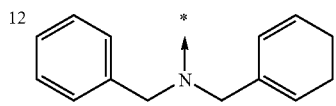 | 4.6 | 463.2 |
| 11 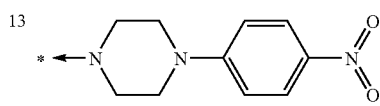 | 5.2 | 467.2 |
| 12 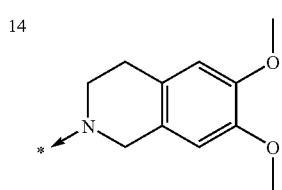 | 5.4 | 468.2 |
| 13 | 4.9 | 478.2 |
| 14 | 4.6 | 464.2 |
-continued
FORMULA 35
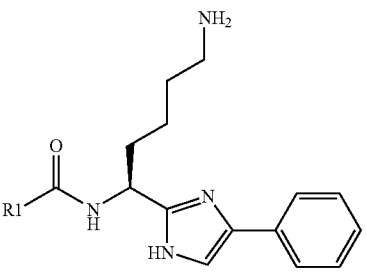
| R1 | Analysis Tr | [M+H]+ |
|---|---|---|
| 15 | 5.2 | 467.2 |
| 16 | 3.5 | 434.2 |
| 17 | 5.3 | 446.2 |
| 18 | 5.0 | 478.2 |
| 19 | 3.8 | 491.2 |
| 20 | 5.5 | 501.2 |
| 21 | 4.6 | 502.3 |
| 22 | 5.1 | 467.2 |

-continued
FORMULA 35
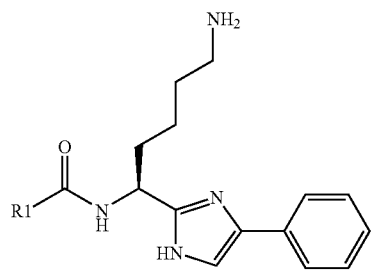
| R1 | | Analysis Tr | [M + H]+ |
|---|---|---|---|
| 23 | 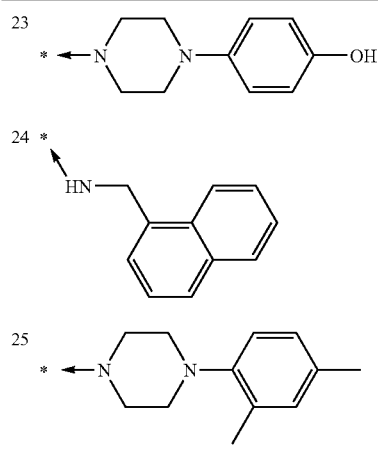 | 3.8 | 449.2 |
| 24 | | 5.0 | 428.2 |
| 25 | | 5.4 | 461.2 |
| 26 | 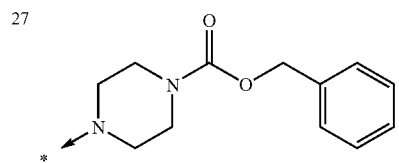 | 5.4 | 468.2 |
| 27 | 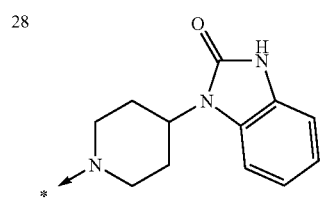 | 5.0 | 491.2 |
| 28 | | 4.5 | 488.2 |
| 29 | 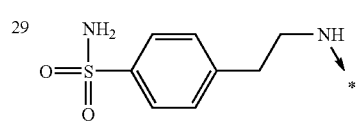 | 4.0 | 471.2 |
-continued
FORMULA 35
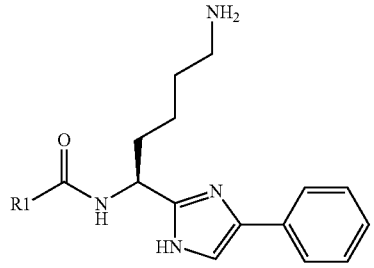
| R1 | | Analysis Tr | [M + H]+ |
|---|---|---|---|
| 30 | 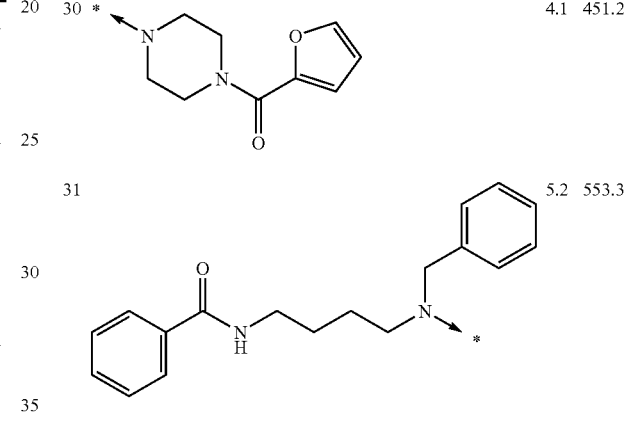 | 4.1 | 451.2 |
| 31 | | 5.2 | 553.3 |
| 32 | | 5.6 | 512.2 |
| 33 | | 4.5 | 463.3 |
| 34 | | 4.7 | 523.3 |
| 35 | | 3.8 | 449.3 |

-continued
FORMULA 35
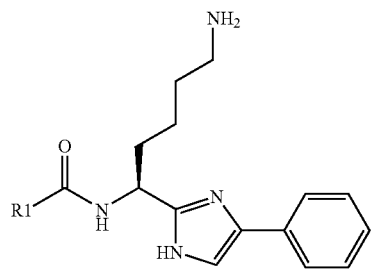
| R1 | | Analysis | |
|---|---|---|---|
| | | Tr | [M+H]+ |
| 36 | 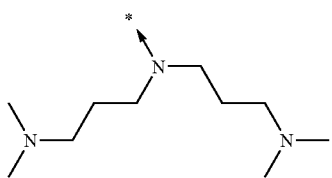 | 3.1 | 458.3 |
| 37 | 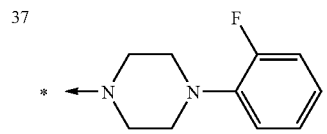 | 4.8 | 451.2 |
FORMULA 36
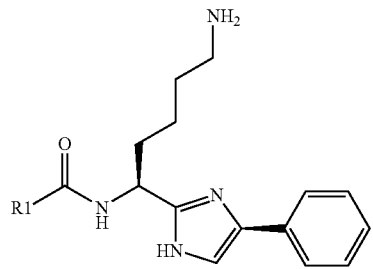
| R1 | | Analysis | |
|---|---|---|---|
| | | Tr | [M+H]+ |
| 1 | 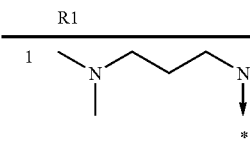 | 3.2 | 373.3 |
| 2 | 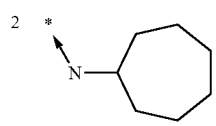 | 4.8 | 384.3 |
| 3 | 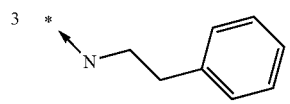 | 4.7 | 392.2 |
-continued
FORMULA 36
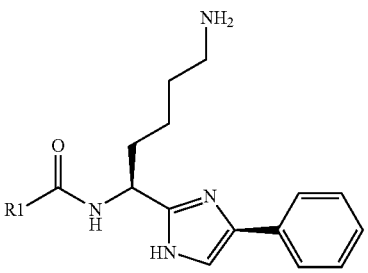
| R1 | | Analysis | |
|---|---|---|---|
| | | Tr | [M+H]+ |
| 4 | 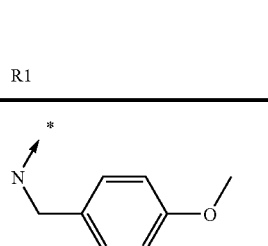 | 4.5 | 408.2 |
| 5 | 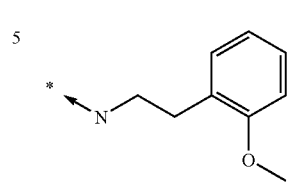 | 4.8 | 422.2 |
| 6 | 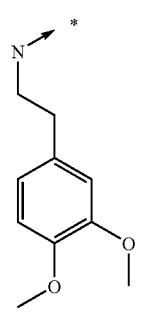 | 4.5 | 452.2 |
| 7 | 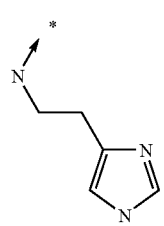 | 3.3 | 382.2 |
| 8 | | 4.4 | 468.2 |

-continued
FORMULA 36
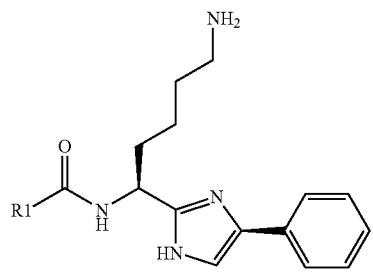
| R1 | Analysis | |
|---|---|---|
| | Tr | [M + H]+ |
| 9 (*-N-CH2CH2-C6H4-NO2) | 4.7 | 437.2 |
| 10 (neopentyl-CH2-N-*) | 4.8 | 372.3 |
| 11 (4-pyridyl-CH2-N-*) | 3.2 | 379.2 |
| 12 (*-N-CH2CH2-2-pyridyl) | 3.3 | 393.2 |
| 13 (*-N-(CH2)3-morpholine) | 3.3 | 415.2 |
| 14 (ethyl N-piperidinyl carbamate-N-*) | 4.4 | 443.3 |
| 15 (*-HN-CH2CH2-NH-5-nitro-2-pyridyl) | 4.4 | 453.2 |
| 16 (BnS-CH2CH2-NH-*) | 5.0 | 438.2 |
| 17 (*-N-CH2-3,4-dihydroxyphenyl) | 3.9 | 410.2 |
-continued
FORMULA 36
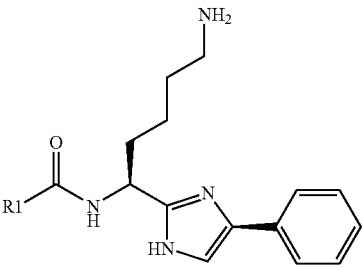
| R1 | Analysis | |
|---|---|---|
| | Tr | [M + H]+ |
| 18 (1,2-diethylpyrazolidin-4-yl-N-*) | 3.6 | 414.3 |
| 19 (tBu-N-*) | 4.3 | 344.3 |
| 20 (3-Cl-phenyl-piperazine-CH2CH2-N-*) | 4.5 | 510.2 |
| 21 (Bn2CH-N-*) | 5.3 | 454.2 |
| 22 (*-N-CH2-2-pyridyl) | 3.4 | 379.2 |
| 23 (3-Cl-phenyl-N(Me)-*) | 4.5 | 412.1 |

-continued
FORMULA 36
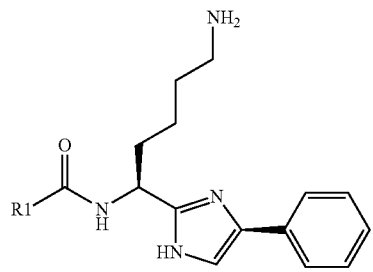
| R1 | Analysis Tr | [M + H]+ |
|---|---|---|
| 24 ![diphenyl propyl amine] | 5.5 | 482.3 |
| 25 * N-CH2CH2CH2-Ph | 5.0 | 406.2 |
| 26 * N-CH2CH2-pyrrolidine | 3.3 | 385.2 |
| 27 * N-CH2CH2-(4-Cl-Ph) | 5.0 | 426.2 |
| 28 N-CH2-(2-F-Ph) * | 4.7 | 410.2 |
| 29 CH3-N-* / (methyl, 4-F-Ph) | 4.8 | 410.2 |
| 30 * N-CH2CH2-(3-Cl-Ph) | 5.0 | 426.2 |
-continued
FORMULA 36
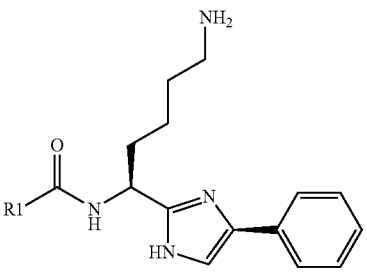
| R1 | Analysis Tr | [M + H]+ |
|---|---|---|
| 31 * N-CH2CH2-(4-Br-Ph) | 5.1 | 470.2 |
| 32 * N-CH2-(3-CF3-Ph) | 5.1 | 446.2 |
| 33 * N-CH2-(4-CF3-Ph) | 5.1 | 446.2 |
| 34 pyridyl-CH2-N-* | 3.3 | 379.2 |
| 35 MeO-(2-OMe-Ph)-CH2-N-* | 4.5 | 408.2 |
| 36 * N-CH2-(2-Cl-Ph) | 4.8 | 412.1 |
| 37 * N-CH2-(3-F-Ph) | 4.6 | 396.2 |
| 38 * N-CH2-(2-F-Ph) | 4.5 | 396.2 |

-continued
FORMULA 36
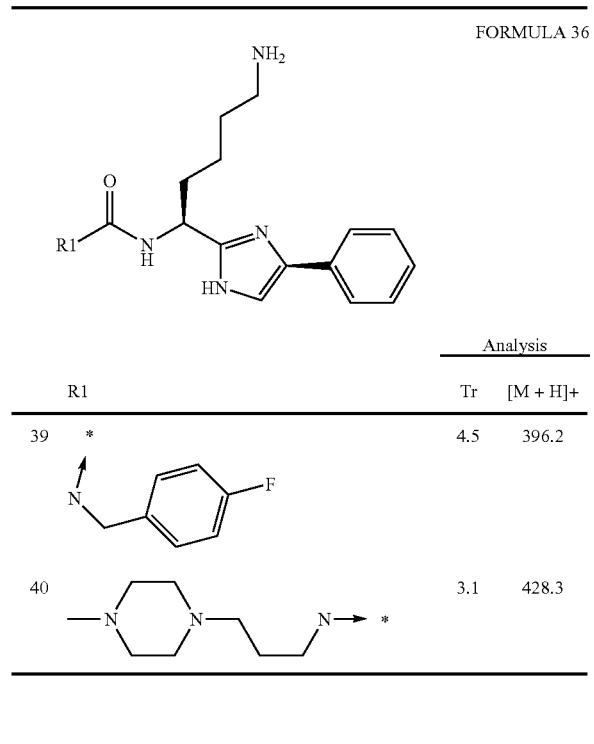
| R1 | Analysis Tr | [M + H]+ |
|---|---|---|
| 39 (4-fluorobenzylamine group) * | 4.5 | 396.2 |
| 40 (4-methylpiperazinyl-propylamine) | 3.1 | 428.3 |
FORMULA 37
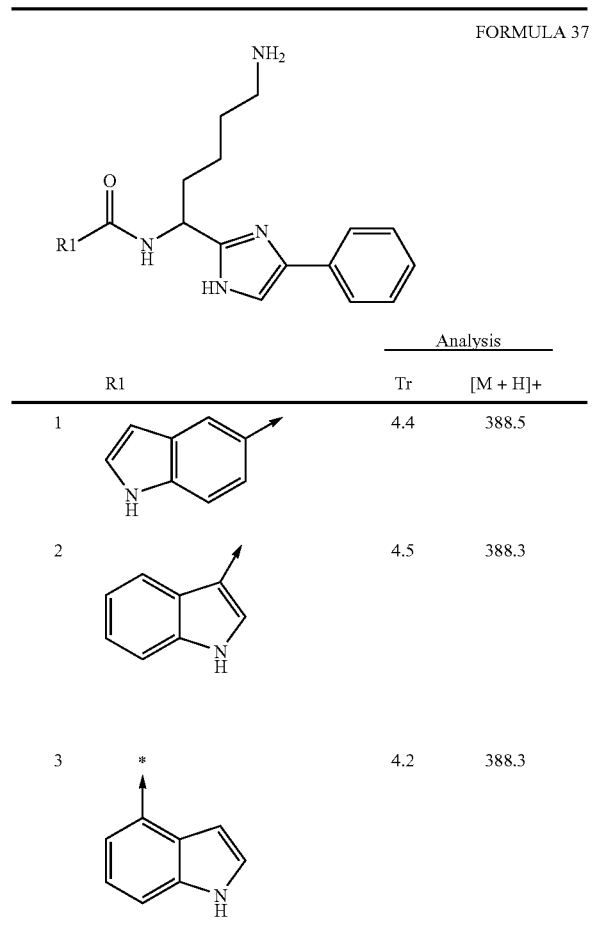
| | R1 | Analysis Tr | [M + H]+ |
|---|---|---|---|
| 1 | 1H-indol-5-yl | 4.4 | 388.5 |
| 2 | 1H-indol-3-yl | 4.5 | 388.3 |
| 3 | 1H-indol-4-yl * | 4.2 | 388.3 |
-continued
FORMULA 37
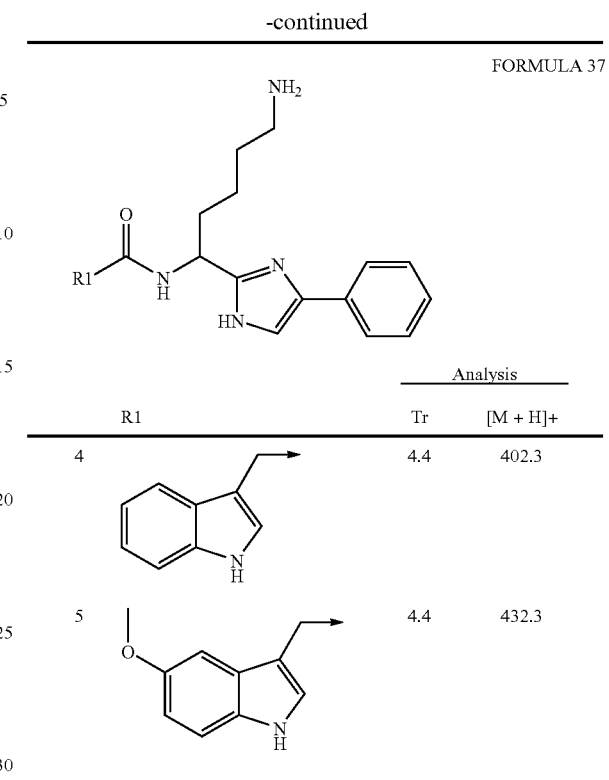
| | R1 | Analysis Tr | [M + H]+ |
|---|---|---|---|
| 4 | 1H-indol-3-yl | 4.4 | 402.3 |
| 5 | 5-methoxy-1H-indol-3-yl | 4.4 | 432.3 |
| 6 | 5-hydroxy-1H-indol-2-yl | 4.2 | 404.3 |
| 7 | 5-oxo-azepinyl | 4.7 | 418.3 |
| 8 | 1H-indol-3-yl (propyl) | 4.9 | 430.5 |
| 9 | 1H-indol-3-yl (ethyl) | 4.6 | 416.4 |
| 10 | 5-hydroxy-1H-indol-3-yl | 3.9 | 418.3 |
| 11 | 5-bromo-1H-indol-3-yl | 4.8 | 480.2 |
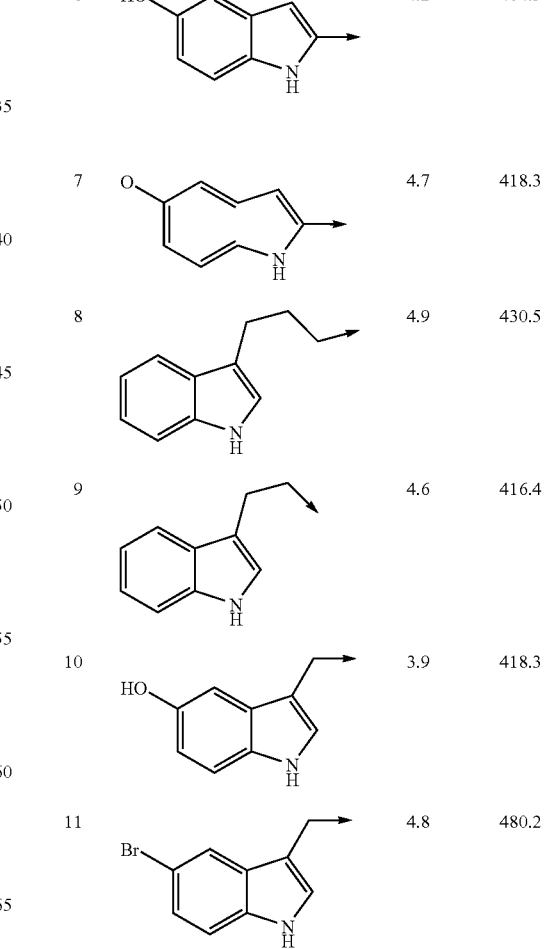

-continued

FORMULA 37

| R1 | Analysis | |
|---|---|---|
|  | Tr | [M + H]+ |
| 12 (2-methyl-1H-indol-3-yl-methyl) | 4.5 | 416.4 |
| 13 (benzo[b]thiophen-2-yl-methyl) | 4.8 | 419.3 |
| 14 (4,5,6,7-tetrahydrobenzo[b]thiophen-3-yl-methyl) | 4.8 | 419.3 |
| 15 (benzofuran-2-yl-methyl) | 4.7 | 389.3 |

FORMULA 38

| R1 | Analysis | |
|---|---|---|
|  | Tr | [M + H]+ |
| 1 (3,4-dichlorobenzyl) | 5.1 | 431.2 |

-continued

FORMULA 38

| R1 | Analysis | |
|---|---|---|
|  | Tr | [M + H]+ |
| 2 (3,4,5-trimethoxybenzyl) | 4.4 | 453.4 |
| 3 (4-methylbenzyl) | 4.6 | 377.4 |
| 4 (4-hydroxybenzyl) | 4.5 | 399.3 |
| 5 (2,4-difluorobenzyl) | 4.5 | 399.3 |
| 6 (furan-2-yl-methyl) | 3.9 | 339.3 |
| 7 (pyridin-2-yl-methyl) | 4.1 | 350.4 |
| 8 (phenylthio-methyl) | 4.5 | 395.3 |
| 9 (naphthalen-1-yl-methyl) * | 4.8 | 399.3 |
| 10 (quinolin-2-yl-methyl) | 4.7 | 400.3 |

-continued

FORMULA 38

Structure: R1-C(=O)-NH-CH(CH2CH2CH2CH2NH2)-[2-imidazolyl with 4-phenyl, NH]

| R1 | Tr | [M + H]+ |
|---|---|---|
| 11  quinolin-8-yl | 4.5 | 400.3 |
| 12  quinolin-3-yl | 4.4 | 400.3 |
| 13  quinolin-4-yl* | 4.2 | 400.3 |
| 14  isoquinolin-1-yl | 4.3 | 441.3 |
| 15  PhSO2CH2CH2- | 4.3 | 441.3 |
| 16  thiophen-2-ylmethyl | 4.2 | 389.3 |
| 17  pyrimidin-2-ylthiomethyl | 3.9 | 397.3 |
| 18  pyridin-3-yl | 3.8 | 350.3 |

FORMULA 39

Structure: R1-C(=O)-NH-CH(CH2CH2CH2CH2NH2)-[2-imidazolyl with 4-phenyl, NH]

| R1 | Tr | [M + H]+ |
|---|---|---|
| 1  2-Cl-benzyl | 4.5 | 397.3 |
| 2  3-Cl-benzyl | 4.7 | 397.3 |
| 3  4-Cl-benzyl | 4.7 | 397.3 |
| 4  2-Br-benzyl | 4.6 | 441.2 |
| 5  3-Br-benzyl | 4.8 | 441.2 |
| 6  4-Br-benzyl | 4.8 | 441.2 |
| 7  2-F-benzyl | 4.3 | 381.3 |
| 8  3-F-benzyl | 4.4 | 381.3 |
| 9  4-F-benzyl | 4.4 | 381.3 |

-continued
FORMULA 39
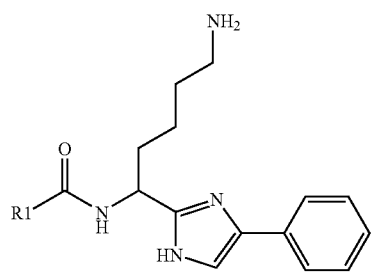
| R1 | Analysis Tr | [M + H]+ |
|---|---|---|
| 10 2-NO2-benzyl | 4.3 | 406.3 |
| 11 3-NO2-benzyl | 4.4 | 406.3 |
| 12 4-NO2-benzyl | 4.5 | 408.3 |
| 13 2-CF3-benzyl | 4.7 | 431.3 |
| 14 3-CF3-benzyl | 4.9 | 431.3 |
| 15 4-CF3-benzyl | 5.0 | 431.3 |
| 16 2-OMe-benzyl | 4.4 | 393.3 |
| 17 3-OMe-benzyl | 4.4 | 393.3 |
-continued
FORMULA 39
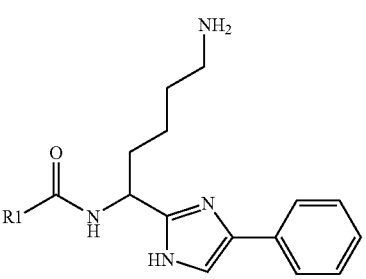
| R1 | Analysis Tr | [M + H]+ |
|---|---|---|
| 18 4-OMe-benzyl | 4.4 | 393.3 |
| 19 benzyl | 4.3 | 363.4 |
| 20 4-NMe2-benzyl | 3.7 | 406.3 |
FORMULA 40
| R1 | Analysis Tr | [M + H]+ |
|---|---|---|
| 1 pyridin-3-ylmethyl | 3.6 | 336.4 |
| 2 (2-chloroquinolin-3-yl)methyl | 4.9 | 420.3 |
| 3 quinolin-2-ylmethyl | 4.5 | 386.4 |

-continued
FORMULA 40
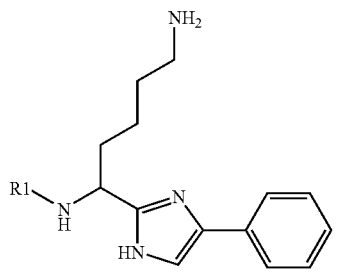
| R1 | | Tr | [M + H]+ |
|---|---|---|---|
| 4 | 4-pyridylmethyl | 3.5 | 336.4 |
| 5 | 2-pyridylmethyl | 3.8 | 336.4 |
| 6 | (6-MeO-carbonyl-1H-indol-3-yl)methyl | 4.9 | 432.3 |
FORMULA 41
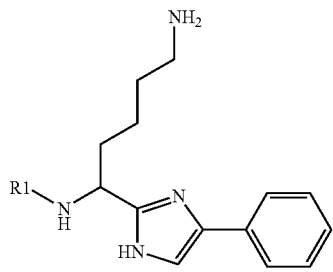
| R1 | | Tr | [M + H]+ |
|---|---|---|---|
| 1 | benzyl | 4.5 | 335.3 |
| 2 | 2-OH-benzyl | 4.3 | 351.3 |
-continued
FORMULA 41
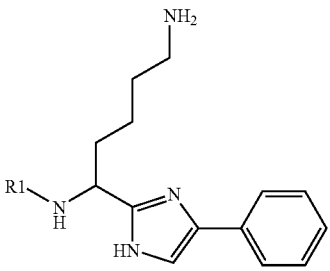
| R1 | | Tr | [M + H]+ |
|---|---|---|---|
| 3 | 4-HO-benzyl | 4.2 | 351.3 |
| 4 | 4-F-benzyl | 4.6 | 353.3 |
| 5 | 3-MeO-benzyl | 4.6 | 365.3 |
| 6 | 4-MeO-benzyl | 4.6 | 365.3 |
| 7 | 2-MeO-benzyl | 4.6 | 365.3 |
| 8 | 2-NO2-benzyl | 4.5 | 380.3 |
| 9 | 4-NO2-benzyl | 4.6 | 380.3 |
| 10 | 3,4-diCl-benzyl | 5.1 | 403.2 |
| 11 | 3-MeO-2-NO2-benzyl | 4.7 | 410.3 |

-continued
FORMULA 41
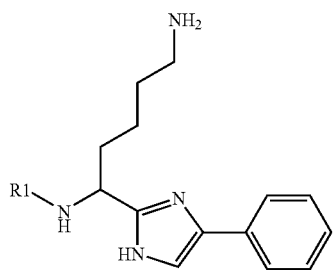
| R1 | | Analysis | |
|---|---|---|---|
| | | Tr | [M + H]+ |
| 12 | 4-Br-C6H4-CH2 | 4.9 | 413.2 |
| 13 | 2-thienyl-CH2 | 4.3 | 341.3 |
| 14 | 3,4,5-(MeO)3-C6H2-CH2 | 4.6 | 425.3 |
| 15 | 4-(PhCH2O)-C6H4-CH2 | 5.4 | 441.3 |
| 16 | 2-F-C6H4-CH2 | 4.5 | 353.3 |
| 17 | 2-CF3-C6H4-CH2 | 4.9 | 403.3 |
| 18 | 4-Ph-C6H4-CH2 | 5.3 | 411.3 |
| 19 | 2-Br-C6H4-CH2 | 4.7 | 415.2 |
-continued
FORMULA 41
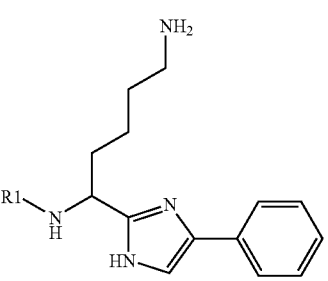
| R1 | | Analysis | |
|---|---|---|---|
| | | Tr | [M + H]+ |
| 20 | 4-(OCF3)-C6H4-CH2 | 5.2 | 419.3 |
| 21 | 4-(Me2N(CH2)3O)-C6H4-CH2 | 3.9 | 436.4 |
| 22 | 3-F-4-MeO-C6H3-CH2 | 4.6 | 383.3 |
| 23 | 4-tBu-C6H4-CH2 | 5.4 | 391.4 |
| 24 | 3-Br-C6H4-CH2 | 4.9 | 413.2 |
| 25 | 3-(4-MeO-C6H4-O)-C6H4-CH2 | 5.4 | 457.4 |

FORMULA 42
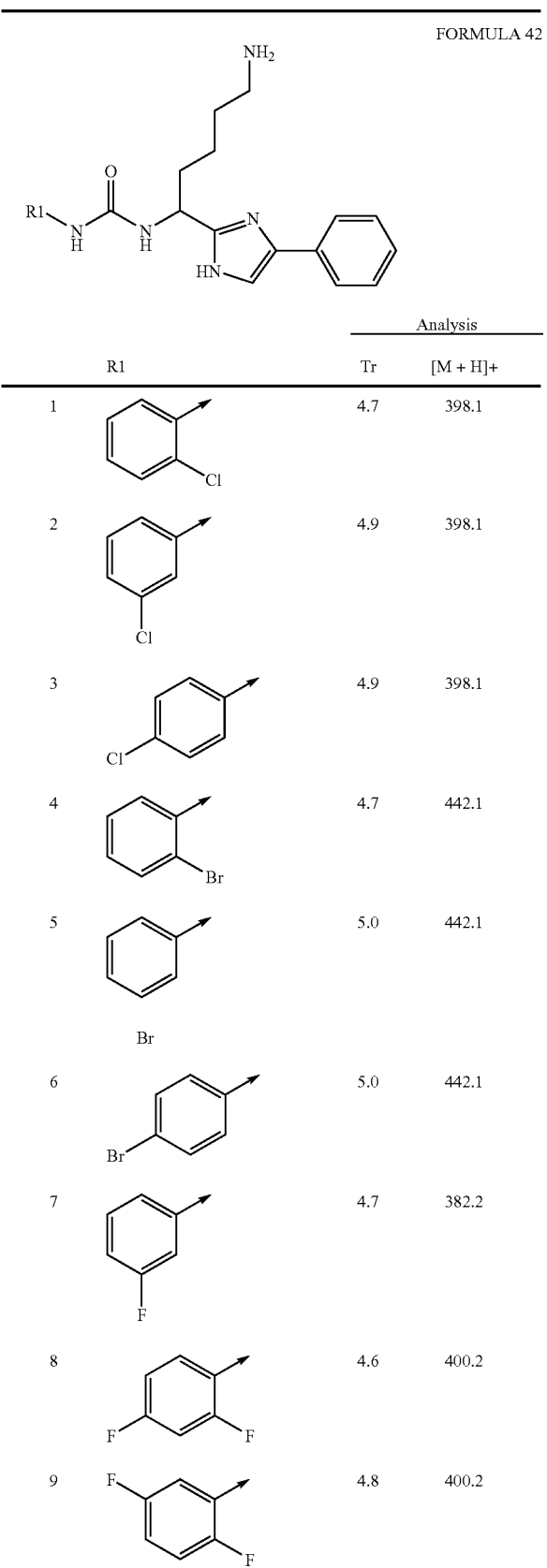
| | R1 | Analysis Tr | [M + H]+ |
|---|---|---|---|
| 1 | 2-Cl-phenyl | 4.7 | 398.1 |
| 2 | 3-Cl-phenyl | 4.9 | 398.1 |
| 3 | 4-Cl-phenyl | 4.9 | 398.1 |
| 4 | 2-Br-phenyl | 4.7 | 442.1 |
| 5 | 3-Br-phenyl | 5.0 | 442.1 |
| 6 | 4-Br-phenyl | 5.0 | 442.1 |
| 7 | 3-F-phenyl | 4.7 | 382.2 |
| 8 | 2,4-diF-phenyl | 4.6 | 400.2 |
| 9 | 2,5-diF-phenyl | 4.8 | 400.2 |
-continued
FORMULA 42
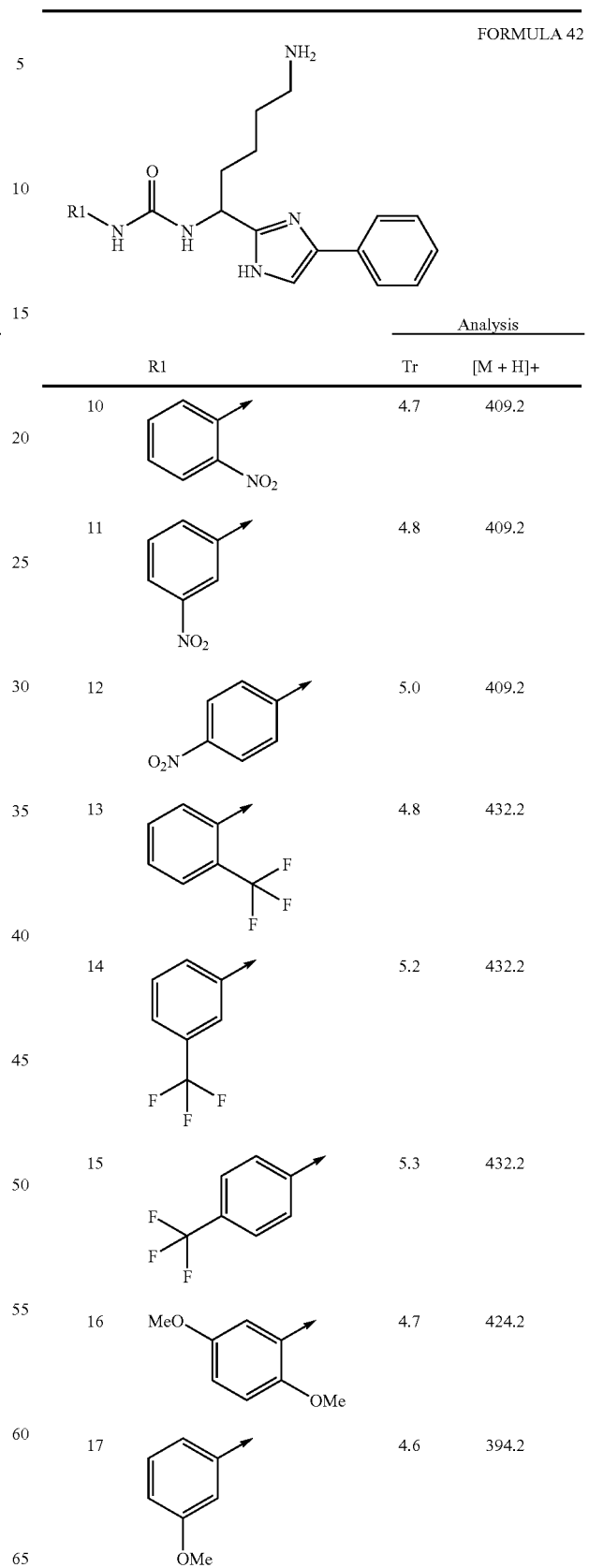
| | R1 | Analysis Tr | [M + H]+ |
|---|---|---|---|
| 10 | 2-NO2-phenyl | 4.7 | 409.2 |
| 11 | 3-NO2-phenyl | 4.8 | 409.2 |
| 12 | 4-NO2-phenyl | 5.0 | 409.2 |
| 13 | 2-CF3-phenyl | 4.8 | 432.2 |
| 14 | 3-CF3-phenyl | 5.2 | 432.2 |
| 15 | 4-CF3-phenyl | 5.3 | 432.2 |
| 16 | 2,5-diOMe-phenyl | 4.7 | 424.2 |
| 17 | 3-OMe-phenyl | 4.6 | 394.2 |

-continued
FORMULA 42
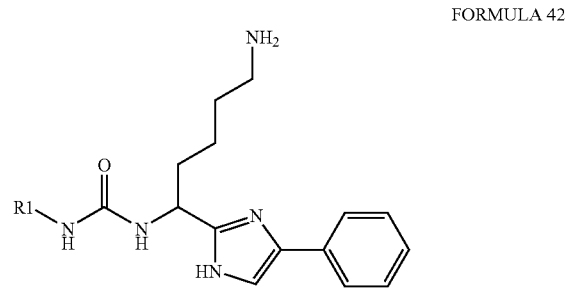
| | R1 | Analysis Tr | [M + H]+ |
|---|---|---|---|
| 18 | 4-MeO-C6H4- | 4.5 | 394.2 |
| 19 | 4-Cl-2-CF3-C6H3- | 5.2 | 468.1 |
| 20 | 4-F-3-NO2-C6H3- | 4.9 | 427.2 |
FORMULA 43
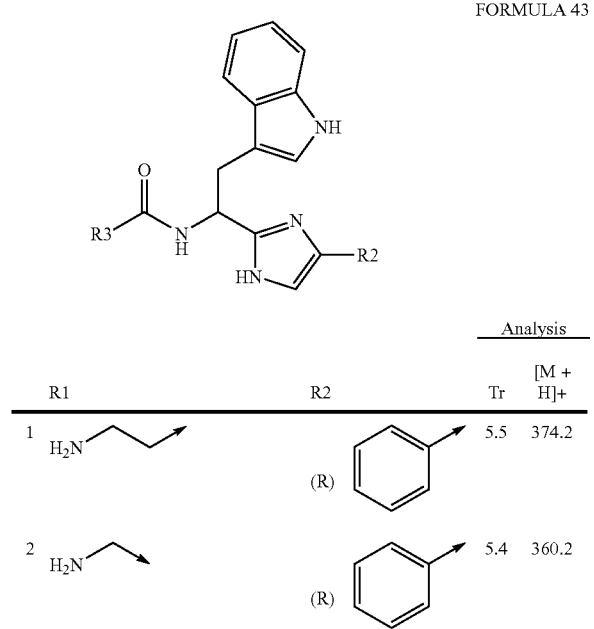
| | R1 | R2 | Analysis Tr | [M + H]+ |
|---|---|---|---|---|
| 1 | H2N-(CH2)2- | Ph (R) | 5.5 | 374.2 |
| 2 | H2N-CH2- | Ph (R) | 5.4 | 360.2 |
-continued
FORMULA 43
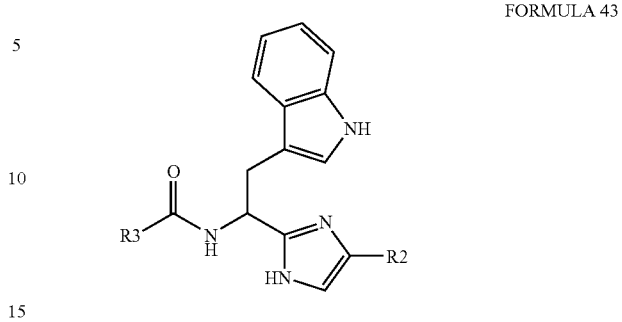
| | R1 | R2 | Analysis Tr | [M + H]+ |
|---|---|---|---|---|
| 3 | H2N-(CH2)3- | Ph (R) | 5.4 | 388.2 |
| 4 | H2N-(CH2)5- | Ph (R) | 5.5 | 416.3 |
| 5 | CH3-NH-CH2- | Ph (R) | 5.4 | 374.2 |
| 6 | 4-H2N-C6H4- | Ph (R) | 6.1 | 422.2 |
| 7 | H2N-C(CH3)2- | Ph (R) | 5.5 | 368.2 |
| 8 | H2N-(CH2)4- | Ph (R) | 5.5 | 402.2 |
| 9 | 4-(H2N-CH2)-C6H4- | Ph (R) | 5.5 | 436.2 |
| 10 | 4-H2N-C6H4-CH2- | Ph (R) | 5.7 | 436.2 |
| 11 | H2N-(CH2)2- | tBu (R,S) | | |
| 12 | H2N-CH2- | tBu (R,S) | 5.3 | 340.3 |
| 13 | H2N-(CH2)3- | tBu (R,S) | 5.4 | 368.3 |

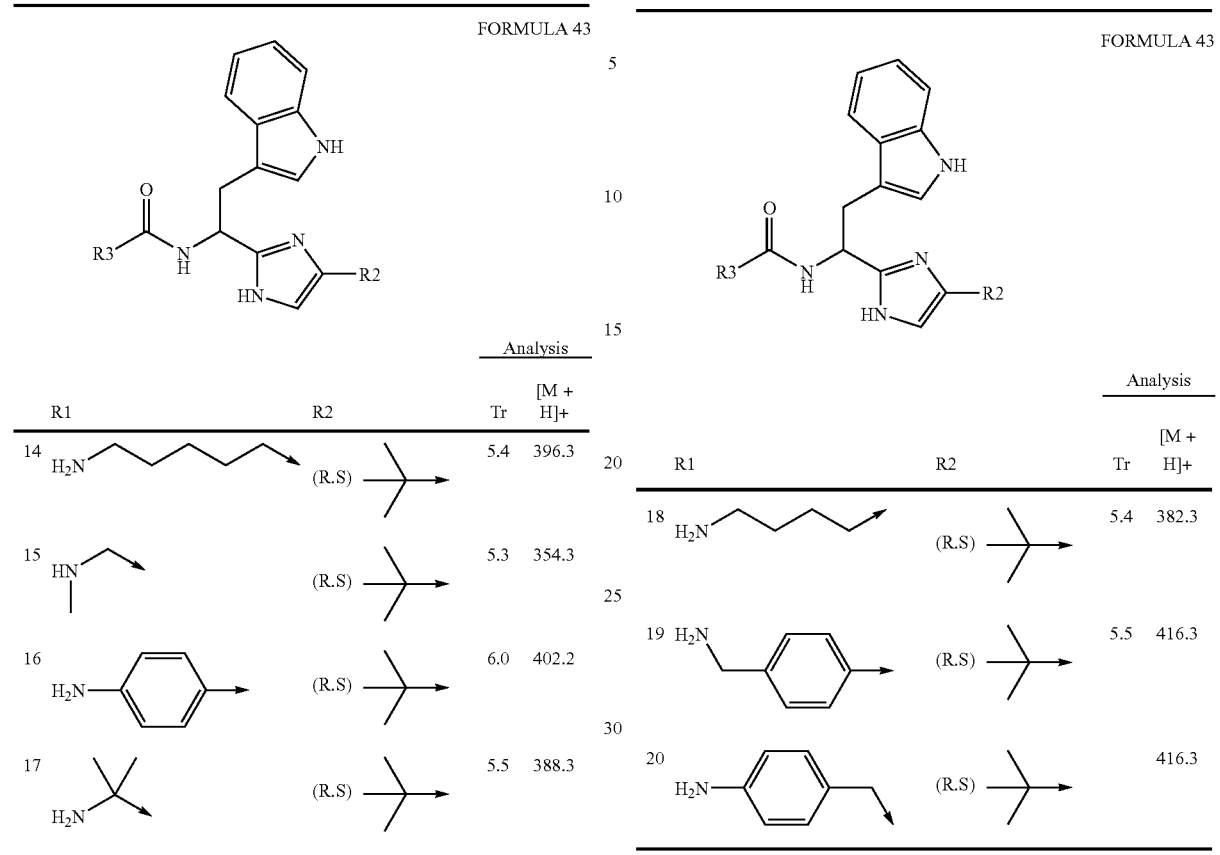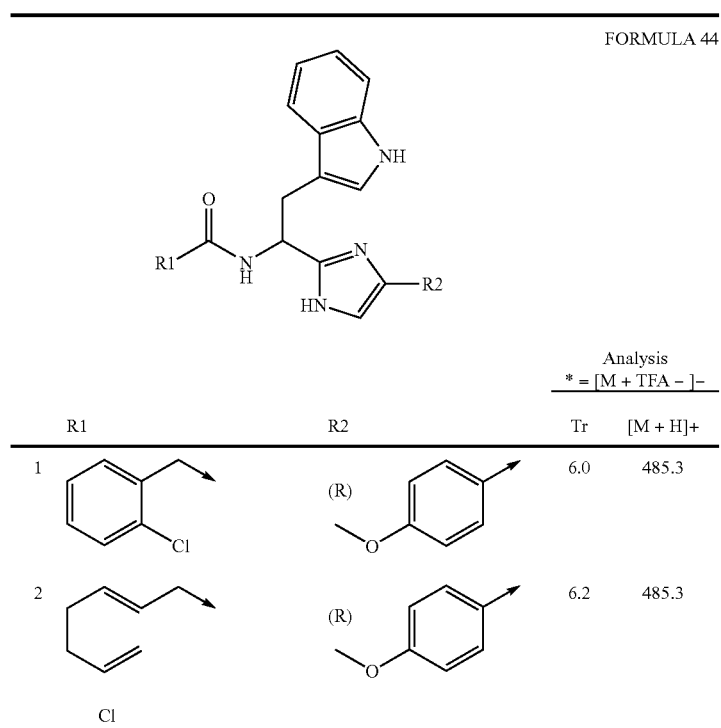

-continued
FORMULA 44
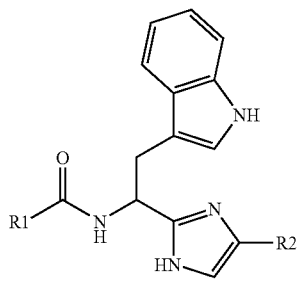
| | R1 | R2 | Tr | Analysis<br>* = [M + TFA − ]−<br>[M + H]+ |
|---|---|---|---|---|
| 3 | 4-Cl-C6H4-CH2- | (R) 4-MeO-C6H4- | 6.2 | 485.3 |
| 4 | (Z)-4-Br-but-2-enyl- | (R) 4-MeO-C6H4- | 6.1 | 529.2 |
| 5 | (E)-but-2-enyl- / 2-Br-allyl- | (R) 4-MeO-C6H4- | 6.2 | 529.2 |
| 6 | 4-Br-C6H4-CH2- | (R) 4-MeO-C6H4- | 6.3 | 529.2 |
| 7 | 2-F-C6H4-CH2- | (R) 4-MeO-C6H4- | 5.9 | 469.3 |
| 8 | 3-F-C6H4-CH2- | (R) 4-MeO-C6H4- | 5.9 | 469.3 |
| 9 | 4-F-C6H4-CH2- | (R) 4-MeO-C6H4- | 5.9 | 469.3 |
| 10 | 2-NO2-C6H4-CH2- | (R) 4-MeO-C6H4- | 5.8 | 496.3 |
| 11 | 3-NO2-C6H4-CH2- | (R) 4-MeO-C6H4- | 5.9 | 496.3 |

-continued
FORMULA 44
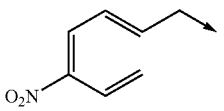
| | R1 | R2 | Analysis * = [M + TFA − ]− | |
|---|---|---|---|---|
| | | | Tr | [M + H]+ |
| 12 | 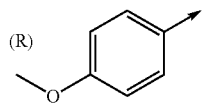 | 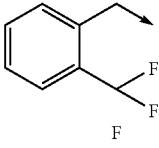 (R) | 6.0 | 496.3 |
| 13 | 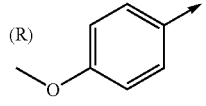 | 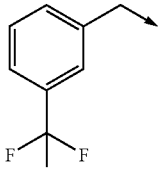 (R) | 6.2 | 519.3 |
| 14 | 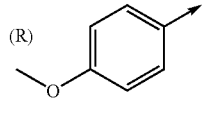 | 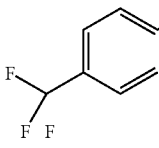 (R) | 6.4 | 519.3 |
| 15 | 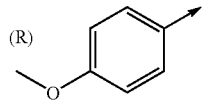 | 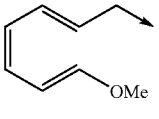 (R) | 6.4 | 519.3 |
| 16 | 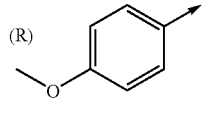 | 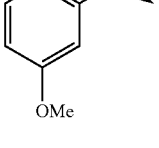 (R) | 6.9 | 481.3 |
| 17 | 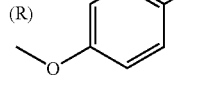 | 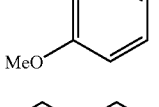 (R) | 5.9 | 481.3 |
| 18 | 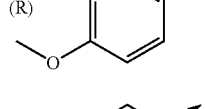 | 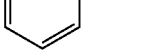 (R) | 5.9 | 481.3 |
| 19 | 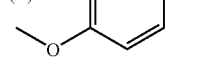 | (R) | 5.8 | 451.3 |

-continued

FORMULA 44

|   | R1 | R2 | Tr | [M + H]+ |
|---|---|---|---|---|
| | | | Analysis * = [M + TFA − ]− | |
| 20 | 4-(dimethylamino)phenyl-CH2- | 4-methoxyphenyl- (R) | 4.9 | 494.4 |
| 21 | 2,4-dichloro-pentyl- | 4-methoxyphenyl- (R) | 6.5 | 519.2 |
| 22 | 3,4,5-trimethoxyphenyl-CH2- | 4-methoxyphenyl- (R) | 5.7 | 541.3 |
| 23 | 4-methylphenyl-CH2- | 4-methoxyphenyl- (R) | 6.0 | 465.3 |
| 24 | HOCH2- pentenyl | 4-methoxyphenyl- (R) | 5.4 | 467.3 |
| 25 | 2,4-difluorophenyl-CH2- | 4-methoxyphenyl- (R) | 5.9 | 487.3 |
| 26 | 2-chlorophenyl-CH2- | 4-methoxyphenyl- (S) | 6.0 | 485.3 |
| 27 | chloro-hexenyl- | 4-methoxyphenyl- (S) | 6.1 | 485.3 |
| 28 | 4-chlorophenyl-CH2- | 4-methoxyphenyl- (S) | 6.2 | 485.3 |

-continued
FORMULA 44
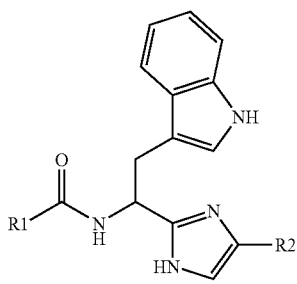
| | R1 | R2 | Tr | [M + H]+ |
|---|---|---|---|---|
| | | | Analysis * = [M + TFA − ]− | |
| 29 | (CH2-CH=CH-CH=CH-CH2Br) | (S)-C6H4-OCH3 | 6.0 | 529.2 |
| 30 | (CH2-CH=CH-CH3) / (CH2=C(Br)-CH3) | (S)-C6H4-OCH3 | 6.2 | 529.2 |
| 31 | 4-Br-C6H4-CH2- | (S)-C6H4-OCH3 | 6.2 | 529.2 |
| 32 | 2-F-C6H4-CH2- | (S)-C6H4-OCH3 | 5.8 | 469.3 |
| 33 | 3-F-C6H4-CH2- | (S)-C6H4-OCH3 | 5.9 | 469.3 |
| 34 | 4-F-C6H4-CH2- | (S)-C6H4-OCH3 | 5.9 | 469.3 |
| 35 | 2-NO2-C6H4-CH2- | (S)-C6H4-OCH3 | 5.8 | 496.3 |
| 36 | 3-NO2-C6H4-CH2- | (S)-C6H4-OCH3 | 5.9 | 496.3 |
| 37 | (O2N-C=CH-CH=CH-CH2-, CH2=) | (S)-C6H4-OCH3 | 5.9 | 496.3 |

-continued
FORMULA 44
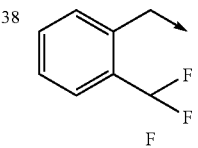
| | R1 | R2 | Analysis * = [M + TFA − ]− Tr | [M + H]+ |
|---|---|---|---|---|
| 38 | 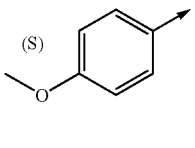 | 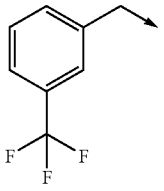 | 6.2 | 519.3 |
| 39 | 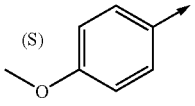 |  | 6.4 | 519.3 |
| 40 | 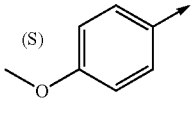 | 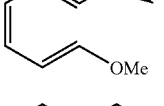 | 6.4 | 519.3 |
| 41 | 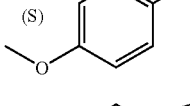 | 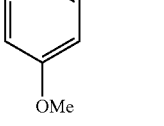 | 5.9 | 481.3 |
| 42 | 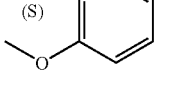 | 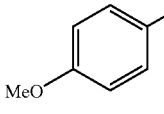 | 5.9 | 481.3 |
| 43 | 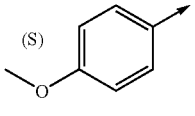 | 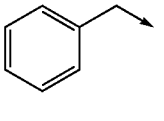 | 5.8 | 481.3 |
| 44 | 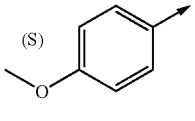 | 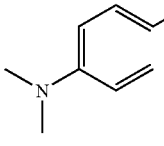 | 5.8 | 563.3* |
| 45 | 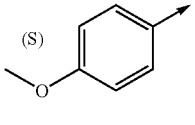 | | 4.8 | 494.4 |

-continued
FORMULA 44
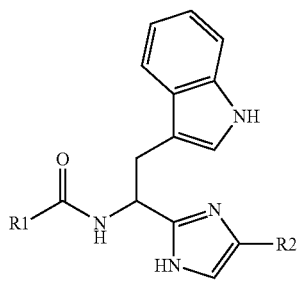
| | R1 | R2 | Tr | [M + H]+ |
|---|---|---|---|---|
| | | | Analysis * = [M + TFA − ]− | |
| 46 | Ethyl/Cl,Cl substituted alkene | (S) 4-methoxyphenyl | 6.4 | 519.2 |
| 47 | 3,4,5-trimethoxybenzyl | (S) 4-methoxyphenyl | 5.7 | 541.3 |
| 48 | 4-methylbenzyl | (S) 4-methoxyphenyl | 6.0 | 485.3 |
| 49 | pentenyl / HO-allyl | (S) 4-methoxyphenyl | 5.4 | 467.3 |
| 50 | 2,4-difluorobenzyl | (S) 4-methoxyphenyl | 6.0 | 487.3 |

FORMULA 45
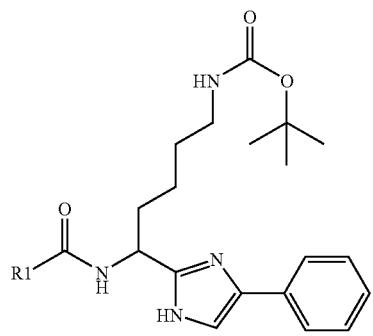
| | R1 | Tr | [M + H]+ |
|---|---|---|---|
| 1 | indol-5-yl | 5.9 | 488.4 |
| 2 | indol-3-yl | 6.1 | 488.4 |
| 3 | indol-4-yl | 5.9 | 488.4 |
| 4 | indol-2-yl | 6.0 | 502.4 |
| 5 | (indol-3-yl)methyl | 6.0 | 502.4 |
| 6 | (5-methoxyindol-3-yl)methyl | 6.0 | 532.4 |
| 7 | 5-hydroxyindol-2-yl | 5.7 | 504.4 |
| 8 | 5-methoxyindol-2-yl | 6.3 | 518.4 |
-continued
FORMULA 45
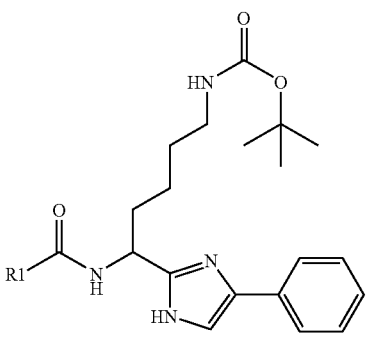
| | R1 | Tr | [M + H]+ |
|---|---|---|---|
| 9 | (indol-3-yl)propyl | 5.4 | 530.4 |
| 10 | (indol-3-yl)ethyl | 6.2 | 516.4 |
| 11 | (5-hydroxyindol-3-yl)methyl | 5.5 | 518.4 |
| 12 | (5-bromoindol-3-yl)methyl | 6.4 | 580.3 |
| 13 | (2-methylindol-3-yl)methyl | 6.1 | 516.4 |
| 14 | benzothiophen-2-yl | 6.4 | 519.3 |
| 15 | (benzothiophen-3-yl)methyl | 5.4 | 519.3 |
| 16 | benzofuran-2-yl | 6.3 | 489.4 |

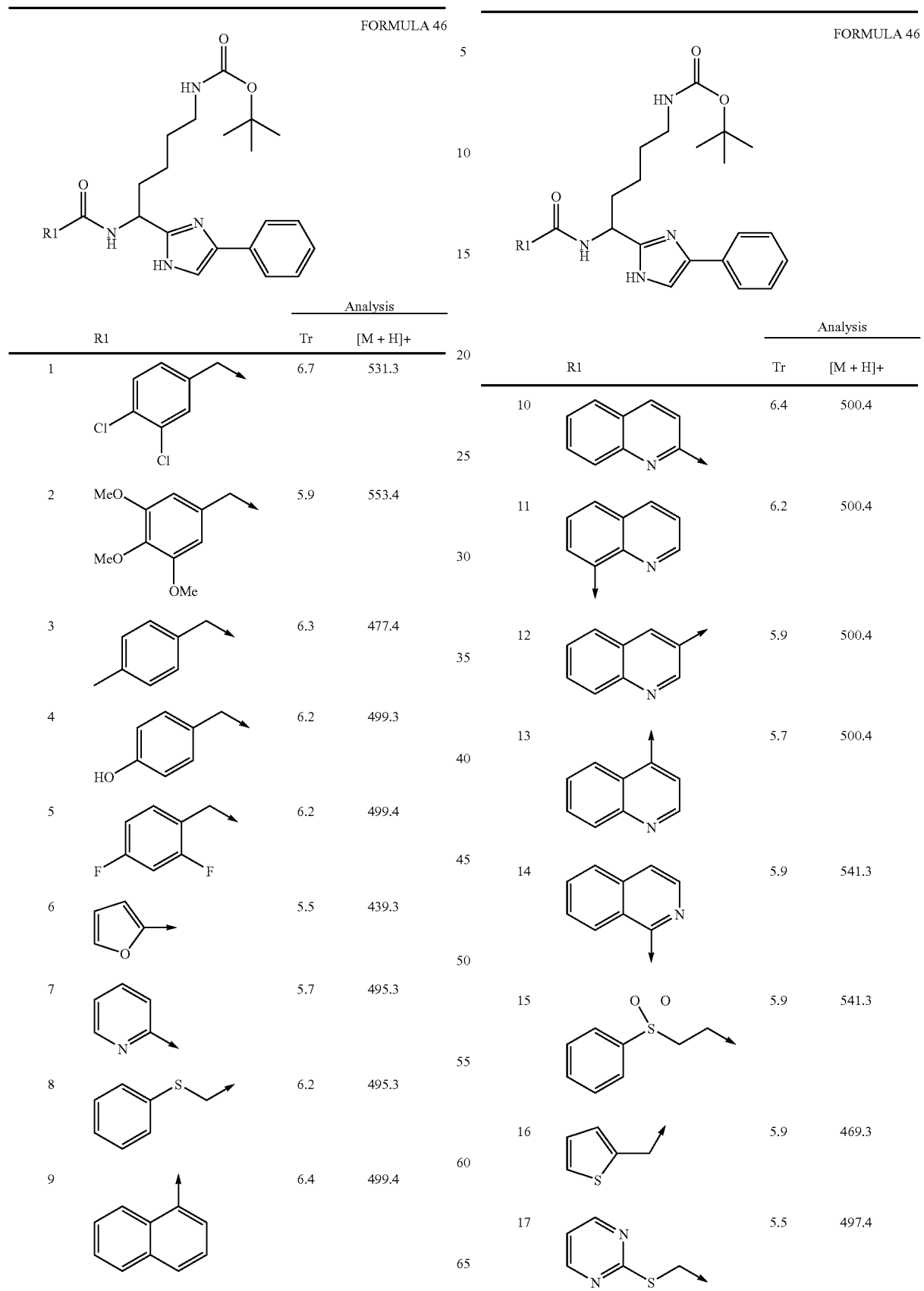

401
-continued
FORMULA 46
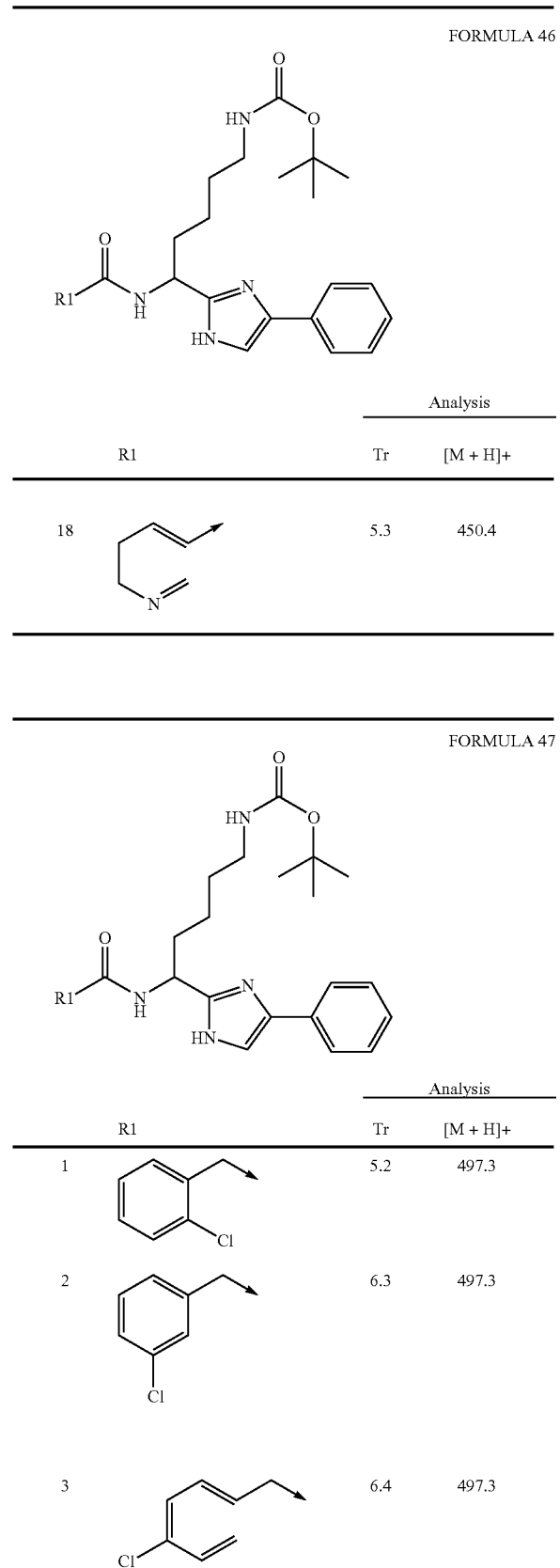
| R1 | Analysis | |
|---|---|---|
| | Tr | [M + H]+ |
| 18 | 5.3 | 450.4 |
FORMULA 47
| R1 | Analysis | |
|---|---|---|
| | Tr | [M + H]+ |
| 1 (2-Cl-benzyl) | 5.2 | 497.3 |
| 2 (3-Cl-benzyl) | 6.3 | 497.3 |
| 3 | 6.4 | 497.3 |
402
-continued
FORMULA 47
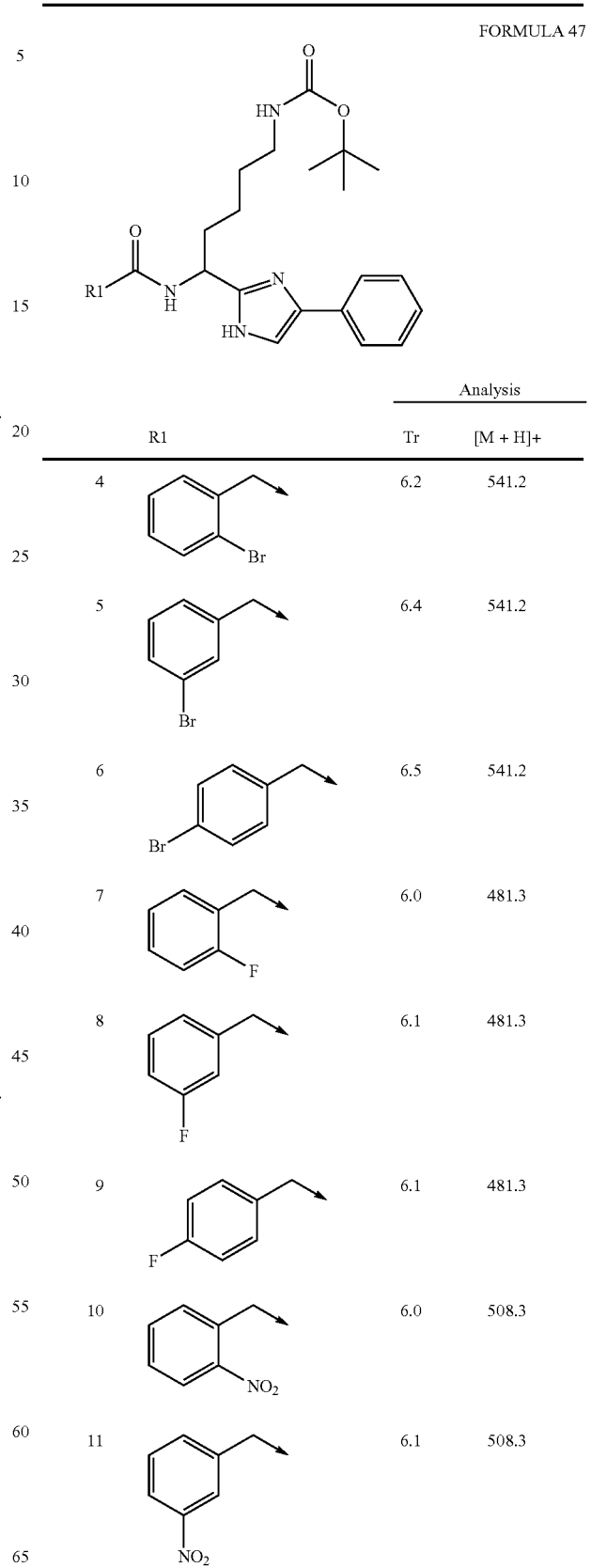
| R1 | Analysis | |
|---|---|---|
| | Tr | [M + H]+ |
| 4 (2-Br-benzyl) | 6.2 | 541.2 |
| 5 (3-Br-benzyl) | 6.4 | 541.2 |
| 6 (4-Br-benzyl) | 6.5 | 541.2 |
| 7 (2-F-benzyl) | 6.0 | 481.3 |
| 8 (3-F-benzyl) | 6.1 | 481.3 |
| 9 (4-F-benzyl) | 6.1 | 481.3 |
| 10 (2-NO₂-benzyl) | 6.0 | 508.3 |
| 11 (3-NO₂-benzyl) | 6.1 | 508.3 |

-continued
FORMULA 47
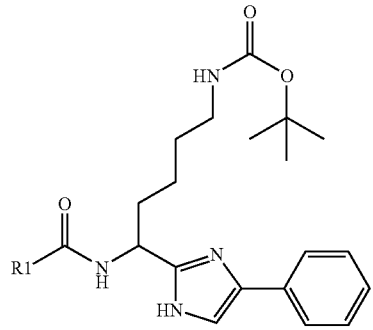
| | R1 | Analysis Tr | [M + H]+ |
|---|---|---|---|
| 12 | 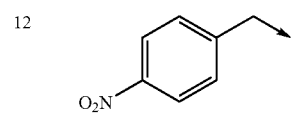 | 5.1 | 508.3 |
| 13 | 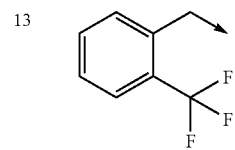 | 6.4 | 531.3 |
| 14 | 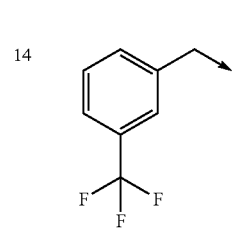 | 6.6 | 531.3 |
| 15 | 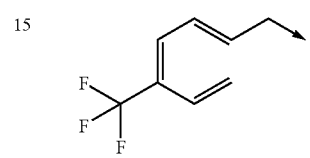 | 5.6 | 531.3 |
| 16 | 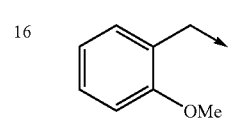 | 6.1 | 493.4 |
-continued
FORMULA 47
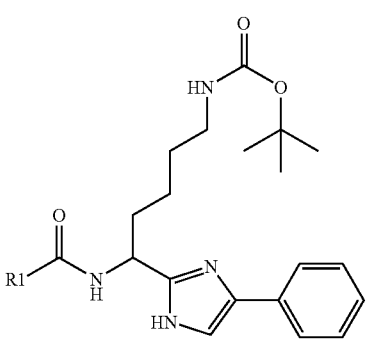
| | R1 | Analysis Tr | [M + H]+ |
|---|---|---|---|
| 17 | 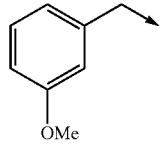 | 6.0 | 493.4 |
| 18 | 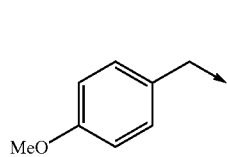 | 6.0 | 493.4 |
| 19 | 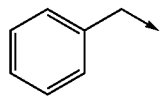 | 6.0 | 463.4 |
| 20 | 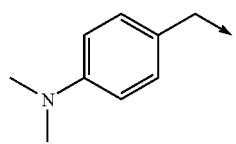 | 6.0 | 506.4 |

FORMULA 48
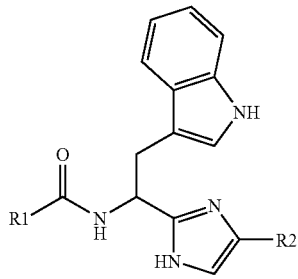
| | R1 | R2 | Tr | [M + H]+ |
|---|---|---|---|---|
| 1 | 3,4-dichlorobenzyl | 2-OMe-phenyl (R,S) | 6.9 | 519.2 |
| 2 | 3,4,5-trimethoxybenzyl | 2-OMe-phenyl (R,S) | 6.5 | 541.3 |
| 3 | 4-methylbenzyl | 2-OMe-phenyl (R,S) | 6.7 | 485.3 |
| 4 | 4-hydroxybenzyl | 2-OMe-phenyl (R,S) | 6.3 | 467.3 |
| 5 | 2,4-difluorobenzyl | 2-OMe-phenyl (R,S) | 6.6 | 487.2 |
| 6 | 3,4-dichlorobenzyl | 4-Br-phenyl (R,S) | 7.0 | 567.0 |
| 7 | 3,4,5-trimethoxybenzyl | 4-Br-phenyl (R,S) | 5.7 | 589.1 |
| 8 | 4-methylbenzyl | 4-Br-phenyl (R,S) | 6.9 | 513.2 |

-continued
FORMULA 48
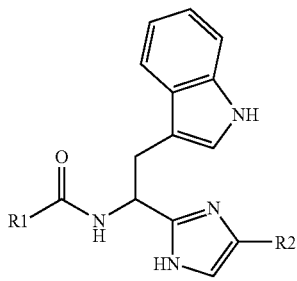
| | R1 | R2 | Analysis Tr | [M + H]+ |
|---|---|---|---|---|
| 9 | HO-C6H4-CH2- | (R.S) 4-Br-C6H4- | 6.5 | 515.1 |
| 10 | 2,4-F2-C6H3-CH2- | (R.S) 4-Br-C6H4- | 6.8 | 535.1 |
| 11 | 3,4-Cl2-C6H3-CH2- | (R.S) 4-O2N-C6H4- | 7.2 | 534.1 |
| 12 | 3,4,5-(MeO)3-C6H2-CH2- | (R.S) 4-O2N-C6H4- | 6.8 | 556.2 |
| 13 | 4-Me-C6H4-CH2- | (R.S) 4-O2N-C6H4- | 6.8 | 480.1 |
| 14 | 4-HO-C6H4-CH2- | (R.S) 4-O2N-C6H4- | 5.8 | 482.1 |
| 15 | 2,4-F2-C6H3-CH2- | (R.S) 4-O2N-C6H4- | 6.7 | 502.1 |
| 16 | 3,4-Cl2-C6H3-CH2- | (R.S) 4-(Et2N)-C6H4- | 6.3 | 560.1 |

-continued
FORMULA 48
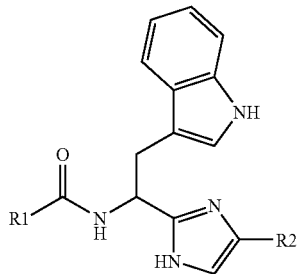
| | R1 | R2 | Tr | [M + H]+ |
|---|---|---|---|---|
| 17 | 3,4,5-triMeO-benzyl | (R,S) 4-(NEt2)-phenyl | 5.5 | 582.2 |
| 18 | 4-Me-benzyl | (R,S) 4-(NEt2)-phenyl | 5.8 | 506.3 |
| 19 | 4-HO-benzyl | (R,S) 4-(NEt2)-phenyl | 5.1 | 506.2 |
| 20 | 2,4-diF-benzyl | (R,S) 4-(NEt2)-phenyl | 5.7 | 528.2 |
| 21 | 3,4-diCl-benzyl | (R) phenyl | 6.5 | 489.1 |
| 22 | 3,4,5-triMeO-benzyl | (R) phenyl | 5.7 | 511.2 |
| 23 | 4-Me-benzyl | (R) phenyl | 5.1 | 435.2 |
| 24 | 4-HO-benzyl | (R) phenyl | 5.4 | 437.2 |

-continued
FORMULA 48
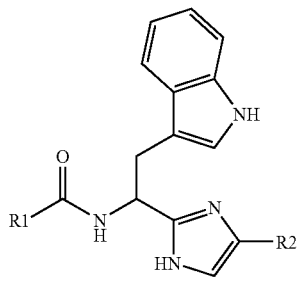
| R1 | R2 | Analysis Tr | [M + H]+ |
|---|---|---|---|
| 25 | (R) | 6.0 | 457.2 |
FORMULA 49
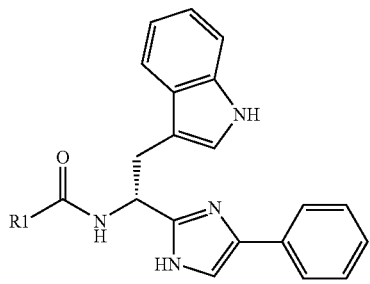
| | R1 | Analysis (min) | [M + H]+ |
|---|---|---|---|
| 1 | 2-Cl-benzyl | 6.6 | 455.2 |
| 2 | 3-Cl-benzyl | 6.5 | 455.2 |
| 3 | 4-Cl-benzyl | 6.6 | 455.2 |
| 4 | 2-Br-benzyl | 6.6 | 499.2 |
-continued
FORMULA 49
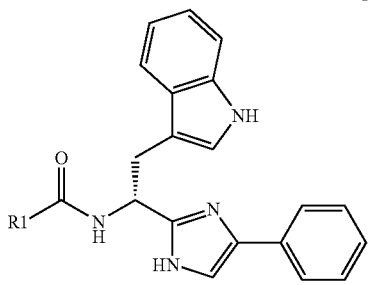
| | R1 | Analysis (min) | [M + H]+ |
|---|---|---|---|
| 5 | 3-Br-benzyl | 6.7 | 499.2 |
| 6 | 4-Br-benzyl | 6.7 | 499.2 |
| 7 | 2-F-benzyl | 6.5 | 439.2 |
| 8 | 3-F-benzyl | 6.5 | 439.2 |

413
-continued
FORMULA 49
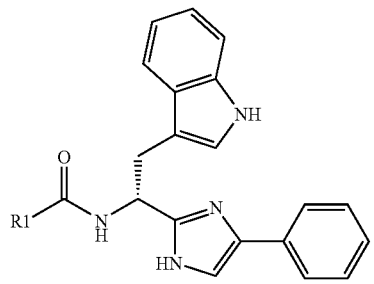
| R1 | Analysis (min) | [M + H]+ |
|---|---|---|
| 9 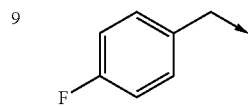 | 6.5 | 439.2 |
| 10 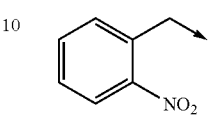 | 6.5 | 466.2 |
| 11 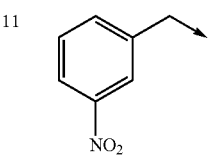 | 6.5 | 466.2 |
| 12 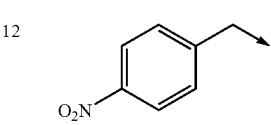 | 6.5 | 466.2 |
| 13 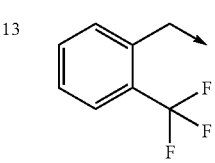 | 6.7 | 489.2 |
| 14 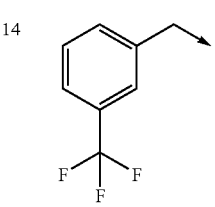 | 6.7 | 489.2 |
| 15 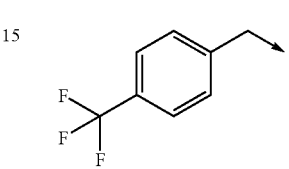 | 6.8 | 489.2 |
414
-continued
FORMULA 49
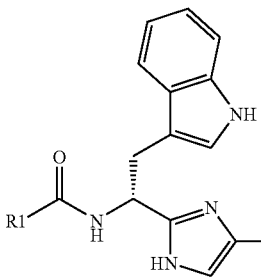
| R1 | Analysis (min) | [M + H]+ |
|---|---|---|
| 16 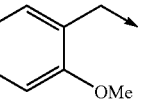 | 6.5 | 451.3 |
| 17 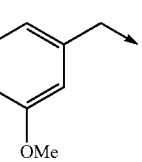 | 6.5 | 451.3 |
| 18 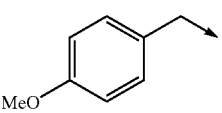 | 6.5 | 451.3 |
| 19 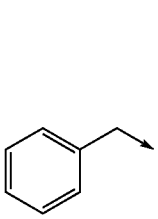 | 6.5 | 421.3 |
| 20 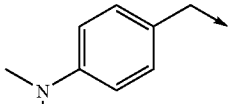 | 5.8 | 464.3 |

FORMULA 50

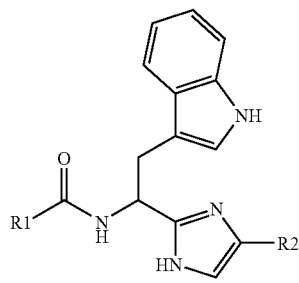

| | R1 | R2 | Tr | [M + H]+ |
|---|---|---|---|---|
| 1 | tert-butyl N-ethylcarbamate (R) | phenyl | 6.3 | 474.3 |
| 2 | tert-butyl N-methylcarbamate (R) | phenyl | 6.3 | 460.3 |
| 3 | tert-butyl N-propylcarbamate (R) | phenyl | 6.3 | 488.3 |
| 4 | tert-butyl N-pentylcarbamate (R) | phenyl | 6.4 | 516.3 |
| 5 | tert-butyl N-methylcarbamate (R) | phenyl | 6.3 | 474.3 |
| 6 | tert-butyl N-(4-phenyl)carbamate (R) | phenyl | 6.5 | 522.3 |
| 7 | tert-butyl N-tert-butylcarbamate (R) | phenyl | 6.5 | 488.3 |
| 8 | tert-butyl N-butylcarbamate (R) | phenyl | 6.4 | 502.3 |
| 9 | tert-butyl N-(4-benzyl)carbamate (R) | phenyl | 6.5 | 536.3 |
| 10 | tert-butyl N-(4-phenethyl)carbamate (R) | phenyl | 6.5 | 536.3 |

-continued
FORMULA 50
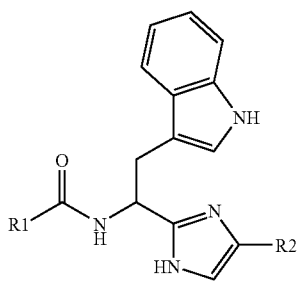
| | R1 | R2 | | Analysis Tr | [M + H]+ |
|---|---|---|---|---|---|
| 11 | tert-butyl N-ethyl carbamate | (R.S) | | 6.2 | 454.3 |
| 12 (R) | phenyl | (R.S) | | 6.2 | 440.3 |
| 13 | tert-butyl N-methyl carbamate | (R.S) | | 6.3 | 468.3 |
| 14 | tert-butyl N-propyl carbamate | (R.S) | | 6.4 | 496.3 |
| 15 | tert-butyl N-pentyl carbamate | (R.S) | | 6.2 | 454.3 |
| 16 | tert-butyl N,N-dimethyl carbamate | (R.S) | | 6.5 | 502.3 |
| 17 | tert-butyl N-(4-phenyl)carbamate | (R.S) | | 6.4 | 468.3 |
| 18 | tert-butyl N-tert-butyl carbamate | (R.S) | | 6.3 | 482.3 |
| 19 | tert-butyl N-butyl carbamate | (R.S) | | 6.4 | 516.3 |
| 20 | tert-butyl N-benzyl carbamate | (R.S) | | 6.4 | 516.3 |

-continued
FORMULA 50
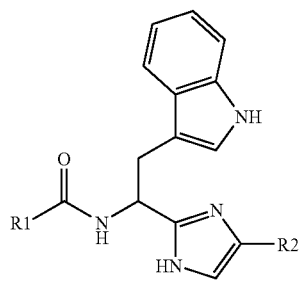
| R1 | R2 | Analysis Tr | [M + H]+ |
|---|---|---|---|
| 21 tert-butyl carbamate-CH2CH2- | (R,S) tert-butyl | 6.2 | 454.3 |
FORMULA 51
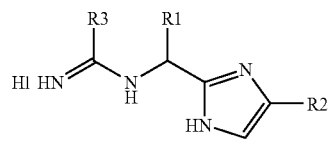
| | R1 | R2 | R3 | Tr | [M + H]+ |
|---|---|---|---|---|---|
| 1 (S) | PhCH2O-CH2-* | Ph-* | Ph-* | 5.6 | 397.2 |
| 2 (S) | PhCH2O-CH2-* | Ph-* | 2-Cl-C6H4-* | 5.9 | 431.2 |
| 3 (S) | PhCH2O-CH2-* | Ph-* | 4-Cl-C6H4-* | 6.0 | 431.2 |
| 4 (S) | PhCH2O-CH2-* | Ph-* | 4-MeO-C6H4-* | 5.8 | 427.2 |
| 5 (S) | PhCH2O-CH2-* | Ph-* | 4-CF3-C6H4-* | 6.3 | 465.2 |

-continued
FORMULA 51
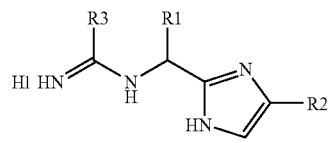
| | R1 | R2 | R3 | Tr | [M + H]+ |
|---|---|---|---|---|---|
| 6 (S) | BnOCH2– | Ph | 4-tBu-C6H4 | 6.7 | 453.3 |
| 7 (S) | BnOCH2– | Ph | 2,4-F2-C6H3 | 5.8 | 433.2 |
| 8 (S) | BnOCH2– | Ph | 4-CF3O-C6H4 | 6.4 | 481.2 |
| 9 (S) | BnOCH2– | Ph | 2,6-Cl2-C6H3-CH2 | 6.3 | 479.1 |
| 10 (S) | BnOCH2– | Ph | tBu-SO2-CH2 | 5.7 | 455.2 |
| 11 (S) | 4-MeO-C6H4-CH2 | Ph | Ph | 5.4 | 397.2 |
| 12 (S) | 4-MeO-C6H4-CH2 | Ph | 2-Cl-C6H4 | 5.0 | 431.2 |
| 13 (S) | 4-MeO-C6H4-CH2 | Ph | 4-Cl-C6H4 | 5.8 | 431.2 |
| 14 (S) | 4-MeO-C6H4-CH2 | Ph | 4-MeO-C6H4 | 5.5 | 427.2 |

-continued

FORMULA 51

| | R1 | R2 | R3 | Tr | [M + H]+ |
|---|---|---|---|---|---|
| 15 | (S) 4-methoxybenzyl | phenyl | 4-CF₃-phenyl | 6.0 | 465.2 |
| 16 | (S) 4-methoxybenzyl | phenyl | 4-tert-butylphenyl | 6.5 | 453.3 |
| 17 | (S) 4-methoxybenzyl | phenyl | 2,4-difluorophenyl | 5.5 | 433.2 |
| 18 | (S) 4-methoxybenzyl | phenyl | 4-CF₃O-phenyl | 6.2 | 481.2 |
| 19 | (S) 4-methoxybenzyl | phenyl | 2,6-dichlorobenzyl | 6.1 | 479.1 |
| 20 | (S) 4-methoxybenzyl | phenyl | tert-butylsulfonylmethyl | 5.5 | 455.2 |
| 21 | (R) indol-3-ylmethyl | phenyl | phenyl | 5.3 | 406.2 |
| 22 | (R) indol-3-ylmethyl | phenyl | 2-chlorophenyl | 5.5 | 440.1 |
| 23 | (R) indol-3-ylmethyl | phenyl | 4-chlorophenyl | 5.7 | 440.2 |

-continued

FORMULA 51

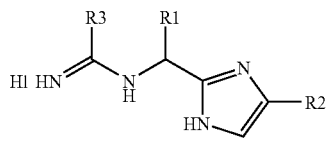

| | R1 | R2 | R3 | Tr | [M + H]+ |
|---|---|---|---|---|---|
| 24 (R) | 3-indolylmethyl | phenyl | 4-methoxyphenyl | 5.5 | 436.2 |
| 25 (R) | 3-indolylmethyl | phenyl | 4-trifluoromethylphenyl | 6.0 | 474.2 |
| 26 (R) | 3-indolylmethyl | phenyl | 4-tert-butylphenyl | 6.4 | 462.3 |
| 27 (R) | 3-indolylmethyl | phenyl | 2,4-difluorophenyl | 5.5 | 442.2 |
| 28 (R) | 3-indolylmethyl | phenyl | 4-trifluoromethoxyphenyl | 6.1 | 490.2 |
| 29 (R) | 3-indolylmethyl | phenyl | 2,6-dichlorobenzyl | 6.0 | 488.1 |
| 30 (R) | 3-indolylmethyl | phenyl | tert-butylsulfonylmethyl | 5.4 | 464.2 |
| 31 (R) | 3-indolylmethyl | 4-methoxyphenyl | phenyl | 5.2 | 436.2 |

-continued
FORMULA 51
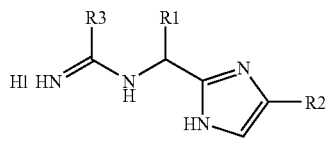
| | R1 | R2 | R3 | Analysis Tr | [M + H]+ |
|---|---|---|---|---|---|
| 32 (R) | indol-3-ylmethyl | 4-MeO-phenyl | 2-Cl-phenyl | 5.4 | 470.2 |
| 33 (R) | indol-3-ylmethyl | 4-MeO-phenyl | 4-Cl-phenyl | 5.6 | 470.2 |
| 34 (R) | indol-3-ylmethyl | 4-MeO-phenyl | 4-MeO-phenyl | 5.4 | 466.2 |
| 35 (R) | indol-3-ylmethyl | 4-MeO-phenyl | 4-CF3-phenyl | 5.9 | 504.2 |
| 36 (R) | indol-3-ylmethyl | 4-MeO-phenyl | 4-tBu-phenyl | 6.2 | 492.3 |
| 37 (R) | indol-3-ylmethyl | 4-MeO-phenyl | 2,4-diF-phenyl | 5.4 | 472.2 |
| 38 (R) | indol-3-ylmethyl | 4-MeO-phenyl | 4-CF3O-phenyl | 6.0 | 520.1 |
| 39 (R) | indol-3-ylmethyl | 4-MeO-phenyl | 2,6-diCl-benzyl | 5.8 | 518.1 |

-continued
FORMULA 51
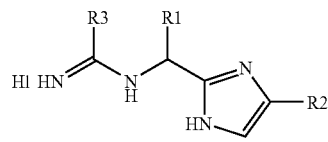
| | R1 | R2 | R3 | Analysis Tr | [M + H]+ |
|---|---|---|---|---|---|
| 40 (R) | indol-3-ylmethyl | 4-MeO-phenyl | tBu-SO2-CH2- | 5.3 | 494.2 |
| 41 (R,S) | indol-3-ylmethyl | 2-OMe-phenyl | phenyl | 5.2 | 436.2 |
| 42 (R,S) | indol-3-ylmethyl | 2-OMe-phenyl | 2-Cl-phenyl | 5.4 | 470.2 |
| 43 (R,S) | indol-3-ylmethyl | 2-OMe-phenyl | 4-Cl-phenyl | 5.5 | 470.2 |
| 44 (R,S) | indol-3-ylmethyl | 2-OMe-phenyl | 4-MeO-phenyl | 5.4 | 466.2 |
| 45 (R,S) | indol-3-ylmethyl | 2-OMe-phenyl | 4-CF3-phenyl | 5.9 | 504.2 |
| 46 (R,S) | indol-3-ylmethyl | 2-OMe-phenyl | 4-tBu-phenyl | 6.2 | 492.3 |
| 47 (R,S) | indol-3-ylmethyl | 2-OMe-phenyl | 2,4-diF-phenyl | 5.4 | 472.2 |

-continued
FORMULA 51
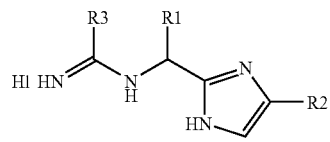
| | R1 | R2 | R3 | Analysis Tr | [M + H]+ |
|---|---|---|---|---|---|
| 48 (R.S) | indol-3-ylmethyl | 2-OMe-phenyl | 4-CF3O-phenyl | 6.0 | 520.1 |
| 49 (R.S) | indol-3-ylmethyl | 2-OMe-phenyl | 2,6-dichlorobenzyl | 5.9 | 518.1 |
| 50 (R.S) | indol-3-ylmethyl | 2-OMe-phenyl | t-Bu-CH2-SO2 | 5.3 | 494.2 |
| 51 (R.S) | indol-3-ylmethyl | t-Bu | phenyl | 4.6 | 386.2 |
| 52 (R.S) | indol-3-ylmethyl | t-Bu | 2-Cl-phenyl | 4.7 | 420.2 |
| 53 (R.S) | indol-3-ylmethyl | t-Bu | 4-Cl-phenyl | 4.9 | 420.2 |
| 54 (R.S) | indol-3-ylmethyl | t-Bu | 4-MeO-phenyl | 4.8 | 416.2 |
| 55 (R.S) | indol-3-ylmethyl | t-Bu | 4-CF3-phenyl | 5.2 | 454.2 |

-continued
FORMULA 51
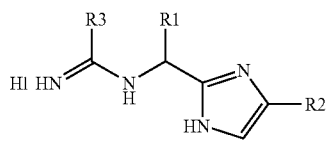
| | R1 | R2 | R3 | Analysis Tr | [M + H]+ |
|---|---|---|---|---|---|
| 56 (R,S) | 3-indolylmethyl | t-Bu | 4-t-butylphenyl | 5.6 | 442.3 |
| 57 (R,S) | 3-indolylmethyl | t-Bu | 2,4-difluorophenyl | 4.7 | 422.2 |
| 58 (R,S) | 3-indolylmethyl | t-Bu | 4-trifluoromethoxyphenyl | 5.3 | 470.2 |
| 59 (R,S) | 3-indolylmethyl | t-Bu | 2,6-dichlorobenzyl | 5.2 | 468.2 |
| 60 (R,S) | 3-indolylmethyl | t-Bu | t-butylsulfonylmethyl | 4.8 | 444.2 |
| 61 (S) | 1-benzyl-imidazol-4-ylmethyl | phenyl | phenyl | 4.9 | 449.2 |
| 62 (S) | 1-benzyl-imidazol-4-ylmethyl | phenyl | 2-chlorophenyl | 5.0 | 483.2 |

-continued
FORMULA 51
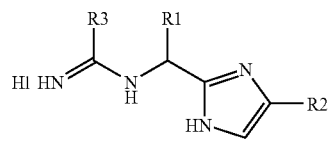
| | R1 | R2 | R3 | Analysis Tr | [M + H]+ |
|---|---|---|---|---|---|
| 63 | (S)-1-benzylimidazol-4-ylmethyl | phenyl | 4-Cl-phenyl | 5.2 | 483.2 |
| 64 | (S)-1-benzylimidazol-4-ylmethyl | phenyl | 4-MeO-phenyl | 5.0 | 477.2 |
| 65 | (S)-1-benzylimidazol-4-ylmethyl | phenyl | 4-CF3-phenyl | 5.4 | 515.1 |
| 66 | (S)-1-benzylimidazol-4-ylmethyl | phenyl | 4-tBu-phenyl | 5.8 | 503.3 |
| 67 | (S)-1-benzylimidazol-4-ylmethyl | phenyl | 2,4-diF-phenyl | 4.9 | 483.2 |
| 68 | (S)-1-benzylimidazol-4-ylmethyl | phenyl | 4-CF3O-phenyl | 5.5 | 531.2 |

-continued
FORMULA 51
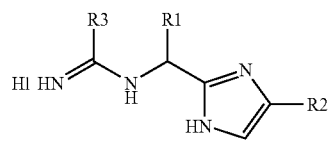
| | R1 | R2 | R3 | Analysis Tr | [M + H]+ |
|---|---|---|---|---|---|
| 69 (S) | 1-benzyl-imidazol-4-yl-methyl | phenyl | 2,6-dichlorobenzyl | 5.4 | 531.1 |
| 70 (S) | 1-benzyl-imidazol-4-yl-methyl | phenyl | tert-butylsulfonylmethyl | 4.9 | 507.2 |
| 71 (S) | benzyl | phenyl | phenyl | 5.3 | 367.2 |
| 72 (S) | benzyl | phenyl | 2-chlorophenyl | 5.6 | 401.2 |
| 73 (S) | benzyl | phenyl | 4-chlorophenyl | 5.7 | 401.1 |
| 74 (S) | benzyl | phenyl | 4-methoxyphenyl | 5.5 | 397.2 |
| 75 (S) | benzyl | phenyl | 4-trifluoromethylphenyl | 6.0 | 435.2 |
| 76 (S) | benzyl | phenyl | 4-tert-butylphenyl | 6.5 | 423.3 |

-continued
FORMULA 51
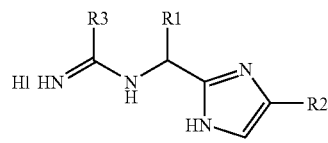
| | R1 | R2 | R3 | Analysis Tr | [M + H]+ |
|---|---|---|---|---|---|
| 77 (S) | benzyl | phenyl | 2,4-difluorophenyl | 5.5 | 403.2 |
| 78 (S) | benzyl | phenyl | 4-(trifluoromethoxy)phenyl | 6.2 | 451.2 |
| 79 (S) | benzyl | phenyl | 2,6-dichlorobenzyl | 6.1 | 449.1 |
| 80 (S) | benzyl | phenyl | tert-butylsulfonylmethyl | 5.4 | 425.2 |
FORMULA 52
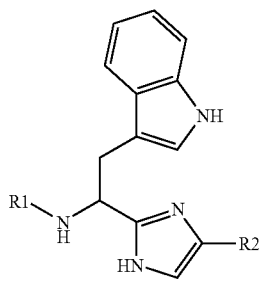
| | R1 | R2 | Analysis Tr | [M + H]+ |
|---|---|---|---|---|
| 1 | benzyl | (S) phenyl | 5.9 | 393.2 |
| 2 | 2-hydroxybenzyl | (S) phenyl | 5.7 | 409.2 |

-continued
FORMULA 52
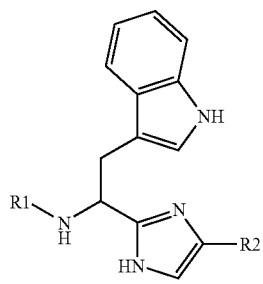
| | R1 | R2 | Tr | [M + H]+ |
|---|---|---|---|---|
| 3 | 4-HO-C6H4-CH2- | (S) phenyl | 5.6 | 409.2 |
| 4 | 4-F-C6H4-CH2- | (S) phenyl | 6.0 | 411.2 |
| 5 | 3-MeO-C6H4-CH2- | (S) phenyl | 6.0 | 423.2 |
| 6 | 4-MeO-C6H4-CH2- (SH2) | (S) phenyl | 6.0 | 423.2 |
| 7 | 2-MeO-C6H4-CH2- | (S) phenyl | 6.0 | 423.2 |
| 8 | 2-NO2-C6H4-CH2- | (S) phenyl | 6.0 | 438.2 |
| 9 | 4-O2N-C6H4-CH2- | (S) phenyl | 6.0 | 438.2 |
| 10 | 3,4-Cl2-C6H3-CH2- | (S) phenyl | 6.5 | 461.1 |
| 11 | 3-MeO-2-NO2-C6H3-CH2- | (S) phenyl | 6.1 | 468.2 |

-continued
FORMULA 52
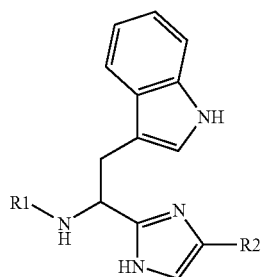
| | R1 | R2 | Tr | [M + H]+ |
|---|---|---|---|---|
| 12 | 4-Br-C6H4-CH2- | (S) Ph | 6.4 | 471.1 |
| 13 | 2-thienyl-CH2- | (S) Ph | 5.8 | 511.2* |
| 14 | 3,4,5-(MeO)3-C6H2-CH2- | (S) Ph | 5.9 | 483.3 |
| 15 | 2-F-CH2-CH=CH-CH=CH2 (2-fluoro-penta-2,4-dienyl) | (S) Ph | 5.9 | 411.2 |
| 16 | 2-CF3-C6H4-CH2- | (S) Ph | 6.4 | 461.2 |
| 17 | 2-Br-C6H4-CH2- | (S) Ph | 6.2 | 471.1 |
| 18 | 4-(NMe2)-C6H4-CH2- | (S) Ph | 5.5 | 436.3 |
| 19 | 4-(OCF3)-C6H4-CH2- | (S) Ph | 6.6 | 477.2 |

-continued
FORMULA 52
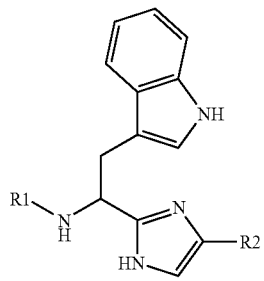
| | R1 | R2 | Tr | [M + H]+ |
|---|---|---|---|---|
| 20 | -N(Me)2-CH2-CH=C(Et)-CH2-O-propyl, SH2 | phenyl (S) | 4.9 | 494.3 |
| 21 | benzyl | 2-OMe-cyclohexadienyl (R.S) | 6.0 | 423.3 |
| 22 | phenyl (S) | 2-OMe-cyclohexadienyl (R.S) | 5.7 | 439.2 |
| 23 | 2-OH-benzyl | 2-OMe-cyclohexadienyl (R.S) | 5.6 | 439.2 |
| 24 | 4-OH-benzyl | 2-OMe-cyclohexadienyl (R.S) | 6.1 | 441.2 |
| 25 | 4-F-benzyl | 2-OMe-cyclohexadienyl (R.S) | 6.0 | 453.2 |
| 26 | 4-MeO-benzyl | 2-OMe-cyclohexadienyl (R.S) | 5.9 | 453.2 |

-continued
FORMULA 52
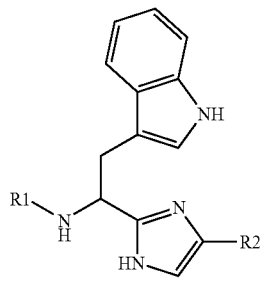
| | R1 | R2 | Tr | [M + H]+ |
|---|---|---|---|---|
| 27 | 2-OMe-benzyl | OMe-benzyl (R.S) | 6.0 | 453.2 |
| 28 | 2-NO2-benzyl | OMe-benzyl (R.S) | 6.2 | 468.2 |
| 29 | 4-O2N-benzyl | OMe-benzyl (R.S) | 6.1 | 468.2 |
| 30 | 3,4-Cl2-benzyl | OMe-benzyl (R.S) | 6.1 | 468.2 |
| 31 | 3-MeO-2-NO2-benzyl | OMe-benzyl (R.S) | 6.7 | 491.2 |
| 32 | 4-Br-benzyl | OMe-benzyl (R.S) | 6.5 | 501.1 |
| 33 | thiophen-2-ylmethyl | OMe-benzyl (R.S) | 6.0 | 429.2 |

-continued
FORMULA 52
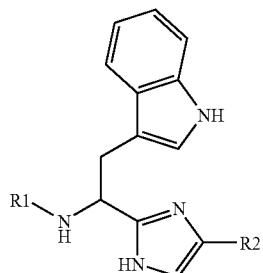
| | R1 | R2 | Tr | [M + H]+ |
|---|---|---|---|---|
| 34 | MeO, MeO, OMe (benzyl) | OMe (R.S) | 5.9 | 513.2 |
| 35 | F (pentadienyl) | OMe (R.S) | 6.1 | 441.2 |
| 36 | CF3-benzyl | OMe (R.S) | 6.6 | 491.2 |
| 37 | Br-benzyl | OMe (R.S) | 6.4 | 501.1 |
| 38 | 4-(dimethylamino)benzyl | OMe (R.S) | 5.5 | 466.3 |
| 39 | 4-(OCF3)benzyl | OMe (R.S) | 6.7 | 507.2 |
| 40 | Me2N-(CH2)3-O-C6H4-CH2 | OMe (R.S) | 4.9 | 524.3 |

-continued
FORMULA 52
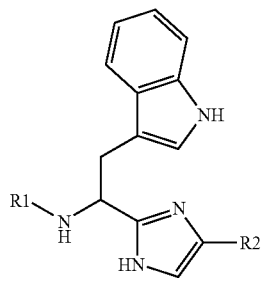
| R1 | R2 | Analysis Tr | [M + H]+ |
|---|---|---|---|
| 41 benzyl | (R) 4-OMe-benzyl | 5.9 | 423.2 |
| 42 (S) benzyl | (R) 4-OMe-benzyl | 5.6 | 439.2 |
| 43 2-OH-benzyl | (R) 4-OMe-benzyl | 5.5 | 439.2 |
| 44 4-HO-benzyl | (R) 4-OMe-benzyl | 6.0 | 441.2 |
| 45 4-F-benzyl | (R) 4-OMe-benzyl | 6.0 | 453.2 |
| 46 3-MeO-benzyl | (R) 4-OMe-benzyl | 5.9 | 453.2 |
| 47 SH$_2$ 4-MeO-benzyl | (R) 4-OMe-benzyl | 6.0 | 453.2 |
| 48 2-OMe-benzyl | (R) 4-OMe-benzyl | 6.1 | 468.2 |
| 49 2-NO$_2$-benzyl | (R) 4-OMe-benzyl | 6.1 | 468.2 |

-continued
FORMULA 52
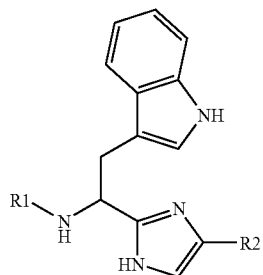
| R1 | R2 | Analysis Tr | [M + H]+ |
|---|---|---|---|
| 50 4-O₂N-C₆H₄-CH₂- | (R) 4-MeO-C₆H₄- | 6.6 | 491.1 |
| 51 3,4-Cl₂-C₆H₃-CH₂- | (R) 4-MeO-C₆H₄- | 6.2 | 498.2 |
| 52 2-NO₂-3-MeO-C₆H₃-CH₂- | (R) 4-MeO-C₆H₄- | 6.4 | 501.1 |
| 53 4-Br-C₆H₄-CH₂- | (R) 4-MeO-C₆H₄- | 5.8 | 429.2 |
| 54 2-thienyl-CH₂- | (R) 4-MeO-C₆H₄- | 5.8 | 513.2 |
| 55 3,4,5-(MeO)₃-C₆H₂-CH₂- | (R) 4-MeO-C₆H₄- | 6.1 | 441.2 |
| 56 2-CF₃-C₆H₄-CH₂- | (R) 4-MeO-C₆H₄- | 6.5 | 491.2 |
| 57 2-Br-C₆H₄-CH₂- | (R) 4-MeO-C₆H₄- | 6.3 | 501.1 |

-continued
FORMULA 52
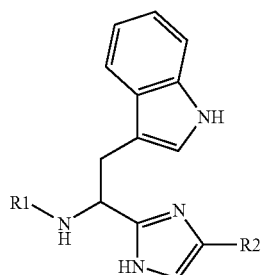
| | R1 | R2 | Tr | [M + H]+ |
|---|---|---|---|---|
| 58 | 4-(dimethylamino)benzyl, SH2 | (R) 4-OMe-phenyl | 5.4 | 466.3 |
| 59 | 4-(trifluoromethoxy)benzyl | (R) 4-OMe-phenyl | 5.6 | 507.2 |
| 60 | SH2, dimethylamino alkenyl propoxy chain | (R) 4-OMe-phenyl | 4.9 | 524.3 |
| 61 | benzyl | (R) 4-OMe-phenyl | 5.9 | 423.2 |
| 62 | (S) cyclohexyl | (S) 4-OMe-phenyl | 5.6 | 439.2 |
| 63 | 2-hydroxybenzyl | (S) 4-OMe-phenyl | 5.5 | 439.2 |
| 64 | 4-hydroxybenzyl | (S) 4-OMe-phenyl | 6.0 | 441.2 |
| 65 | 4-fluorobenzyl | (S) 4-OMe-phenyl | 6.0 | 453.2 |
| 66 | 3-methoxybenzyl | (S) 4-OMe-phenyl | 5.9 | 453.2 |

-continued
FORMULA 52
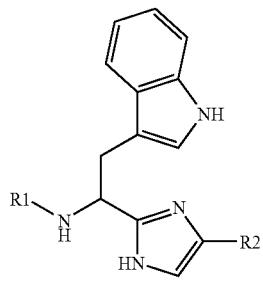
| | R1 | R2 | Tr | [M + H]+ |
|---|---|---|---|---|
| 67 | SH₂, 4-MeO-benzyl | (S) 4-OMe-phenyl | 6.0 | 453.2 |
| 68 | 2-OMe-benzyl | (S) 4-OMe-phenyl | 6.0 | 468.2 |
| 69 | 2-NO₂-benzyl | (S) 4-OMe-phenyl | 6.0 | 468.2 |
| 70 | 3,4-diCl-benzyl, SH₂ | (S) 4-OMe-phenyl | 6.8 | 491.1 |
| 71 | 3-MeO-2-NO₂-benzyl, SH₂ | (S) 4-OMe-phenyl | 6.2 | 498.2 |
| 72 | 4-Br-benzyl | (S) 4-OMe-phenyl | 6.4 | 501.1 |
| 73 | 2-thienylmethyl | (S) 4-OMe-phenyl | 5.9 | 429.2 |
| 74 | 3,4,5-triMeO-benzyl | (S) 4-OMe-phenyl | 5.8 | 513.3 |

-continued
FORMULA 52
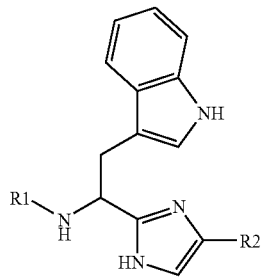
| | R1 | R2 | Tr | [M + H]+ |
|---|---|---|---|---|
| 75 | 2-fluoro-penta-2,4-dienyl | (S) 4-OMe-phenyl | 6.0 | 441.2 |
| 76 | 2-(trifluoromethyl)benzyl | (S) 4-OMe-phenyl | 6.5 | 491.2 |
| 77 | 2-bromobenzyl | (S) 4-OMe-phenyl | 6.3 | 501.1 |
| 78 | 4-(dimethylamino)benzyl | (S) 4-OMe-phenyl | 5.4 | 466.3 |
| 79 | 4-(trifluoromethoxy)benzyl-SH₂ | (S) 4-OMe-phenyl | 6.6 | 507.2 |

FORMULA 53
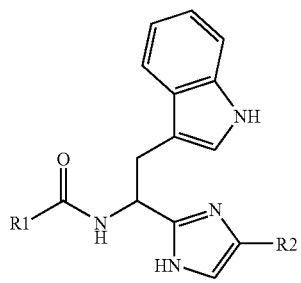
| | R1 | R2 | Tr (min) | [M + H]+ |
|---|---|---|---|---|
| 1 | morpholine | (R) phenyl | 5.2 | 416.2 |
| 2 * | thiazolidine | (R) phenyl | 5.5 | 418.1 |
| 3 | 4-hydroxypiperidine | (R) phenyl | 5.0 | 430.2 |
| 4 | piperidine-4-carboxamide | (R) phenyl | 5.0 | 457.2 |
| 5 | N-benzyl-N-(2-hydroxyethyl)amine * | (R) phenyl | 5.9 | 480.2 |
| 6 | 4-phenylpiperazine | (R) phenyl | 6.1 | 491.2 |
| 7 | 2,3,4,9-tetrahydro-1H-β-carboline | (R) phenyl | 6.4 | 501.2 |
| 8 * | 4-benzylpiperazine | (R) phenyl | 4.9 | 505.2 |
| 9 | 4-(4-fluorophenyl)piperazine | (R) phenyl | 6.3 | 509.2 |
| 10 | 4-(2-methoxyphenyl)piperazine | (R) phenyl | 5.9 | 521.2 |

-continued
FORMULA 53
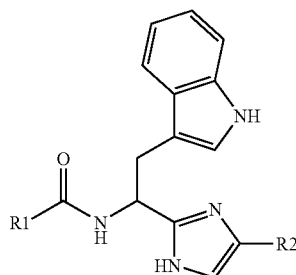
| | R1 | R2 | Tr (min) | [M + H]+ |
|---|---|---|---|---|
| 11 | N-piperazine-N-(3-chlorophenyl) | (R) phenyl | 6.7 | 525.2 |
| 12 | N(CH2Ph)2 (dibenzylamino) | (R) phenyl | 7.0 | 525.2 |
| 13 | N-piperazine-N-(4-nitrophenyl) | (R) phenyl | 6.3 | 536.2 |
| 14 | 6,7-dimethoxy-1,2,3,4-tetrahydroisoquinolin-2-yl | (R) phenyl | 5.9 | 522.2 |
| 15 | N-piperazine-N-(4-chlorophenyl) | (R) phenyl | 6.7 | 525.2 |
| 16 | N-piperazine-N-(2-pyridyl) | (R) phenyl | 4.6 | 492.2 |
| 17 | 4-benzylpiperidin-1-yl | (R) phenyl | 6.9 | 504.2 |
| 18 | 1,4-dioxa-8-azaspiro[4.5]decan-8-yl | (R) phenyl | 5.4 | 472.2 |
| 19 | 4-hydroxy-4-phenylpiperidin-1-yl | (R) phenyl | 5.9 | 506.2 |

-continued
FORMULA 53
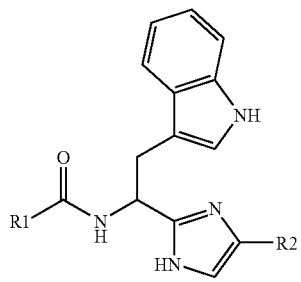
| | R1 | R2 | Analysis Tr (min) | [M + H]+ |
|---|---|---|---|---|
| 20 | ethyl ester-CH2CH2-N(*)-CH2-cyclohexenyl | (R) phenyl | 6.6 | 536.2 |
| 21 | benzodioxole-CH2-piperazine-N* | (R) phenyl | 4.9 | 549.2 |
| 22 | 4-[3-(trifluoromethyl)phenyl]piperidine | (R) phenyl | 6.9 | 559.2 |
| 23 | 1-phenyl-1,3,8-triazaspiro[4.5]decan-4-one-N8* | (R) phenyl | 6.0 | 560.2 |
| 24 | 4-(2-chlorophenyl)piperazine | (R) phenyl | 6.7 | 525.2 |
| 25 | 4-(4-hydroxyphenyl)piperazine | (R) phenyl | 5.0 | 507.2 |
| 26 | 4-(2,4-dimethylphenyl)piperazine | (R) phenyl | 6.9 | 519.2 |

-continued
FORMULA 53
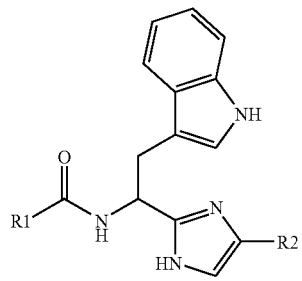
| | R1 | R2 | Analysis Tr (min) | [M + H]+ |
|---|---|---|---|---|
| 27 | (3-hydroxypyrrolidin-1-yl), Chiral | (R) phenyl | 5.0 | 416.2 |
| 28 | 4-(benzyloxycarbonyl)piperazin-1-yl | (R) phenyl | 6.4 | 549.2 |
| 29 | 4-(2-oxo-2,3-dihydro-1H-benzimidazol-1-yl)piperidin-1-yl | (R) phenyl | 5.8 | 546.2 |
| 30 | 4-(furan-2-carbonyl)piperazin-1-yl | (R) phenyl | 5.5 | 509.2 |
| 31 | N-benzyl-N-(4-benzamidobutyl)amino | (R) phenyl | 6.8 | 611.2 |
| 32 | N-benzyl-N-[2-(2-methoxyphenyl)ethyl]amino | (R) phenyl | 7.2 | 570.2 |
| 33 | 4-(4-methoxyphenyl)piperazin-1-yl | (R) phenyl | 5.8 | 521.2 |

-continued
FORMULA 53
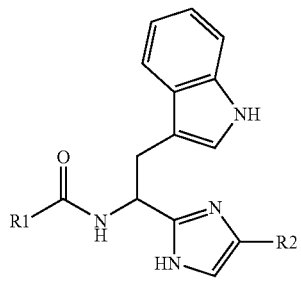
| | R1 | R2 | Tr (min) | [M + H]+ |
|---|---|---|---|---|
| 34 | *-N(piperazine)-CH(Ph)2 | (R) phenyl | 5.8 | 581.2 |
| 35 | *-N(Bn)-CH2CH2-N(Me)2 | (R) phenyl | 5.1 | 507.2 |
| 36 | *-N(CH2CH2CH2NMe2)2 | (R) phenyl | 4.2 | 516.3 |
| 37 | 4-(2-fluorophenyl)piperazin-1-yl | (R) phenyl | 6.4 | 509.2 |
| 38 | 4-(2-methylthiophenyl)piperazin-1-yl | (R) phenyl | 5.7 | 537.2 |
| 39 | morpholin-4-yl | (R,S) tert-butyl | 5.1 | 396.2 |
| 40 | (R) phenyl | (R,S) tert-butyl | 5.4 | 398.2 |

-continued
FORMULA 53
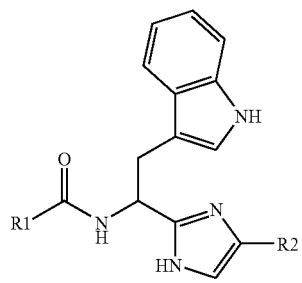
| | R1 | R2 | | Analysis | |
|---|---|---|---|---|---|
| | | | | Tr (min) | [M + H]+ |
| 41 * | thiazolidine | (R,S) | | 5.0 | 410.2 |
| 42 | 4-hydroxypiperidine | (R,S) | | 4.9 | 437.2 |
| 43 | 4-carbamoylpiperidine | (R,S) | | 5.8 | 460.2 |
| 44 | N-benzyl-N-(2-hydroxyethyl)amino | (R,S) | | 6.0 | 471.3 |
| 45 | 4-phenylpiperazine | (R,S) | | 6.4 | 481.2 |
| 46 | 1,2,3,4-tetrahydro-β-carboline | (R,S) | | 4.5 | 485.2 |
| 47 * | 4-benzylpiperazine | (R,S) | | 6.2 | 489.2 |
| 48 | 4-(4-fluorophenyl)piperazine | (R,S) | | 5.8 | 501.3 |
| 49 | 4-(2-methoxyphenyl)piperazine | (R,S) | | 6.7 | 505.2 |
| 50 | 4-(3-chlorophenyl)piperazine | (R,S) | | 6.9 | 506.3 |

-continued
FORMULA 53
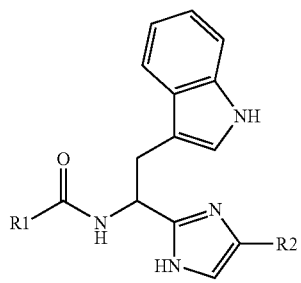
| | R1 | R2 | Tr (min) | [M + H]+ |
|---|---|---|---|---|
| 51 | (benzyl)₂N– | (R.S) | 6.2 | 516.2 |
| 52 | 4-(4-nitrophenyl)piperazin-1-yl | (R.S) | 5.9 | 502.2 |
| 53 | 6,7-dimethoxy-1,2,3,4-tetrahydroisoquinolin-2-yl | (R.S) | 6.6 | 505.2 |
| 54 | 4-(4-chlorophenyl)piperazin-1-yl | (R.S) | 4.5 | 472.3 |
| 55 | 4-(pyridin-2-yl)piperazin-1-yl | (R.S) | 6.8 | 484.3 |
| 56 | 4-benzylpiperidin-1-yl | (R.S) | 5.3 | 452.3 |
| 57 | 1,4-dioxa-8-azaspiro[4.5]decan-8-yl | (R.S) | 5.8 | 486.3 |
| 58 | 4-hydroxy-4-phenylpiperidin-1-yl | (R.S) | 6.5 | 516.3 |
| 59 | ethyl 3-(N-benzyl-N-*)propanoate | (R.S) | 4.8 | 529.2 |

-continued
FORMULA 53
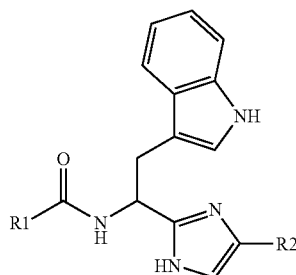
| | R1 | R2 | Tr (min) | [M + H]+ |
|---|---|---|---|---|
| 60 | benzo[1,3]dioxol-5-ylmethyl-piperazinyl | (R,S) | 6.9 | 539.2 |
| 61 | 1-[3-(trifluoromethyl)phenyl]piperidin-4-yl | (R,S) | 6.0 | 540.2 |
| 62 | 1-phenyl-4-oxo-1,3,8-triazaspiro[4.5]decan-8-yl | (R,S) | 6.6 | 505.2 |
| 63 | 4-(2-chlorophenyl)piperazin-1-yl | (R,S) | 4.9 | 487.3 |
| 64 | 4-(4-hydroxyphenyl)piperazin-1-yl | (R,S) | 6.9 | 499.3 |
| 65 | 4-(2,4-dimethylphenyl)piperazin-1-yl | (R,S) | 4.9 | 396.2 |
| 66 | (3R)-3-hydroxypyrrolidin-1-yl (Chiral) | (R,S) | 6.3 | 529.2 |

-continued
FORMULA 53
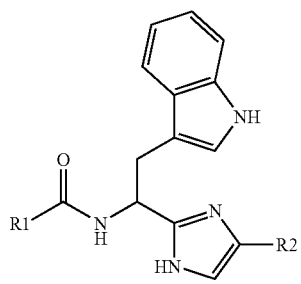
| R1 | R2 | Analysis | |
|---|---|---|---|
| | | Tr (min) | [M + H]+ |
| 67 [benzyl piperazine-1-carboxylate] | (R.S) [t-Bu] | 5.7 | 526.3 |
| 68 [1-(piperidin-4-yl)-1,3-dihydro-2H-benzimidazol-2-one] | (R.S) [t-Bu] | 5.4 | 489.2 |
| 69 [4-(furan-2-carbonyl)piperazine] | (R.S) [t-Bu] | 6.7 | 591.3 |
| 70 [N-(4-(benzylamino)butyl)benzamide] | (R.S) [t-Bu] | 7.2 | 550.3 |
| 71 [N-benzyl-N-(2-methoxyphenethyl)amine] | (R.S) [t-Bu] | 5.7 | 501.3 |

-continued
FORMULA 53
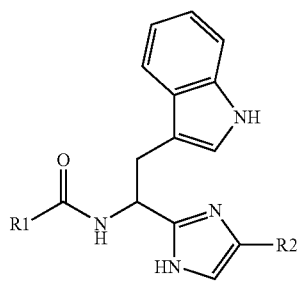
| R1 | R2 | | Analysis Tr (min) | [M + H]+ |
|---|---|---|---|---|
| 72 ~N(piperazine)N-C6H4-OCH3 | (R.S) | ⟩⟨ (t-Bu) | 5.7 | 561.3 |
| 73 *N(piperazine)N-CH(Ph)2 | (R.S) | ⟩⟨ | 5.0 | 487.3 |
| 74 (CH3)2N-CH2CH2-N(*)-CH2Ph | (R.S) | ⟩⟨ | 4.1 | 496.4 |
| 75 (CH3)HN-(CH2)3-N(*)-(CH2)3-N(CH3) | (R.S) | ⟩⟨ | 6.3 | 489.3 |
| 76 ~N(piperazine)N-C6H4-F | (R.S) | ⟩⟨ | 6.7 | 517.2 |

FORMULA 54
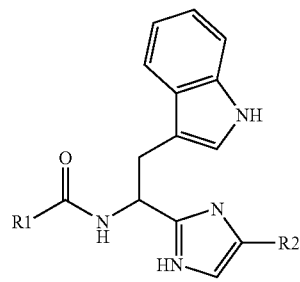
| | R1 | R2 | Tr (min) | [M + H]+ |
|---|---|---|---|---|
| 1 | *N(CH3)-CH2CH2CH2-NH-* | phenyl (R) * | 4.4 | 431.2 |
| 2 | *-NH-cycloheptyl | phenyl (R) * | 6.3 | 442.2 |
| 3 | *-NH-CH2CH2-phenyl | phenyl (R) * | 6.1 | 450.2 |
| 4 | *-NH-CH2-(4-methoxyphenyl) | phenyl (R) * | 5.9 | 466.2 |
| 5 | *-N-CH2CH2-(2-methoxyphenyl) | phenyl (R) * | 6.2 | 480.2 |
| 6 | *-N-CH2CH2-(3,4-dimethoxyphenyl) | phenyl (R) * | 5.9 | 510.2 |
| 7 | *-N-CH2CH2-(imidazol-4-yl) | phenyl (R) * | 4.5 | 440.2 |

-continued
FORMULA 54
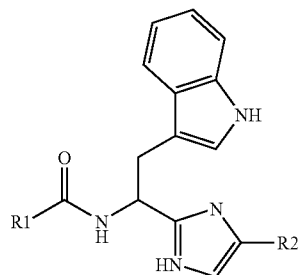
| R1 | R2 | Analysis Tr (min) | [M + H]+ |
|---|---|---|---|
| 8 3,4,5-trimethoxybenzyl-NH- | (R) phenyl | 5.8 | 526.2 |
| 9 4-nitrophenethyl-NH- | (R) phenyl | 6.1 | 495.2 |
| 10 neopentyl-N- | (R) phenyl | 6.2 | 430.3 |
| 11 pyridin-4-ylmethyl-N- | (R) phenyl | 4.5 | 437.2 |
| 12 2-(pyridin-2-yl)ethyl-N- | (R) phenyl | 4.5 | 451.2 |
| 13 3-morpholinopropyl-N- | (R) phenyl | 4.5 | 473.3 |
| 14 ethyl 4-aminopiperidine-1-carboxylate- | (R) phenyl | 5.7 | 501.3 |
| 15 2-(5-nitropyridin-2-ylamino)ethyl-NH- | (R) phenyl | 5.8 | 511.2 |

-continued
FORMULA 54
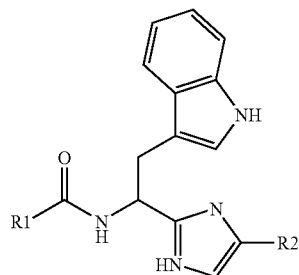
| | R1 | R2 | Tr (min) | [M + H]+ |
|---|---|---|---|---|
| 16 | benzyl-S-CH2CH2-N | phenyl (R) | 6.4 | 496.2 |
| 17 | 3,4-dihydroxybenzyl-N | phenyl (R) | 5.3 | 468.2 |
| 18 | 1,2-diethylpyrazolidin-4-yl-N | phenyl (R) | 4.7 | 472.3 |
| 19 | tert-butyl-N | phenyl (R) | 5.8 | 402.2 |
| 20 | 4-(3-chlorophenyl)piperazin-1-yl-CH2CH2-NH | phenyl (R) | 5.6 | 568.2 |
| 21 | diphenylmethyl-NH | phenyl (R) | 5.8 | 437.2 |
| 22 | pyridin-2-ylmethyl-NH | phenyl (R) | 4.6 | 437.2 |

-continued
FORMULA 54
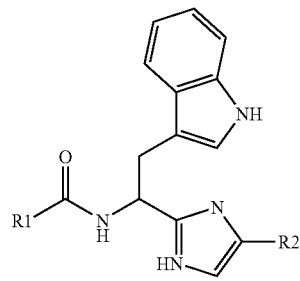
| | R1 | R2 | Tr (min) | [M + H]+ |
|---|---|---|---|---|
| 23 | *↑HN— (3-chlorobenzyl) | (R) phenyl * | 6.3 | 470.2 |
| 24 | Ph2CH-CH2-CH2-NH—* | (R) phenyl * | 7.0 | 540.2 |
| 25 | *↑HN—(CH2)3-Ph | (R) phenyl * | 5.4 | 464.2 |
| 26 | *←HN—(CH2)2-pyrrolidinyl | (R) phenyl * | 4.5 | 443.3 |
| 27 | *↑HN—(CH2)2-(4-Cl-C6H4) | (R) phenyl * | 6.5 | 484.2 |
| 28 | *←NH—(CH2)2-(2-F-C6H4) | (R) phenyl * | 6.2 | 468.2 |

-continued
FORMULA 54
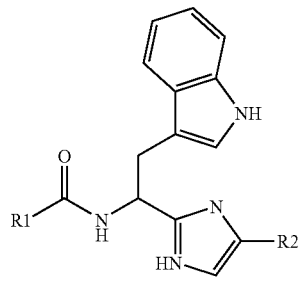
| | R1 | R2 | Analysis Tr (min) | [M + H]+ |
|---|---|---|---|---|
| 29 | 4-F-phenethyl-NH- | phenyl (R) | 6.2 | 468.2 |
| 30 | 3-Cl-phenethyl-NH- | phenyl (R) | 6.5 | 484.2 |
| 31 | 4-Br-phenethyl-NH- | phenyl (R) | 6.6 | 528.1 |
| 32 | 3-CF3-benzyl-NH- | phenyl (R) | 6.5 | 504.2 |
| 33 | 4-CF3-benzyl-NH- | phenyl (R) | 6.5 | 504.2 |
| 34 | pyridin-3-ylmethyl-NH- | phenyl (R) | 4.5 | 437.2 |
| 35 | 2-methoxybenzyl-NH- | phenyl (R) | 6.1 | 486.2 |

-continued
FORMULA 54
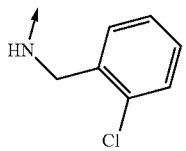
| | R1 | R2 | Analysis Tr (min) | [M + H]+ |
|---|---|---|---|---|
| 36 | 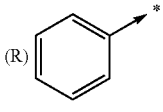 | 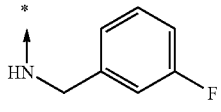 (R) | 6.2 | 470.2 |
| 37 | 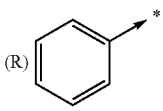 | 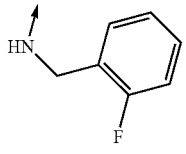 (R) | 6.0 | 454.2 |
| 38 | 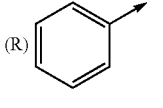 | 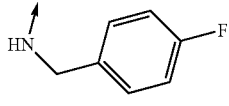 (R) | 6.0 | 454.2 |
| 39 | 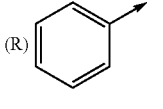 | 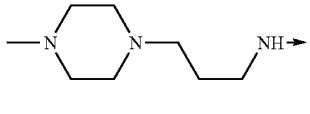 (R) | 5.0 | 454.2 |
| 40 | 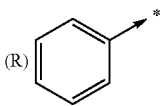 | 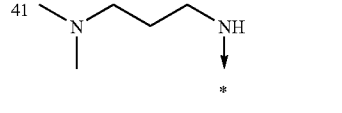 (R) | 4.3 | 486.3 |
| 41 | 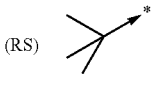 | 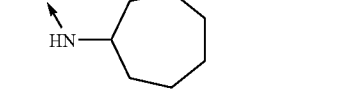 (RS) | 4.4 | 411.3 |
| 42 | 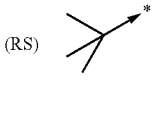 | 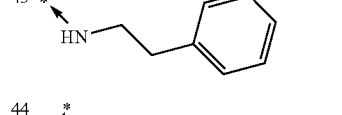 (RS) | 6.3 | 422.3 |
| 43 | 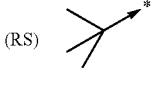 | 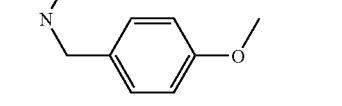 (RS) | 6.0 | 430.3 |
| 44 | 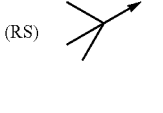 | (RS) | 5.9 | 446.2 |

-continued
FORMULA 54
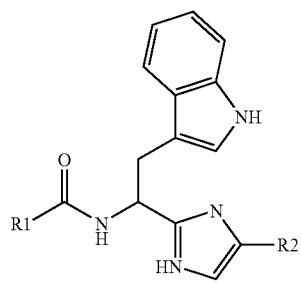
| R1 | R2 | Tr (min) | [M + H]+ |
|---|---|---|---|
| 45 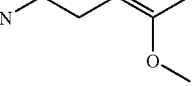 | (RS)  | 6.2 | 460.3 |
| 46 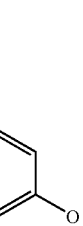 | (RS)  | 5.5 | 490.3 |
| 47 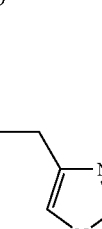 | (RS)  | 4.4 | 420.3 |
| 48 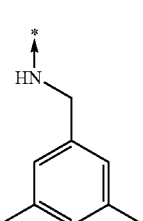 | (RS)  | 5.7 | 506.3 |
| 49 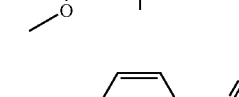 | (RS)  | 6.1 | 475.2 |
| 50 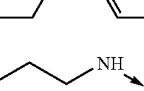 | (RS)  | 6.2 | 410.3 |

-continued
FORMULA 54
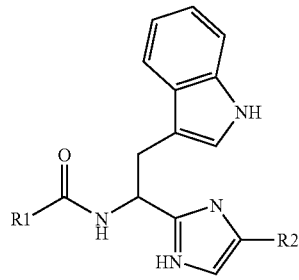
| R1 | R2 | Analysis Tr (min) | [M + H]+ |
|---|---|---|---|
| 51 pyridin-4-ylmethyl-NH—* | (RS) tert-butyl* | 4.4 | 417.2 |
| 52 *HN—CH2CH2-(2-pyridyl) | (RS) tert-butyl* | 4.4 | 431.2 |
| 53 *HN—(CH2)3-morpholino | (RS) tert-butyl* | 4.4 | 453.3 |
| 54 ethyl 4-(NH*)piperidine-1-carboxylate | (RS) tert-butyl* | 5.7 | 481.3 |
| 55 *HN—CH2CH2—NH—(5-nitropyridin-2-yl) | (RS) tert-butyl* | 5.7 | 491.2 |
| 56 PhCH2—S—CH2CH2—N* | (RS) tert-butyl* | 6.4 | 476.3 |
| 57 *HN—CH2-(3,4-dihydroxyphenyl) | (RS) tert-butyl* | 5.2 | 448.2 |
| 58 *HN—CH2-(3,4-dihydroxyphenyl) | (RS) tert-butyl* | 4.6 | 452.3 |
| 59 (CH3)2C(NH*)— | (RS) tert-butyl* | 5.7 | 382.3 |

-continued
FORMULA 54
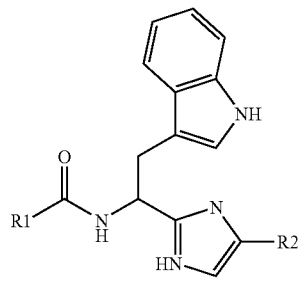
| R1 | R2 | Tr (min) | [M + H]+ |
|---|---|---|---|
| 60 3-Cl-phenyl-piperazine-N-CH2CH2-NH-* | (RS) tBu-* | 5.5 | 548.2 |
| 61 (Ph)2CH-NH-* | (RS) tBu-* | 6.7 | 492.3 |
| 62 2-pyridyl-CH2-NH-* | (RS) tBu-* | 4.5 | 417.2 |
| 63 3-Cl-benzyl-NH-* | (RS) tBu-* | 6.2 | 450.2 |
| 64 (Ph)2CH-CH2CH2-NH-* | (RS) tBu-* | 7.0 | 520.3 |
Analysis column header spans Tr (min) and [M + H]+.

-continued
FORMULA 54
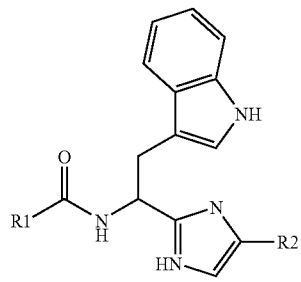
| | R1 | R2 | Analysis Tr (min) | [M + H]+ |
|---|---|---|---|---|
| 65 | * HN—(CH2)3—Ph | (RS) tBu* | 6.3 | 444.3 |
| 66 | *HN—(CH2)2—N-pyrrolidine | (RS) tBu* | 4.4 | 423.3 |
| 67 | *HN—(CH2)2—C6H4—Cl | (RS) tBu* | 6.4 | 464.2 |
| 68 | *NH—(CH2)2—C6H4(2-F) | (RS) tBu* | 6.1 | 448.2 |
| 69 | NH—(CH2)2—C6H4(4-F)* | (RS) tBu* | 6.2 | 448.2 |
| 70 | *NH—(CH2)2—C6H4(3-Cl) | (RS) tBu* | 6.4 | 464.2 |
| 71 | *HN—(CH2)2—C6H4—Br | (RS) tBu* | 6.5 | −510.1 |

-continued
FORMULA 54
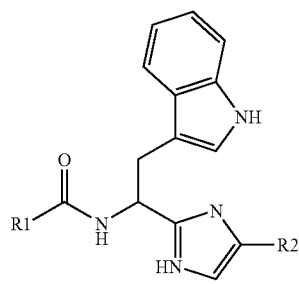
| R1 | R2 | Analysis Tr (min) | [M + H]+ |
|---|---|---|---|
| 72 HN—CH2—C6H4-3-CF3 | (RS) tBu | 6.5 | 484.2 |
| 73 HN—CH2—C6H4-4-CF3 | (RS) tBu | 6.5 | 484.2 |
| 74 3-pyridyl-CH2—NH— | (RS) tBu | 4.4 | 417.2 |
| 75 2-MeO-C6H4-CH2—NH— | (RS) tBu | 6.0 | 446.2 |
| 76 HN—CH2—C6H4-2-Cl | (RS) tBu | 6.2 | 450.2 |
| 77 HN—CH2—C6H4-3-F | (RS) tBu | 6.0 | 434.2 |
| 78 HN—CH2—C6H4-2-F | (RS) tBu | 6.9 | 434.2 |
| 79 HN—CH2—C6H4-4-F | (RS) tBu | 6.0 | 434.2 |
| 80 4-Me-piperazinyl-(CH2)3—NH— | (RS) tBu | 4.1 | 466.3 |

FORMULA 55
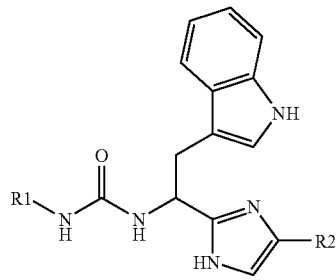
| | R1 | R2 | Analysis | |
|---|---|---|---|---|
| | | | Tr (min) | [M + H]+ |
| 1 | 2-Cl-phenyl | 2-OMe-phenyl (RS) | 8.4 | 486.2 |
| 2 | 3-Cl-phenyl | 2-OMe-phenyl (RS) | 6.6 | 486.2 |
| 3 | 4-Cl-phenyl | 2-OMe-phenyl (RS) | 6.6 | 486.2 |
| 4 | 2-Br-phenyl | 2-OMe-phenyl (RS) | 6.4 | 530.1 |
| 5 | 3-Br-phenyl | 2-OMe-phenyl (RS) | 6.7 | 530.1 |
| 6 | 4-Br-phenyl | 2-OMe-phenyl (RS) | 6.6 | 530.1 |
| 7 | 3-F-phenyl | 2-OMe-phenyl (RS) | 6.3 | 470.2 |

-continued
FORMULA 55
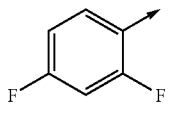
| | R1 | R2 | Analysis Tr (min) | [M + H]+ |
|---|---|---|---|---|
| 8 | 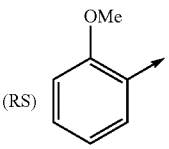 | 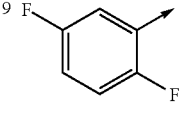 (RS) | 6.3 | 488.2 |
| 9 | 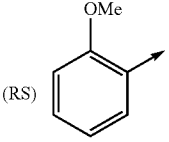 | 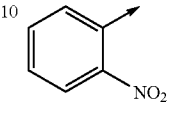 (RS) | 6.4 | 488.2 |
| 10 | 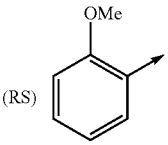 | 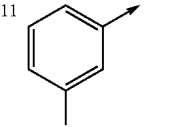 (RS) | 6.3 | 497.2 |
| 11 | 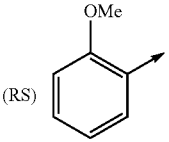 | 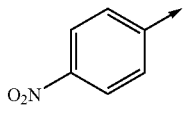 (RS) | 6.4 | 497.2 |
| 12 | 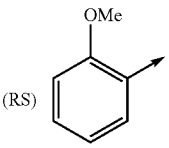 | 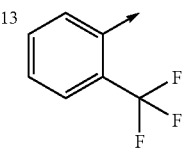 (RS) | 6.4 | 497.2 |
| 13 | 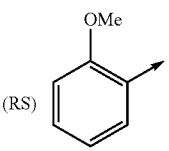 | 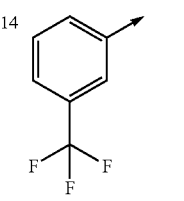 (RS) | 6.4 | 520.2 |
| 14 | 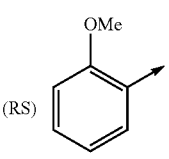 | (RS) | 6.8 | 520.2 |

-continued
FORMULA 55
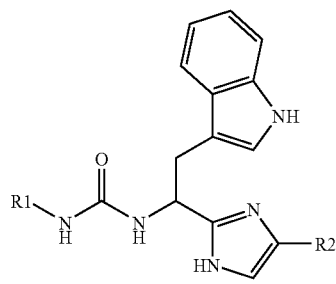
| R1 | R2 | Analysis Tr (min) | [M + H]+ |
|---|---|---|---|
| 15 3-(trifluoromethyl)phenyl | 2-OMe-phenyl (RS) | 6.8 | 520.2 |
| 16 2,5-dimethoxyphenyl (MeO, OMe) | 2-OMe-phenyl (RS) | 6.3 | 512.2 |
| 17 3-OMe-phenyl | 2-OMe-phenyl (RS) | 6.2 | 482.2 |
| 18 4-OMe-phenyl | 2-OMe-phenyl (RS) | 6.1 | 482.2 |
| 19 4-Cl-2-(trifluoromethyl)phenyl | 2-OMe-phenyl (RS) | 6.8 | 554.1 |
| 20 4-F-3-NO$_2$-phenyl | 2-OMe-phenyl (RS) | 6.4 | 515.1 |
| 21 2-Cl-phenyl | 4-Br-phenyl (R,S) | 6.7 | 534.0 |
| 22 3-Cl-phenyl | 4-Br-phenyl (R,S) | 6.9 | 534.0 |

-continued
FORMULA 55
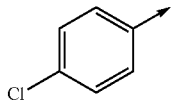
| | R1 | R2 | Tr (min) | [M + H]+ |
|---|---|---|---|---|
| 23 | 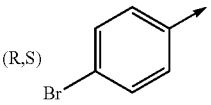 Cl | (R,S) 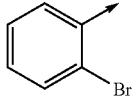 Br | 6.8 | 534.0 |
| 24 | 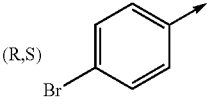 Br | (R,S) 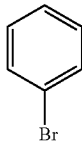 Br | 6.7 | 578.0 |
| 25 | 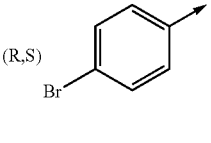 Br | (R,S) 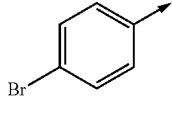 Br | 6.9 | 578.0 |
| 26 | 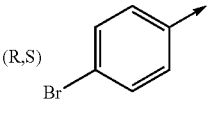 Br | (R,S) 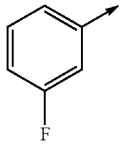 Br | 6.9 | 578.0 |
| 27 | 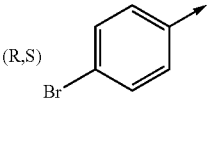 F | (R,S) 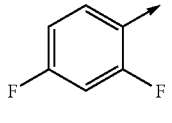 Br | 6.6 | 518.1 |
| 28 | 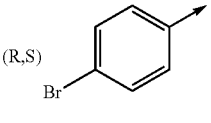 F, F | (R,S) 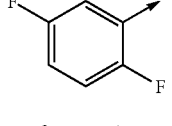 Br | 6.6 | 536.1 |
| 29 | 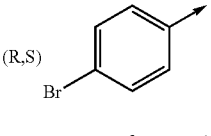 F, F | (R,S) 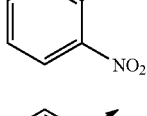 Br | 6.7 | 536.0 |
| 30 | 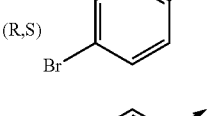 NO₂ | (R,S) 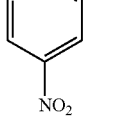 Br | 6.6 | 545.0 |
| 31 | 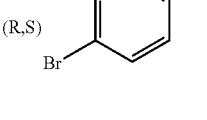 NO₂ | (R,S) 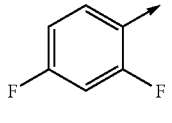 Br | 6.7 | 545.0 |

-continued
FORMULA 55
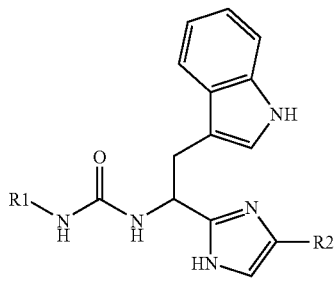
| | R1 | R2 | Tr (min) | [M + H]+ |
|---|---|---|---|---|
| 32 | 4-O$_2$N-C$_6$H$_4$ | 4-Br-C$_6$H$_4$ (R,S) | 6.7 | 545.0 |
| 33 | 2-CF$_3$-C$_6$H$_4$ | 4-Br-C$_6$H$_4$ (R,S) | 6.7 | 568.0 |
| 34 | 3-CF$_3$-C$_6$H$_4$ | 4-Br-C$_6$H$_4$ (R,S) | 7.1 | 568.0 |
| 35 | 4-CF$_3$-C$_6$H$_4$ | 4-Br-C$_6$H$_4$ (R,S) | 7.1 | 568.0 |
| 36 | 2,5-(MeO)$_2$-C$_6$H$_3$ | 4-Br-C$_6$H$_4$ (R,S) | 6.6 | 560.1 |
| 37 | 3-MeO-C$_6$H$_4$ | 4-Br-C$_6$H$_4$ (R,S) | 6.5 | 530.1 |
| 38 | 4-MeO-C$_6$H$_4$ | 4-Br-C$_6$H$_4$ (R,S) | 6.4 | 530.1 |
| 39 | 4-Cl-2-CF$_3$-C$_6$H$_3$ | 4-Br-C$_6$H$_4$ (R,S) | 7.1 | 602.0 |

-continued
FORMULA 55
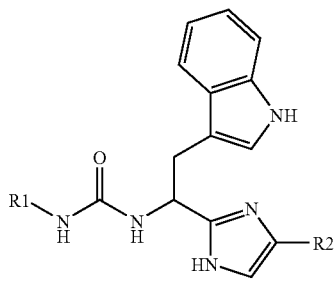
| | R1 | R2 | Tr (min) | [M + H]+ |
|---|---|---|---|---|
| 40 | 4-F, 3-NO₂-phenyl | (R,S) 4-Br-phenyl | 6.7 | 563.0 |
| 41 | 2-Cl-phenyl | (R,S) 4-O₂N-phenyl | 6.6 | 501.1 |
| 42 | 3-Cl-phenyl | (R,S) 4-O₂N-phenyl | 6.8 | 501.1 |
| 43 | 4-Cl-phenyl | (R,S) 4-O₂N-phenyl | 6.8 | 501.1 |
| 44 | 2-Br-phenyl | (R,S) 4-O₂N-phenyl | 6.7 | 545.0 |
| 45 | 3-Br-phenyl | (R,S) 4-O₂N-phenyl | 6.9 | 545.0 |
| 46 | 4-Br-phenyl | (R,S) 4-O₂N-phenyl | 6.9 | 545.0 |
| 47 | 3-F-phenyl | (R,S) 4-O₂N-phenyl | 6.5 | 485.1 |

-continued
FORMULA 55
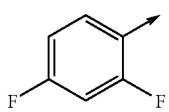
| | R1 | R2 | Analysis Tr (min) | [M + H]+ |
|---|---|---|---|---|
| 48 | 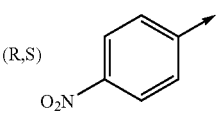 2,4-F | (R,S) 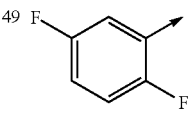 4-O$_2$N | 6.5 | 503.2 |
| 49 | 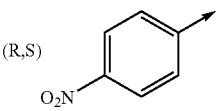 2,5-F | (R,S) 4-O$_2$N | 6.7 | 503.2 |
| 50 | 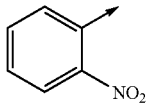 2-NO$_2$ | (R,S) 4-O$_2$N | 6.6 | 512.2 |
| 51 | 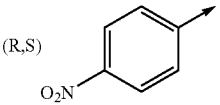 3-NO$_2$ | (R,S) 4-O$_2$N | 6.6 | 512.2 |
| 52 | 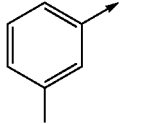 4-O$_2$N | (R,S) 4-O$_2$N | 6.6 | 512.2 |
| 53 | 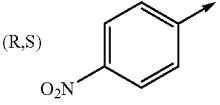 2-CF$_3$ | (R,S) 4-O$_2$N | 6.7 | 535.1 |
| 54 | 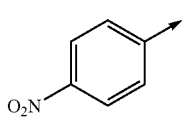 3-CF$_3$ | (R,S) 4-O$_2$N | 7.1 | 535.1 |
| 55 | 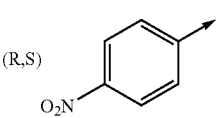 CF$_3$ | (R,S) 4-O$_2$N | 7.1 | 535.1 |

-continued
FORMULA 55
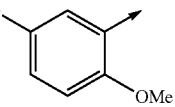
| | R1 | R2 | Tr (min) | [M + H]+ |
|---|---|---|---|---|
| 56 | MeO-phenyl-OMe | (R,S) O$_2$N-phenyl | 6.4 | 527.2 |
| 57 | 3-MeO-phenyl | (R,S) O$_2$N-phenyl | 6.3 | 497.2 |
| 58 | 4-MeO-phenyl | (R,S) O$_2$N-phenyl | 6.2 | 497.2 |
| 59 | Cl,CF$_3$-phenyl | (R,S) O$_2$N-phenyl | 7.2 | 569.1 |
| 60 | F,NO$_2$-phenyl | (R,S) O$_2$N-phenyl | 6.7 | 530.1 |
| 61 | 2-Cl-phenyl | (R,S) Et$_2$N-phenyl | 5.9 | 527.2 |
| 62 | 3-Cl-phenyl | (R,S) Et$_2$N-phenyl | 6.2 | 527.2 |
| 63 | 4-Cl-phenyl | (R,S) Et$_2$N-phenyl | 6.1 | 527.2 |

-continued
FORMULA 55
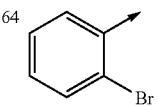
| | R1 | R2 | Tr (min) | [M + H]+ |
|---|---|---|---|---|
| 64 | 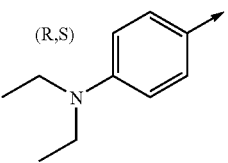 | (R,S) 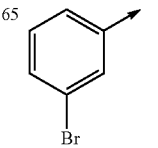 | 5.9 | 571.1 |
| 65 | 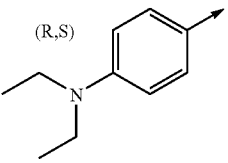 | (R,S) 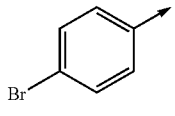 | 6.3 | 571.1 |
| 66 | 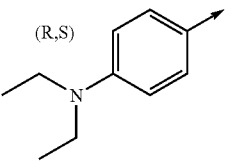 | (R,S) 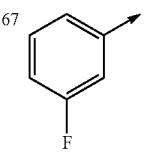 | 6.2 | 571.1 |
| 67 | 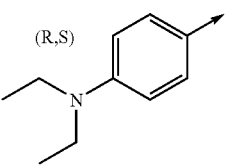 | (R,S) 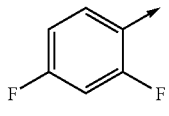 | 5.9 | 511.3 |
| 68 | 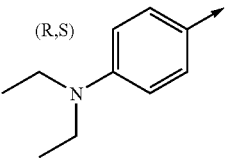 | (R,S) 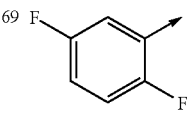 | 5.8 | 529.2 |
| 69 | 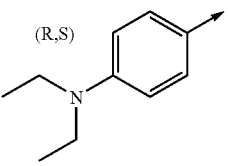 | (R,S) 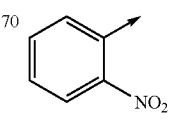 | 6.0 | 529.2 |
| 70 | 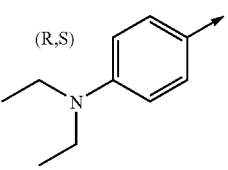 | (R,S) | 5.8 | 538.2 |

-continued
FORMULA 55
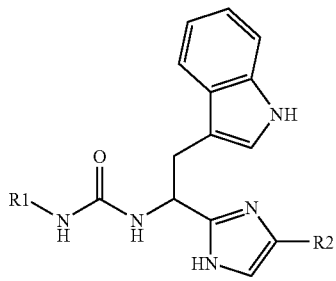
| | R1 | R2 | Tr (min) | [M + H]+ |
|---|---|---|---|---|
| 71 | 3-NO2-phenyl | (R,S) 4-NEt2-phenyl | 5.9 | 538.2 |
| 72 | 4-NO2-phenyl | (R,S) 4-NEt2-phenyl | 6.0 | 538.2 |
| 73 | 2-CF3-phenyl | (R,S) 4-NEt2-phenyl | 6.0 | 561.2 |
| 74 | 3-CF3-phenyl | (R,S) 4-NEt2-phenyl | 6.4 | 561.2 |
| 75 | CF3-benzyl | (R,S) 4-NEt2-phenyl | 6.5 | 561.0 |

-continued
FORMULA 55
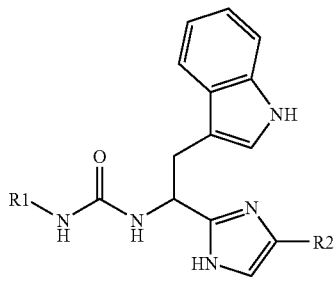
| | R1 | R2 | Tr (min) | [M + H]+ |
|---|---|---|---|---|
| 76 | MeO-C6H3(OMe)- | (R,S) -CH2-C6H4-N(Et)2 | 5.8 | 553.3 |
| 77 | 3-MeO-C6H4- | (R,S) -CH2-C6H4-N(Et)2 | 5.7 | 523.3 |
| 78 | 4-MeO-C6H4- | (R,S) -CH2-C6H4-N(Et)2 | 5.6 | 523.3 |
| 79 | 5-Cl-2-CF3-C6H3- | (R,S) -CH2-C6H4-N(Et)2 | 6.5 | 595.2 |
| 80 | 4-F-3-NO2-C6H3- | (R,S) -CH2-C6H4-N(Et)2 | 6.0 | 556.2 |

FORMULA 56
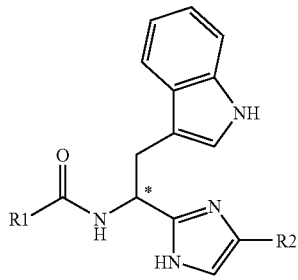
| | R1 | R2 | Tr (min) | [M + H]+ |
|---|---|---|---|---|
| 1 | 2-Cl-benzyl | 2-OMe-phenyl (R,S) | 5.6 | 485.2 |
| 2 | 3-Cl-benzyl | 2-OMe-phenyl (R,S) | 5.8 | 485.2 |
| 3 | 4-Cl-benzyl | 2-OMe-phenyl (R,S) | 6.0 | 485.2 |
| 4 | 2-Br-benzyl | 2-OMe-phenyl (R,S) | 5.8 | 529.2 |
| 5 | 3-Br-benzyl | 2-OMe-phenyl (R,S) | 6.0 | 529.2 |
| 6 | 4-Br-benzyl | 2-OMe-phenyl (R,S) | 6.0 | 529.2 |
| 7 | 2-F-benzyl | 2-OMe-phenyl (R,S) | 5.5 | 469.2 |
| 8 | 3-F-benzyl | 2-OMe-phenyl (R,S) | 5.7 | 469.3 |

-continued
FORMULA 56
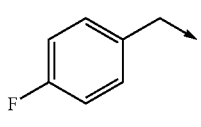
| | R1 | R2 | Analysis Tr (min) | [M + H]+ |
|---|---|---|---|---|
| 9 | 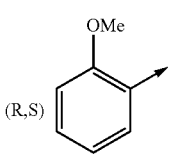 | 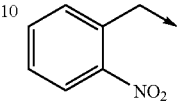 (R,S) | 5.6 | 469.2 |
| 10 | 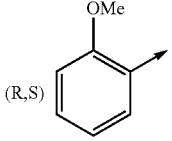 | 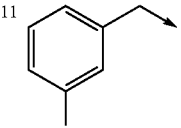 (R,S) | 5.5 | 496.3 |
| 11 | 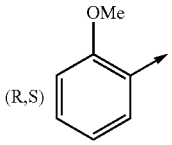 | 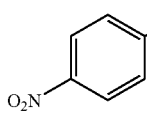 (R,S) | 5.6 | 496.3 |
| 12 | 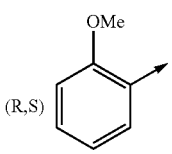 | 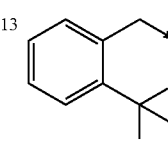 (R,S) | 5.6 | 496.3 |
| 13 | 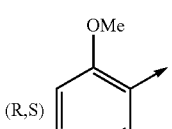 | 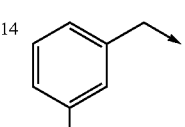 (R,S) | 6.0 | 519.2 |
| 14 | 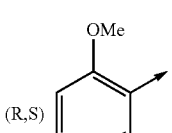 | 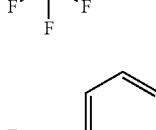 (R,S) | 6.2 | 519.2 |
| 15 | 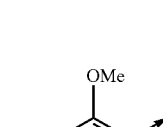 | (R,S) | 6.2 | 519.2 |

-continued
FORMULA 56
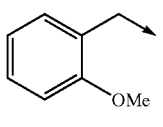
| | R1 | R2 | Analysis Tr (min) | [M + H]+ |
|---|---|---|---|---|
| 16 | 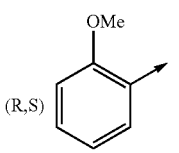 | 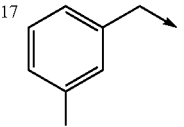 (R,S) | 5.5 | 481.1 |
| 17 | 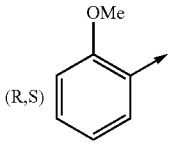 | 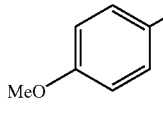 (R,S) | 5.5 | 481.2 |
| 18 | 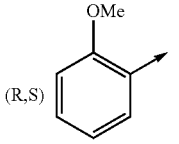 | 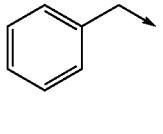 (R,S) | 5.4 | 481.2 |
| 19 | 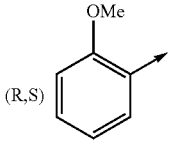 | 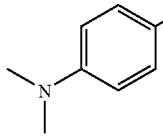 (R,S) | 5.4 | 451.2 |
| 20 | 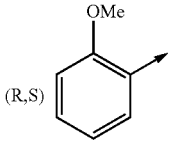 | 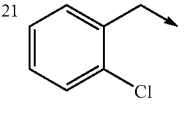 (R,S) | 4.3 | 494.2 |
| 21 | 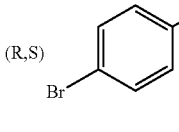 | (R,S) 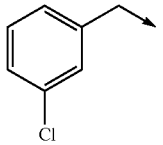 | 6.1 | 533.1 |
| 22 | 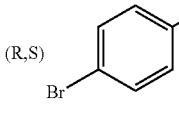 | (R,S) 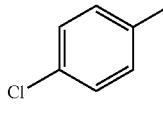 | 6.2 | 533.1 |
| 23 | 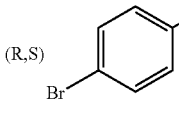 | (R,S)  | 6.3 | 533.1 |

-continued
FORMULA 56
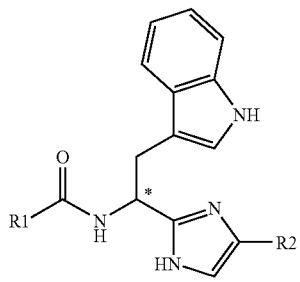
| | R1 | R2 | Analysis Tr (min) | [M + H]+ |
|---|---|---|---|---|
| 24 | 2-Br-benzyl | (R,S) 4-Br-phenyl | 6.1 | 577.0 |
| 25 | 3-Br-benzyl | (R,S) 4-Br-phenyl | 6.3 | 577.0 |
| 26 | 4-Br-benzyl | (R,S) 4-Br-phenyl | 6.3 | 577.0 |
| 27 | 2-F-benzyl | (R,S) 4-Br-phenyl | 5.9 | 517.1 |
| 28 | 3-F-benzyl | (R,S) 4-Br-phenyl | 6.0 | 517.1 |
| 29 | 4-F-benzyl | (R,S) 4-Br-phenyl | 6.0 | 517.1 |
| 30 | 2-NO$_2$-benzyl | (R,S) 4-Br-phenyl | 5.8 | 544.1 |
| 31 | 3-NO$_2$-benzyl | (R,S) 4-Br-phenyl | 6.0 | 544.1 |
| 32 | 4-NO$_2$-benzyl | (R,S) 4-Br-phenyl | 6.0 | 544.1 |

-continued
FORMULA 56
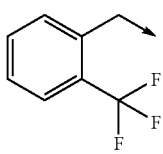
| R1 | R2 | Analysis Tr (min) | [M + H]+ |
|---|---|---|---|
| 33 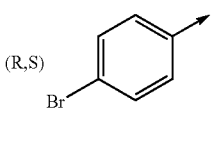 | (R,S) 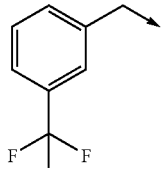 | 6.3 | 567.1 |
| 34 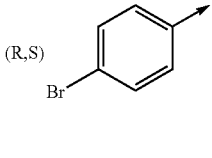 | (R,S)  | 6.5 | 567.1 |
| 35 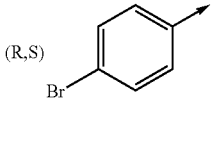 | (R,S) 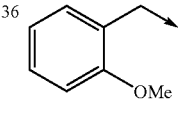 | 6.5 | 567.1 |
| 36 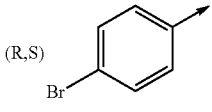 | (R,S) 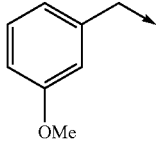 | 5.9 | 529.1 |
| 37 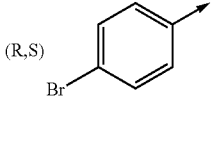 | (R,S) 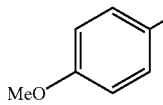 | 5.9 | 529.1 |
| 38 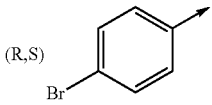 | (R,S) 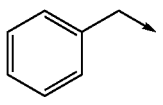 | 5.9 | 529.1 |
| 39 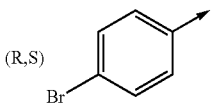 | (R,S) 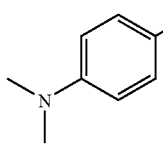 | 5.9 | 499.1 |
| 40 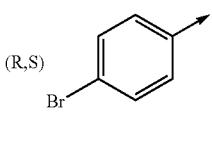 | (R,S) | 4.7 | 542.1 |

-continued
FORMULA 56
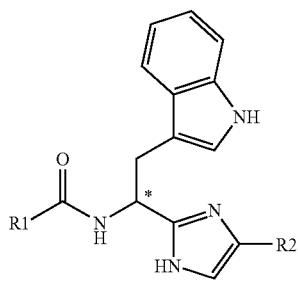
| | R1 | R2 | Tr (min) | [M + H]+ |
|---|---|---|---|---|
| 41 | 2-Cl-benzyl | (R,S) 4-O₂N-phenyl | 6.2 | 500.2 |
| 42 | 3-Cl-benzyl | (R,S) 4-O₂N-phenyl | 6.4 | 500.2 |
| 43 | 4-Cl-benzyl | (R,S) 4-O₂N-phenyl | 6.9 | 500.1 |
| 44 | 2-Br-benzyl | (R,S) 4-O₂N-phenyl | 6.8 | 544.0 |
| 45 | 3-Br-benzyl | (R,S) 4-O₂N-phenyl | 7.0 | 544.0 |
| 46 | 4-Br-benzyl | (R,S) 4-O₂N-phenyl | 7.0 | 544.0 |
| 47 | 2-F-benzyl | (R,S) 4-O₂N-phenyl | 6.5 | 484.2 |
| 48 | 3-F-benzyl | (R,S) 4-O₂N-phenyl | 6.6 | 484.2 |
| 49 | 4-F-benzyl | (R,S) 4-O₂N-phenyl | 6.6 | 484.2 |

-continued
FORMULA 56
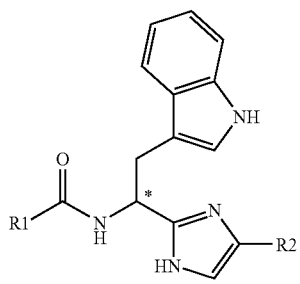
| R1 | R2 | Tr (min) | [M + H]+ |
|---|---|---|---|
| 50 2-NO2-benzyl | (R,S) 4-O2N-phenyl | 6.4 | 511.2 |
| 51 3-NO2-benzyl | (R,S) 4-O2N-phenyl | 6.6 | 511.2 |
| 52 4-O2N-benzyl | (R,S) 4-O2N-phenyl | 6.6 | 511.2 |
| 53 2-CF3-benzyl | (R,S) 4-O2N-phenyl | 7.0 | 534.1 |
| 54 3-CF3-benzyl | (R,S) 4-O2N-phenyl | 7.1 | 534.1 |
| 55 4-CF3-benzyl | (R,S) 4-O2N-phenyl | 7.2 | 534.2 |
| 56 2-OMe-benzyl | (R,S) 4-O2N-phenyl | 6.6 | 496.2 |
| 57 3-OMe-benzyl | (R,S) 4-O2N-phenyl | 6.5 | 496.2 |

-continued
FORMULA 56
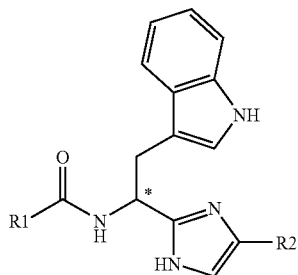
| | R1 | R2 | Analysis Tr (min) | [M + H]+ |
|---|---|---|---|---|
| 58 | 4-MeO-C6H4-CH2- | (R,S) 4-O2N-C6H4- | 6.5 | 496.2 |
| 59 | C6H5-CH2- | (R,S) 4-O2N-C6H4- | 6.5 | 466.2 |
| 60 | 4-(Me2N)-C6H4-CH2- | (R,S) 4-O2N-C6H4- | 5.4 | 509.2 |
| 61 | 2-Cl-C6H4-CH2- | (R,S) 4-(Et2N)-C6H4- | 5.8 | 526.2 |
| 62 | 3-Cl-C6H4-CH2- | (R,S) 4-(Et2N)-C6H4- | 6.0 | 526.3 |
| 63 | 4-Cl-C6H4-CH2- | (R,S) 4-(Et2N)-C6H4- | 6.0 | 526.3 |
| 64 | 2-Br-C6H4-CH2- | (R,S) 4-(Et2N)-C6H4- | 5.9 | 570.2 |
| 65 | 3-Br-C6H4-CH2- | (R,S) 4-(Et2N)-C6H4- | 6.1 | 570.1 |

-continued
FORMULA 56
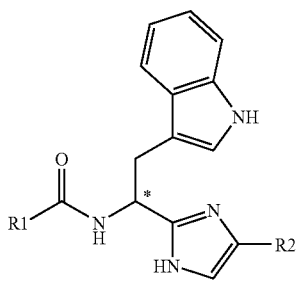
| | R1 | R2 | Tr (min) | [M + H]+ |
|---|---|---|---|---|
| 66 | 4-Br-benzyl | (R,S) 4-(N,N-diethylamino)phenyl | 6.1 | 570.1 |
| 67 | 2-F-benzyl | (R,S) 4-(N,N-diethylamino)phenyl | 5.6 | 510.3 |
| 68 | 3-F-benzyl | (R,S) 4-(N,N-diethylamino)phenyl | 5.7 | 510.3 |
| 69 | 2-NO₂-benzyl | (R,S) 4-(N,N-diethylamino)phenyl | 5.6 | 537.2 |
| 70 | 3-NO₂-benzyl | (R,S) 4-(N,N-diethylamino)phenyl | 5.7 | 537.2 |
| 71 | 4-NO₂-benzyl | (R,S) 4-(N,N-diethylamino)phenyl | 5.7 | 537.3 |
| 72 | 2-CF₃-benzyl | (R,S) 4-(N,N-diethylamino)phenyl | 6.1 | 560.2 |

-continued
FORMULA 56
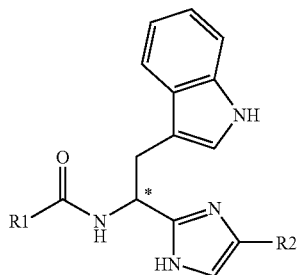
| | R1 | R2 | Tr (min) | [M + H]+ |
|---|---|---|---|---|
| 73 | 3-(trifluoromethyl)benzyl | (R,S) 4-(diethylamino)phenyl | 6.2 | 560.2 |
| 74 | 4-(trifluoromethyl)benzyl | (R,S) 4-(diethylamino)phenyl | 6.3 | 560.2 |
| 75 | 2-methoxybenzyl | (R,S) 4-(diethylamino)phenyl | 5.7 | 522.3 |
| 76 | 3-methoxybenzyl | (R,S) 4-(diethylamino)phenyl | 5.6 | 522.3 |
| 77 | 4-methoxybenzyl | (R,S) 4-(diethylamino)phenyl | 5.5 | 522.3 |
| 78 | benzyl | (R,S) 4-(diethylamino)phenyl | 5.6 | 492.3 |
| 79 | 4-(dimethylamino)benzyl | (R,S) 4-(diethylamino)phenyl | 4.7 | 535.3 |

FORMULA 57
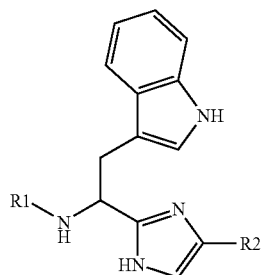
| | R1 | R2 | Tr (min) | [M + H]+ |
|---|---|---|---|---|
| 1 | cyclopentyl-NHC(O)- | Ph (R) | 14.4 | 474.2 |
| 2 | HO-(CH2)4-NHC(O)- | Ph (R) | 5.4 | 418.2 |
| 3 | Et2N-CH2CH2-NHC(O)- | Ph (R) | 11.1 | 445.3 |
| 4 | (1-methylpyrrolidin-2-yl)-CH2CH2-NHC(O)- | Ph (R) | 10.8 | 457.3 |
| 5 | (EtO)2CH-CH2-NHC(O)- | Ph (R) | 14.3 | 462.2 |
| 6 | PhO-CH2CH2-NHC(O)- | Ph (R) | 14.5 | 466.1 |
| 7 | (1H-indol-3-yl)-CH2CH2-NHC(O)- | Ph (R) | 14.5 | 489.2 |
| 8 | (1-benzylpiperidin-4-yl)-NHC(O)- | Ph (R) | 12.2 | 519.4 |
| 9 | (4-hydroxyphenyl)-CH2CH2-NHC(O)- | Ph (R) | 10.1 | 466.1 |

-continued
FORMULA 57
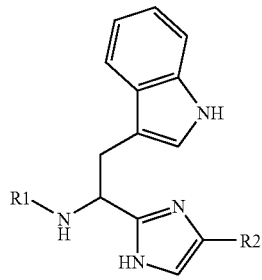
| | | Analysis | |
|---|---|---|---|
| R1 | R2 | Tr (min) | [M + H]+ |
| 10 ![naphthylmethyl amide] | (R) phenyl | 14.8 | 485.1 |
| 11 ![morpholinoethyl amide] | (R) phenyl | 12.1 | 459.3 |
| 12 ![benzodioxolylmethyl amide] | (R) phenyl | 14.4 | 480.1 |
| 13 ![tetrahydronaphthyl amide] | (R) phenyl | 14.8 | 476.1 |
| 14 ![thiophenylmethyl amide] | (R) phenyl | 14.4 | 442.1 |
| 15 ![2-CF3-benzyl amide] | (R) phenyl | 14.8 | 504.1 |
| 16 ![4-Cl-benzyl amide] | (R) phenyl | 14.7 | 470.1 |

-continued
FORMULA 57
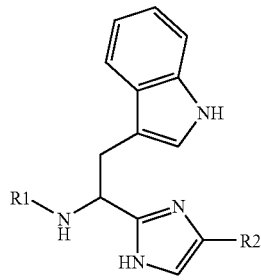
| | | Analysis | |
|---|---|---|---|
| R1 | R2 | Tr (min) | [M + H]+ |
| 17 ⌬-CH2-NH-C(O)- with 2-((2-(hydroxymethyl)phenyl)thio)phenyl (R) | phenyl | 14.7 | 574.1 |
| 18 Ph2CH-CH2-NH-C(O)- (R) | phenyl | 15.0 | 526.2 |
| 19 imidazol-1-yl-(CH2)3-NH-C(O)- (R) | phenyl | 12.0 | 454.3 |
| 20 4-(H2NSO2)-C6H4-CH2CH2-NH-C(O)- (R) | phenyl | 8.0 | 529.1 |
| 21 cyclopentyl-NH-C(O)- (S) | phenyl | 14.4 | 414.2 |
| 22 HO-(CH2)4-NH-C(O)- (S) | phenyl | 6.3 | 418.2 |
| 23 Et2N-CH2CH2-NH-C(O)- (S) | phenyl | 11.3 | 445.3 |

-continued
FORMULA 57
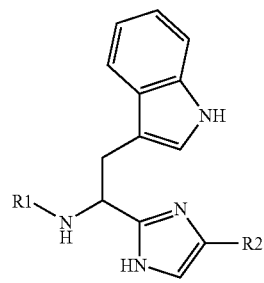
| | R1 | R2 | Tr (min) | [M + H]+ |
|---|---|---|---|---|
| 24 | 1-methyl-pyrrolidin-2-yl-ethyl-NH-C(O)- (S) | Ph | 10.7 | 457.3 |
| 25 | (EtO)₂CH-CH₂-NH-C(O)- (S) | Ph | 14.3 | 462.2 |
| 26 | PhO-CH₂CH₂-NH-C(O)- (S) | Ph | 14.6 | 466.1 |
| 27 | indol-3-yl-CH₂CH₂-NH-C(O)- (S) | Ph | 14.5 | 489.2 |
| 28 | 1-benzyl-piperidin-4-yl-NH-C(O)- (S) | Ph | 12.2 | 519.2 |
| 29 | 4-HO-C₆H₄-CH₂CH₂-NH-C(O)- (S) | Ph | 11.7 | 466.1 |
| 30 | naphthalen-1-yl-CH₂-NH-C(O)- (S) | Ph | 14.8 | 486.1 |
| 31 | morpholin-4-yl-CH₂CH₂-NH-C(O)- (S) | Ph | 12.0 | 459.3 |

-continued
FORMULA 57
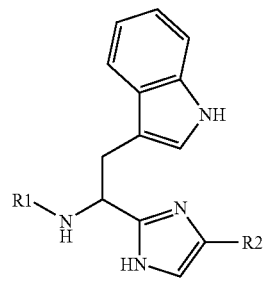
| R1 | R2 | Tr (min) | [M + H]+ |
|---|---|---|---|
| 32 ![structure: benzodioxole-CH2-NH-C(O)-] | (S) ![phenyl] | 14.4 | 480.1 |
| 33 ![structure: tetrahydronaphthalene-NH-C(O)-] | (S) ![phenyl] | 14.8 | 476.2 |
| 34 ![structure: thiophene-CH2-NH-C(O)-] | (S) ![phenyl] | 14.4 | 442.1 |
| 35 ![structure: 2-CF3-phenyl-CH2-NH-C(O)-] | (S) ![phenyl] | 14.7 | 504.1 |
| 36 ![structure: 4-Cl-phenyl-CH2-NH-C(O)-] | (S) ![phenyl] | 14.7 | 470.1 |
| 37 ![structure: 2-(2-hydroxymethylphenylthio)phenyl-CH2-NH-C(O)-] | (S) ![phenyl] | 14.7 | 574.1 |

-continued
FORMULA 57
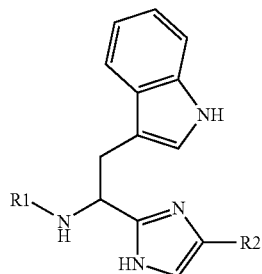
| | R1 | R2 | Tr (min) | [M + H]+ |
|---|---|---|---|---|
| 38 | (S) 2,2-diphenylethyl acetamide | phenyl | 14.9 | 526.2 |
| 39 | (S) 3-(imidazol-1-yl)propyl acetamide | phenyl | 11.8 | 454.3 |
| 40 | (S) 4-sulfamoylphenethyl acetamide | phenyl | 8.5 | 529.1 |
| 41 | (R) cyclopentyl acetamide | tert-butyl | 14.3 | 394.2 |
| 42 | (R) 4-hydroxybutyl acetamide | tert-butyl | 6.0 | 396.2 |
| 43 | (R) 2,2-diethoxyethyl acetamide | tert-butyl | 14.2 | 442.2 |
| 44 | (R) 2-phenoxyethyl acetamide | tert-butyl | 14.6 | 446.2 |

-continued
FORMULA 57
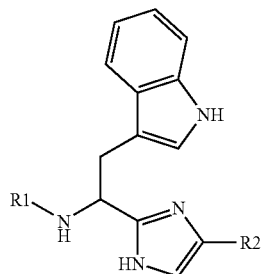
| R1 | R2 | Tr (min) | [M + H]+ |
|---|---|---|---|
| 45 [tryptamine-NHC(O)-] | (R) tBu | 14.6 | 459.2 |
| 46 [4-HO-phenethyl-NHC(O)-] | (R) tBu | 10.7 | 446.2 |
| 47 [naphthalen-1-ylmethyl-NHC(O)-] | (R) tBu | 14.8 | 466.2 |
| 48 [morpholinoethyl-NHC(O)-] | (R) tBu | 11.8 | 439.3 |
| 49 [benzo[d][1,3]dioxol-5-ylmethyl-NHC(O)-] | (R) tBu | 14.4 | 460.1 |
| 50 [1,2,3,4-tetrahydronaphthalen-1-yl-NHC(O)-] | (R) tBu | 14.8 | 456.2 |
| 51 [thiophen-2-ylmethyl-NHC(O)-] | (R) tBu | 14.4 | 422.1 |

-continued
FORMULA 57
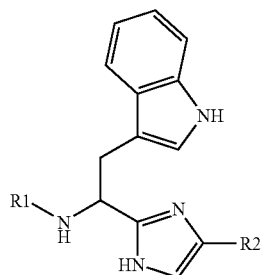
| R1 | R2 | Analysis Tr (min) | [M + H]+ |
|---|---|---|---|
| 52 (2-CF3-benzyl-NHC(O)CH2-) | (R) tBu | 14.8 | 484.1 |
| 53 (4-Cl-benzyl-NHC(O)CH2-) | (R) tBu | 14.7 | 450.1 |
| 54 (2-((2-hydroxymethyl)phenylthio)benzyl-NHC(O)CH2-) | (R) tBu | 14.7 | 554.1 |
| 55 (2,2-diphenylethyl-NHC(O)CH2-) | (R) tBu | 15.0 | 506.2 |
| 56 (3-(imidazol-1-yl)propyl-NHC(O)CH2-) | (R) tBu | 11.5 | 434.3 |
| 57 (4-sulfamoylphenethyl-NHC(O)CH2-) | (R) tBu | 8.1 | 509.1 |
| 58 (cyclopentyl-NHC(O)CH2-) | (S) tBu | 14.4 | 394.2 |

-continued
FORMULA 57
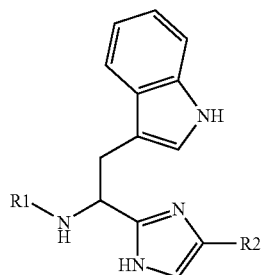
| | R1 | R2 | Analysis Tr (min) | [M + H]+ |
|---|---|---|---|---|
| 59 | HO~~~NH-C(=O)- | (S) tBu | 11.4 | 398.2 |
| 60 | EtO-CH(OEt)-CH2-NH-C(=O)- | (S) tBu | 14.2 | 442.2 |
| 61 | PhO-CH2CH2-NH-C(=O)- | (S) tBu | 14.6 | 446.2 |
| 62 | indol-3-yl-CH2CH2-NH-C(=O)- | (S) tBu | 14.6 | 469.2 |
| 63 | 4-HO-C6H4-CH2CH2-NH-C(=O)- | (S) tBu | 11.0 | 446.2 |
| 64 | naphth-1-yl-CH2-NH-C(=O)- | (S) tBu | 14.8 | 466.2 |
| 65 | morpholin-4-yl-CH2CH2-NH-C(=O)- | (S) tBu | 11.8 | 439.3 |
| 66 | 3,4-methylenedioxyphenyl-CH2-NH-C(=O)- | (S) tBu | 14.4 | 460.2 |

-continued
FORMULA 57
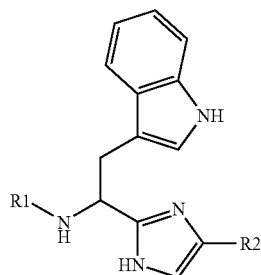
| | R1 | R2 | Analysis Tr (min) | [M + H]+ |
|---|---|---|---|---|
| 67 | (S)-1-acetamido-1,2,3,4-tetrahydronaphthalen-1-yl | tert-butyl | 14.8 | 456.2 |
| 68 | (S)-thiophen-2-ylmethyl acetamide | tert-butyl | 14.3 | 422.1 |
| 69 | (S)-2-(trifluoromethyl)benzyl acetamide | tert-butyl | 14.7 | 484.2 |
| 70 | (S)-4-chlorobenzyl acetamide | tert-butyl | 14.6 | 450.2 |
| 71 | (S)-2-((2-(hydroxymethyl)phenylthio)benzyl acetamide | tert-butyl | 14.7 | 554.1 |
| 72 | (S)-2,2-diphenylethyl acetamide | tert-butyl | 14.9 | 506.2 |

FORMULA 57
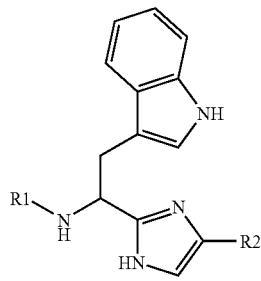
| R1 | R2 | Tr (min) | [M + H]+ |
|---|---|---|---|
| 73 ![imidazole-propyl-NHC(O)] | (S) tBu | 11.7 | 434.3 |
| 74 ![sulfamoylphenethyl-NHC(O)] | (S) tBu | 8.4 | 509.2 |
FORMULA 58
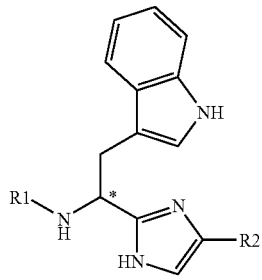
| R1 | R2 | Tr (min) | [M + H]+ |
|---|---|---|---|
| 1 ![PhNHC(O)] | (R) Ph | 12.9 | 422.2 |
| 2 ![2-Cl-PhNHC(O)] | (R) Ph | 13.3 | 456.2 |

-continued
FORMULA 58
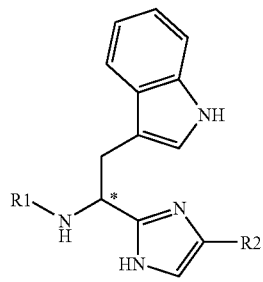
| | R1 | R2 | Tr (min) | [M + H]+ |
|---|---|---|---|---|
| 3 | benzyl-NHC(O)- | (R) phenyl | 12.9 | 436.2 |
| 4 | naphth-1-yl-NHC(O)- | (R) phenyl | 13.6 | 472.3 |
| 5 | 4-phenoxyphenyl-NHC(O)- | (R) phenyl | 14.5 | 514.2 |
| 6 | 2,6-diisopropylphenyl-NHC(O)- | (R) phenyl | 14.5 | 506.3 |
| 7 | 3-trifluoromethylphenyl-NHC(O)- | (R) phenyl | 14.2 | 490.2 |
| 8 | 4-(ethoxycarbonyl)phenyl-NHC(O)- | (R) phenyl | 13.5 | 494.2 |

-continued
FORMULA 58
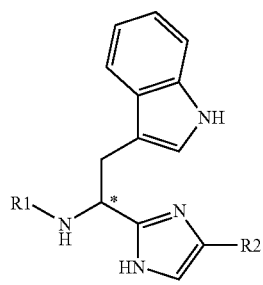
| R1 | R2 | Analysis Tr (min) | [M + H]+ |
|---|---|---|---|
| 9 — 2,4-difluorophenyl-NHC(O)- | (R) phenyl | 13.3 | 458.2 |
| 10 — 3-nitrophenyl-NHC(O)- | (R) phenyl | 13.3 | 467.2 |
| 11 — phenyl-NHC(S)- | (R) phenyl | 13.8 | 438.2 |
| 12 — PhC(O)NHC(S)- | (R) phenyl | 13.8 | 466.2 |
| 13 — benzyl-NHC(S)- | (R) phenyl | 13.9 | 452.2 |
| 14 — 1-naphthyl-NHC(S)- | (R) phenyl | 13.8 | 488.2 |
| 15 — 4-(PhCH2O)phenyl-NHC(S)- | (R) phenyl | 14.8 | 544.2 |

-continued
FORMULA 58
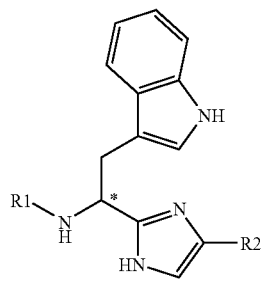
| R1 | R2 | Tr (min) | [M + H]+ |
|---|---|---|---|
| 16 isopropyl-phenyl-NH-C(=S)- | (R) phenyl | 14.3 | 480.2 |
| 17 3-chlorophenyl-NH-C(=S)- | (R) phenyl | 14.2 | 472.2 |
| 18 n-hexyl-NH-C(=S)- | (R) phenyl | 14.7 | 446.3 |
| 19 morpholinoethyl-NH-C(=S)- | (R) phenyl | 10.4 | 475.2 |
| 20 (benzo[d][1,3]dioxol-5-yl)methyl-NH-C(=S)- | (R) phenyl | 13.8 | 496.2 |
| 21 phenyl-NH-C(=O)- | (S) phenyl | 13.1 | 422.2 |
| 22 2-chlorophenyl-NH-C(=O)- | (S) phenyl | 13.4 | 456.2 |
| 23 benzyl-NH-C(=O)- | (S) phenyl | 13.1 | 436.2 |

-continued
FORMULA 58
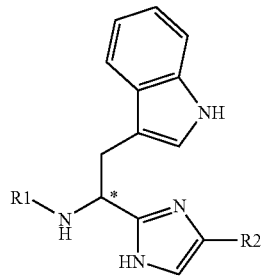
|  | R1 | R2 | Tr (min) | [M + H]+ |
|---|---|---|---|---|
| 24 | N-(naphthalen-1-yl)acetamido | (S) phenyl | 13.7 | 472.3 |
| 25 | N-(4-phenoxyphenyl)acetamido | (S) phenyl | 14.7 | 514.2 |
| 26 | N-(2,6-diisopropylphenyl)acetamido | (S) phenyl | 14.7 | 506.3 |
| 27 | N-(3-trifluoromethylphenyl)acetamido | (S) phenyl | 14.3 | 490.2 |
| 28 | N-(4-ethoxycarbonylphenyl)acetamido | (S) phenyl | 13.7 | 494.2 |
| 29 | N-(2,4-difluorophenyl)acetamido | (S) phenyl | 13.4 | 458.2 |

-continued
FORMULA 58
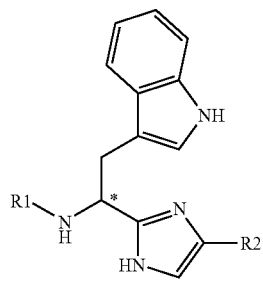
| | R1 | R2 | Tr (min) | [M + H]+ |
|---|---|---|---|---|
| 30 | 3-nitrophenyl-NH-C(=O)- | (S) phenyl | 13.6 | 467.2 |
| 31 | phenyl-NH-C(=S)- | (S) phenyl | 13.3 | 438.2 |
| 32 | phenyl-C(=O)-NH-C(=S)- | (S) phenyl | 13.9 | 466.2 |
| 33 | benzyl-NH-C(=S)- | (S) phenyl | 13.9 | 452.2 |
| 34 | naphthalen-1-yl-NH-C(=S)- | (S) phenyl | 14.0 | 488.2 |
| 35 | 4-(benzyloxy)phenyl-NH-C(=S)- | (S) phenyl | 15.1 | 544.2 |
| 36 | 2-isopropylphenyl-NH-C(=S)- | (S) phenyl | 14.5 | 480.2 |

-continued
FORMULA 58
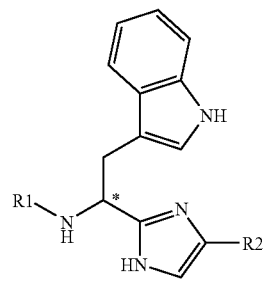
| | R1 | R2 | Analysis Tr (min) | [M + H]+ |
|---|---|---|---|---|
| 37 | 3-chlorophenyl-NH-C(=S)- | (S) phenyl | 14.2 | 472.2 |
| 38 | hexyl-NH-C(=S)- | (S) phenyl | 13.8 | 496.2 |
| 39 | phenyl-NH-C(=O)- | (R) tert-butyl | 13.1 | 402.2 |
| 40 | 2-chlorophenyl-NH-C(=O)- | (R) tert-butyl | 13.6 | 438.2 |
| 41 | 1-naphthyl-NH-C(=O)- | (R) tert-butyl | 13.5 | 452.2 |
| 42 | 4-phenoxyphenyl-NH-C(=O)- | (R) tert-butyl | 14.8 | 494.2 |
| 43 | 2,6-diisopropylphenyl-NH-C(=O)- | (R) tert-butyl | 14.9 | 486.3 |

-continued
FORMULA 58
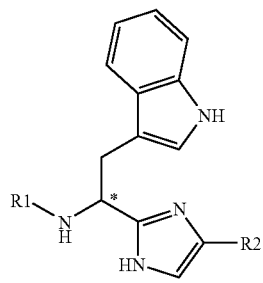
| | R1 | R2 | Analysis Tr (min) | [M + H]+ |
|---|---|---|---|---|
| 44 | 3-(CF3)-C6H4-NH-C(O)-CH2- | (R) tBu | 14.3 | 470.2 |
| 45 | 4-(EtO-C(O))-C6H4-NH-C(O)-CH2- | (R) tBu | 13.7 | 474.3 |
| 46 | 2,4-F2-C6H3-NH-C(O)-CH2- | (R) tBu | 13.4 | 438.2 |
| 47 | 3-(NO2)-C6H4-NH-C(O)-CH2- | (R) tBu | 13.2 | 418.2 |
| 48 | Ph-C(O)-NH-C(S)-CH2- | (R) tBu | 13.6 | 446.2 |
| 49 | Ph-CH2-NH-C(S)-CH2- | (R) tBu | 10.0 | 432.1 |
| 50 | 1-naphthyl-NH-C(S)-CH2- | (R) tBu | 10.1 | 468.1 |

-continued
FORMULA 58
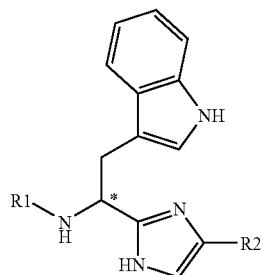
| | R1 | R2 | Tr (min) | [M + H]+ |
|---|---|---|---|---|
| 51 | 2-isopropylphenyl-NH-C(=S)- | (R) tBu | 14.2 | 460.2 |
| 52 | 3-chlorophenyl-NH-C(=S)- | (R) tBu | 14.0 | 452.2 |
| 53 | n-hexyl-NH-C(=S)- | (R) tBu | 14.8 | 426.3 |
| 54 | morpholinoethyl-NH-C(=S)- | (R) tBu | 10.4 | 455.3 |
| 55 | benzo[1,3]dioxol-5-ylmethyl-NH-C(=S)- | (R) tBu | 13.9 | 476.2 |
| 56 | 2-chlorophenyl-NH-C(=O)- | (S) tBu | 13.6 | 436.2 |
| 57 | 2,6-diisopropylphenyl-NH-C(=O)- | (S) tBu | 14.9 | 486.3 |

-continued
FORMULA 58
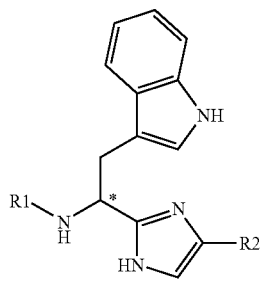
| | R1 | R2 | Tr (min) | [M + H]+ |
|---|---|---|---|---|
| 58 | 3-CF3-C6H4-NH-C(O)- | (S) tBu | 14.4 | 470.2 |
| 59 | 4-(EtO2C)-C6H4-NH-C(O)- | (S) tBu | 13.8 | 474.3 |
| 60 | 2,4-F2-C6H3-NH-C(O)- | (S) tBu | 13.4 | 438.2 |
| 61 | 3-NO2-C6H4-NH-C(O)- | (S) tBu | 13.3 | 447.2 |
| 62 | Ph-NH-C(S)- | (S) tBu | 13.1 | 418.2 |
| 63 | Ph-C(O)-NH-C(S)- | (S) tBu | 13.5 | 446.2 |
| 64 | Ph-CH2-NH-C(S)- | (S) tBu | 13.5 | 432.2 |

-continued

FORMULA 58

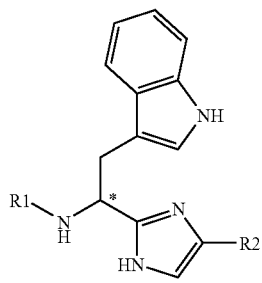

| R1 | R2 | Analysis | |
|---|---|---|---|
| | | Tr (min) | [M + H]+ |
| 65 (naphthylthiourea) | (S) t-Bu | 13.7 | 466.2 |
| 66 (4-benzyloxyphenylthiourea) | (S) t-Bu | 14.7 | 524.2 |
| 67 (2-isopropylphenylthiourea) | (S) t-Bu | 14.3 | 460.2 |
| 68 (3-chlorophenylthiourea) | (S) t-Bu | 14.2 | 452.2 |
| 69 (n-hexylthiourea) | (S) t-Bu | 13.8 | 476.2 |

EXAMPLE 13777

N-{1-(4-(3-bromophenyl)-1H-imidazol-2-yl)-5-methylhexyl}-N-cyclohexylamine 13777.1) 2-((tert-butoxycarbonyl)amino)-6-methylheptanoic acid A solution of diisopropylamine (13.2 ml; 0.094 mol) in 130 ml tetrahydrofurane (THF) was cooled down to about −40° C. n-Butyllithium (37 ml of a 2.5 M solution in hexane; 0.094 mol) was added dropwise. The temperature was left to return to about 0° C. At this temperature, Boc-glycine (5 g; 0.028 mol) in solution in 30 ml THF was introduced into the mixture. After ten minutes at this temperature, 1-bromo-4-methylpentane (7.9 ml; 0.056 mol) in solution in 20 ml THF was quickly added. The temperature was then left to return to about 23° C. and the mixture agitated for about one hour at this temperature. After hydrolysis with 100 ml water and acidification with 150 ml of a saturated potassium hydrogenosulfate solution, the obtained mixture was extracted with 2 times 50 ml ethyl acetate. The organic phase was washed with 100 ml water followed by 100 ml of a saturated sodium chloride solution. After drying on magnesium sulfate and evaporation of the solvent, the residue obtained was purified on a silica column (eluent: ethyl acetate-heptane/6-4) to produce a white-colored powder with a yield of 50%. MH+=260.3.

13777.2) tert-butyl 1-(4-(3-bromophenyl)-1H-imidazol-2-yl)-5-methylhexylcarbamate A mixture of 2-((tert-butoxycarbonyl)amino)-6-methylheptanoic acid (3.5 g; 0.0135 mol) and cesium carbonate (4.89 g; 0.015 mol) in 100 ml ethanol was agitated at about 23° C. for about 1 hour. The ethanol was eliminated by evaporation under reduced pressure in a rotative evaporator. The mixture obtained was dissolved in 100 ml of dimethylformamide and 3-bromophenacyl bromide (3.75 g; 0.0135 mol) was then added. After about 16 hours agitation, the solvent was evaporated under reduced pressure. The mixture obtained was taken up in ethyl acetate and the cesium bromide was then filtered. The ethyl acetate of the filtrate was evaporated and the reaction oil was taken up in a mixture of xylene (100 ml) and ammonium acetate (46.2 g; 0.6 mol). The mixture was then heated to reflux for about one hour and a half and, after cooling, a mixture of icy water and ethyl acetate was poured in the reaction medium. After phase separation, the organic phase was washed with a sodium saturated bicarbonate solution, dried over magnesium sulfate and then evaporated under vacuum. The solid obtained was filtered and then washed with ether to produce a white powder (yield of 63%). Melting point: 134-136° C. MH+=436.2.

13777.3) 1-(4-(3-bromophenyl)-1H-imidazol-2-yl)-5-methyl-1-hexanamine tert-Butyl 1-(4-(3-bromophenyl)-1H-imidazol-2-yl)-5-methylhexylcarbamate (obtained at stage 13777.2; 3.5 g; 0.008 mol) was agitated in 120 ml of an ethyl acetate solution saturated in hydrochloric acid for about 2.5 at a temperature of about 55° C. The solid obtained was filtered and washed with ether. A white powder was obtained with a yield of 97%. Melting point: 200-202° C. MH+=336.2.

13777.4) N-{1-(4-(3-bromophenyl)-1H-imidazol-2-yl)-5-methylhexyl}-N-cyclohexylamine A mixture containing 1-(4-(3-bromophenyl)-1H-imidazol-2-yl)-5-methyl-1-hexanamine (obtained at stage 13777.3; 0.8 g; 0.0019 mol), triethylamine (0.4 ml; 0.003 mol) and cyclohexanone (0.32 ml; 0.0023 mol) in 10 ml methanol was agitated for about 30 minutes at about 23° C. Sodium triacetoxyborohydride (630 mg; 0.003 mol) was then added. The reaction mixture was agitated for about 16 hours and then poured into water. After extraction with ethyl acetate, the organic phase was washed with a saturated sodium chloride solution and then dried over magnesium sulfate. The solvent was evaporated and the residue purified over a silica column (eluent mixture $CH_2Cl_2$-MeOH/95-05). A white-colored powder was obtained with a yield of 38%. Melting point: 236-238° C. MH+=418.2.

EXAMPLE 13778

N-{1-(4-(4-fluorophenyl)-1H-imidazol-2-yl)heptyl}cyclohexanamine 13778.1) tert-butyl 1-(4-(4-fluorophenyl)-1H-imidazol-2-yl)heptylcarbamate This compound was obtained according to a protocol analogous to that of stage 13777.2 of example 13777, using 2-((tert-butoxycarbonyl)amino)octanoic acid (6.2 g; 0.024 mol) instead of 2-((tert-butoxycarbonyl)amino)-6-methylheptanoic acid and 2-bromo-4-fluoroacetophenone (5.2 g; 0.024 mol) instead of 3-bromophenacyl bromide. A white powder was obtained (yield: 58%), which was sufficiently clean to be used as was for the following stage.

13778.2) 1-(4-(4-fluorophenyl)-1H-imidazol-2-yl)-1-heptanamine

This compound was obtained according to a protocol analogous to that of stage 13777.3 of example 13777, using tert-butyl 1-(4-(4-fluorophenyl)-1H-imidazol-2-yl)heptylcarbamate (5.2 g; 0.014 mol) as starting compound. After purification over a silica column (eluent: $CH_2Cl_2$-MeOH-$NH_4OH$/89-10-1), a gray powder was obtained (yield of 72%). Melting point: 148-150° C. MH+=276.2.

13778.3) N-{1-(4-(4-fluorophenyl)-1H-imidazol-2-yl)heptyl}cyclohexanamine

This compound was obtained according to a protocol analogous to that of stage 13777.4 of example 13777, using 1-(4-(4-fluorophenyl)-1H-imidazol-2-yl)-1-heptanamine (0.5 g; 0.0014 mol) as starting amine and cyclohexanone (0.17 ml; 0.0014 mol) as starting ketone. A white powder was obtained with a yield of 15%. Melting point: 190-192° C. MH+=358.2.

EXAMPLE 13779

(1R)-N-benzyl-1-(1-benzyl-4-tert-butyl-1H-imidazol-2-yl)-2-(1H-indol-3-yl)ethanamine Triethylamine (0.83 ml; 0.006 mol) was added at about 23° C. to a solution of (1R)-1-(1-benzyl-4-tert-butyl-1H-imidazol-2-yl)-2-(1H-indol-3-yl)ethanamine (0.7 g; 0.002 mol; prepared according to experimental conditions analogous to the preceding examples and using the appropriate starting compounds and reaction products) in 15 ml acetonitrile. The mixture was agitated about one hour at about 23° C. and benzyl chloride (0.23 ml; 0.002 mol) was added. Agitation was maintained for about 16 hours. The reaction mixture was concentrated using a rotative evaporator and the oil obtained was taken up in ethyl acetate and water. The aqueous phase was extracted with ethyl acetate and washed with water and then with a saturated solution of sodium chloride. The solvents were evaporated under vacuum. After purification over a silica column (eluent: ethyl acetate-heptane/7-3), a strong beige solid was obtained in the form of a glue (yield of 5%). Free base. Melting point: 60-62° C. MH+=463.3.

EXAMPLE 13780

(R,S)-N-benzyl-1-(1-benzyl-4-phenyl-1H-imidazol-2-yl)-1-heptanamine (R,S)-1-(4-phenyl-1H-imidazol-2-yl)heptylamine (1 g; 0.003 mol; prepared according to experimental conditions analogous to the preceding examples and using the appropriate starting compounds and reaction products) was diluted in 20 ml dimethylformamide. Potassium carbonate (2.2 g; 0.016 mol) was added at about 23° C. and then benzyl bromide (1.2 ml; 0.010 mol) was added quite slowly. The mixture was agitated about 72 hours at about 23° C. before being poured in icy water. The mixture was extracted with ethyl acetate. The organic phase was washed with water and then a saturated solution of sodium chloride. After drying over magnesium sulfate, the solvents were concentrated using a rotative evaporator. After purification over a silica column (eluent: ethyl acetate-heptane/10-90), a white powder was obtained (yield of 31%). Free base. Melting point 94-96° C. MH+=438.3.

EXAMPLE 13781

N-benzyl-N-((4-(1,1'-biphenyl)-4-yl-1H-imidazol-2-yl)methyl)-1-hexanamine

N-benzyl(4-(1,1'-biphenyl)-4-yl-1H-imidazol-2-yl)methanamine (1 g; 0.0024 mol; prepared according to experimental conditions analogous to the preceding examples and using the appropriate starting compounds and reaction products) was diluted in 15 ml dimethylformamide. Potassium carbonate (1 g; 0.0073 mol) was added at about 23° C. and then hexane bromide (0.34 ml; 0.0024 mol) was added quite slowly. The reaction mixture was brought around the temperature of about 70° C. for about 3 hours before being poured in icy water. The mixture was extracted with ethyl acetate and the organic phase washed with water. After drying over magnesium sulfate, the solvents were concentrated using a rotative evaporator. After purification over a silica column (eluent: ethyl acetate-heptane/7-3), a light yellow solid was obtained in the form of a glue (yield of 13%). Free base. Melting point: 120-122° C. MH+=424.3.

EXAMPLE 13782

N-benzyl(4-(1,1'-biphenyl)-4-yl-1H-imidazol-2-yl)-N-methylmethanamine (4-(1,1'-biphenyl)-4-yl-1H-imidazol-2-yl)-N-methylmethanamine (1 g; 0.003 mol; prepared according to experimental conditions analogous to the preceding examples and using the appropriate starting compounds and reaction products) was diluted in 20 ml dimethylformamide. Potassium carbonate (1.23 g; 0.009 mol) was added at about 23° C. and then benzyl bromide (0.34 ml; 0.003 mol) was added quite slowly. The reaction mixture was agitated at this temperature for about 48 hours then poured in icy water. The mixture was extracted with ethyl acetate and the organic phase washed with water. After drying over magnesium sulfate, the solvents were concentrated using a rotative evaporator. After purification over a silica column (eluent: ethyl acetate-heptane/8-2), a white solid was obtained in the form of a glue (yield of 16%). Free base. Melting point: 106-108° C. MH+=354.2.

EXAMPLE 13783

(R,S)-N,N-dihexyl-1-(4-phenyl-1H-imidazol-2-yl)-1-heptanamine (R,S)-1-(4-phenyl-1H-imidazol-2-yl)-1-heptanamine (1 g; 0.003 mol; prepared according to experimental conditions analogous to the preceding examples and using the appropriate starting compounds and reaction products) was diluted in 10 ml methanol. Triethylamine (0.9 ml; 0.006 mol) was added dropwise and the mixture was agitated for about 30 minutes at about 23° C. Hexanal (0.45 ml; 0.0036 mol) was then added and the mixture was agitated for about one hour at about 23° C. Sodium triacetoxyborohydride (1.3 g; 0.006 mol) was finally added. After about two hours agitation at about 23° C., water was added and the reaction mixture extracted with ethyl acetate. The organic phase was washed with water and dried over magnesium sulfate before evaporation of the solvents. After purification over a silica column (eluent: ethyl acetate-heptane/6-4), a chestnut solid was obtained in the form of a glue (yield of 3%). Free base. The melting point could not be measured (sticks). MH+=426.4.

EXAMPLE 13784

N-((1R)-2-(1H-indol-3-yl)-1-(4-phenyl-1H-imidazol-2-yl)ethyl)-2-pyrimidinamine (1R)-2-(1H-indol-3-yl)-1-(4-phenyl-1H-imidazol-2-yl)ethanamine (2 g; 0.0066 mol; prepared according to experimental conditions analogous to the preceding examples and using the appropriate starting compounds and reaction products) was diluted in 10 ml n-butanol. 2-bromopyrimidine (1 g; 0.0066 mol) and then diisoethylamine (1.15 ml; 0.0066 mol) were added dropwise. The mixture was then heated to around 80° C. for about 16 hours. The n-butanol was evaporated and the residue taken up in water and ethyl acetate. The organic phase was washed with water and then with a saturated solution of sodium chloride before being dried over magnesium sulfate and concentrated using a rotative evaporator. After purification over a silica column (eluent: ethyl acetate-heptane/7-3, followed by $CH_2Cl_2$-MeOH-$NH_4OH$/95-4.5-0.5 and ethyl acetate). A white powder was obtained (yield of 20%). Free base. Melting point: 138-140° C. MH+=381.2.

EXAMPLE 13785

(1R)-N-benzyl-2-(1H-indol-3-yl)-N-methyl-1-(4-phenyl-1H-imidazol-2-yl)ethanamine (1R)-N-benzyl-2-(1H-indol-3-yl)-1-(4-phenyl-1H-imidazol-2-yl)ethanamine (0.5 g; 0.00127 mol; prepared according to experimental conditions analogous to that of example 38 using the appropriate starting compounds and reaction products) was diluted in 25 ml tetrahydrofurane. Methyl tosylate (0.24 g; 0.00127 mol) was added to the preceding at about 23° C. and then potassium tert-butylate (0.15 g; 0.00127 mol) was added quite slowly. Agitation at about 23° C. was maintained for about two hours and then the mixture was heated to around 60° C. for about 8 hours. The solvent was evaporated and the residue obtained taken up in ethyl acetate and a 10% sodium bicarbonate solution. After phase separation, the organic phase was washed with water and dried over magnesium sulfate. The solvent was then evaporated. After purification over a silica column (eluent: ethyl acetate-heptane/7-3), a light beige solid was obtained in the form of a glue (yield of 4%). Free base. Melting point: 110-112° C. MH+=407.3.

EXAMPLE 13786

(1-benzyl-4-phenyl-1H-imidazol-2-yl)-N,N-dimethylmethanamine (1-benzyl-4-phenyl-1H-imidazol-2-yl)methanamine (0.6 g; 0.0018 mol; prepared according to experimental conditions analogous to the preceding examples and using the appropriate starting compounds and reaction products) was diluted in 15 ml tetrahydrofurane. Triethylamine (1.12 ml; 0.008 mol) and then methyl 4-toluenesulfonate (0.75 g; 0.004 mol) were added dropwise. The mixture was agitated about 48 hours at about 23° C. and then poured in icy water. After extraction with ether and phase separation, the organic phase was washed with water and afterwards with a saturated solution of sodium chloride. The organic phase was then dried over magnesium sulfate and concentrated using a rotative evaporator.

After purification over a silica column (eluent: ethyl acetate-heptane/7-3 followed by CH$_2$Cl$_2$-MeOH/95-5), a white powder was obtained (yield of 44%). Free base. Melting point: 78-80° C. MH+=292.2.

The following further examples were made according to the procedures described in examples 13777 to 13786 and to the general procedures described in this application.

EXAMPLE 13787 tert-butyl (1R)-1-(4-tert-butyl-1H-imidazol-2-yl)-2-(1H-indol-3-yl)-ethylcarbamate Free base. Melting point: 104-106° C.

EXAMPLE 13788

(4-phenyl-1H-imidazol-2-yl)methanamine

Hydrochloride. Melting point: 228-230° C.

EXAMPLE 13789

N-((1S)-2-(1H-indol-3-yl)-1-(4-phenyl-1H-imidazol-2-yl)ethyl)-1-hexanamine

Hydrochloride. Melting point: 132-134° C.

EXAMPLE 13790 tert-butyl (R,S)-1-(4-phenyl-1H-imidazol-2-yl)heptylcarbamate

Free base. Melting point: 102-104° C.

EXAMPLE 13791

(4-(1,1'-biphenyl)-4-yl-1-methyl-1H-imidazol-2-yl)methanamine

Hydrochloride. Melting point: 279-280° C.

EXAMPLE 13792

(1S)-3-methyl-1-(4-phenyl-1H-imidazol-2-yl)-1-butanamine

Hydrochloride. Melting point: 150-152° C.

EXAMPLE 13793

(R,S)-N-(2-(1-methyl-1H-indol-3-yl)-1-(4-phenyl-1H-imidazol-2-yl)ethyl)-1-butanamine Free base. The melting point could not be measured (sticks).

EXAMPLE 13794

(R,S)-N-benzyl-2-(6-fluoro-1H-indol-3-yl)-1-(4-phenyl-1H-imidazol-2-yl)ethanamine Free base. Melting point: 98-100° C.

EXAMPLE 13795

(R,S)-4-(2-{1-((tert-butoxycarbonyl)amino)pentyl}-1H-imidazol-4-yl)-1,1'-biphenyl Free base. Melting point: 172-176° C.

EXAMPLE 13796

(R,S)-N-benzyl-1-(4-(1,1'-biphenyl)-4-yl-1H-imidazol-2-yl)-1-pentanamine

Free base. Melting point: 201-203° C.

EXAMPLE 13797

(1R)-N-benzyl-2-phenyl-1-(4-phenyl-1H-imidazol-2-yl)ethanamine

Free base. Melting point: 228-230° C.

EXAMPLE 13798 tert-butyl (R,S)-1-(4-phenyl-1H-imidazol-2-yl)hexylcarbamate

Free base. The melting point could not be measured (sticks).

EXAMPLE 13799

(R,S)-N-hexyl-1-(4-phenyl-1H-imidazol-2-yl)-1-heptanamine

Free base. Melting point: 140-142° C.

EXAMPLE 13800

(R,S)-1-(4-phenyl-1H-imidazol-2-yl)hexylamine

Hydrochloride. Melting point: 146-148° C.

EXAMPLE 13801

(R,S)-N-benzyl-1-(4-(4-methoxyphenyl)-1H-imidazol-2-yl)-1-heptanamine

Hydrochloride. Melting point: starting from 115° C.

EXAMPLE 13802

(R,S)-N-(2,6-dichlorobenzyl)-1-(4-phenyl-1H-imidazol-2-yl)-1-heptanamine

Free base. The melting point could not be measured (sticks).

EXAMPLE 13803

(R,S)-N-(4-chlorobenzyl)-1-(4-phenyl-1H-imidazol-2-yl)-1-heptanamine

Free base. The melting point could not be measured (sticks).

EXAMPLE 13804

(R,S)-1-(4-(3-methoxyphenyl)-1H-imidazol-2-yl) heptylamine

Hydrochloride. Melting point: 110-112° C.

EXAMPLE 13805

(R,S)-N-(2-chlorobenzyl)-1-(4-phenyl-1H-imidazol-2-yl)-1-heptanamine

Free base. The melting point could not be measured (sticks).

EXAMPLE 13806

(R,S)-N-(2-fluorobenzyl)-1-(4-phenyl-1H-imidazol-2-yl)-1-heptanamine

Free base. The melting point could not be measured (sticks).

EXAMPLE 13807

(R,S)-N-butyl-1-(4-phenyl-1H-imidazol-2-yl)-1-heptanamine

Free base. The melting point could not be measured (sticks).

EXAMPLE 13808

(R,S)-N-isopentyl-N-(1-(4-phenyl-1H-imidazol-2-yl) heptyl)amine

Free base. The melting point could not be measured (sticks).

EXAMPLE 13809

(R,S)-1-(4-(3-bromophenyl)-1H-imidazol-2-yl)-N-hexyl-1-heptanamine

Free base. The melting point could not be measured (sticks).

EXAMPLE 13810

(R,S)-N-pentyl-1-(4-phenyl-1H-imidazol-2-yl)-1-heptanamine

Free base. Melting point: 118-120° C.

EXAMPLE 13811

(R,S)-N-(1-(4-phenyl-1H-imidazol-2-yl)heptyl)cyclohexanamine

Free base. Melting point: 68-70° C.

EXAMPLE 13812

(R,S)-N-benzyl-1-(4-(3,4-dichlorophenyl)-1H-imidazol-2-yl)-1-heptanamine

Free base. Melting point: 192-194° C.

EXAMPLE 13813 butyl (4-(1,1'-biphenyl)-4-yl-1H-imidazol-2-yl)methylcarbamate

Free base. Melting point 130-132° C.

EXAMPLE 13814

(R,S)-N-(1-(4-phenyl-1H-imidazol-2-yl)heptyl)cyclopentanamine

Free base. The melting point could not be measured (sticks).

EXAMPLE 13815

(R,S)-N-{1-(4-(2-chlorophenyl)-1H-imidazol-2-yl) heptyl}-cyclohexanamine

Hydrochloride. Melting point: 155-157° C.

EXAMPLE 13816

(R,S)-N-{1-(4-(4-fluorophenyl)-1H-imidazol-2-yl) heptyl}-cyclobutanamine

Hydrochloride. Melting point: 144-146° C.

EXAMPLE 13817

(1R)-N-benzyl-2-(1H-indol-3-yl)-1-(4-phenyl-1H-imidazol-2-yl)ethanamine

Free base. Melting point 100-102° C.

EXAMPLE 13818

(R,S)-2-(1H-indol-3-yl)-1-(5-methyl-4-phenyl-1H-imidazol-2-yl)ethanamine

Hydrochloride. Melting point: 208-210° C.

EXAMPLE 13819

(R,S)-2-phenyl-1-(4-phenyl-1H-imidazol-2-yl)ethanamine

Hydrochloride. Melting point: 180-182° C.

EXAMPLE 13820

(R,S)-2-(1-methyl-1H-indol-3-yl)-1-(4-phenyl-1H-imidazol-2-yl)ethylamine

Hydrochloride. Melting point: 110-114° C.

EXAMPLE 13821

(1S)-N-benzyl-2-(1H-indol-3-yl)-1-(4-phenyl-1H-imidazol-2-yl)ethanamine

Free base. Melting point 118-120° C.

EXAMPLE 13822

(1R)-N-benzyl-2-(1H-indol-3-yl)-1-(5-methyl-4-phenyl-1H-imidazol-2-yl)ethanamine Free base. Melting point: 120-122° C.

EXAMPLE 13823 tert-butyl (1R)-2-(1H-indol-3-yl)-1-(4-phenyl-1H-imidazol-2-yl)ethylcarbamate

Free base. Melting point: 208-210° C.

EXAMPLE 13824

(1R)-2-(1H-indol-3-yl)-1-(4-phenyl-1H-imidazol-2-yl)ethanamine

Hydrochloride. The melting point could not be measured (sticks).

EXAMPLE 13825

N-((1R)-2-(1H-indol-3-yl)-1-(4-phenyl-1H-imidazol-2-yl)ethyl)-benzamide

Free base. Melting point: 218-220° C.

EXAMPLE 13826 benzyl (1R)-2-(1H-indol-3-yl)-1-(4-phenyl-1H-imidazol-2-yl)-ethylcarbamate

Free base. Melting point: 105-108° C.

EXAMPLE 13827 tert-butyl (1R)-2-(1H-indol-3-yl)-1-(4-(4-nitrophenyl)-1H-imidazol-2-yl)ethylcarbamate Free base. Melting point 220-222° C.

EXAMPLE 13828 tert-butyl (4-phenyl-1H-imidazol-2-yl)methylcarbamate

Free base. Melting point: 170-172° C.

EXAMPLE 13829 tert-butyl (1-benzyl-4-phenyl-1H-imidazol-2-yl)methylcarbamate

Free base. Melting point: 140-142° C.

EXAMPLE 13830

(1R)-2-(1H-indol-3-yl)-N-(2-phenylethyl)-1-(4-phenyl-1H-imidazol-2-yl)ethanamine Free base. The melting point could not be measured (sticks).

EXAMPLE 13831

(1R)-2-(1H-indol-3-yl)-1-(4-(4-nitrophenyl)-1H-imidazol-2-yl)ethanamine

Hydrochloride. Melting point: begins to stick around 220° C.

EXAMPLE 13832

(1-benzyl-4-phenyl-1H-imidazol-2-yl)methanamine

Hydrochloride. Melting point: 248-250° C.

EXAMPLE 13833

(1R)-2-(1H-indol-3-yl)-N-(2-phenoxyethyl)-1-(4-phenyl-1H-imidazol-2-yl)ethanamine Free base. Melting point: 94-96° C.

EXAMPLE 13834

(1R)-1-(4-tert-butyl-1H-imidazol-2-yl)-2-(1H-indol-3-yl)ethylamine

Hydrochloride. Melting point: 230-232° C.

EXAMPLE 13835

N-benzyl(1-benzyl-4-phenyl-1H-imidazol-2-yl)methanamine

Free base. Melting point: 60-62° C.

EXAMPLE 13836

(1R)-2-(1-benzothien-3-yl)-N-benzyl-1-(4-phenyl-1H-imidazol-2-yl)ethanamine

Free base. Melting point: 152-154° C.

EXAMPLE 13837 tert-butyl (R,S)-2-(6-chloro-1H-indol)-3-yl)-1-(4-phenyl-1H-imidazol-2-yl)ethylcarbamate Free base. Melting point: 208-210° C.

EXAMPLE 13838

(R,S)-2-(6-chloro-1H-indol-3-yl)-1-(4-phenyl-1H-imidazol-2-yl)-ethylamine

Hydrochloride. Melting point: 210-212° C.

EXAMPLE 13839 tert-butyl (1R)-3-methyl-1-(4-phenyl-1H-imidazol-2-yl)butylcarbamate

Free base. Melting point: 88-90° C.

EXAMPLE 13840

(1R)-N-benzyl-3-methyl-1-(4-phenyl-1H-imidazol-2-yl)-1-butanamine

Free base. Melting point 134-135° C.

EXAMPLE 13841 tert-butyl (R,S)-phenyl(4-phenyl-1H-imidazol-2-yl)-methylcarbamate

Free base. Melting point: 134-136° C.

EXAMPLE 13842

(R,S)-phenyl(4-phenyl-1H-imidazol-2-yl)methylamine

Hydrochloride. The melting point could not be measured (sticks).

EXAMPLE 13843 tert-butyl (1R)-3-phenyl-1-(4-phenyl-1H-imidazol-2-yl)-propylcarbamate

Free base. Melting point 72-74° C.

EXAMPLE 13844

(1R)-3-phenyl-1-(4-phenyl-1H-imidazol-2-yl)-1-propanamine

Hydrochloride. Melting point: 174-176° C.

EXAMPLE 13845

(R,S)-N-benzyl(phenyl)(4-phenyl-1H-imidazol-2-yl)methanamine

Free base. Melting point 144-146° C.

EXAMPLE 13846

(1R)-N-benzyl-3-phenyl-1-(4-phenyl-1H-imidazol-2-yl)-1-propanamine

Free base. Melting point: 142-144° C.

EXAMPLE 13847

4-(2-{((tert-butoxycarbonyl)amino)methyl}-1H-imidazol-4-yl)-1,1'-biphenyl

Free base. Melting point: 100-102° C.

EXAMPLE 13848

N-benzyl(4-phenyl-1H-imidazol-2-yl)methanamine

Free base. The melting point could not be measured (sticks).

EXAMPLE 13849

4-(1-benzyl-2-{((tert-butoxycarbonyl)amino)methyl}-1H-imidazol-4-yl)-1,1'-biphenyl Free base. Melting point: 167-169° C.

EXAMPLE 13850

(4-(1,1'-biphenyl)-4-yl-1H-imidazol-2-yl)methanamine

Hydrochloride. Melting point: 240-242° C.

EXAMPLE 13851

(R,S) 1-(4-phenyl-1H-imidazol-2-yl)heptylamine

Hydrochloride. Melting point: 131-134° C.

EXAMPLE 13852

(1-benzyl-4-(1,1'-biphenyl)-4-yl-1H-imidazol-2-yl)methanamine

Hydrochloride. Melting point: 170-174° C.

EXAMPLE 13853

(R,S)-N-benzyl-1-(4-phenyl-1H-imidazol-2-yl)-1-heptanamine

Free base. Melting point: 160-162° C.

EXAMPLE 13854

4-(2-{((tert-butoxycarbonyl)amino)methyl}-1-methyl-1H-imidazol-4-yl)-1,1'-biphenyl Free base. Melting point 208-210° C.

EXAMPLE 13855 tert-butyl (1R)-2-(1H-indol-3-yl)-1-(1-methyl-4-phenyl-1H-imidazol-2-yl)ethylcarbamate Free base. Melting point: 96-100° C.

EXAMPLE 13856

4-(2-{((tert-butoxycarbonyl)(methyl)amino)methyl}-1H-imidazol-4-yl)-1,1'-biphenyl Free base. Melting point: 72-74° C.

EXAMPLE 13857

(1R)-2-(1H-indol-3-yl)-1-(1-methyl-4-phenyl-1H-imidazol-2-yl)-ethanamine

Hydrochloride. Melting point: 206-210° C.

EXAMPLE 13858 tert-butyl methyl((5-methyl-4-phenyl-1H-imidazol-2-yl)-methyl)carbamate

Free base. Melting point: 70-72° C.

EXAMPLE 13859

(4-(1,1'-biphenyl)-4-yl-1H-imidazol-2-yl)-N-methyl-methanamine

Hydrochloride. Melting point: 218-220° C.

EXAMPLE 13860

N-methyl-(5-methyl-4-phenyl-1H-imidazol-2-yl)methanamine

Hydrochloride. Melting point: 218-220° C.

EXAMPLE 13861

4-(2-{(benzyl(tert-butoxycarbonyl)amino)methyl}-1H-imidazol-4-yl)-1,1'-biphenyl

Free-base. Melting point: 130-132° C.

EXAMPLE 13862

(1R)-1-(4-(1,1'-biphenyl)-4-yl-1H-imidazol-2-yl)-3-phenyl-1-propanamine

Hydrochloride. Melting point: 215-218° C.

EXAMPLE 13863

N-benzyl(4-(1,1'-biphenyl)-4-yl-1H-imidazol-2-yl)methanamine

Hydrochloride. Melting point: >250° C.

EXAMPLE 13864

(1R)-N-benzyl-1-(4-(1,1'-biphenyl)-4-yl-1H-imidazol-2-yl)-3-phenyl-1-propanamine Free base. Melting point: 210-213° C.

EXAMPLE 13865 tert-butyl (R,S)-1-(4-phenyl-1H-imidazol-2-yl)pentylcarbamate

Free base. Melting point: 126° C.

EXAMPLE 13866

(R,S)-1-(4-(1,1'-biphenyl)-4-yl-1H-imidazol-2-yl)-1-pentanamine

Hydrochloride. Melting point: 197-200° C.

EXAMPLE 13867

(R,S)-1-(4-phenyl-1H-imidazol-2-yl)pentylamine

Hydrochloride. Melting point: 178-180° C.

EXAMPLE 13868 tert-butyl (R,S)-1-(4-(4-methylphenyl)-1H-imidazol-2-yl)-heptylcarbamate

Free base. Melting point: 77-80° C.

EXAMPLE 13869 tert-butyl (R,S)-1-(4-(2-methoxyphenyl)-1H-imidazol-2-yl)-heptylcarbamate

Free base. Melting point: 64-65° C.

EXAMPLE 13870

(R,S)-1-(4-(4-methylphenyl)-1H-imidazol-2-yl)-1-heptanamine

Hydrochloride. Melting point: 157-160° C.

EXAMPLE 13871

(R,S)-1-(4-(2-methoxyphenyl)-1H-imidazol-2-yl)heptylamine

Hydrochloride. Melting point: 238-240° C.

EXAMPLE 13872

(R,S)-N-benzyl-1-(4-phenyl-1H-imidazol-2-yl)-1-pentanamine

Free base. Melting point: 200-202° C.

EXAMPLE 13873 tert-butyl (R,S)-1-(4-(4-methoxyphenyl)-1H-imidazol-2-yl)-heptylcarbamate

Free base. Melting point: 125-127° C.

EXAMPLE 13874

(R,S)-1-(4-(1,1'-biphenyl)-4-yl-1H-imidazol-2-yl)-1-heptanamine

Hydrochloride. Melting point: 182-184° C.

EXAMPLE 13875 tert-butyl (R,S)-1-(4-(3-bromophenyl)-1H-imidazol-2-yl)-heptylcarbamate

Free base. Melting point: 141-143° C.

EXAMPLE 13876

(R,S)-1-(4-(4-methoxyphenyl)-1H-imidazol-2-yl)heptylamine

Hydrochloride. Melting point: 231-232° C.

EXAMPLE 13877

(R,S)-1-(4-(3-bromophenyl)-1H-imidazol-2-yl)-1-heptanamine

Hydrochloride. Melting point: 230-231° C.

EXAMPLE 13878

(R,S)-4-(2-{1-((tert-butoxycarbonyl)amino)heptyl}-1H-imidazol-4-yl)-1,1'-biphenyl Free base. Melting point: 142-144° C.

EXAMPLE 13879

(R,S)-N-benzyl-1-(4-(3-bromophenyl)-1H-imidazol-2-yl)-1-heptanamine

Acetate. Melting point: 115-116° C.

EXAMPLE 13880

4-(2-{(1S)-1-((tert-butoxycarbonyl)amino)propyl}-1H-imidazol-4-yl)-1,1'-biphenyl Free base. Melting point 138-140° C.

EXAMPLE 13881

(R,S)-N-benzyl-1-(4-(1,1'-biphenyl)-4-yl-1H-imidazol-2-yl)-1-heptanamine

Free base. Melting point: 100-102° C.

EXAMPLE 13882

(1S)-1-(4-(1,1'-biphenyl)-4-yl-1H-imidazol-2-yl)-1-propanamine

Hydrochloride. Melting point: >250° C.

EXAMPLE 13883

(1S)-N-benzyl-1-(4-(1,1'-biphenyl)-4-yl-1H-imidazol-2-yl)-1-propanamine

Free base. Melting point: 220-222° C.

EXAMPLE 13884

(R,S)-N-benzyl-1-(4-(4-methylphenyl)-1H-imidazol-2-yl)-1-heptanamine

Hydrochloride. Melting point: 185-188° C.

EXAMPLE 13885

(R,S)-N-benzyl-1-(4-(2-methoxyphenyl)-1H-imidazol-2-yl)-1-heptanamine

Free base. Melting point: 155-157° C.

EXAMPLE 13886

(R,S)-N-benzyl-1-(4-phenyl-1H-imidazol-2-yl)-1-hexanamine

Free base. Melting point 192-194° C.

EXAMPLE 13887

(R,S)-4-(2-(1-aminoheptyl)-1H-imidazol-4-yl)benzonitrile

Hydrochloride. Melting point: 218-220° C.

EXAMPLE 13888

(R,S)-1-(4-(4-bromophenyl)-1H-imidazol-2-yl)-1-heptanamine

Free base. Melting point: starting from 126° C.

EXAMPLE 13889 tert-butyl (1R)-1-(4-phenyl-1H-imidazol-2-yl)butylcarbamate

Free base. Melting point: 156-158° C.

EXAMPLE 13890

4-(2-{(1R)-1-((tert-butoxycarbonyl)amino)butyl}-1H-imidazol-4-yl)-1,1'-biphenyl

Free base. Melting point: 145.6° C.

EXAMPLE 13891

(1R)-1-(4-(1,1'-biphenyl)-4-yl-1H-imidazol-2-yl)-1-butanamine

Hydrochloride. Melting point: 155.4° C.

EXAMPLE 13892

(R,S)-4-(2-(1-aminoheptyl)-1H-imidazol-4-yl)-2,6-di(tert-butyl)-phenol

Hydrochloride. Melting point: 204-206° C.

EXAMPLE 13893

(1R)-1-(4-phenyl-1H-imidazol-2-yl)-1-butanamine

Hydrochloride. Melting point: 182-184° C.

EXAMPLE 13894

(R,S)-N-benzyl-1-(4-(4-bromophenyl)-1H-imidazol-2-yl)-1-heptanamine

Free base. Melting point: begins to stick around 130° C.

EXAMPLE 13895

(1R)-N-benzyl-1-(4-(1,1'-biphenyl)-4-yl-1H-imidazol-2-yl)-1-butanamine

Free base. Melting point: 78.6° C.

EXAMPLE 13896

(1R)-N-benzyl-1-(4-phenyl-1H-imidazol-2-yl)-1-butanamine

Free base. Melting point: 218-220° C.

EXAMPLE 13897

(R,S)-N-(3-chlorobenzyl)-1-(4-phenyl-1H-imidazol-2-yl)-1-heptanamine

Free base. The melting point could not be measured (sticks).

EXAMPLE 13898

(R,S)-N-benzyl-1-(4-(3-methoxyphenyl)-1H-imidazol-2-yl)-1-heptanamine

Free base. Melting point 141-142° C.

EXAMPLE 13899

(R,S)-4-{2-(1-(benzylamino)heptyl)-1H-imidazol-4-yl}benzonitrile

Free base. Melting point: 188-189° C.

EXAMPLE 13900

(R,S)-4-(2-(1-aminoheptyl)-1H-imidazol-4-yl)-N,N-diethylaniline

Hydrochloride. Melting point: 192° C.

EXAMPLE 13901

(1R)-1-(4-phenyl-1H-imidazol-2-yl)ethanamine

Hydrochloride. Melting point: 178-181° C.

EXAMPLE 13902

(R,S)-1-(4-(4-fluorophenyl)-1H-imidazol-2-yl)-1-heptanamine

Hydrochloride. Melting point: 148-150° C.

EXAMPLE 13903

(R,S)-1-(4-(2-chlorophenyl)-1H-imidazol-2-yl)-1-heptanamine

Hydrochloride. Melting point: 138-140° C.

EXAMPLE 13904

N-((1S)-1-(4-(1,1'-biphenyl)-4-yl-1H-imidazol-2-yl)propyl)-1-butanamine

Free base. The melting point could not be measured (sticks).

EXAMPLE 13905

(1R)-N-benzyl-1-(4-phenyl-1H-imidazol-2-yl)ethanamine

Free base. The melting point could not be measured (sticks).

EXAMPLE 13906

(R,S)-N-(1-(4-phenyl-1H-imidazol-2-yl)heptyl)-N-propylamine

Free base. Melting point: 94-98° C.

EXAMPLE 13907

(R,S)-N-benzyl-1-(4-(3-methoxyphenyl)-1H-imidazol-2-yl)-1-heptanamine

Hydrochloride. Melting point: starting from 120° C.

EXAMPLE 13908

(R,S)-4-{2-(1-(benzylamino)heptyl)-1H-imidazol-4-yl}benzonitrile Hydrochloride. Melting point: starting from 185° C.

EXAMPLE 13909

(R,S)-N-(4-methoxybenzyl)-1-(4-phenyl-1H-imidazol-2-yl)-1-heptanamine

Free base. Melting point: 126-128° C.

EXAMPLE 13910

(R,S)-N-benzyl-1-(4-(4-fluorophenyl)-1H-imidazol-2-yl)-1-heptanamine

Hydrochloride. Melting point: starting from 110° C.

EXAMPLE 13911

(R,S)-N-benzyl-1-(4-(2-chlorophenyl)-1H-imidazol-2-yl)-1-heptanamine

Hydrochloride. Melting point: starting from 90° C.

EXAMPLE 13912

(R,S)-N-benzyl-N-(1-{4-(4-(diethylamino)phenyl)-1H-imidazol-2-yl}heptyl)amine

Hydrochloride. Melting point: 170° C.

EXAMPLE 13913

(R,S)-1-(4-(3,4-dichlorophenyl)-1H-imidazol-2-yl)-1-heptanamine

Hydrochloride. Melting point: 148-150° C.

EXAMPLE 13914 tert-butyl (R,S)-1-(4-(3-bromophenyl)-1H-imidazol-2-yl)-5-methylhexylcarbamate

Free base. Melting point: 134-136° C.

EXAMPLE 13915

(R,S)-1-(4-(3-bromophenyl)-1H-imidazol-2-yl)-5-methyl-1-hexanamine

Hydrochloride. Melting point: 200-202° C.

EXAMPLE 13916

(R,S)-N-isobutyl-1-(4-phenyl-1H-imidazol-2-yl)-1-heptanamine

Acetate. Melting point 70-72° C.

EXAMPLE 13917

(R,S)-N-benzyl-1-(4-(3-bromophenyl)-1H-imidazol-2-yl)-5-methyl-1-hexanamine

Free base. Melting point: 92-94° C.

EXAMPLE 13918

(R,S)-N-benzyl-1-(4-(4-methoxyphenyl)-1H-imidazol-2-yl)-1-heptanamine

Free base. Oil.

EXAMPLE 13919

(R,S)-N-(1-(4-phenyl-1H-imidazol-2-yl)heptyl)cyclobutanamine

Free base. Melting point: 148-150° C.

EXAMPLE 13920

4-(2-{(1S)-1-((butoxycarbonyl)amino)ethyl}-1H-imidazol-4-yl)-1,1'-biphenyl

Free base. Melting point: 118-122° C.

EXAMPLE 13921

4-(2-{(1R)-1-((butoxycarbonyl)amino)ethyl}-1H-imidazol-4-yl)-1,1'-biphenyl

Free base. Melting point: 114-116° C.

EXAMPLE 13922

(R,S)-N-isopropyl-N-(1-(4-phenyl-1H-imidazol-2-yl)heptyl)amine

Free base. Melting point: 114-116° C.

EXAMPLE 13923

(R,S)-N-{1-(4-(3,4-dichlorophenyl)-1H-imidazol-2-yl)heptyl}-cyclohexanamine

Hydrochloride. Melting point: 194° C.

EXAMPLE 13924

(R,S)-N-(1-(4-(1,1'-biphenyl)-4-yl-1H-imidazol-2-yl)heptyl)-cyclohexanamine

Hydrochloride. Melting point: 168-170° C.

EXAMPLE 13925

(R,S)-2-(5-fluoro-1H-indol-3-yl)-1-(4-(4-fluorophenyl)-1H-imidazol-2-yl)ethylamine Hydrochloride. Melting point: 220-222° C.

EXAMPLE 13926

N-{(4-(3-bromophenyl)-1H-imidazol-2-yl)methyl}cyclohexanamine

Free base. Melting point: 202-204° C.

EXAMPLE 13927

(R,S)-N-{2-(5-fluoro-1H-indol-3-yl)-1-(4-(4-fluorophenyl)-1H-imidazol-2-yl)ethyl}cyclobutanamine Hydrochloride. Melting point: 180-190° C.

EXAMPLE 13928

(R,S)-N-{1-(4-(4-fluorophenyl)-1H-imidazol-2-yl)-4-methylpentyl}-cyclohexanamine Hydrochloride. Melting point: 230-232° C.

EXAMPLE 13929

(R,S)-N-(cyclohexylmethyl)-1-(4-phenyl-1H-imidazol-2-yl)-1-heptanamine

Hydrochloride. Melting point: 142-144° C.

EXAMPLE 13930

(R,S)-N-{1-(4-(3-bromophenyl)-1H-imidazol-2-yl)-5-methylhexyl}-cyclohexanamine

Hydrochloride. Melting point: 216.7° C.

EXAMPLE 13931

N-{(1R)-1-(4-(4-fluorophenyl)-1H-imidazol-2-yl)-2-methylpropyl}-cyclohexanamine

Free base. Melting point: 224-226° C.

What is claimed is:

1. A compound selected from the group consisting of:
N-{1-(4-(3-bromophenyl)-1H-imidazol-2-yl)-5-methylhexyl}-N-cyclohexylamine;
N-{1-(4-(4-fluorophenyl)-1H-imidazol-2-yl)heptyl}cyclohexanamine;
(4-phenyl-1H-imidazol-2-yl)methanamine;
(1S)-3-methyl-1-(4-phenyl-1H-imidazol-2-yl)-1-butanamine;
(1R)-N-benzyl-2-phenyl-1-(4-phenyl-1H-imidazol-2-yl)ethanamine;
N-benzyl(4-phenyl-1H-imidazol-2-yl)methanamine;
tert-butyl (R,S)-1-(4-phenyl-1H-imidazol-2-yl)heptylcarbamate;
(4-(1,1'-biphenyl)-4-yl-1-methyl-1H-imidazol-2-yl)methanamine;
(R,S)-N-benzyl-1-(1-benzyl-4-phenyl-1H-imidazol-2-yl)-1-heptanamine;
N-benzyl-N-((4-(1,1'-biphenyl)-4-yl-1H-imidazol-2-yl)methyl)-1-hexanamine;
N-benzyl(4-(1,1'-biphenyl)-4-yl-1H-imidazol-2-yl)-N-methylmethanamine;
(R,S)-4-(2-{1-((tert-butoxycarbonyl)amino)pentyl}-1H-imidazol-4-yl)-1,1'-biphenyl;
(R,S)-N-benzyl-1-(4-(1,1'-biphenyl)-4-yl-1H-imidazol-2-yl)-1-pentanamine;
(R,S)-N,N-dihexyl-1-(4-phenyl-1H-imidazol-2-yl)-1-heptanamine;
tert-butyl (R,S)-1-(4-phenyl-1H-imidazol-2-yl)hexylcarbamate;
(R,S)-N-hexyl-1-(4-phenyl-1H-imidazol-2-yl)-1-heptanamine;
(R,S)-1-(4-phenyl-1H-imidazol-2-yl)hexylamine;
(R,S)-N-benzyl-1-(4-(4-methoxyphenyl)-1H-imidazol-2-yl)-1-heptanamine;
(R,S)-N-(2,6-dichlorobenzyl)-1-(4-phenyl-1H-imidazol-2-yl)-1-heptanamine;
(R,S)-N-(4-chlorobenzyl)-1-(4-phenyl-1H-imidazol-2-yl)-1-heptanamine;
(R,S)-1-(4-(3-methoxyphenyl)-1H-imidazol-2-yl)heptylamine;
(R,S)-N-(2-chlorobenzyl)-1-(4-phenyl-1H-imidazol-2-yl)-1-heptanamine;
(R,S)-N-(2-fluorobenzyl)-1-(4-phenyl-1H-imidazol-2-yl)-1-heptanamine;
(R,S)-N-butyl-1-(4-phenyl-1H-imidazol-2-yl)-1-heptanamine;
(R,S)-N-isopentyl-N-(1-(4-phenyl-1H-imidazol-2-yl)heptyl)amine;
(R,S)-1-(4-(3-bromophenyl)-1H-imidazol-2-yl)-N-hexyl-1-heptanamine;
(R,S)-N-pentyl-1-(4-phenyl-1H-imidazol-2-yl)-1-heptanamine;
(R,S)-N-(1-(4-phenyl-1H-imidazol-2-yl)heptyl)cyclohexanamine;
(R,S)-N-benzyl-1-(4-(3,4-dichlorophenyl)-1H-imidazol-2-yl)-1-heptanamine;
butyl (4-(1,1'-biphenyl)-4-yl-1H-imidazol-2-yl)methylcarbamate;
(R,S)-N-(1-(4-phenyl-1H-imidazol-2-yl)heptyl)cyclopentanamine;
(R,S)-N-{1-(4-(2-chlorophenyl)-1H-imidazol-2-yl)heptyl}-cyclohexanamine;
(R,S)-N-{1-(4-(4-fluorophenyl)-1H-imidazol-2-yl)heptyl}-cyclobutanamine;
(R,S)-2-phenyl-1-(4-phenyl-1H-imidazol-2-yl)ethanamine;
tert-butyl (4-phenyl-1H-imidazol-2-yl)methylcarbamate;
tert-butyl (1-benzyl-4-phenyl-1H-imidazol-2-yl)methylcarbamate;
(1-benzyl-4-phenyl-1H-imidazol-2-yl)methanamine;
N-benzyl(1-benzyl-4-phenyl-1H-imidazol-2-yl)methanamine;
(1R)-2-(1-benzothien-3-yl)-N-benzyl-1-(4-phenyl-1H-imidazol-2-yl)ethanamine;
tert-butyl (1R)-3-methyl-1-(4-phenyl-1H-imidazol-2-yl)butylcarbamate;
(1R)-N-benzyl-3-methyl-1-(4-phenyl-1H-imidazol-2-yl)-1-butanamine;
tert-butyl (R,S)-phenyl(4-phenyl-1H-imidazol-2-yl)methylcarbamate;
(R,S)-phenyl(4-phenyl-1H-imidazol-2-yl)methylamine;
tert-butyl (1R)-3-phenyl-1-(4-phenyl-1H-imidazol-2-yl)propylcarbamate;
(1R)-3-phenyl-1-(4-phenyl-1H-imidazol-2-yl)-1-propanamine;
(R,S)-N-benzyl(phenyl)(4-phenyl-1H-imidazol-2-yl)methanamine;
(1R)-N-benzyl-3-phenyl-1-(4-phenyl-1H-imidazol-2-yl)-1-propanamine;
4-(2-{((tert-butoxycarbonyl)amino)methyl}-1H-imidazol-4-yl)-1,1'-biphenyl;
(1-benzyl-4-phenyl-1H-imidazol-2-yl)-N,N-dimethylmethanamine;
4-(1-benzyl-2-{((tert-butoxycarbonyl)amino)methyl}-1H-imidazol-4-yl)-1,1'-biphenyl;
(4-(1,1'-biphenyl)-4-yl-1H-imidazol-2-yl)methanamine;
(R,S) 1-(4-phenyl-1H-imidazol-2-yl)heptylamine;
(1-benzyl-4(1,1'-biphenyl)-4-yl-1H-imidazol-2-yl)methanamine;
(R,S)-N-benzyl-1-(4-phenyl-1H-imidazol-2-yl)-1-heptanamine;
4-(2-{((tert-butoxycarbonyl)amino)methyl}-1-methyl-1H-imidazol-4-yl)-1,1'-biphenyl;
4-(2-{((tert-butoxycarbonyl)(methyl)amino)methyl}-1H-imidazol-4-yl)-1,1'-biphenyl;
tert-butyl methyl((5-methyl-4-phenyl-1H-imidazol-2-yl)methyl)carbamate;
(4-(1,1'-biphenyl)-4-yl-1H-imidazol-2-yl)-N-methylmethanamine;
N-methyl-(5-methyl-4-phenyl-1H-imidazol-2-yl)methanamine;
4-(2-{(benzyl(tert-butoxycarbonyl)amino)methyl}-1H-imidazol-4-yl)-1,1'-biphenyl;
(1R)-1-(4-(1,1'-biphenyl)-4-yl-1H-imidazol-2-yl)-3-phenyl-1-propanamine;
N-benzyl(4-(1,1'-biphenyl)-4-yl-1H-imidazol-2-yl)methanamine;
(1R)-N-benzyl-1-(4-(1,1'-biphenyl)-4-yl-1H-imidazol-2-yl)-3-phenyl-1-propanamine;

tert-butyl (R,S)-1-(4-phenyl-1H-imidazol-2-yl)pentylcarbamate;
(R,S)-1-(4-(1,1'-biphenyl)-4-yl-1H-imidazol-2-yl)-1-pentanamine;
(R,S)-1-(4-phenyl-1H-imidazol-2-yl)pentylamine;
tert-butyl (R,S)-1-(4-(4-methylphenyl)-1H-imidazol-2-yl)-heptylcarbamate;
tert-butyl (R,S)-1-(4-(2-methoxyphenyl)-1H-imidazol-2-yl)-heptylcarbamate;
(R,S)-1-(4-(4-methylphenyl)-1H-imidazol-2-yl)-1-heptanamine;
(R,S)-1-(4-(2-methoxyphenyl)-1H-imidazol-2-yl)heptylamine;
(R,S)-N-benzyl-1-(4-phenyl-1H-imidazol-2-yl)-1-pentanamine;
tert-butyl (R,S)-1-(4-(4-methoxyphenyl)-1H-imidazol-2-yl)heptylcarbamate;
(R,S)-1-(4-(1,1'-biphenyl)-4-yl-1H-imidazol-2-yl)-1-heptanamine;
tert-butyl (R,S)-1-(4-(3-bromophenyl)-1H-imidazol-2-yl)-heptylcarbamate;
(R,S)-1-(4-(4-methoxyphenyl)-1H-imidazol-2-yl)heptylamine;
(R,S)-1-(4-(3-bromophenyl)-1H-imidazol-2-yl)-1-heptanamine;
(R,S)-4-(2-{1-((tert-butoxycarbonyl)amino)heptyl}-1H-imidazol-4-yl)-1,1'-biphenyl;
(R,S)-N-benzyl-1-(4-(3-bromophenyl)-1H-imidazol-2-yl)-1-heptanamine;
4-(2-{(1S)-1-((tert-butoxycarbonyl)amino)propyl}-1H-imidazol-4-yl)-1,1'-biphenyl;
(R,S)-N-benzyl-1-(4-(1,1'-biphenyl)-4-yl-1H-imidazol-2-yl)-1-heptanamine;
(1S)-1-(4-(1,1'-biphenyl)-4-yl-1H-imidazol-2-yl)-1-propanamine;
(1S)-N-benzyl-1-(4-(1,1'-biphenyl)-4-yl-1H-imidazol-2-yl)-1-propanamine;
(R,S)-N-benzyl-1-(4-(4-methylphenyl)-1H-imidazol-2-yl)-1-heptanamine;
(R,S)-N-benzyl-1-(4-(2-methoxyphenyl)-1H-imidazol-2-yl)-1-heptanamine;
(R,S)-N-benzyl-1-(4-phenyl-1H-imidazol-2-yl)-1-hexanamine;
(R,S)-4-(2-(1-aminoheptyl)-1H-imidazol-4-yl)benzonitrile;
(R,S)-1-(4-(4-bromophenyl)-1H-imidazol-2-yl)-1-heptanamine;
tert-butyl (1R)-1-(4-phenyl-1H-imidazol-2-yl)butylcarbamate;
4-(2-{(1R)-1-((tert-butoxycarbonyl)amino)butyl}-1H-imidazol-4-yl)-1,1'-biphenyl;
(1R)-1-(4-(1,1'-biphenyl)-4-yl-1H-imidazol-2-yl)-1-butanamine;
(R,S)-4-(2-(1-aminoheptyl)-1H-imidazol-4-yl)-2,6-di(tert-butyl)-phenol;
(1R)-1-(4-phenyl-1H-imidazol-2-yl)-1-butanamine;
(R,S)-N-benzyl-1-(4-(4-bromophenyl)-1H-imidazol-2-yl)-1-heptanamine;
(1R)-N-benzyl-1-(4-(1,1'-biphenyl)-4-yl-1H-imidazol-2-yl)-1-butanamine;
(1R)-N-benzyl-1-(4-phenyl-1H-imidazol-2-yl)-1-butanamine;
(R,S)-N-(3-chlorobenzyl)-1-(4-phenyl-1H-imidazol-2-yl)-1-heptanamine;
(R,S)-N-benzyl-1-(4-(3-methoxyphenyl)-1H-imidazol-2-yl)-1-heptanamine;
(R,S)-4-{2-(1-(benzylamino)heptyl)-1H-imidazol-4-yl}benzonitrile;
(R,S)-4-(2-(1-aminoheptyl)-1H-imidazol-4-yl)-N,N-diethylaniline;
(1R)-1-(4-phenyl-1H-imidazol-2-yl)ethanamine;
(R,S)-1-(4-(4-fluorophenyl)-1H-imidazol-2-yl)-1-heptanamine;
(R,S)-1-(4-(2-chlorophenyl)-1H-imidazol-2-yl)-1-heptanamine;
N-((1S)-1-(4-(1,1'-biphenyl)-4-yl-1H-imidazol-2-yl)propyl)-1-butanamine;
(1R)-N-benzyl-1-(4-phenyl-1H-imidazol-2-yl)ethanamine;
(R,S)-N-(1-(4-phenyl-1H-imidazol-2-yl)heptyl)-N-propylamine;
(R,S)-N-benzyl-1-(4-(3-methoxyphenyl)-1H-imidazol-2-yl)-1-heptanamine;
(R,S)-4-{2-(1-(benzylamino)heptyl)-1H-imidazol-4-yl}benzonitrile;
(R,S)-N-(4-methoxybenzyl)-1-(4-phenyl-1H-imidazol-2-yl)-1-heptanamine;
(R,S)-N-benzyl-1-(4-(4-fluorophenyl)-1H-imidazol-2-yl)-1-heptanamine;
(R,S)-N-benzyl-1-(4-(2-chlorophenyl)-1H-imidazol-2-yl)-1-heptanamine;
(R,S)-N-benzyl-N-(1-{4-(4-(diethylamino)phenyl)-1H-imidazol-2-yl}heptyl)amine;
(R,S)-1-(4-(3,4-dichlorophenyl)-1H-imidazol-2-yl)-1-heptanamine;
tert-butyl (R,S)-1-(4-(3-bromophenyl)-1H-imidazol-2-yl)-5-methylhexylcarbamate;
(R,S)-1-(4-(3-bromophenyl)-1H-imidazol-2-yl)-5-methyl-1-hexanamine;
(R,S)-N-isobutyl-1-(4-phenyl-1H-imidazol-2-yl)-1-heptanamine;
(R,S)-N-benzyl-1-(4-(3-bromophenyl)-1H-imidazol-2-yl)-5-methyl-1-hexanamine;
(R,S)-N-benzyl-1-(4-(4-methoxyphenyl)-1H-imidazol-2-yl)-1-heptanamine;
(R,S)-N-(1-(4-phenyl-1H-imidazol-2-yl)heptyl)cyclobutanamine;
4-(2-{(1S)-1-((butoxycarbonyl)amino)ethyl}-1H-imidazol-4-yl)-1,1'-biphenyl;
4-(2-{(1R)-1-((butoxycarbonyl)amino)ethyl}-1H-imidazol-4-yl)-1,1'-biphenyl;
(R,S)-N-isopropyl-N-(1-(4-phenyl-1H-imidazol-2-yl)heptyl)amine;
(R,S)-N-{1-(4-(3,4-dichlorophenyl)-1H-imidazol-2-yl)heptyl}-cyclohexanamine;
(R,S)-N-(1-(4(1,1'-biphenyl)-4-yl-1H-imidazol-2-yl)heptyl)-cyclohexanamine;
N-{(4-(3-bromophenyl)-1H-imidazol-2-yl)methyl}cyclohexanamine;
(R,S)-N-{1-(4-(4-fluorophenyl)-1H-imidazol-2-yl)-4-methylpentyl}-cyclohexanamine;
(R,S)-N-(cyclohexylmethyl)-1-(4-phenyl-1H-imidazol-2-yl)-1-heptanamine;
(R,S)-N-{1-(4-(3-bromophenyl)-1H-imidazol-2-yl)-5-methylhexyl}-cyclohexanamine; and
N-{(1R)-1-(4-(4-fluorophenyl)-1H-imidazol-2-yl)-2-methylpropyl}-cyclohexanamine;
or a pharmaceutically acceptable salt thereof.

2. A pharmaceutical composition comprising a compound according to claim 1 or a pharmaceutically acceptable salt thereof and a pharmaceutically acceptable carrier.

3. A method of treating acromegaly, restenosis, Crohn's disease, systemic sclerosis, external and internal pancreatic pseudocysts and ascites, VIPoma, nesidoblastosis, hyperinsulinism, gastrinoma, Zollinger-Ellison Syndrome, diarrhea, AIDS related diarrhea, chemotherapy related diarrhea, scleroderma, Irritable Bowel Syndrome, pancreatitis, small bowel obstruction, gastroesophageal reflux, duodenogastric reflux, Cushing's Syndrome, hyperparathyroidism, Graves' Disease, Paget's disease, polycystic ovary disease, TSH secreting adenomas, in a subject in need thereof, which comprises administering an effective amount of a compound according to claim 1 or a pharmaceutically acceptable salt thereof to said subject.

4. A method of treating peptic ulcers, enterocutaneous and pancreaticocutaneous fistula, Dumping syndrome, watery diarrhea syndrome, acute or chronic pancreatitis, gastrointestinal hormone secreting tumors, chronic allograft rejection, graft vessel bleeding or gastrointestinal bleeding in a subject in need thereof, which comprises administering an effective amount of a compound according to claim 1 or a pharmaceutically acceptable salt thereof to said subject.

* * * * *